(12) United States Patent
John et al.

(10) Patent No.: US 11,376,138 B2
(45) Date of Patent: *Jul. 5, 2022

(54) MEDICAL DEVICE FOR SENSING AND OR STIMULATING TISSUE

(71) Applicant: The University of Melbourne

(72) Inventors: Sam Emmanuel John, Parkville (AU); Nicholas Lachlan Opie, Parkville (AU); Thomas James Oxley, New York, NY (US)

(73) Assignee: The University of Melbourne

( * ) Notice: Subject to any disclaimer, the term of this patent is extended or adjusted under 35 U.S.C. 154(b) by 0 days.

This patent is subject to a terminal disclaimer.

(21) Appl. No.: 16/683,077

(22) Filed: Nov. 13, 2019

(65) Prior Publication Data

US 2020/0078195 A1      Mar. 12, 2020

Related U.S. Application Data

(63) Continuation of application No. 16/054,657, filed on Aug. 3, 2018, now Pat. No. 10,512,555.
(Continued)

(51) Int. Cl.
*A61F 2/68*       (2006.01)
*A61B 5/24*       (2021.01)
(Continued)

(52) U.S. Cl.
CPC ............... *A61F 2/68* (2013.01); *A61B 5/24* (2021.01); *A61B 5/4851* (2013.01);
(Continued)

(58) Field of Classification Search
CPC ...... A61F 2/68; A61F 2/72; A61F 2/86; A61F 2250/0002; A61F 2002/705;
(Continued)

(56) References Cited

U.S. PATENT DOCUMENTS 6,360,122 B1 * 3/2002 Fischell ................ A61B 5/369
600/544
7,826,894 B2   11/2010 Musallam et al.
(Continued)

FOREIGN PATENT DOCUMENTS

CN       106922125        7/2017
CN       101300045        11/2018
WO     WO 2019/028394     2/2019

*Primary Examiner* — Basil T. Jos
(74) *Attorney, Agent, or Firm* — Levine Bagade Han LLP

(57) ABSTRACT

Devices, methods and systems for transmitting signals through a device located in a blood vessel of an animal for stimulating and/or sensing activity of media proximal to the devices. The media can include tissue and/or fluid. A method of controlling an apparatus in communication with a brain machine interface. The method can include measuring a first neural activity in a first neural area and measuring a second neural activity in a second neural area. The first neural activity can be associated with a first intent. The method can include creating and delivering, via the processor, one or more first control signals to the apparatus upon comparing the second neural activity with the first neural activity, and confirming, based on this comparison, that the second neural activity is associated with the first intent.

20 Claims, 80 Drawing Sheets

Related U.S. Application Data

(60) Provisional application No. 62/545,875, filed on Aug. 15, 2017, provisional application No. 62/540,997, filed on Aug. 3, 2017.

(51) Int. Cl.

| | |
|---|---|
| *A61N 1/36* | (2006.01) |
| *A61F 2/86* | (2013.01) |
| *A61B 5/00* | (2006.01) |
| *A61F 2/72* | (2006.01) |
| *B25J 9/00* | (2006.01) |
| *G06F 3/01* | (2006.01) |
| *A61F 2/70* | (2006.01) |
| *A61N 1/05* | (2006.01) |
| *A61B 5/291* | (2021.01) |

(52) U.S. Cl.
CPC .......... *A61B 5/6862* (2013.01); *A61B 5/6868* (2013.01); *A61B 5/6876* (2013.01); *A61F 2/72* (2013.01); *A61F 2/86* (2013.01); *A61N 1/36003* (2013.01); *B25J 9/00* (2013.01); *G06F 3/015* (2013.01); *A61B 5/291* (2021.01); *A61B 2562/227* (2013.01); *A61F 2002/6827* (2013.01); *A61F 2002/705* (2013.01); *A61F 2250/0002* (2013.01); *A61N 1/0531* (2013.01); *A61N 1/0534* (2013.01); *A61N 1/0536* (2013.01); *A61N 1/36067* (2013.01); *A61N 1/36078* (2013.01); *A61N 1/36085* (2013.01); *A61N 1/36089* (2013.01); *A61N 1/36096* (2013.01); *A61N 1/36178* (2013.01)

(58) Field of Classification Search
CPC .... A61F 2002/6827; G06F 3/015; B25J 9/00; A61B 5/24; A61B 5/6862; A61B 5/6868; A61B 5/4851; A61B 5/6876; A61B 5/291; A61B 2562/227; A61N 1/36003; A61N 1/36089; A61N 1/0531; A61N 1/36067; A61N 1/36178; A61N 1/36096; A61N 1/0536; A61N 1/0534; A61N 1/36078; A61N 1/36085
See application file for complete search history.

(56) References Cited

U.S. PATENT DOCUMENTS

| | | |
|---|---|---|
| 2004/0199235 A1* | 10/2004 | Younis ................ A61N 1/0539 607/116 |
| 2005/0228515 A1 | 10/2005 | Musallam et al. |
| 2006/0167371 A1 | 7/2006 | Flaherty et al. |
| 2010/0271051 A1 | 10/2010 | Sankai et al. |
| 2011/0137212 A1 | 6/2011 | Hahn et al. |
| 2012/0035765 A1 | 2/2012 | Sato et al. |
| 2012/0071780 A1 | 3/2012 | Barachant et al. |
| 2013/0184558 A1 | 7/2013 | Gallant et al. |
| 2014/0288667 A1 | 9/2014 | Oxley |
| 2014/0330404 A1 | 11/2014 | Abdelghani |
| 2015/0012111 A1 | 1/2015 | Contreras-Vidal et al. |
| 2016/0048753 A1 | 2/2016 | Sussillo et al. |
| 2017/0172497 A1 | 6/2017 | Marquez |
| 2018/0199840 A1 | 7/2018 | Loureiro et al. |
| 2019/0025917 A1 | 1/2019 | Francis et al. |
| 2019/0038438 A1 | 2/2019 | John et al. |

\* cited by examiner

"THINK ABOUT MOVING YOUR LEGS"

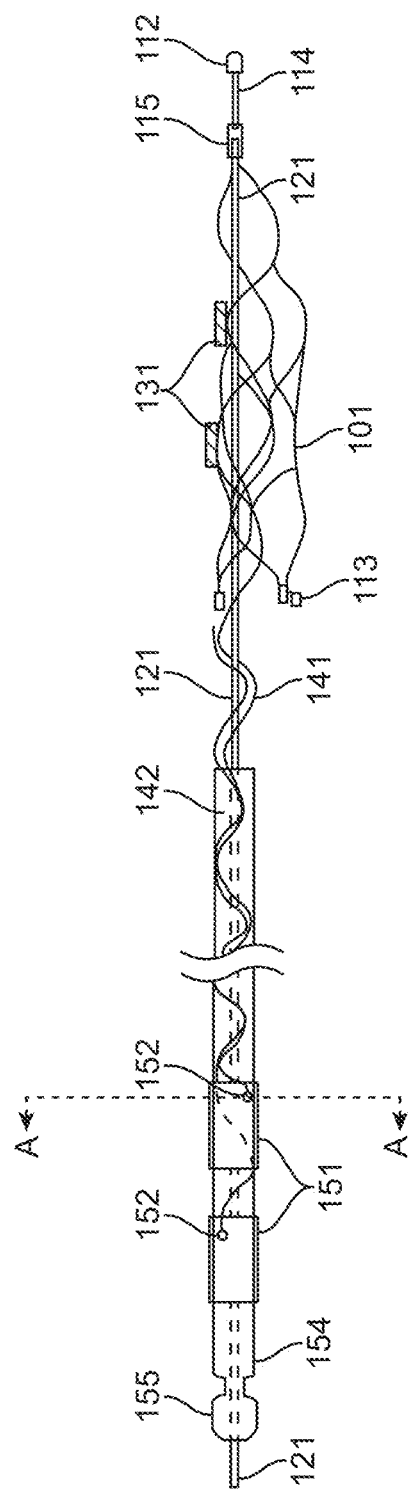
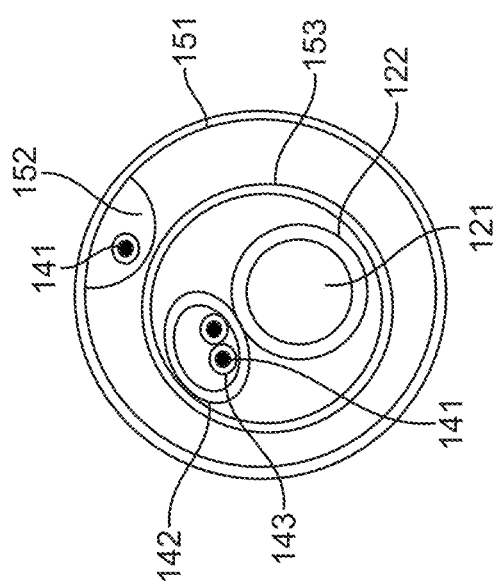
FIG. 5A
FIG. 5B

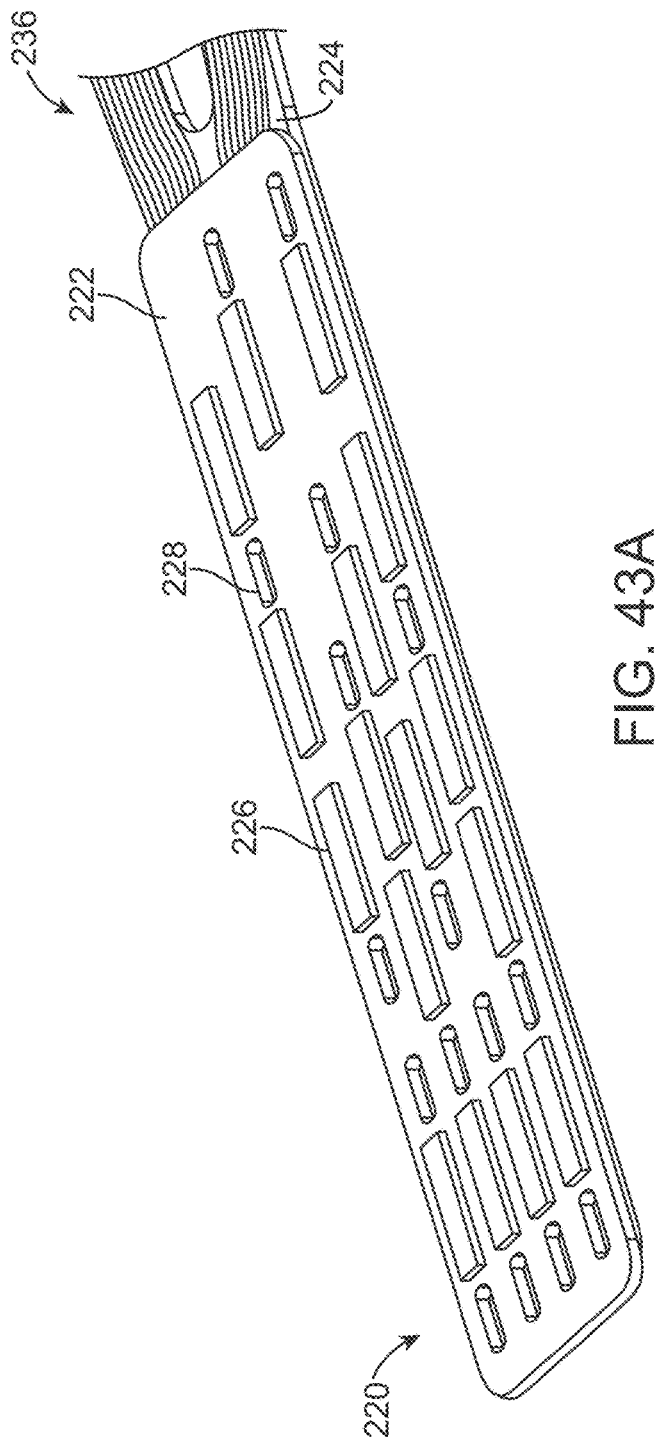
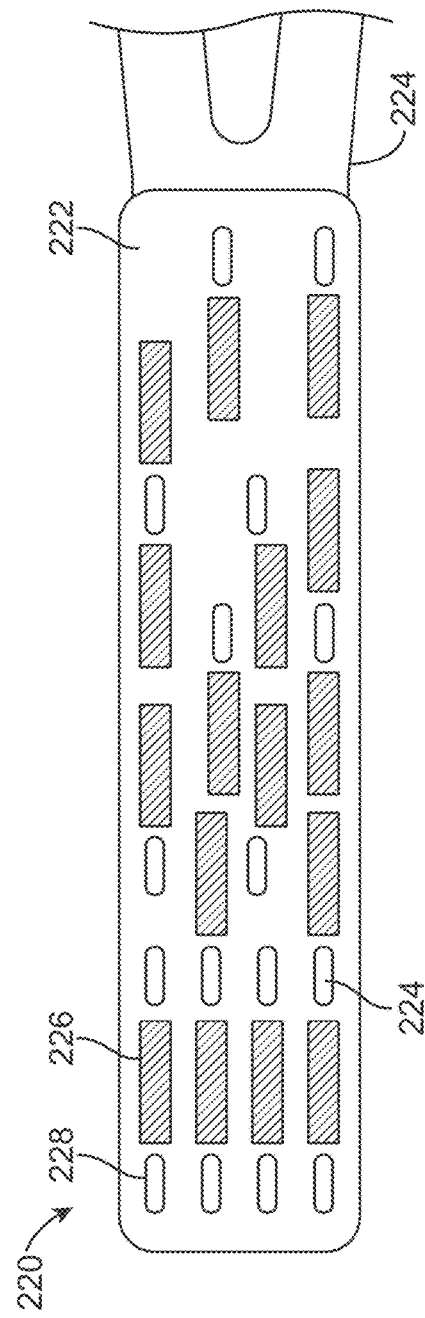
FIG. 43A
FIG. 43B

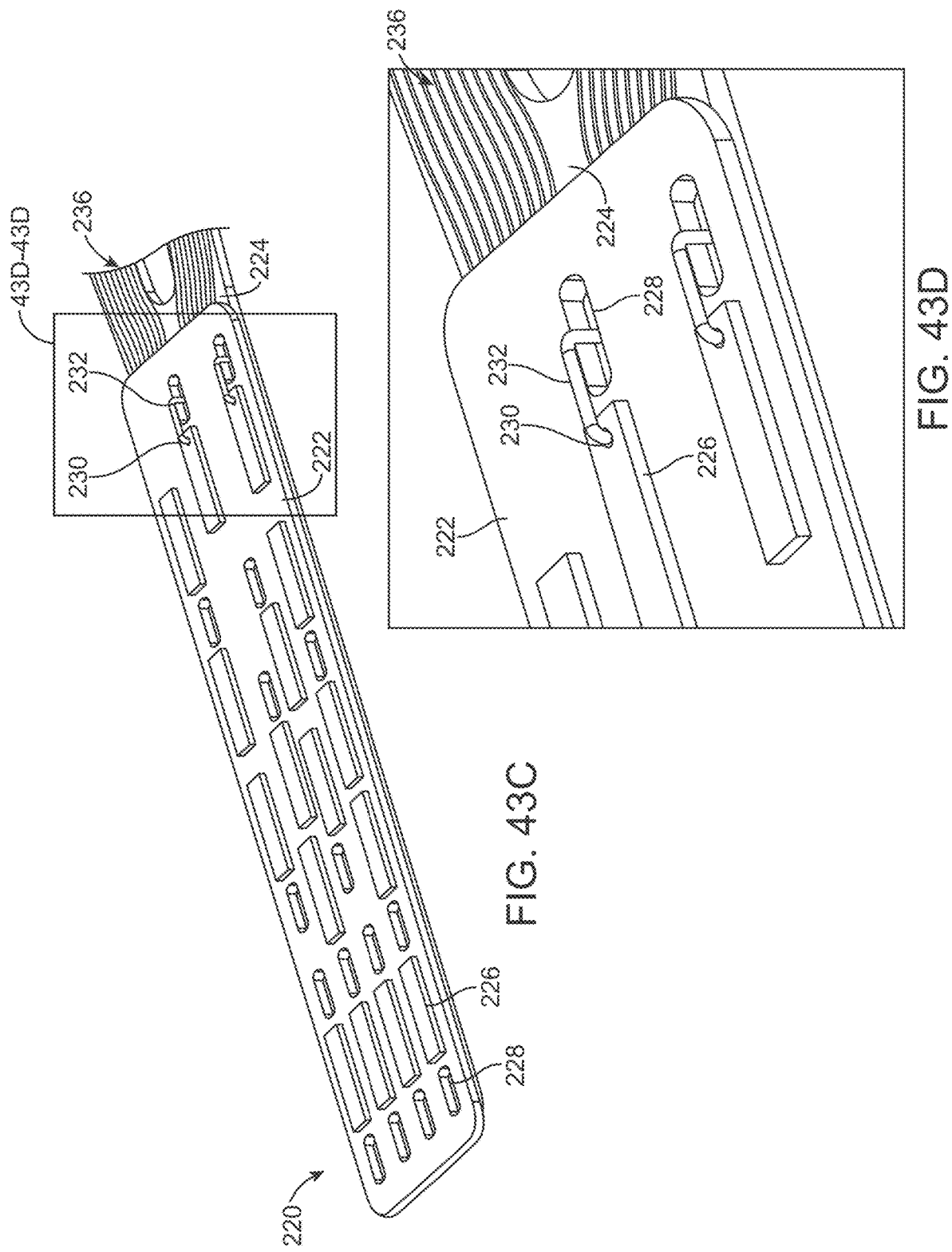

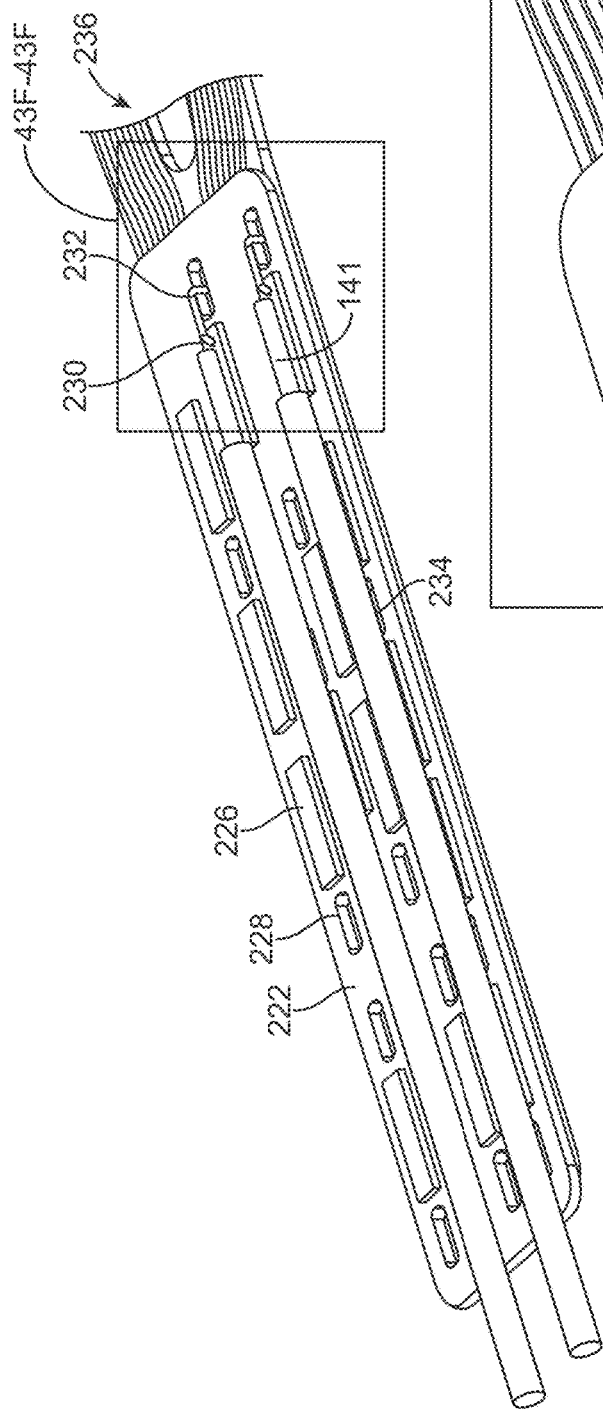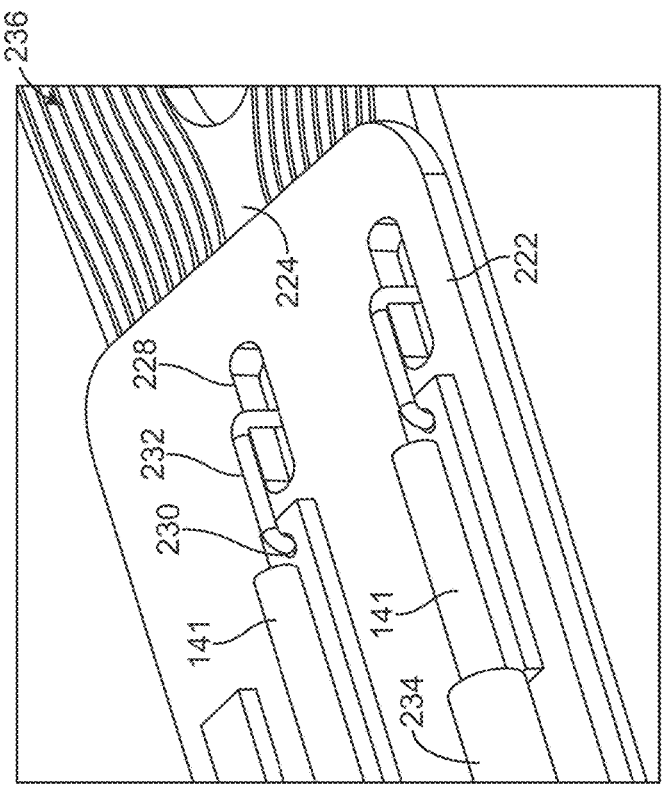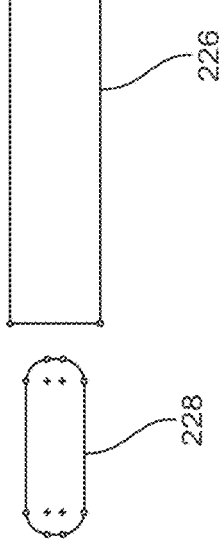

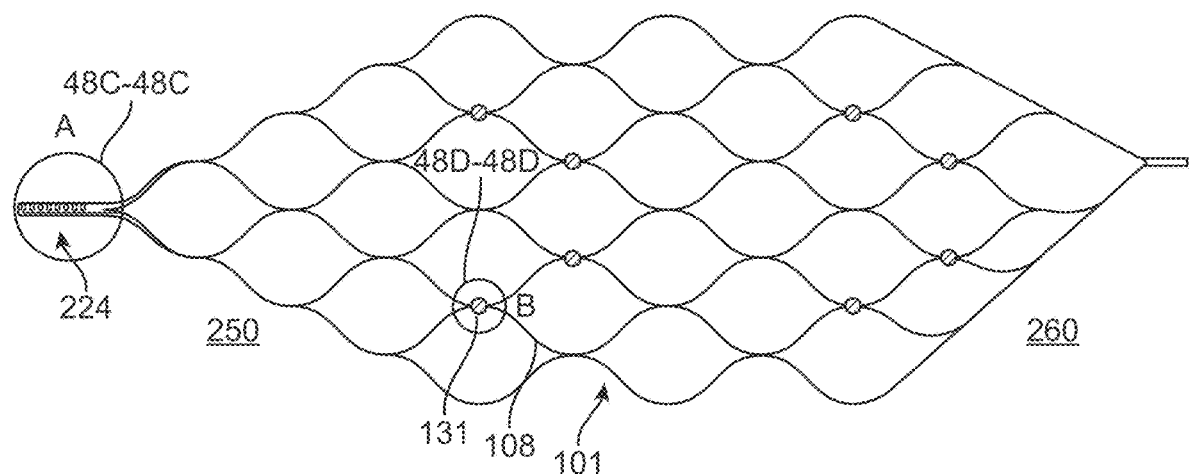
FIG. 48A
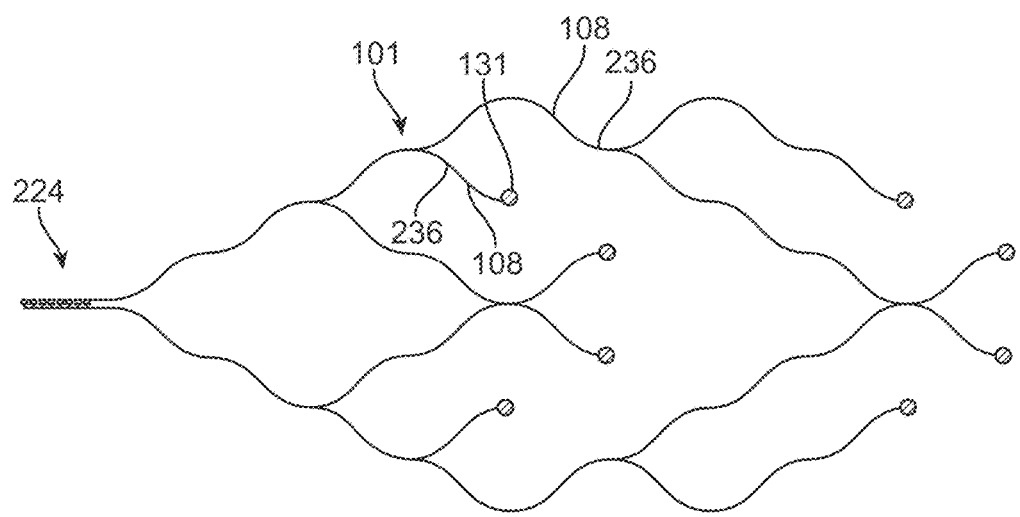
FIG. 48B
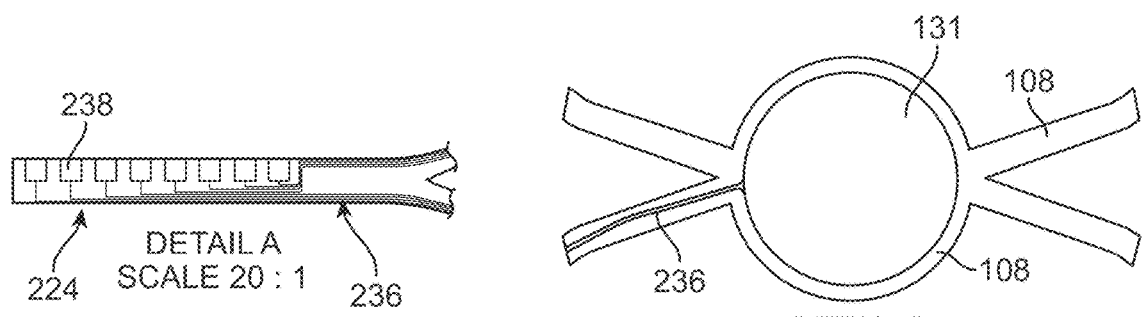
FIG. 48C
FIG. 48D

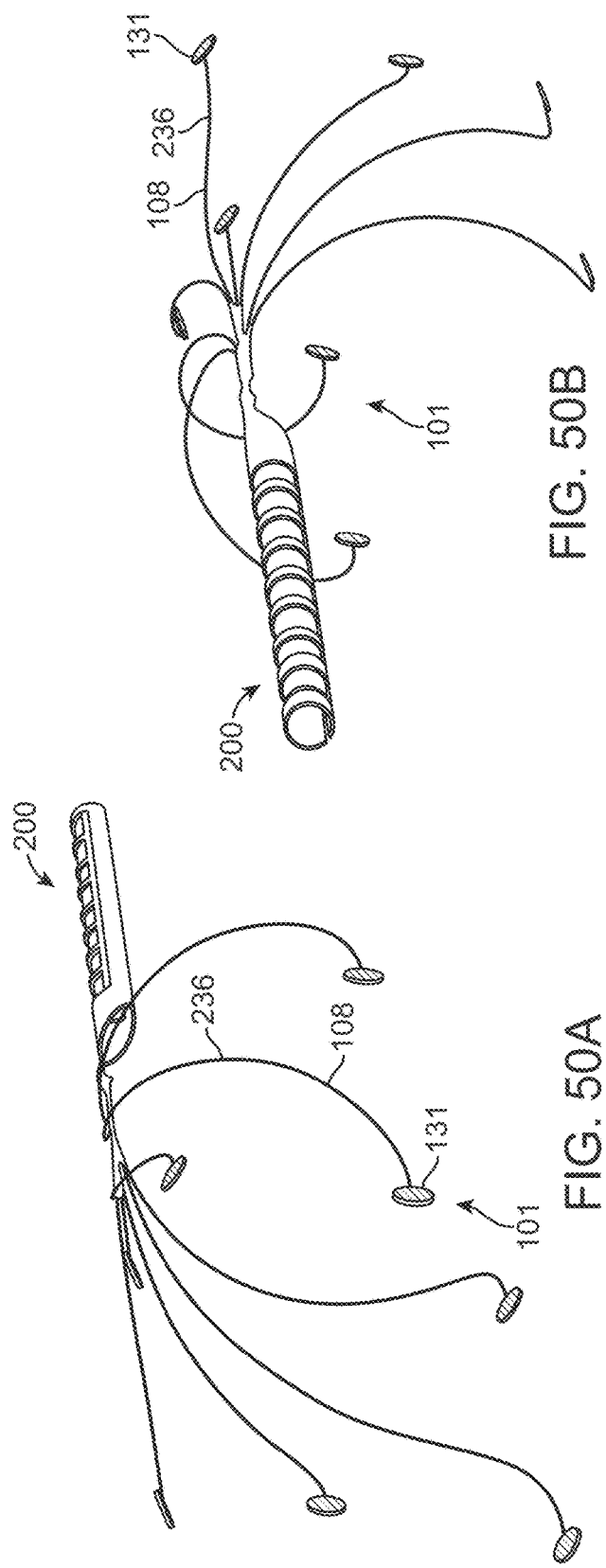
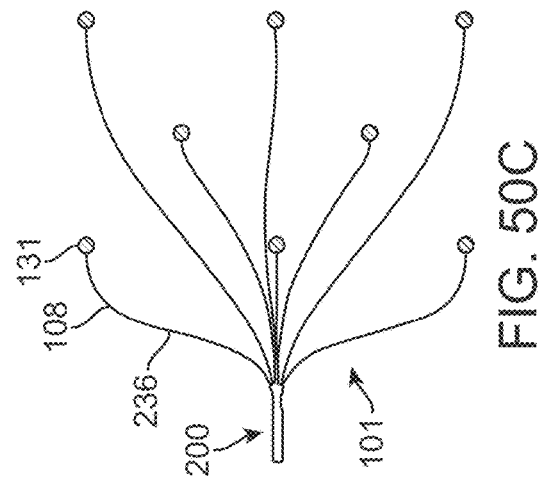

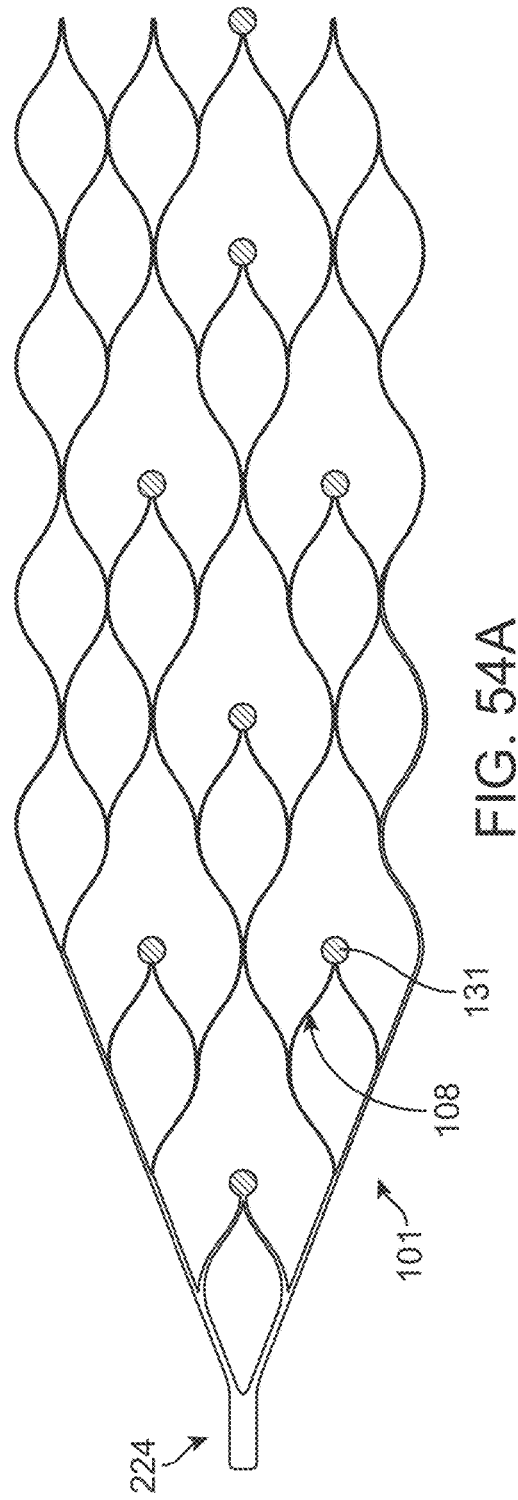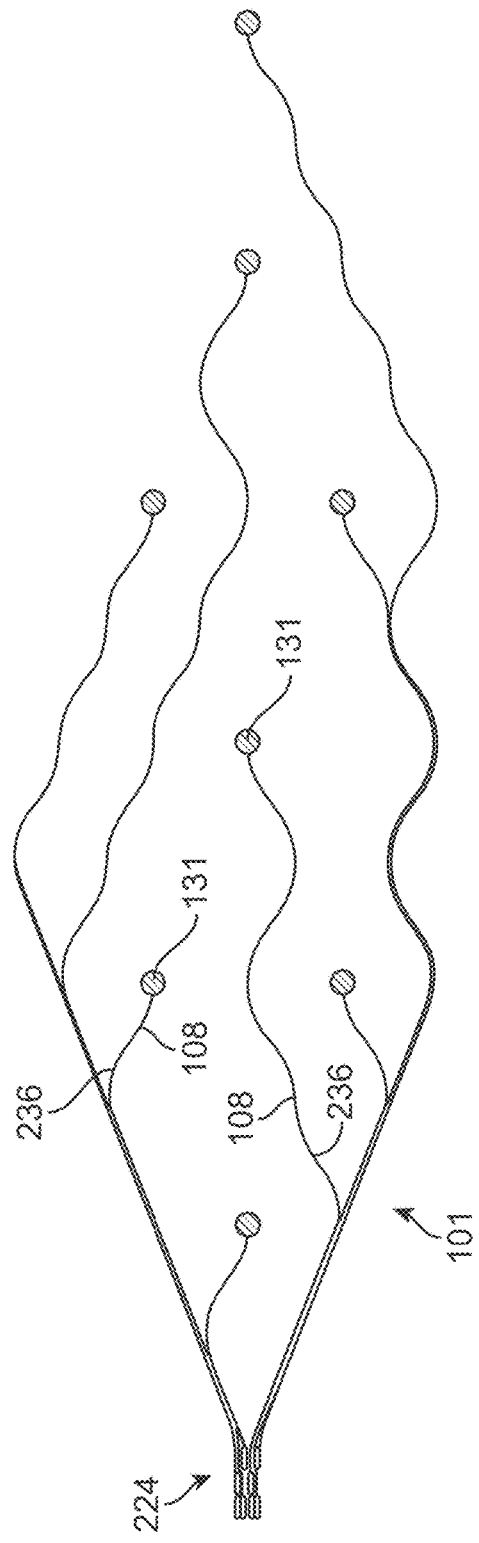

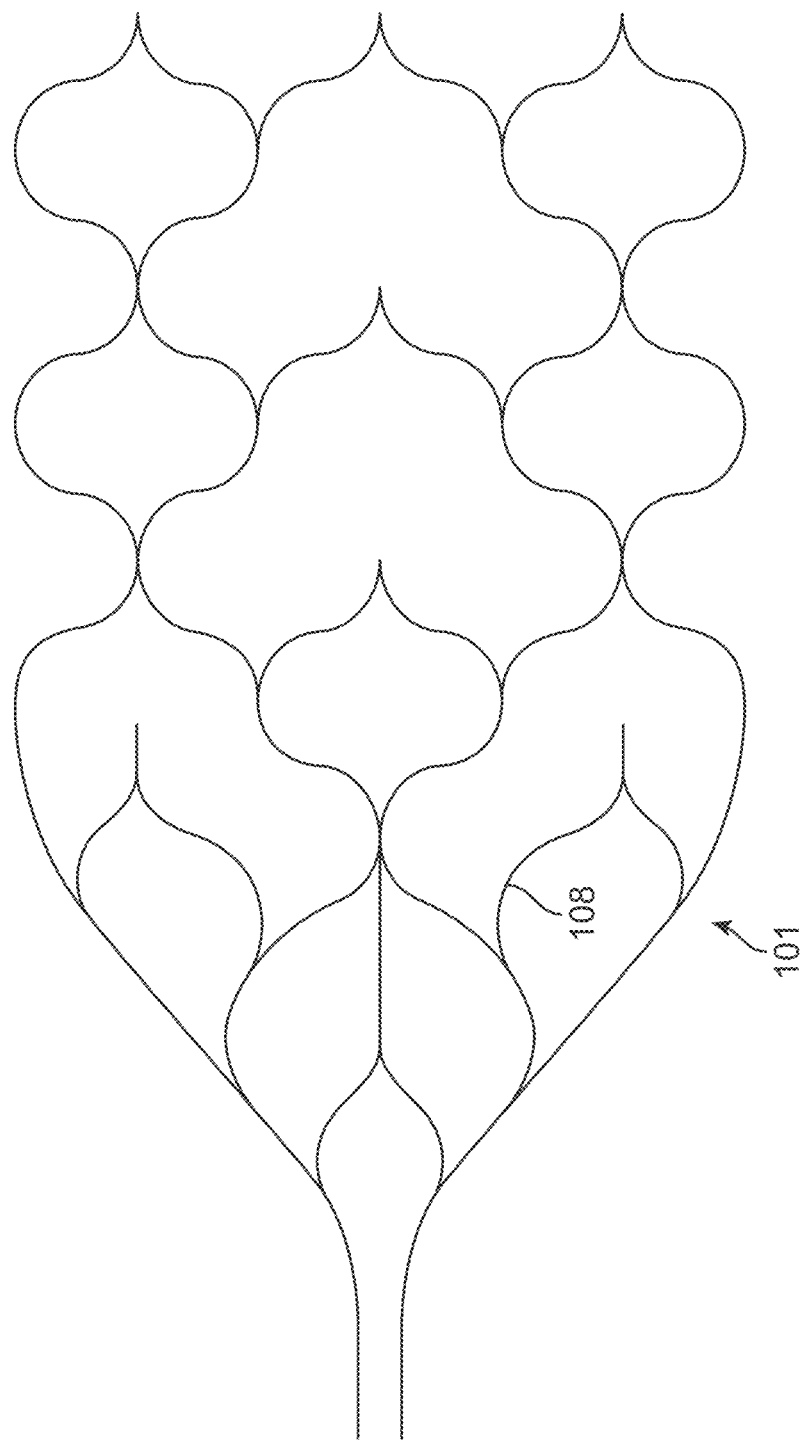

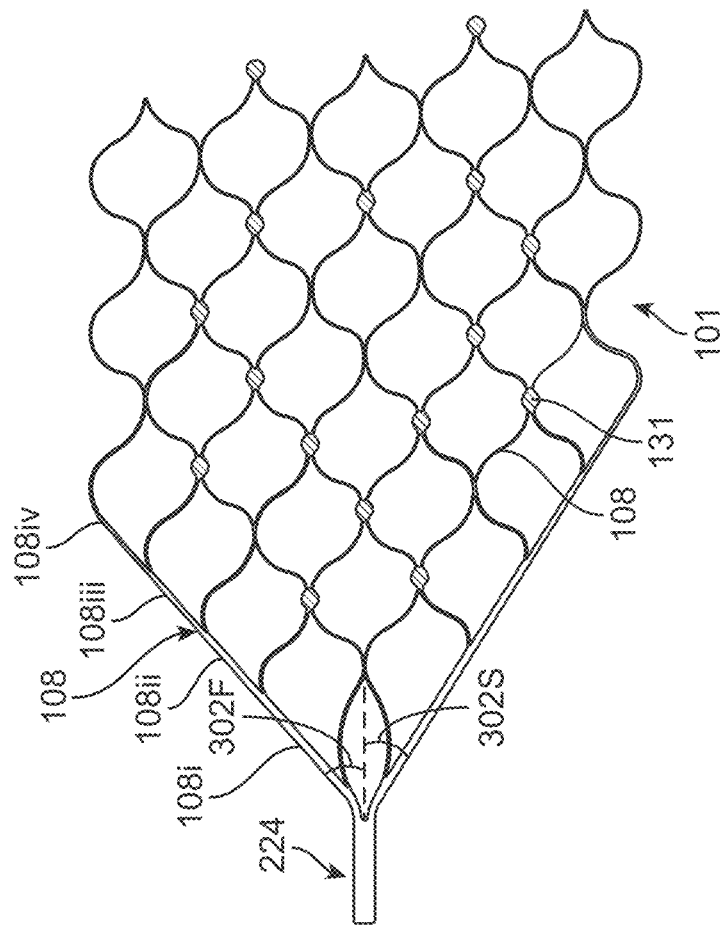
FIG. 58C
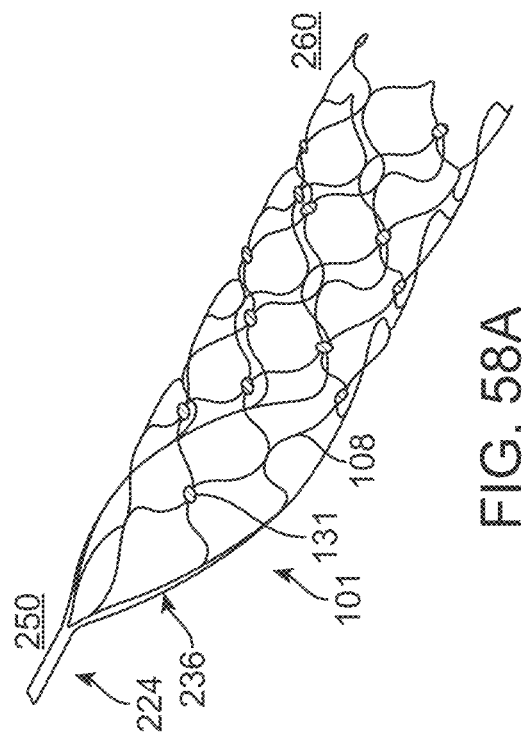
FIG. 58A
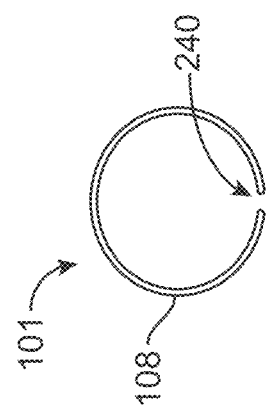
FIG. 58B
FIG. 58D

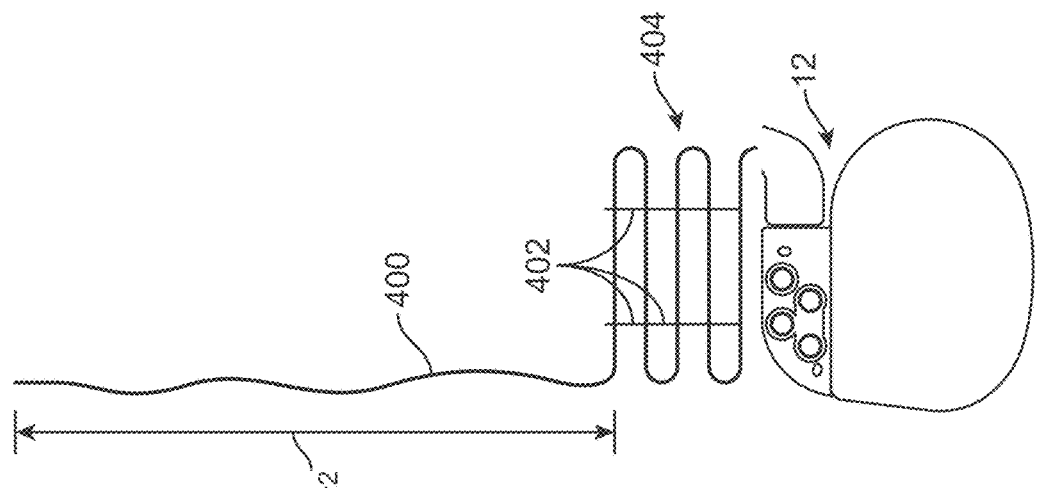
FIG. 59C Increase lead length
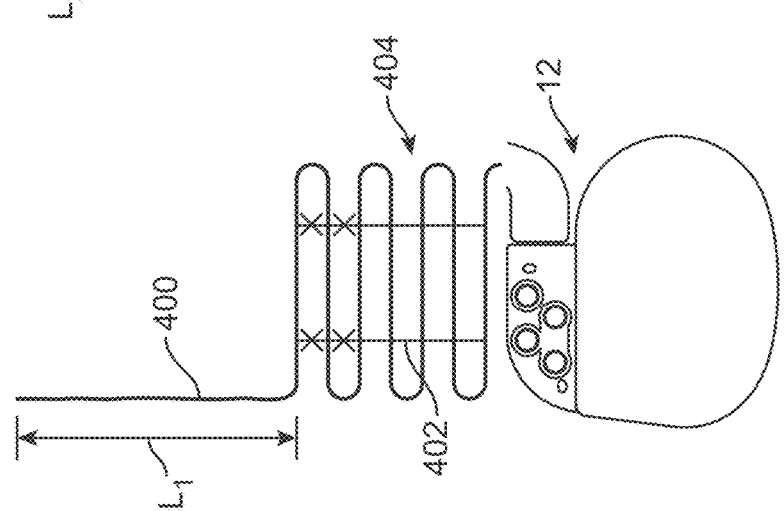
FIG. 59B Cut at X's
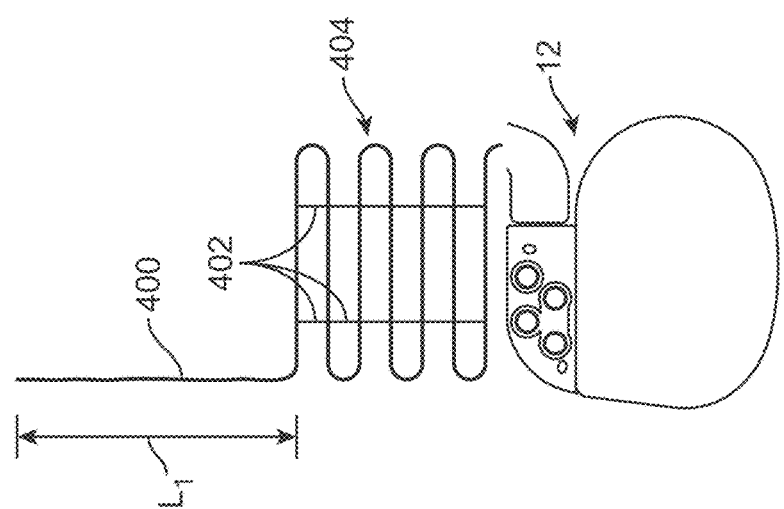
FIG. 59A Starting position

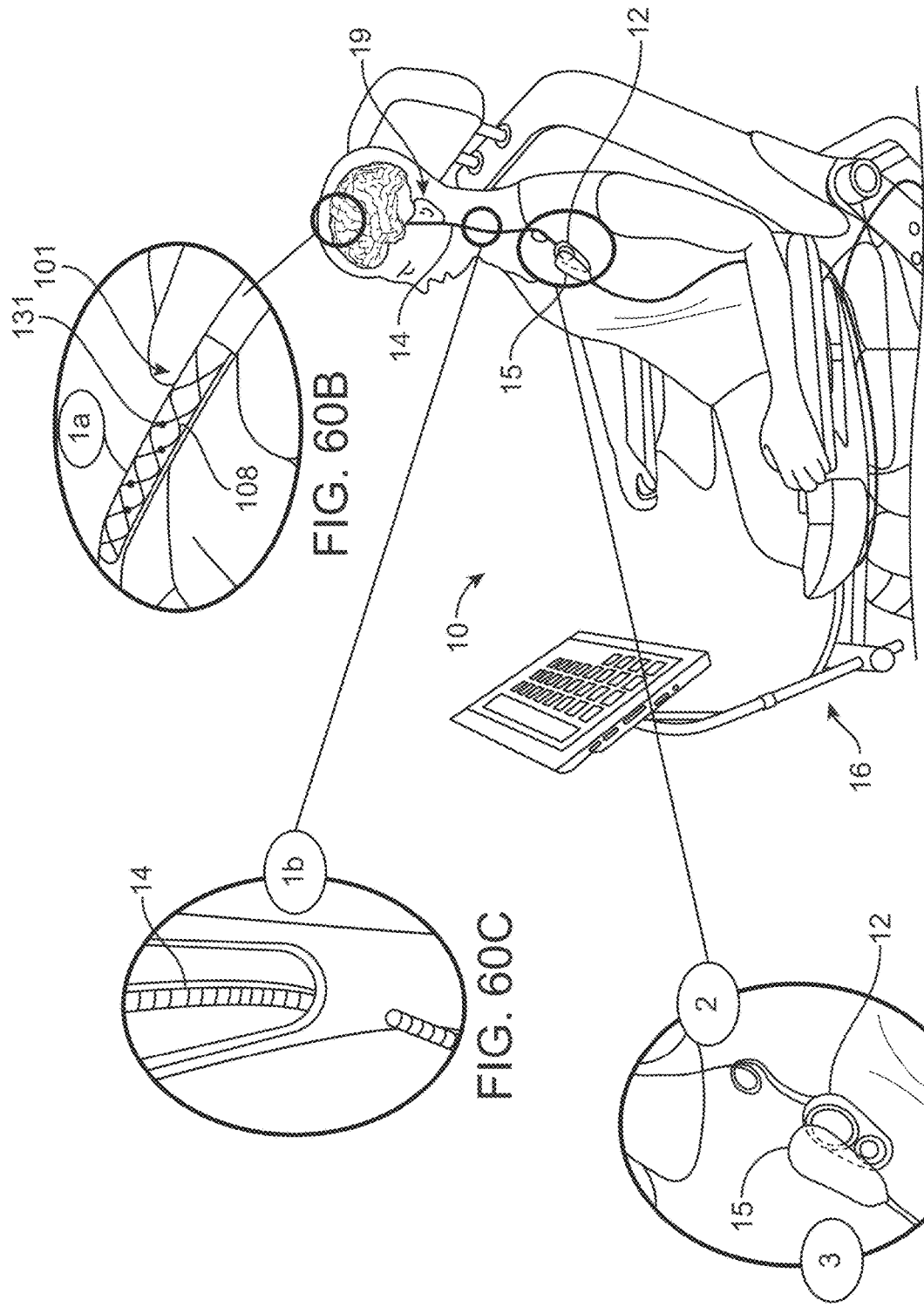

Monopolar Stent monopolar
External return stimulation

Dual Stent multipolar stimulation

Bipolar Stent stimulation

Dual Stent dual multipolar

Dual Stent monopolar stimulation

Dual Stent
Dual multipolar stimulation

Dual Stent monopolar stimulation

Dual Stent dual multipolar

MEDICAL DEVICE FOR SENSING AND OR STIMULATING TISSUE

CROSS-REFERENCE TO RELATED APPLICATIONS

This application is a continuation of U.S. patent application Ser. No. 16/054,657 filed Aug. 3, 2018, which claims priority to U.S. Provisional Application No. 62/540,997 filed Aug. 3, 2017 and to U.S. Provisional Application No. 62/545,875 filed Aug. 15, 2017, each of which is incorporated herein by reference in its entirety for all purposes.

TECHNICAL FIELD OF THE INVENTION

The present invention relates to a medical device for implantation into a blood vessel of an animal.

BACKGROUND OF THE INVENTION

Any discussion of document, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and broad consistory statements herein.

In the United States alone, nearly two million people suffer from various neuromuscular disorders where control of limbs is severely impaired. In many of these patients, however, the portion of the brain responsible for movement remains intact, and it is disease and trauma to the spinal cord, nerves and muscles that limit mobility, function and independence. For these people, the ability to restore lost control at even a rudimentary level could lead to a greatly improved quality of life.

At present, there are two primary options for restoring function. One option is to increase the capabilities of the remaining pathways, substituting paralyzed or amputated muscles with those under voluntary control. While this method has been highly successful for amputees by re-innervating forearm nerves into abdominal muscles which control a bionic arm, the restored function greatly depends on the site of damage or condition, with people paralyzed by brainstem or high cervical injuries only able to achieve minor functional improvement. A second option is to provide the brain with a new communication and control channel to convey messages to the external world. Currently, these brain controlled interfaces (BCIs) measure electroencephalographic or other electrophysiological activity via surgically implanted epidural, subdural, and intracortical electrodes. While cortical measurements performed with electrodes placed on the scalp enable non-invasive neuronal measurements, they require daily application and are prone to noise and movement related artefacts. Penetrating and non-penetrating intracranial electrodes, implanted after a craniotomy directly onto the surface of a cortical area, have much better signal to noise ratios (relative to scalp electrodes) and have been shown to enable rudimentary prosthetic hand operation. These methods, however, require invasive surgery and carry a relatively high risk of complication, which can involve infections and bleeding. Furthermore, craniotomies are limited in access to the central nervous system, with many motor and sensory cortex areas hidden and inaccessible within cortical folds. These approaches are restricted in position and cannot be relocated once implanted and are subject to signal deterioration due to glial scar formation surrounding penetrating electrodes.

Thus, there remains a need to record and stimulate from cortical tissue in a method which is minimally invasive whilst also ensuring longevity and efficacy of recorded and induced signals.

By using blood vessels as a conduit to the brain, the risks associated with craniotomies, and the invasive creation of a burr hole in the skull of the patient is removed whilst also removing current noise and movement related artefacts observed with non-invasive scalp electrodes. Despite the minimally invasive benefits provided by these types of procedures, it is preferable that thrombus formation caused by the blockage of blood flow through a vessel is prevented. It is also preferable that the electrical energy delivered to the electrodes be as efficient as possible, which will reduce the burden placed on the electrical circuitry. Optimization of wireless telemetry aimed to send power and data directly through the body to the implanted device, will enhance device functionality and negate the risk of infection caused through lead wires creating a direct passage between the vessel and the external environment. The ability to implant coils inside blood vessels will similarly reduce surgical risks associated with perforated vasculature.

Thus, there remains a need to provide improved intravascular electrodes, telemetry circuitry and implantation positions that are capable of more efficiently transmitting and receiving electrical energy between vessels and external circuitry, while minimizing the occlusion of blood flow.

It is generally desirable to overcome or ameliorate one or more of the above mentioned difficulties, or at least provide a useful alternative.

SUMMARY OF THE INVENTION

According to the present invention, there is provided a medical device for implantation into a blood vessel of an animal, including: (a) a stent movable between a collapsed condition of use for insertion into said vessel and an expanded condition of use for resiliently bearing against a wall of said vessel; (b) one or more electrodes coupled to the stent for stimulating and/or sensing activity of media proximal to the device, wherein the media includes tissue and/or fluid. The term stent is meant to include any support structure that maintains, carries, supports or incorporates the one or more electrodes within the tissue and/or fluid. The term stent can include conventionally designed medical stents, alternatively, the term stent can include any mechanical framework or scaffolding that positions electrode elements within a body lumen, such as a vessel, and facilitates electrical coupling of the electrode element(s) to a lead or other conductive structure. In certain variations, portions of the support structure itself can function as electrodes.

According to the present invention, there is also provided a method of recording of neural information or stimulation of neurons from the superior sagittal sinus or branching cortical veins of a patient using the above described device, including the steps of: (a) implanting the device in either the superior sagittal sinus or branching cortical veins; (b) receiving activity; and (c) generating data representing said activity; and (d) transmitting said data to a control unit.

According to the present invention, there is also provided a method of for stimulation and recording neural information or stimulation of neurons from the visual cortex of a patient using the above-described device, including the steps of: (a) implanting the device in a vessel in the visual cortex of the patient; and (b) recording neural information associated with the vessel or stimulating neurons in accordance with received stimulation data.

According to the present invention, there is also provided a system for controlling use of apparatus coupled to an animal or human, including: (a) the above-described device, said device being adapted for placement within a vessel of an animal or human to stimulate and/or sense the activity of media proximal to the device; (b) a control unit adapted for communication with the device; (c) apparatus coupleable to the animal or human, said apparatus adapted for in communication with the control unit, wherein the control unit is adapted to perform the steps of: (i) receiving data from the device representing activity of media proximal to the device; (ii) generating control signals for the apparatus; and (iii) sending said control signals to said apparatus.

According to the present invention, there is also provided a control unit for controlling operation of apparatus coupled to an animal or a human, said control unit being adapted to perform the steps of: (a) receiving data from the above-described device, said data representing activity of media proximal to a vessel within which the device is placed; (b) generating control signals for controlling operation of the apparatus; and (c) sending said control signals to the apparatus.

The present disclosure further includes a medical device for use within a tubular body having a lumen, the medical device comprising: a frame structure forming a plurality of struts, where the frame structure is moveable between a reduce profile and an expanded profile in which a diameter of the frame structure increases; where at least one of the plurality of struts forming the frame structure comprises an electrically conductive material on a support material, the electrically conductive material extending along at least a portion of the strut and being covered with a non-conductive material; at least one electrode formed by an opening in the non-conductive material on the portion of the strut; and a lead located at an end of the frame structure and configured to be in electrical communication with the electrically conductive portion, the lead extending from the frame structure.

The medical device can further include a connector block configuredto electrically couple the medical device to an external device, where the lead extends from the frame structure to the connector block.

In another variation, the present disclosure includes a method of recording of neural information or stimulation of neurons a patient the method comprising: receiving a signal representative of neural activity from a device positioned in a vessel of the patient; generating data representing said activity using the signal; and transmitting said data to a control unit; generating a control signal from the control unit; and transmitting the control signal to an apparatus coupled to the patient.

The present disclosure also includes a system for controlling an apparatus coupled to an animal or human. In one example, the system comprises a device adapted for placement within a vessel of the animal or human to stimulate and/or sense the activity of media proximal to the device; a control unit adapted for communication with the device, wherein the control unit is adapted to: (i) receive data from the device representing activity of media proximal to the device; (ii) generate a control signal; and (iii) transmit the control signal to said apparatus.

The system can include an apparatus selected from or more of the following: an exoskeleton; a prosthetic limb; a wheelchair; a computer; and/or an electrical or electro-mechanical device.

BRIEF DESCRIPTION OF THE DRAWINGS

Variations of the present invention are hereafter described, by way of non-limiting example only, with reference to the accompanying drawing. Like reference numerals in the drawings indicate identical or functionally similar features/elements throughout. All dimensions shown in the drawings are exemplary.

FIG. 5A is a diagrammatic illustration of a medical device of the system shown in FIG. 1.

FIG. 5B is a cross-section view through the line A-A of the device shown in FIG. 5a.

FIGS. 43A-43G illustrate various views of a variation of a connection panel.

FIGS. 48A-48D illustrate a variation of a stent.

FIGS. 50A-50C illustrate a variation of a stent.

FIGS. 54A and 54B illustrate a variation of a stent.

FIG. 57 illustrates a variation of a stent lattice structure.

FIGS. 58A-58D illustrate a variation of a stent.

FIGS. 59A-59C illustrate a telemetry unit lead having a snake and rung configuration.

FIGS. 60A-60D illustrate a variation of a system having a stent in communication with an external apparatus.

DETAILED DESCRIPTION

Figure 1:
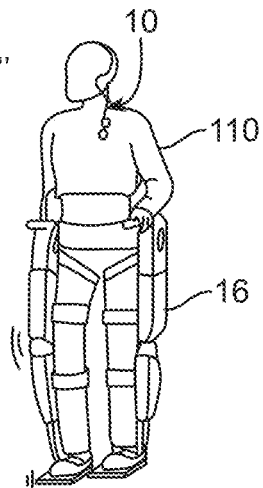
FIG. 1 is a diagrammatic illustration of a system for controlling use of apparatus coupled to an animal or a human.

The system 10 shown in FIGS. 1 to 4 includes: 1) a medical device 100 designed for placement within a vessel 103 of an animal or human 110 to stimulate and/or sense the activity of media (tissue and fluids) proximal (adjacent or touching) to the device 100, whether this be located inside or outside the vessel 103; 2) a control unit 12 (also referred to as a connector block and telemetry system) adapted for communication with the device; 3) a communication conduit 14 for facilitating communications between the device 100 and the control unit 12; and 4) apparatus 16 coupleable to the animal or human 110, the apparatus 16 adapted for communication with the control unit.

The control unit 12 can be adapted to perform the steps of: (a) receiving data from the device 100 representing activity of media proximal to the device 100; (b) generating control signals for the apparatus 16; and (c) sending the control signals to the apparatus 16. In some variations, the system includes connector block (illustrated by element 12) that functions as connector and acts as an extension of the communication conduit. In variations of the system, the control unit/connector block: is hermetically sealed and insulates the leads from the device to the control unit; can be inserted using zero-contact force attachments or attachments that do not require excessive force to insert (i.e., using balseal spring contacts); has a portion of the lead that is made from a stiffer silicone or similar material for handling and insertion into the connector. Variations of the device can include markers to identify portions of the leads that are stiffer (and can be handled) to distinguish from leads that cannot be handled. Such markers can include line-style markers, different colours or other indicators to clearly identify the regions. Variations of the connector block can have a fitting (e.g., clasp) such that multiple connectors can be inserted (i.e., two contact connectors (with 8 contacts each) for a 16 electrode Stentrode lead). The fitting can ensure securing of the contacts, alignment and prevention of water ingress When the medical device 100 is inserted adjacent to the motor cortex in the manner shown in FIGS. 2A, 2B, and 3, the system 10 can be used, for example, to control operation of an exoskeleton, and/or an artificial limb in the manner shown in FIG. 1.

This device 100 is implanted into blood vessels 103, from which, it will utilise electrodes mounted on a self-expanding member 101 to record or stimulate neighbouring tissue. Information is to be passed from or to the electrodes through the communication conduit 14, inside of the blood vessel 103, to a telemetry system 12 that, in turn, passes information (using wires or wirelessly) to or from an external apparatus 16, which includes (but is not limited to) one or more of the following:

(a) an exoskeleton; (b) wheelchair; (c) computer; and/or (d) other electrical or electro-mechanical device.

As such, in one specific application, the implanted medical device 100 has the capability to enable a paralysed patient 110 to use their thoughts directly to command and control a gait aid such as an exoskeleton or robotic legs 16.

Other applications for the implantable medical device 100 include (but are not limited to): (a) detection and prevention of seizures; (b) detection and prevention of involuntary muscular or neural control (for example to alleviate symptoms associated with: (i) multiple sclerosis; (ii) muscular dystrophy; (iii) cerebral palsy; (iv) paralysis and (v) Parkinsons'; (c) detection and therapeutic alleviation of neurological conditions, such as: (i) post-traumatic stress disorder; (ii) obsessive compulsive disorder; (iii) depression; and (iv) obesity; (d) direct brain control of computers and equipment, such as: (i) vehicles; (ii) wheelchairs; (iii) gait aids; robotic limbs; (e) direct input for sensory stimulation for: (i) blindness (connection to a camera); (ii) deafness (connection to microphone); (iiii) proprioception (connection to touch-sensitive robotic and computer systems); (f) internal assessment of personal health and wellbeing: (i) heart rate; (ii) respiration rate; (iii) temperature; (iv) environmental conditions; (v) blood sugar levels; and (vi) other biochemical and neurological markers; (g) internal communication (telepathy) between implanted groups of people utilising the device for information transmission, auditory, visual and proprioceptive feedback (for example, real time communication of what the implantee sees or hears); and (h) augmentation and optimisation of musculskeletal control and dexterity (for performance enhancement or rehabilitation).

Figure 2A:
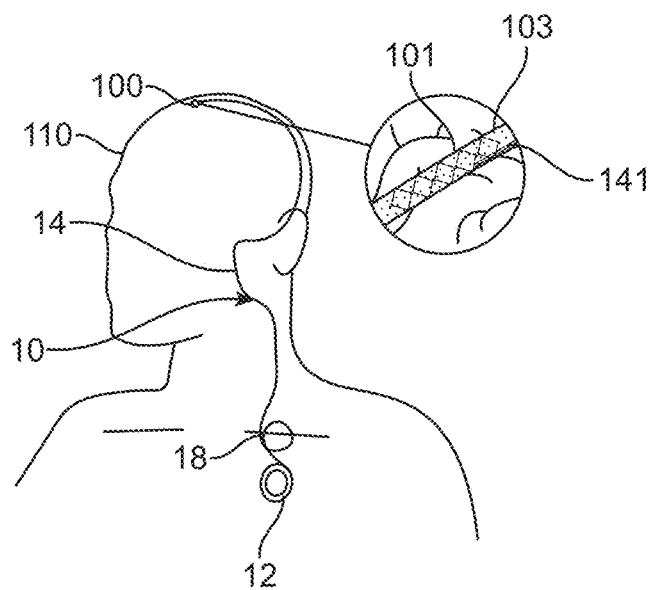
FIG. 2A is a diagrammatic illustration showing parts of the system shown in FIG. 1.
Figure 2B:
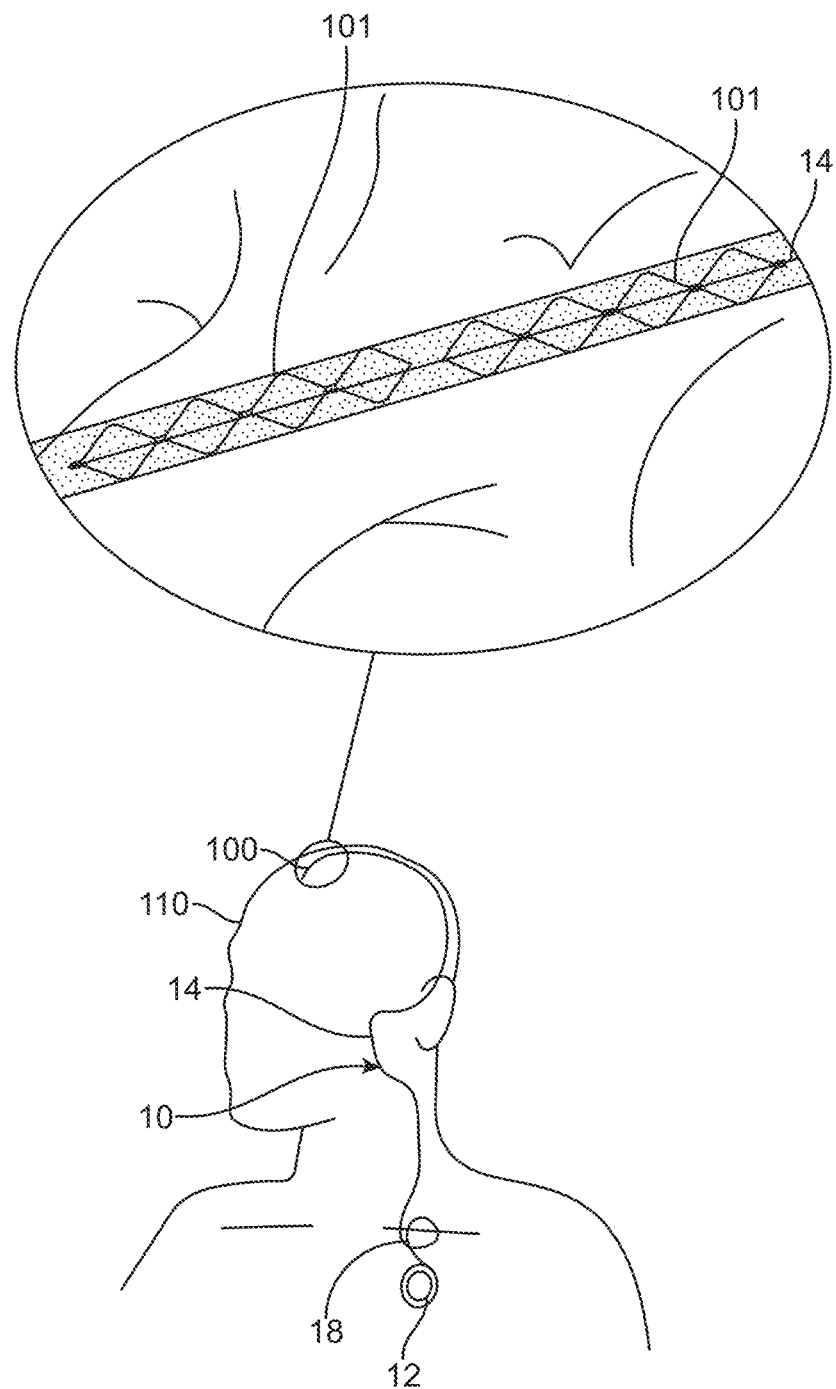
FIG. 2B is a diagrammatic illustration showing of an additional variation of the system comprising two or more stents.
Figure 3:
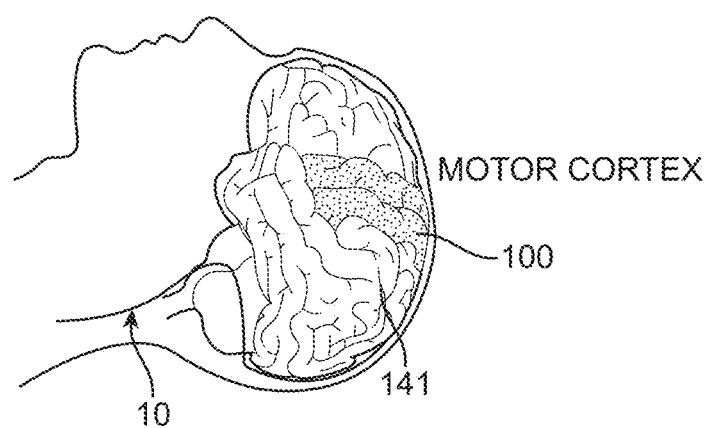
FIG. 3 a diagrammatic illustration showing parts of the system shown in FIG. 1.
Figure 4:
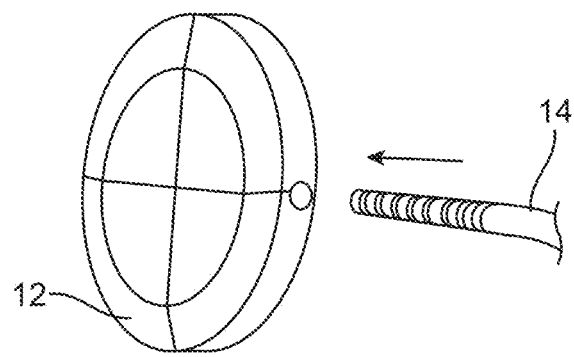
FIG. 4 is a diagrammatic illustration of a control unit of the system shown in FIG. 1.

FIG. 2B illustrates a two-stent 101 system. For purposes of illustration, the stents are positioned in a single vessel. However, the stents can be configured such that they can be positioned in separate vessels. The stents 101 can be joined by non-conductive material to form a power receiver and transmitting antenna. Alternatively, the stents can be coupled by one or more wires or conductive elements. Moreover, the system can include active electronics between the stents 101.

The devices described herein can be positioned in any number of areas of brain structures depending upon the desired outcome. For example, as discussed in Teplitzky, Benjamin A., et al. "Computational modeling of an endovascular approach to deep brain stimulation." *Journal of Neural Engineering* 11.2 (2014): 026011.stents can be positioned as follows: Internal capsule for depression and obsessive compulsive disorder (OCD); thalamus for epilepsy (E), Parkinsons' Disease, essential tremor, Tourette syndrome, consciousness disorder, chronic pain, obsessive compulsive behavior; fornix for Alzheimer's disease; globus pallidus internus for dystonia, depression, Tourette syndrome; hippocampus for epilepsy; hypothalamus for obesity, anorexia mentosa; inferior thalamic pduncle for depression and obsessive compulsive disorder; lateral habenula for depression, obesity, anorexia mentosa; nucleus accumbens for depression, obsessive compulsive disorder, addiction, obesity, anorexia mentosa; periaqueductal/periventricular for chronic pain; subgenal cingulate white matter for depression; subthalamic nucleus for Parkinson's Disease, dystonia, depression, obsessive compulsive disorder, epilepsy; and ventral capsule for obsessive compulsive disorder.

1. Medical Device

As shown in FIGS. 5a, 5b, 5d and 6, the medical device 100 generally includes: a. a collapsible and expandable stent 101; b. a plurality of electrodes 131 coupled to the stent 101; c. electrode lead wires 141 electrically coupled to electrodes 131; d. an olive 112 coupled to the stent 101 by an olive wire 114 for preventing perforation of vessels during implantation; e. implanted chips; f. contacts 151 couple to the lead wires 141 to enable communication between the device 100 to the control unit 12; and g. a stent shaft 121 is used to deploy the device 100.

Electrode lead wires 141 can be electrically connected to at least one electrode and will be wound around the stent strut lattice 108 such that mechanical compression and extension is not interfered with. Electrode wires 141 may be wound around the stent shaft 121, thread through a stylet shaft or may form part of the stent shaft directly. Lead wires 141 will form connections with electrode contacts 151 on the opposite end of the stent shaft to the stent, whereby electrical contact a connector block mechanism 12 enables the connection path with external equipment 16, which included but is not limited to computers, wheelchairs, exoskeletons, robotic prosthesis, cameras, vehicles and other electrical stimulation, diagnostic and measurement hardware and software.

The term electrode 131 is used in this specification to refer to any electrical conductor used to make contact with media in and/or around a blood vessel 103.

A detailed description of the operation of each of these components is set out below.

The Stent

The stent 101 includes a plurality of struts 108 coupled together with strut crosslinks 109.

Figure 7A:
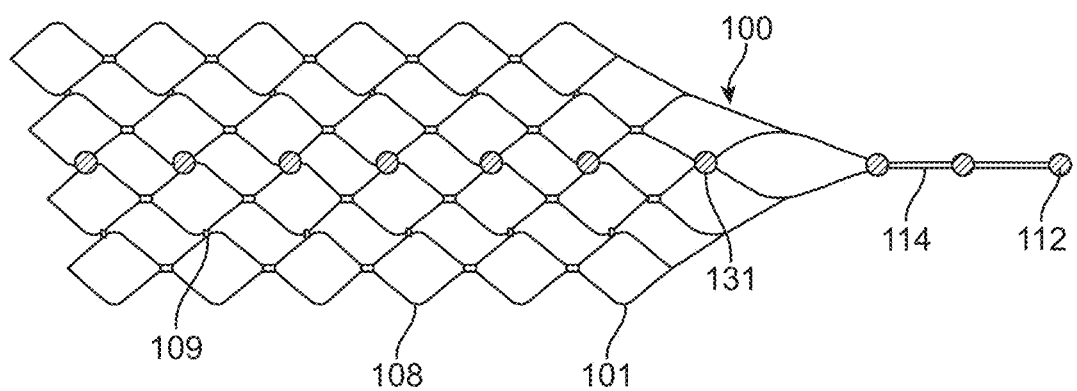
FIGS. 7A to 7E are diagrammatic illustrations of medical device of the system shown in FIG. 1.

In the arrangement shown in FIG. 7a, the device 100 includes nine electrodes coupled to the stent 101 in a linear pattern. As shown, the stent 101 appears flat. The top of the stent 101 may be directly joined to the bottom of the stent 101 or will curve around to meet (without permanent attachment) the bottom of the stent 101.

Figure 7B:
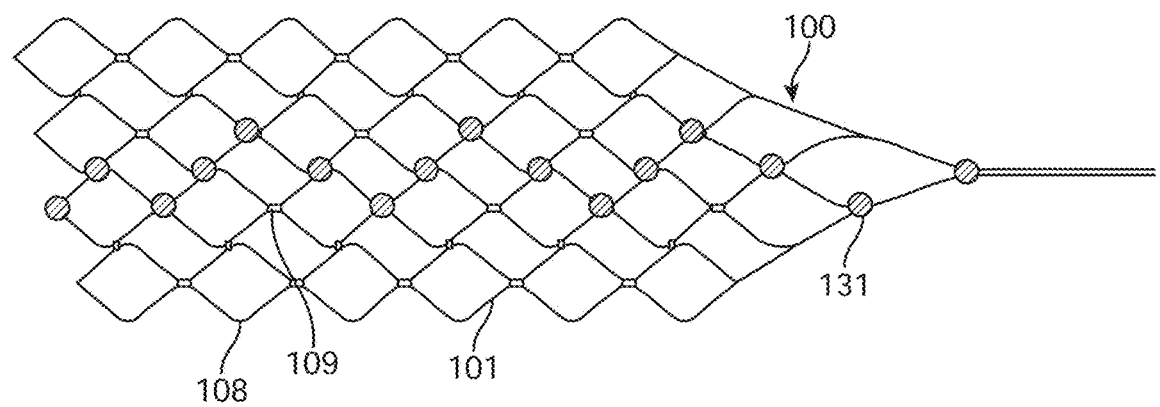
Figure 7C:
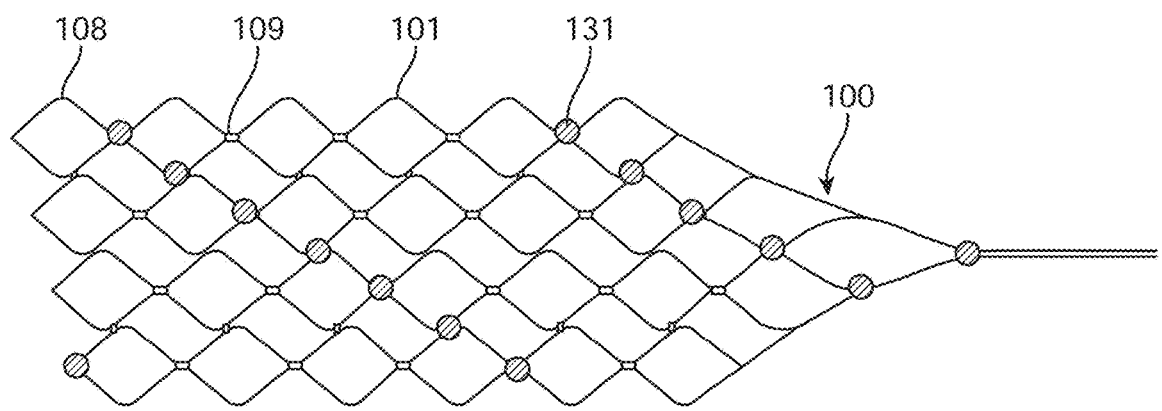
Figure 7D:
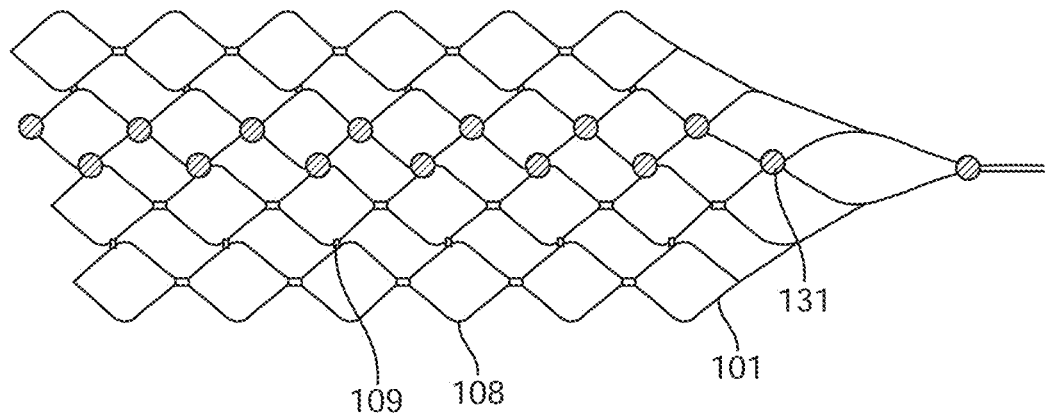
Figure 7E:
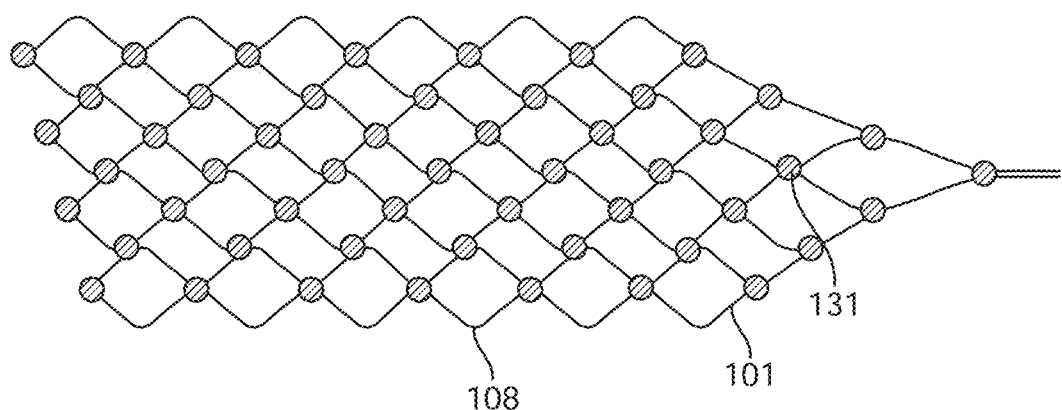
Figure 8A:
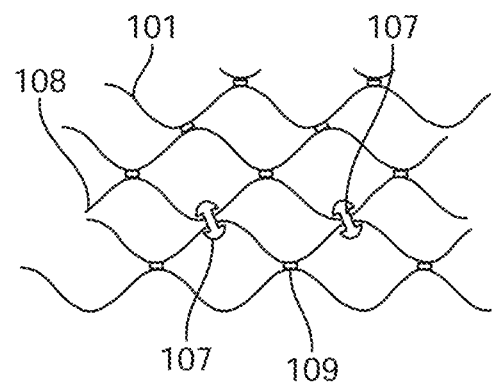
FIG. 8A is a diagrammatic illustration showing electrode mounting platforms of a medical device of the system shown in FIG. 1.
Figure 8B:
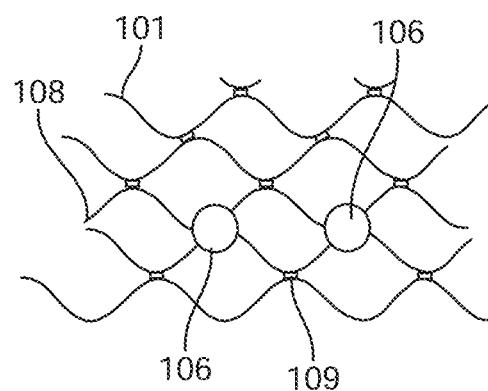
FIG. 8B is a diagrammatic illustration showing placements of a medical device of the system shown in FIG. 1.

Alternatively, the device 100 includes a stent with any suitable number of electrodes 131 arranged in any suitable configuration. For example, the electrodes can be configured as follows: the sinusoidal arrangement of electrodes 131 shown in FIG. 7b; the spiral arrangement of electrodes 131 shown in FIG. 7c to enable 360 degree contact of an electrode to the vessel wall once deployed; the reduced amplitude sinusoidal arrangement of electrodes 131 shown in FIG. 7d for increased coverage whilst still ensuring only one stent is at each vertical segment; and the dense arrangement of electrodes shown in FIG. 7e for increased coverage. The stent 101 is laser cut or woven in a manner such that there is additional material or markers where the electrodes 131 are to be placed to assist with attachment of electrodes and uniformity of electrode locations. For example, if a stent 101 was fabricated by laser cutting material away from a cylindrical tube (original form of stent), and, for example, electrodes are to be located at 5 mm intervals on the one axis, then electrode mounting platforms 107, 108 can be created by not cutting these areas from the tube. Similarly, if the stent is made by wire wrapping, then additional material 107, 108 can be welded or attached to the stent wires providing a platform on which to attach the electrodes. Alternatively, stents can be manufactured using thin-film technology, whereby material (Nitinol and or platinum and or other materials or combinations of) is deposited in specific locations to grow or build a stent structure and/or electrode array Electrodes As particularly shown in FIG. 8a, the device 100 includes electrode placements 107 coupled to strut crosslinks 109. The placements 107 are used to coupled the electrodes 131 to the stent. An alternative embodiment of the placements 106 is shown in FIG. 8b. In this embodiment, the placements are circular.

As shown, the electrodes 131 are located on or at the stent crosslinks 109. Locating the electrodes in these positions allows for changes in shape of the stent 101 (i.e expanding and collapsing) without significantly affecting the integrity of the electrodes. Alternatively, may also be located in between the stent strut crosslinks (not depicted).

Figure 9:
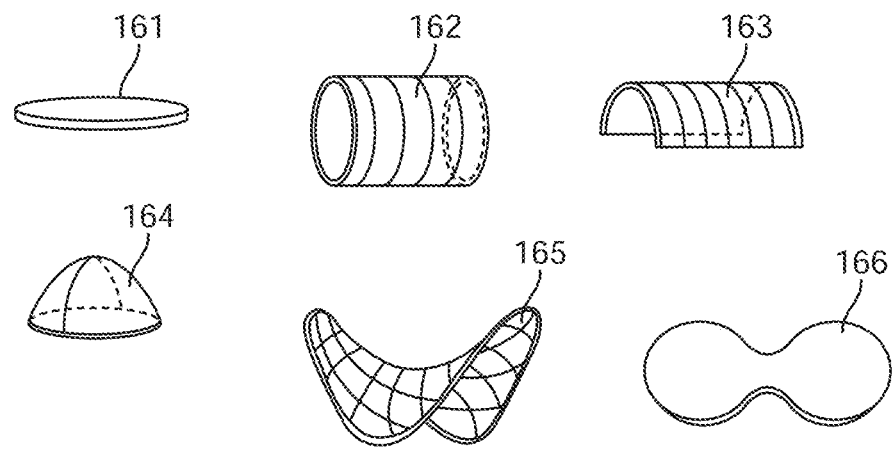
FIG. 9 shows diagrammatic illustrations of different electrode configurations.

FIG. 9 depicts different electrode geometries which include but are not limited to: flat discs 161; cylinders or rings 162; half-cylinders or rings 163; spheres, domes or hemispheres 164; hyperbolic parabaloids 165; and double electrodes or electrodes whereby they are longer along one axis 166.

Figure 10:
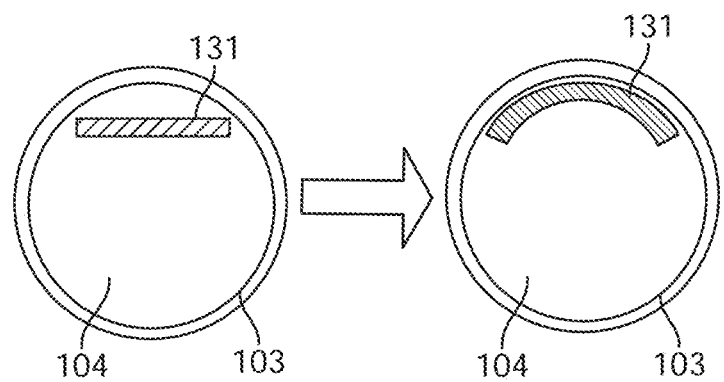
FIG. 10 shows diagrammatic illustrations of different electrode configurations.

As shown in FIG. 10, the electrodes 131 can include shape memory material and hence the electrodes 131 may be uninsulated sections of the device 100. As shown, the electrode 131 inside a patient and the vessel 104 is unobstructed. After activation of shape memory, the electrode 131 conforms to better fit the vessel wall 103.

To enhance contact and functionality of the device 100, electrodes 131 include the attachment of additional material (shape memory alloy or other conducting material) through soldering, welding, chemical deposition and other attachment methods to the stent 101 including but not limited to: directly on or between the stent struts 108; to lead wires 14 passing from the electrodes 131 to wireless telemetry links or circuitry; and directly to an olive 112 placed on the distal aspect of the device 100 to or stent shafts.

To further enhance the device 100 performance, there may be one or more electrodes 131 per wire strand 141 and there may be one or more strands 141 utilised per device 100. These strands 141 may be grouped to form a bundle 144, which may be woven in alternate sinusoidal paths around the stent struts 108 in the manner shown in FIG. 11. Similarly, there may be one or more wires 141 designated to each electrode 131 and hence there may be one or more electrodes 131 per device 100. Thus, multiple electrodes 131 may be used simultaneously.

To optimise the ability of the electrodes 131 to stimulate or record from medium (including but not limited to neural tissue, vascular tissue, blood, bone, muscle, cerebrospinal fluid), the electrodes 131 may be positioned at pre-determined intervals based on the diameter of the target vessel 103 to allow each of the electrodes 131 to be in contact with the vessel 103 in the same orientation (ie, all electrodes facing to and in contact with the left vessel wall upon deposition). Electrodes 131 may be mounted such that recordings or stimulation can be directed to all 360 degrees of the vessel simultaneously. Similarly, to enhance the recording and stimulation parameters of the electrodes 131, the electrode sizes may be varied, with larger electrodes 131 used to assess greater areas of neighbouring medium with smaller electrodes 131 utilised for localisation specificity.

Alternatively, the electrodes 131 are made from electrically conductive material and attached to one or more stents, which form the device 100 and allow for multiple positions. In this embodiment, the electrodes 131 are made from common electrically active materials such as platinum, platinum-iridium, nickel-cobalt alloys, or gold, and may be attached by soldering, welding, chemical deposition and other attachment methods to one or more lead wires 141, which may be directly attached to the shape memory shaft(s). The electrodes 131 can be one or more exposed sections on the insulated lead wire 141 and the electrode lead wires may be wrapped around one or more shape memory backbones. There may be one or more electrodes and lead wires wrapped around a single shape memory backbone, and, where multiple shape memory backbones are used in the one device, the backbones may have different initial insertion and secondary deposition positions. Thus, they may be used for targeting multiple vessels simultaneously.

Figure 12:
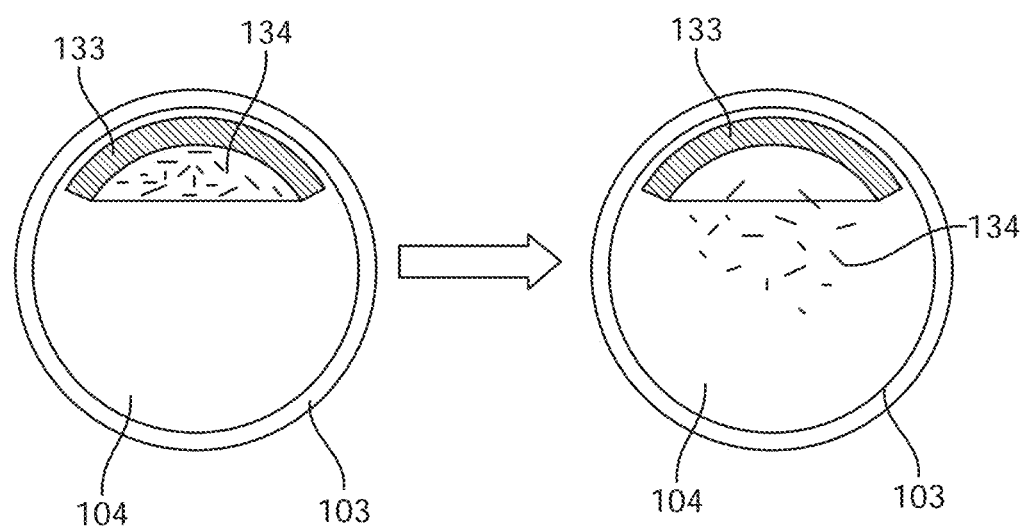
FIG. 12 shows diagrammatic illustrations of different electrode configurations.

As shown in FIG. 12, the electrodes 131 can be designed such that they are carriers of substances 134 and solutions such as therapeutic drugs, including but not limited to anti-thrombogenic, and materials. In this embodiment, the electrodes 131 are designed to release the drugs, either passively through diffusion or through control by an implanted electrical clock or manually through electrical stimulation of the electrodes 131. In this embodiment, the electrodes 131 are made from materials that have portions of the electrodes 131 that are not electrically conductive.

The drug 134 can be released into the vessel 104 upon timed, natural, electrical or otherwise activation, or into the vessel wall 103.

In variations of the device, an insulation layer between the nitinol substrate and the electrodes (e.g., platinum, silicone oxide) comprises a silicone carbide or other insulation material. Alternatively, a layer of silicone carbide can be provided to prevent the degradation and erosion of the silicone oxide layer.

Electrode Wires

Figure 13A:
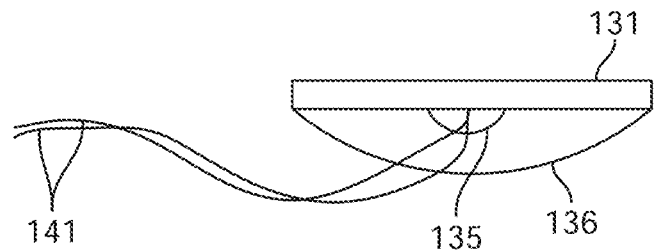
FIG. 13a is a diagrammatic illustration showing wire attachments to an electrode.

The electrode wires 141 are electrically coupled to respective electrodes in the manner shown in FIG. 13a. As shown, the electrical attachment 135 and the back face of the electrode is covered in a non-conductive substance 136.

The lead wires 141 can be wrapped around the stent 101 and along a shaft 121.

Figure 13B:
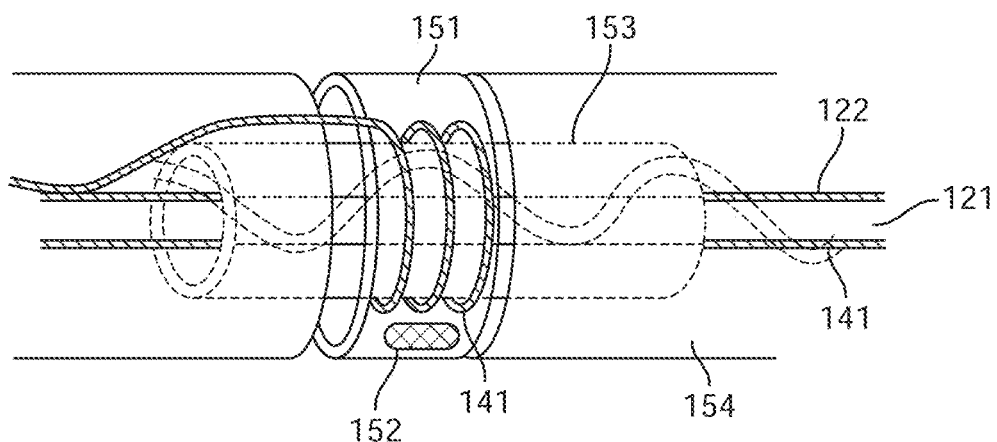
FIG. 13b is a diagrammatic illustration showing electrode lead wires wrapped around a shaft and covered in insulation forming a wire bundle or cable.

As shown in FIGS. 5a, 5b and 13b, the electrode lead wires 141 are wrapped around the shaft 121 and covered in insulation 122 forming a wire bundle or cable. A sleeve 153 wraps around the wire bundle at the location of the contact 151, whereby at least one wire 141 is wrapped around the sleeve 153 and connected to the contact 151 at a connection weld point 152. The over-molding 154 ensures a uniform diameter is present between contacts.

The sleeve 153 covers the wire bundle 142 with an exposed section of wire 141 attached 152 to a contact 151.

Distal electrodes and/or markers and/or buffers are also depicted 112 attached via a wire 114 to the stent 101. The shaft 121 is attached at the end of the stent at the attachment/detachment zone 115 and is shown passing through the sleeve 142 and electrode contacts 151 to exit behind past the connector securement point 155.

The lead wires 141 shown to be inside the sleeve 142 where they are wrapped around the shaft 121 where they make electrical contact at a contact weld 152 to the electrode contacts 151. An overcoat 154 is shown to ensure uniform diameter of the device between the contacts. The shaft 121 may be detached at the detachment zone 115 and removed following deployment in a vessel.

As shown in FIG. 13b, lead wires 141 are connected to electrode contacts 151. Electrode lead wires 141 are initially wrapped around a shaft 121 covered in insulation 122 forming a wire bundle or cable. A sleeve 153 is placed around the wire bundle at the location of the contact, whereby at least one wire 141 is wrapped around the sleeve and connected to the contact 151 at a connection weld point 152. Over-molding 154 may be used to ensure a uniform diameter is present between contacts.

As particularly shown in FIG. 5b, the stent shaft 121 is coated in an insulative layer 122, has a plurality of wires 141 that are insulated 143 and grouped in an insulated bundle 142 wrapped around it. A sleeve 153 covers the wire bundle 142 with an exposed section of wire 141 attached 152 to a contact 141.

The wires 141 are made from electrically conductive materials including but not limited to Platinum, Platinum/Tungsten, Stainless Steel, Nitinol, Platinum/Iridium, Nickel-Cobalt Alloys, or other conductive and biocompatible materials.

The wires 141 are between 10 um and 100 um thick (diameter), stranded cable or monofilament, and connect the electrodes 131 to the contacts 151. Alternatively, the wires 141 connect the electrode 131 to wireless circuitry retained on the stent or shaft.

Figure 11:
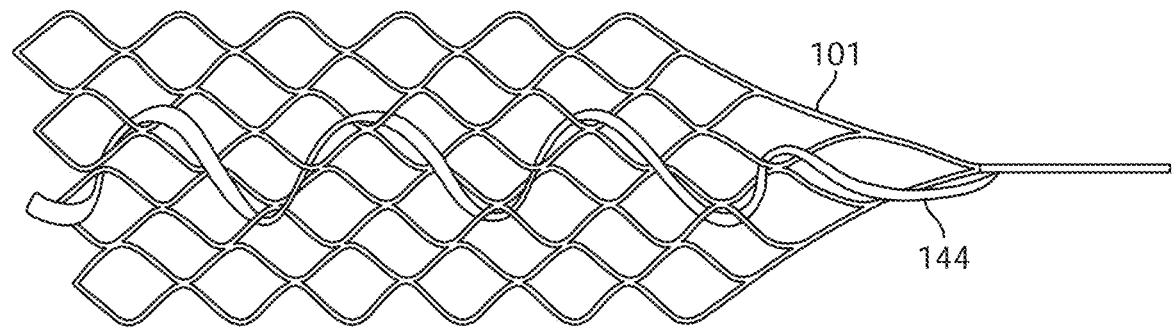
FIG. 11 is a diagrammatic illustration of a medical device of the system shown in FIG. 1.

The wires 141 are insulated with non-conductive material (ie, Teflon or polyimide). The wires 141 are wrapped around the stent struts in a sinusoidal pattern as shown in FIG. 11. Alternatively, the wires 141 are wrapped in a helical tube or wire bundle or cable, with the wire or bundle between 300 um and 2 mm in diameter (thickness)

The wires 141 are connected to contacts 151 using wire wrapping, conductive epoxy, welding, or other electrically conductive adhesion or connection means.

Figure 13C:
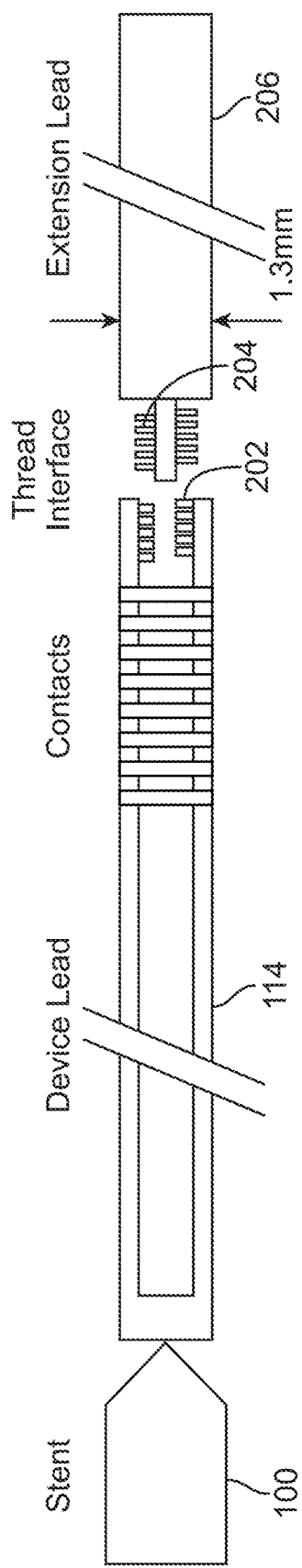
FIGS. 13C and 13D illustrate variations of leads coupled to a device and, which are configured for repositioning of the lead or device.

FIG. 13C illustrates a variation of a lead 114 coupled to a device 100. In some circumstances, there may be a need retract the device for repositioning of the device after a sub optimal placement. FIG. 13C illustrates one variation of a lead 114 having a threaded screw terminal 202 that connects the existing lead to an extension lead 206. The lead include a female threaded portion 202, which mates with a male portion 204 on the extension lead. Placement of the threaded portion on the interior of the lead reduces the risk that the male portion damages the spring contacts that the device 100 lead fits into after the extension lead has been removed.

Figure 13D:
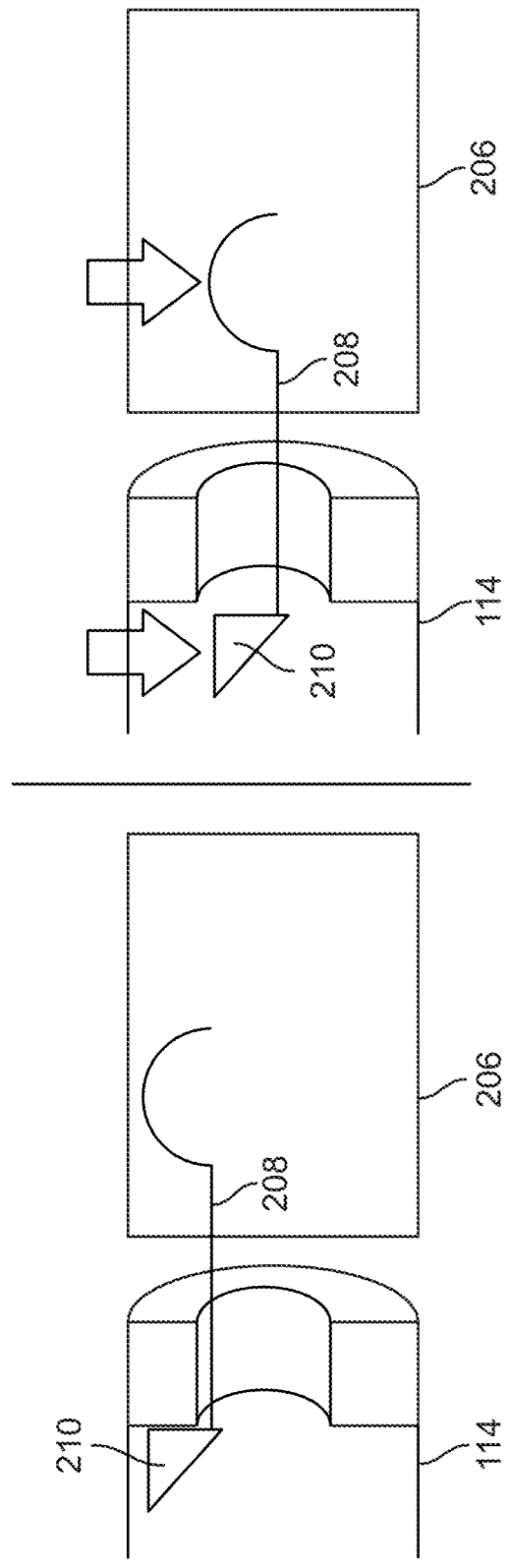

FIG. 13D illustrates an alternative to the screw terminal design shown in FIG. 13C. In this variation, the lead 114 includes a locking mechanism 208. A variation of the locking mechanism can be based on pressure, where pressure on a selected portion of the lead would enable a latch 208 to open or close. Benefits of this would be to reduce the likelihood of any twisting of the device during delivery to detach the prematurely. In this variation, the latch 210 on the extension 206 locks into the lead 114. When an area on the extension is pushed (red arrows) the latch 210 releases from the lead 114 and can be either pushed into the lead (to attach) or be pulled from the lead (to release). Multiple latches would be placed around the circumference of the extension 114 lead, although one is shown here for purposes of illustration.

Olive

In the embodiment shown in FIG. 5a, the device 100 includes an olive 112 mounted at the distal tip to reduce risk of perforation and to improve device 100 safety during the implantation and deposition phase. In this arrangement, the olive 112 is directly connected to the front of the device 100 and act as a buffer, which is the first aspect of the device that comes in contact with the deployment catheter or the vessel during deployment. The olive 112 can additionally be used as a radiopaque distal marker. The olive 112 can be configured and attached to the stent 101 in many different forms including, but not limited to, the following:

i. Flexible Cord

As shown in FIG. 5a, the olive 112 is placed at a distance from the front of the stent 101, connecting with the stent 101 via a flexible cord 114.

ii. Spring Olive

Figure 14:
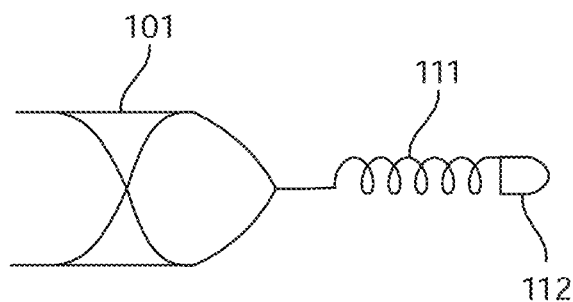
FIGS. 14 to 20 are diagrammatic illustrations showing different embodiments of the stent.

FIG. 14 depicts an olive placed on the distal end of a stent 101 whereby the olive is comprised of a buffer which may or may not be electrically active and function as an electrode 112 connected to the stent 101 by a flexible spring or helically wound wire 111.

iii. Multiple Olives

Figure 15:
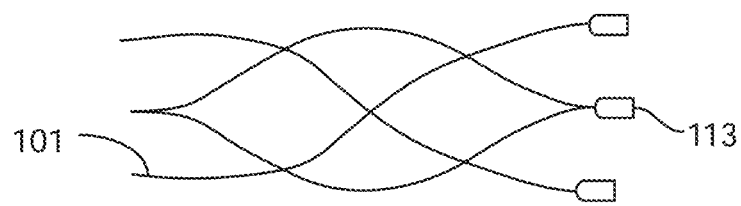

FIG. 15 depicts a plurality of olives placed on the distal end of a stent 101 whereby the olive is comprised of a plurality of buffers which may or may not be electrically active and function as an electrode 113.

iv. Short Olive

Figure 16:
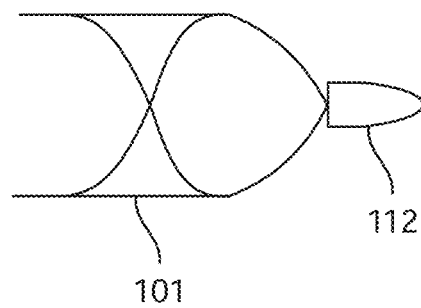

FIG. 16 depicts an olive placed on the distal end of a stent 101 whereby the olive is connected directly to the end of the stent which may or may not be electrically active and function as an electrode 112.

v. Shaped Wire Olive

Figure 17:
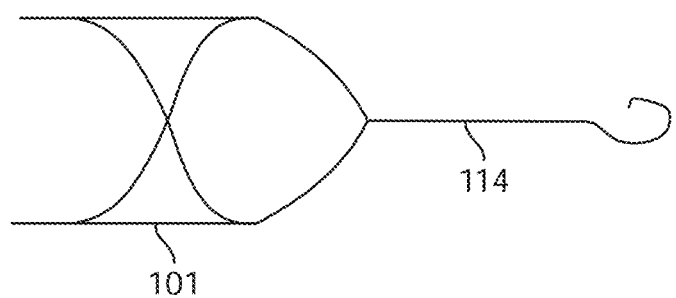

FIG. 17 depicts an olive placed on the distal end of a stent 101 whereby the olive is a flexible wire which may or may not be electrically active and function as an electrode and may or may not be shaped as a shepherds crook 114.

vi. Wire Olive

Figure 18:
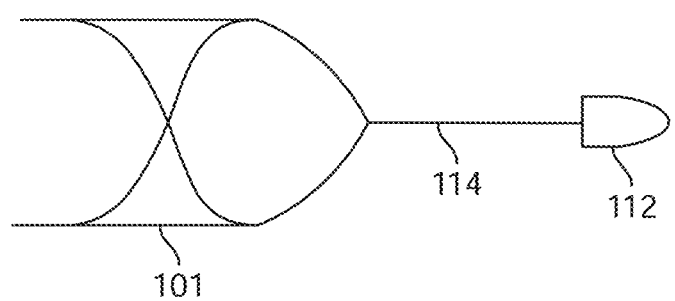

FIG. 18 depicts an olive placed on the distal end of a stent 101 whereby the olive is comprised of a buffer which may or may not be electrically active and function as an electrode 112 connected to the stent 101 by a flexible wire 114.

vii. Olive with Detachment Zone

Figure 19:
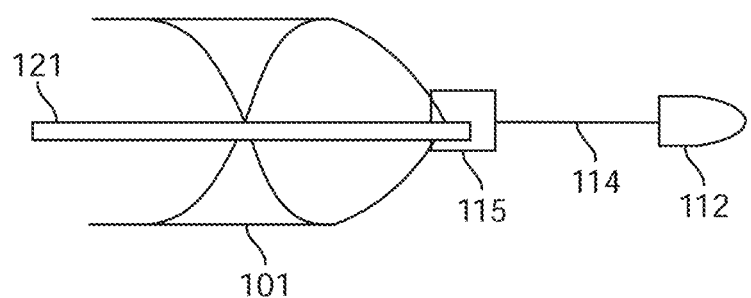

FIG. 19 depicts an olive placed on the distal end of a stent 101 whereby the olive is comprised of a buffer which may or may not be electrically active and function as an electrode 112 connected to the stent 101 by a flexible wire 114. This figure further depicts a shaft 121 that is connected to the stent 101 via an attachment and/or detachment zone 115.

Figure 20:
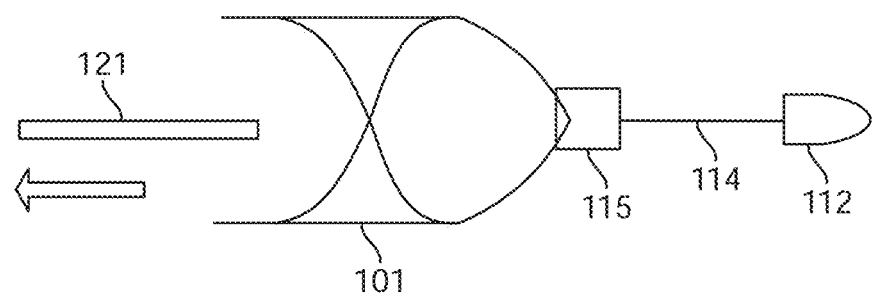

FIG. 20 further depicts the shaft 121 that is detached from the stent 101 via the attachment and/or detachment zone 115.

The flexible wire 114 includes but is not limited to electrically conductive and electrically insulating wires, springs, helical leads and tubes which may have a buffer at the front. Alternatively, the buffer is electrically conductive and acts as an electrode, comprising all the features of stent-mounted electrodes.

Implanted Chips

Implanted electrical circuitry (chips) can be used to control the stimulation and measurement of the electrodes 131. The chip can be implanted in place of an electrode (or elsewhere mounted on the stent), where the chip has the capacity to transmit the signals. The chip includes circuitry for: (a) signal amplification; (b) signal multiplexing; and (c) transmission of power and data.

The electrodes 131 are attached to one or more electrical chips (whereby the chip is defined as the electrical circuitry as well as the substrate which the chip is built on). Miniaturised chips are mounted on the stent 101 in a similar manner and position to the electrodes 131.

Alternatively, these chips may be attached at a distance from the neural recording or stimulation site such as the neck or pectoral region, or the chip may connect directly to external hardware, such as current sources, recording equipment or prostheses.

The chips can include circuitry for stimulation of neural tissue (current and/or voltage sources, batteries and/or capacitors or charge/energy storing components and switch matrices, etc) and circuitry for the recording of neural activity (amplifiers, power sources, switch matrices, etc) and blood composition (such as pH meters, salts and saline composition, glucose etc).

Further, chips may have circuitry required for the transmission of power and data through telemetry coils and self-monitoring hardware such as thermal sensors.

Figure 5C:
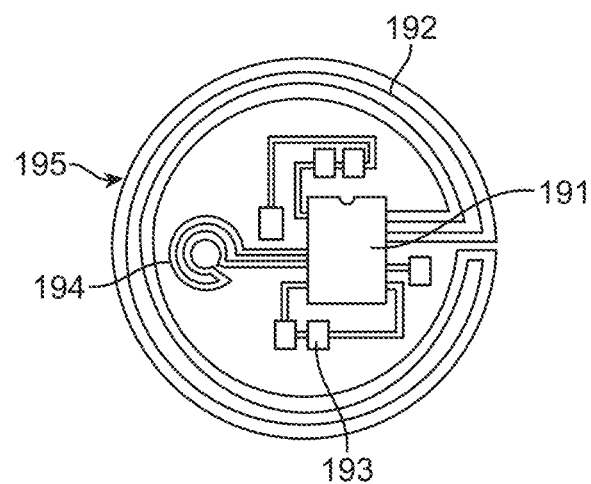
FIG. 5C is a schematic diagram of a wireless chip.
Figure 5D:
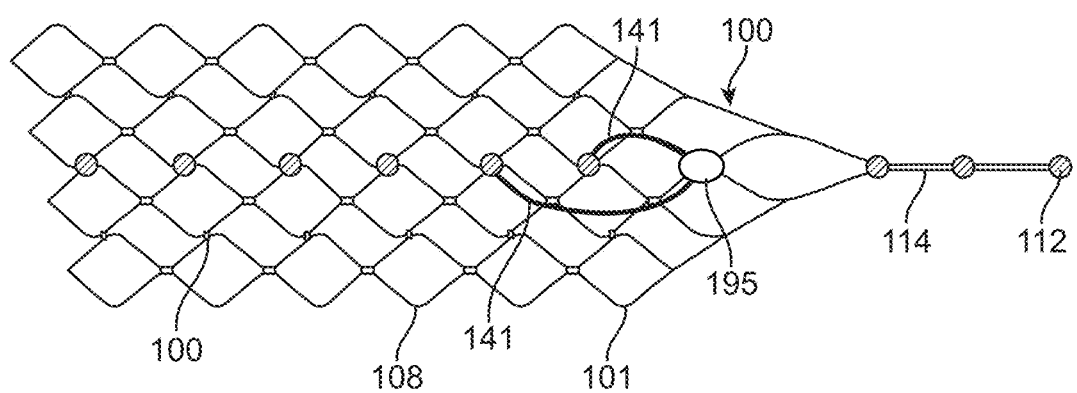
FIG. 5D is a diagrammatic illustration of a medical device of the system shown in FIG. 1.

The depiction of the wireless chip 195 shown in FIG. 5*c*, whereby the microprocessor 191 is shown as well as other components 193 (eg, capacitors, multiplexors, clocks, wireless transmitters, receivers etc). This depiction has two coils that can be used for transmission and receiving of both power and data, shown as a large coil 192 and a small coil 194.

The chip itself may contain a telemetry coil for the transmitting and receiving power and data and may contain a magnet to enable alignment with adjacent chips and telemetry coils or may be attached to shape memory alloys or other materials in which the telemetry coils are comprised.

The chip can be flexible, and may be pre-curved to the diameter of the vessel to allow for the deposition of the chip within a vessel. Thus, the chip may contain shape memory alloys or polymers to conform the chip to the curvature of the vessel during the deposition phase. The chip may also be mounted on a bioabsorbable or biodegradable substrate to allow for integration within a vessel. Multiple chips may be used simultaneously.

f. Contacts

As particularly shown in FIGS. 5*a* and 5*b*, electrode contacts 151 are required to enable connection of the device 100 to external equipment in the situation where wireless circuitry is not employed. The electrode contacts 151 can be made from materials similar to those used by the electrodes and will be of similar diameters. The contacts 151 are electrically insulated from each other and will be connected to the electrode lead wires 141 by (but not limited to) conductive epoxy, laser or resistance welding, soldering, crimping and/or wire wrapping.

The contacts 151 are platinum rings or rings of other conductive, biocompatible materials. The contacts can be made from or contain magnetic materials (ie, Neodinium).

The contacts 151 can be: (a) between 500 um and 2 mm in diameter; (b) between 500 um and 5 mm in length; and (c) between 10 um and 100 um in thickness.

The contacts 151 are shaped as discs, tubes, parabaloids or other shapes similar to those used for the electrodes 131.

The contacts are placed over non-conducting sleeve (including but not limited to a silicone tube, heat shrink, polymer coating) to assist with electrical insulation of other lead wires and electrode and stent wire, and to assist in retaining shape tubular shape whilst allowing some flexibility.

The contacts 151 can have a contact to contact separation of between 100 um and 10 mm, for example, between 1.0 mm and 3.0 mm (e.g., 2 mm or 2.46 mm). Other contact separation dimensions, more or less, as well as other ranges, narrower or wider, are also appreciated.

The contacts 151 are formed through wire wrapping of the wires 141.

At least one contact 151 can be a dummy connector (including but not limited to a metal ring, magnetic ring, plastic tube). A dummy connector in this instance is a connector that is not in electrical contact with an electrode, instead, the purpose is to enable a connection or securing point (ie, through a screw terminal) to the device in a desired location and such that the contacts (connected to electrodes) are not damaged.

The contacts 151 are separated by a non-conductive sleeve (including but not limited to a silicone tube, heat shrink, polymer coating) to reduce electrical noise and prevent contact between superficial lead wires 141.

g. Shaft

Figure 21A:
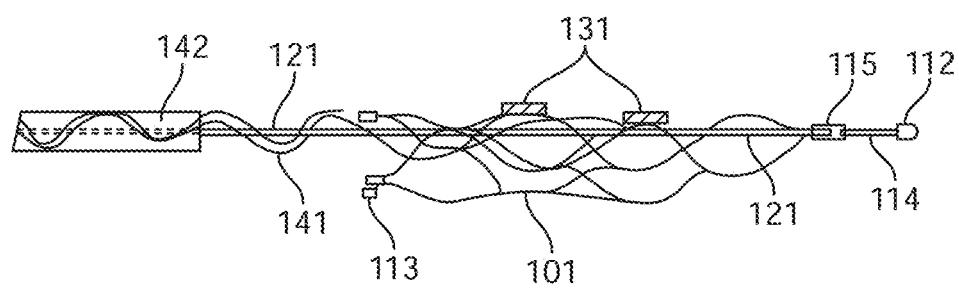
FIGS. 21a to 21c are diagrammatic illustrations showing deployment of different embodiments of the device.

As shown in FIG. 21*a*, to enable deployment, a flexible shaft 121 is connected to the device 100. In the example shown in FIG. 21*a*, the shaft 121 is connected at the distal end of the device 100 such that it acts to pull the device 100 from the front.

Figure 21B:
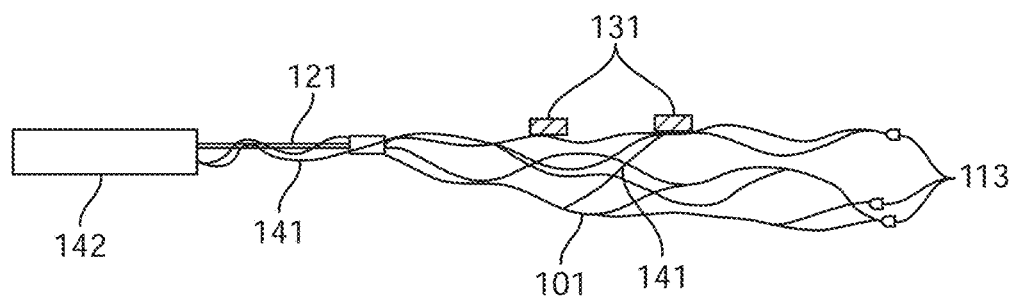

In the alternate embodiment shown in FIG. 21*b*, the shaft 121 is attached to the proximal end of the device 100 such that the shaft 121 pushes the device 100 from the back of the stent 101. In this embodiment, medical device 100 includes a plurality of electrodes 131 mounted to a stent 101 with electrode lead wires 141 wrapped around the stent 101 and the shaft 121 and covered in a sleeve 142. Distal electrodes and/or markers and/or buffers are also depicted 113 as is the stent detachment zone 105.

Figure 21C:
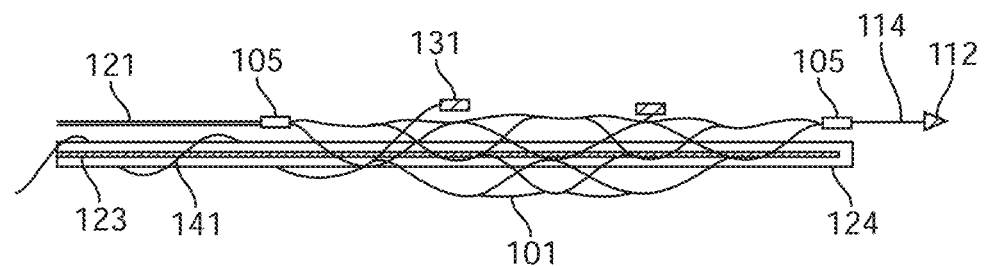

The further embodiment shown in FIG. 21*c* includes a double tapered stent 101 with mounted electrodes 131 and a stent shaft 121 attached to the stent 101 at the stent attachment/detachment zone 105. Another attachment/detachment zone 115 at the front of the stent 101 connects the stent 101 to the olive wire 114 and a stylet sleeve 124, through which, a removable stylet 123 is placed. Electrode wires 141 are shown as wrapped around the outside of the stylet sleeve 123 or as being fed through the centre.

There may be a plurality of wires, with both pushing and pulling abilities. The stent shafts 121 may be implanted permanently or may be designed to be detached and removed. In this embodiment, the attachment/detachment zone will be located at the junction of the stent shaft 121 and the stent 101. Detachment methods include, but are not limited to, electrochemical detachment, mechanical detachment and thermo-electrical detachment.

The stent shaft 121 can be used as a backbone for electrode lead wires 141, assisting the stability of the electrode lead wires 141 as they traverse from the electrodes 131 to the electrode contacts. In this embodiment, the electrode wires 141 are in a polymer 142, (including but not limited to shrink wrap, heat shrink, parylene, silicone, Teflon, etc) to provide additional mechanical support, assist in water retention and to enable coatings to be deposited onto the stent shaft where wires are present.

The stent shaft 121 may be a stylet that is removed following implantation and deposition of the device 100. In this embodiment, the stent shaft 121 may be a cylindrical tube such that the stylet 123 can be fed through the centre of the tube 121.

The wires 141 can be thread through the middle of a stylet sleeve.

The wires 141 can be wrapped around the stent shaft or stylet sleeve.

In a further embodiment, the electrode wires 141 that connect the electrodes 131 to the contacts 152 are wrapped in a wire bundle 144 and wrapped around an internal lumen tubing 145 in a helical form such that there is an internal lumen 147 whereby a removable stylet 148 can be thread during insertion and removed following deployment. This embodiment enabled removability of the stylet 148 and flexibility of the wire bundle 144 that is over coated in an external tubing 146.

Figure 21D:
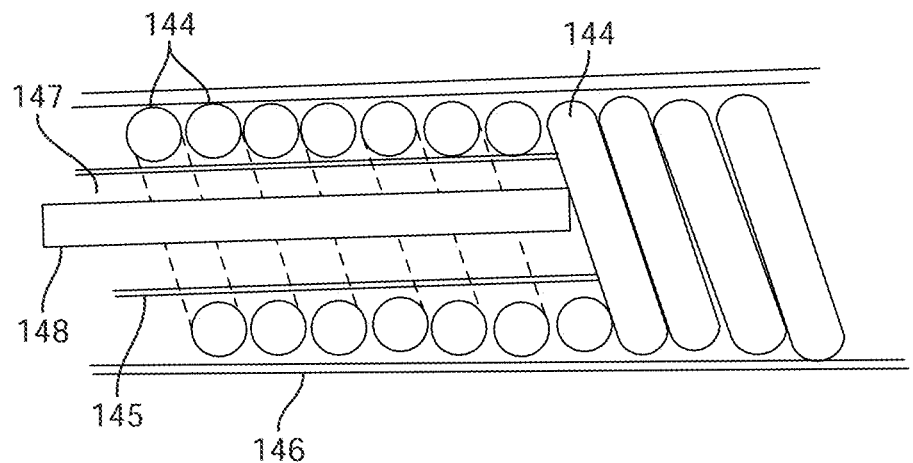
FIGS. 21d and 21e show additional information regarding a helical lead 114.
Figure 21E:
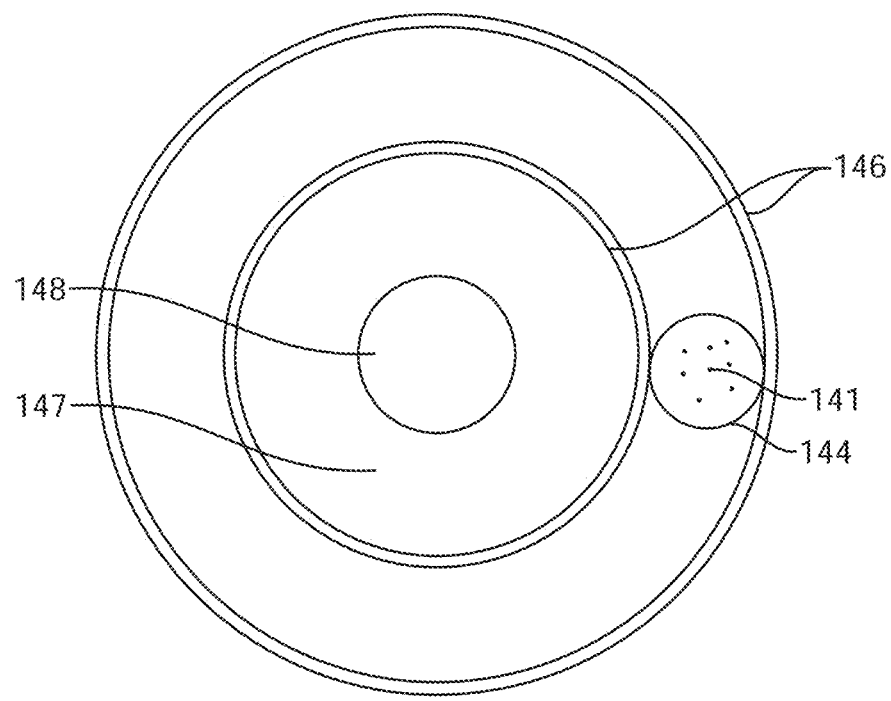

FIGS. 21*d* and 21*e* show additional information regarding a helical lead 114. As depicted, the helical 114 lead includes wire bundle 144 wrapped around an internal lumen tube 145. Through the internal lumen 147, a removable stylet 148 can be thread during delivery and removed following device placement Control Unit The control unit 12 shown in FIG. 2 is a wireless controller, relaying information and power through the skin wirelessly.

Figure 22:
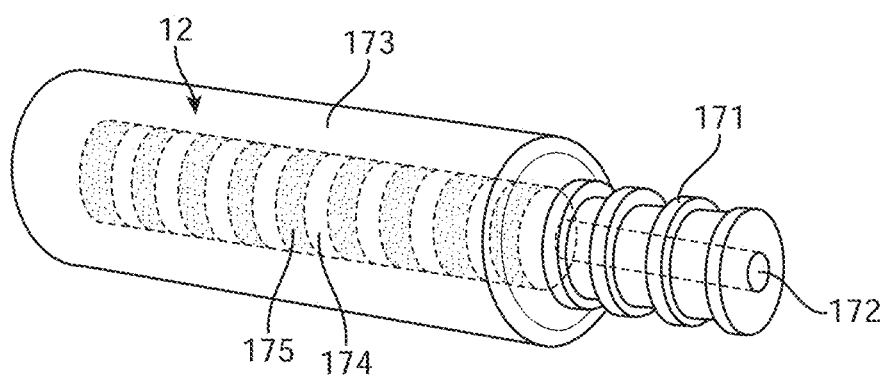
FIGS. 22 to 24 are diagrammatic illustrations of a control unit of the system shown in FIG. 1.
Figure 23:
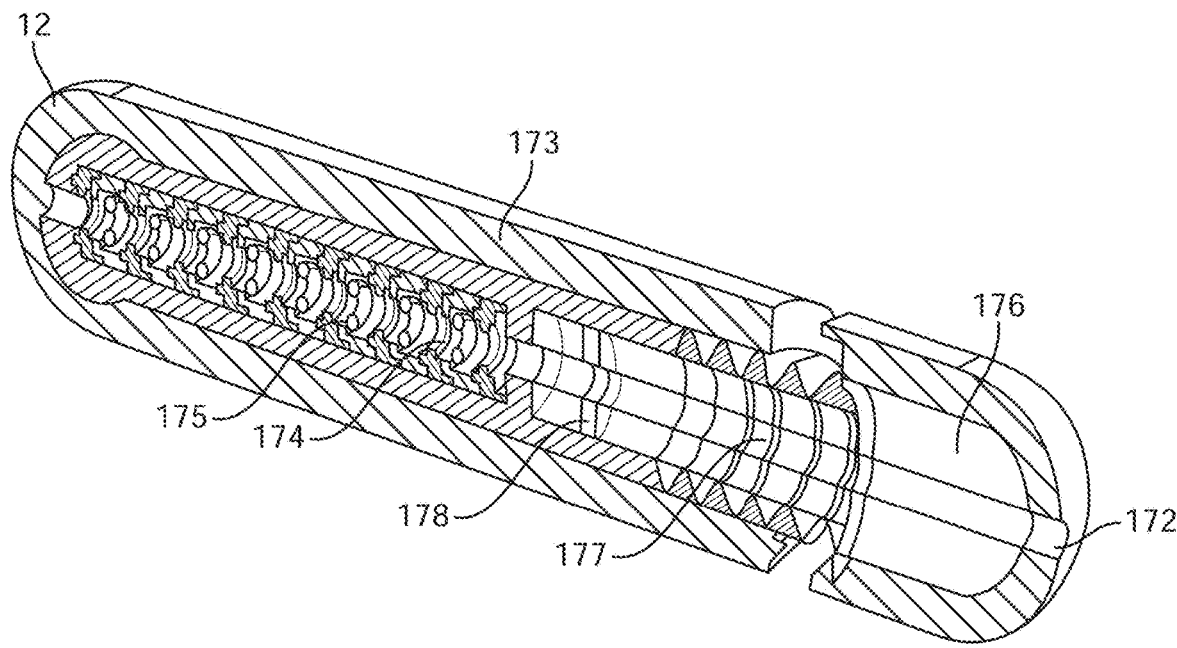
Figure 24:
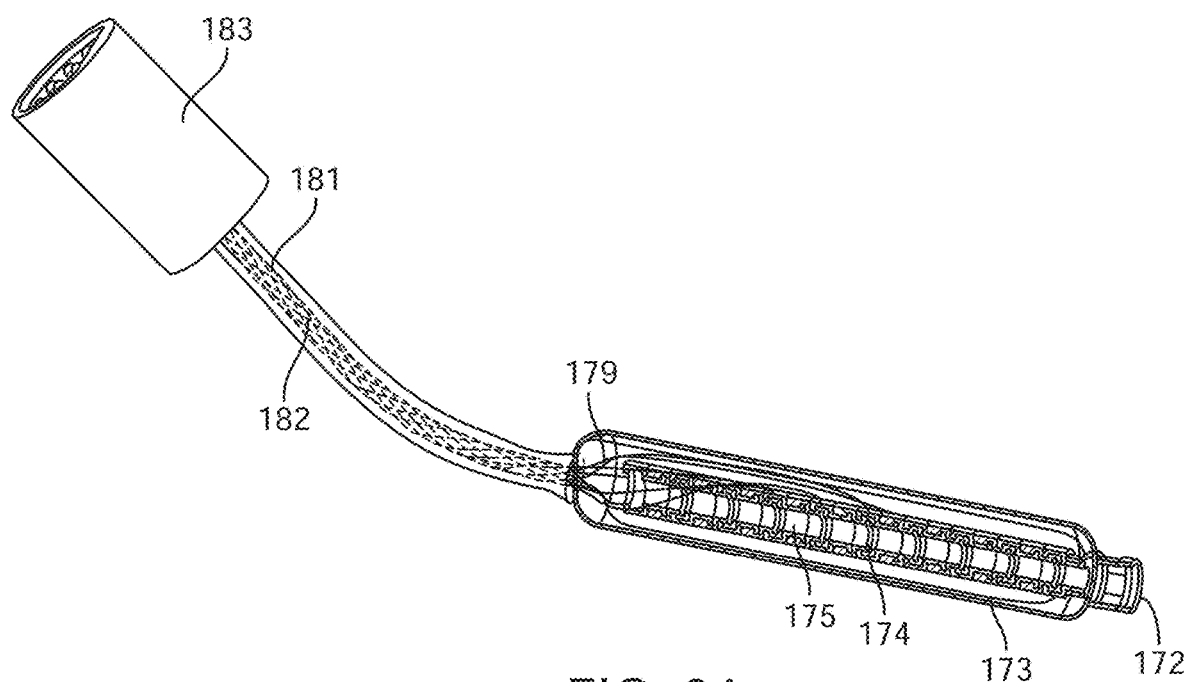

The connector block 12 in FIGS. 22, 23, and 24 are passive devices (ie, no circuitry). Essentially, it functions as an intermediate connection between the device 100 and external equipment. The device 100 is inserted into the connector block 12 whereby the device 100 contacts make electrical contact with internal contacts contained within the connector block 12. These internal contacts of the connector block 12 then form a thicker wire bundle which passes through the skin (the rest of the connector block is implanted) and can be connected to external equipment.

Essentially, as we are limited in space (the entire device must pass through a catheter as the catheter needs to be removed over the device after implantation) the connector block enables attachment of larger items to the thin device 100.

The embodiments shown in FIGS. 22, 23 and 24 are the same, although only FIG. 24 shows the wire that goes through the skin.

The control unit 12 shown in FIG. 22 is shaped to receive and make electrical connection with the lead 14. The control unit include contacts rings mounted on the inside. Here, the connector block 12 is secured and ensured water-tight through attachment of silicone and/or sutures at the grooved end.

The wireless system that is implanted on the stent directly is essentially the same (although a miniaturised version) of the wireless system 12 in FIG. 2.

As shown in FIG. 23, the electrode lead 14 is inserted and a silicone gasket is used to make a watertight seal following FIG. 24 depicts a connector block whereby the electrode lead 14 is thread through the connection opening 172 whereby the contacts connect with the electrically conductive connectors 175 inside the connector block body 173. Separation and electrical insulation and water-tightness is increased through silicone (or otherwise) separators 174. Contacts 175 are welded (or otherwise) to connector block wires 179 that may form a silicone or otherwise 181 encased bundle 181 to terminate at a wireless or direct electrical connection port 183.

Method of Using the System

Figure 25:
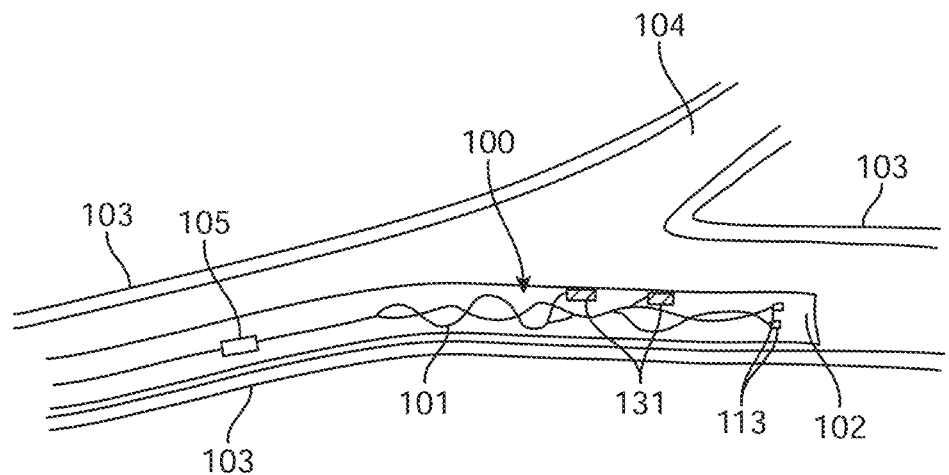
FIGS. 25 and 26 are diagrammatic illustrations showing different stages of deployment of the device.
Figure 26:
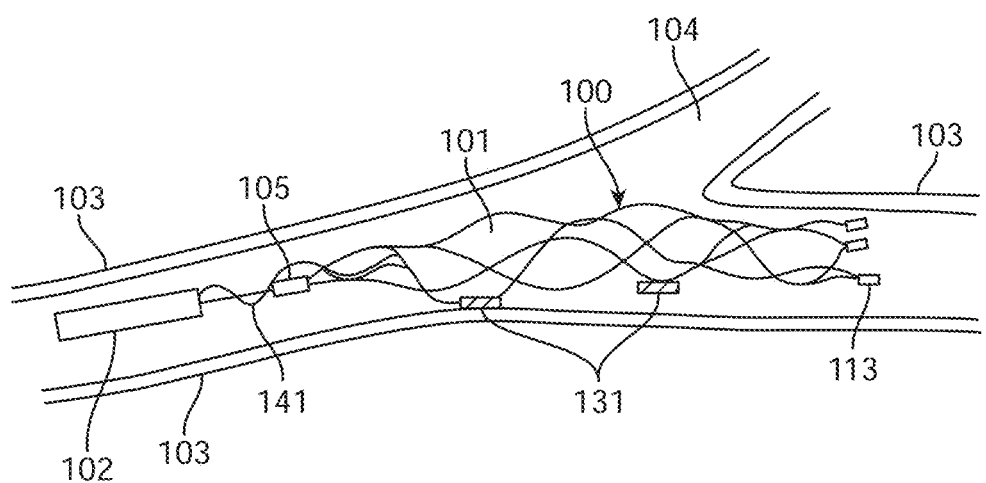

The device 100 is movable between an insertion position shown in FIG. 25 and the deposition or scaffolding position shown in FIG. 26.

In the insertion position, the device 100 is contracted and thus thin enough to be threaded through the vasculature pathway from within a catheter from an entry point (ie, the jugular vein) to a deposition point (eg, the motor cortex).

When arranged in the deposition or scaffolding position, the device 100 is in an expanded condition where scaffold electrodes mounted on the outside of the stent 101 as pressed against the vessel wall. This expanded position anchors the device 100 in its location within the vessel 103. Further, this deposition position is designed such that it has a minimal effect on blood flow integrity through the vessel 103 in which the device 100 is deposited. The scaffolding position may be synonymous to a spring, coil or helical strand, whereby the device 100 is in contact with the vessel wall only, reducing the effect on blood flow. Electrodes 131 may also be mounted on the inside of the stent 101 such that information from fluid flowing through the expanded stent 101 can be measured. For a stent 101 to be removed or relocated, additional shafts (other than that used for initial deployment) are required. These are explained in the context of this invention, with both single tapered and double tapered designs used.

To enable the device 100 to be arranged in multiple positions, the material used is such that multiple states are possible. These materials include, but are not limited to, Nitinol and other shape memory alloys and polymers. Further, to enhance the long term biocompatibility of the device 100, the polymers may be bioabsorbable or biodegradable, with a time of degradation similar to the time in which fibrosis occurs over the device 100. Hence, the electrodes 131 (which preferably are not designed to degrade, and may be made from Nitinol, shape memory alloys, conductive polymers, other non-shape memory alloys and inert and biocompatible metals such as platinum, iridium, stainless steel and gold) will be all that remains of the initial device 100 and will become embed inside the blood vessel 103, further enhancing the stability of the device 100 at the location of deposition Device in Blood Vessel (After Deployment)

Figure 6:
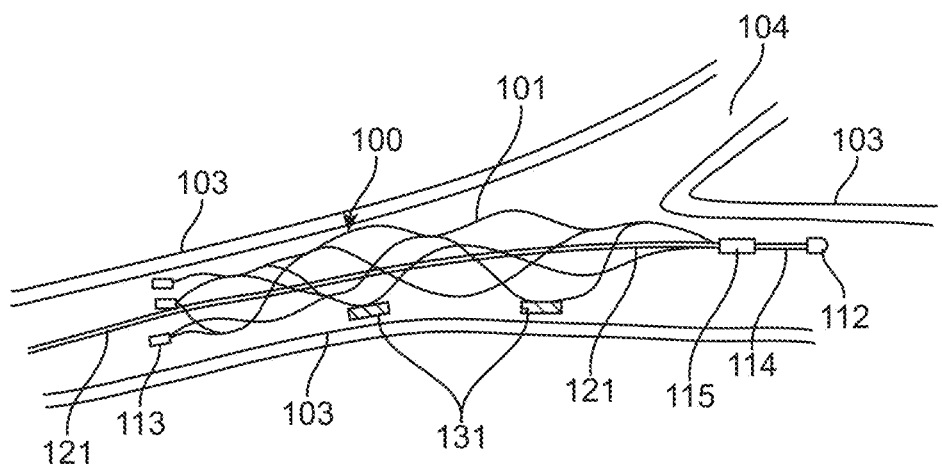
FIG. 6 is a diagrammatic illustration of a medical device located in a vessel.

FIG. 6 depicts a medical device 100 in the expanded or deposition or scaffolding position. The device 100 includes a stent 101, distal olives and/or proximity markers 112, a wire 114 attaching the stent 101 to the olive 112, a plurality of electrodes 131, and an attachment/detachment zone 115 whereby the shaft is connected to the stent 101 having been deployed in a blood vessel 104. Stent 101 mounted electrodes 131 are in direct apposition with the vessel wall 131 and are depicted as not interruptive of blood flow to any vessel (both the vessel the device is deployed in and other connected vessels). Here, the olive 112 can be used to direct the medical device into the desired vessel 104.

Device in Blood Vessel Pre-Deployment

FIG. 25 depicts a medical device 100 during implantation (surgical deployment phase) as it is being thread through vessels 104 inside a catheter 102. The stent 101, electrodes 131, stent detachment zone 105 and stent distal markers/electrodes/buffers 113 are shown, as are the vessel walls 103. Here, the catheter 102 is being used to select and direct the device into the desired vessel 104.

Device In Blood Vessel After Deployment

FIG. 26 depicts a medical device 100 in the expanded or deposition or scaffolding position comprising a stent 101, distal olives and/or proximity markers 113, a plurality of electrodes 131, lead wires 141 and a stent detachment zone 105 being deployed in a blood vessel 104 through a deposition catheter 102. Stent 101 mounted electrodes 131 are in direct apposition with the vessel wall 103 and are depicted as not interruptive of blood flow to any vessel (both the vessel the device is deployed in and other connected vessels).

Ground Electrode

Figure 27:
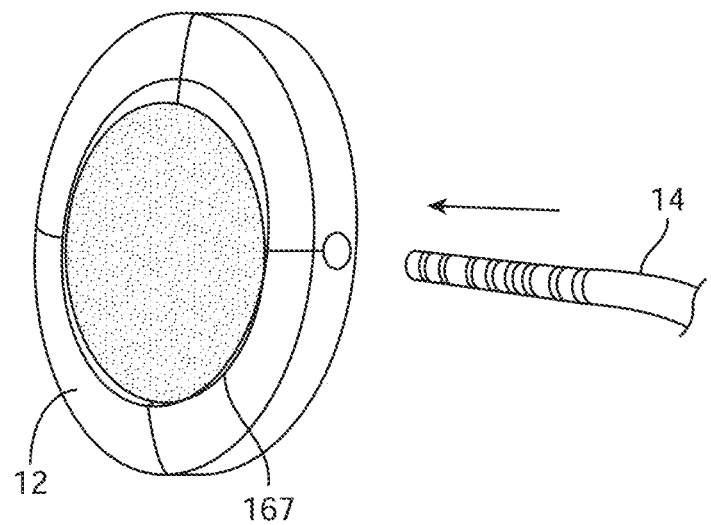
FIGS. 27 and 28 are diagrammatic illustrations of control units having ground electrodes attached thereto.

The system can include a ground electrode 167, configured in the manner shown in FIG. 27, which is used to assist and improve the quality of the recorded signals or to provide an electrical return path for stimulation applications. Here the ground electrode may be placed on the connector block provided it is implanted. Ground electrode 167 can be directly attached to the outside of the wireless controller 12.

Figure 28:
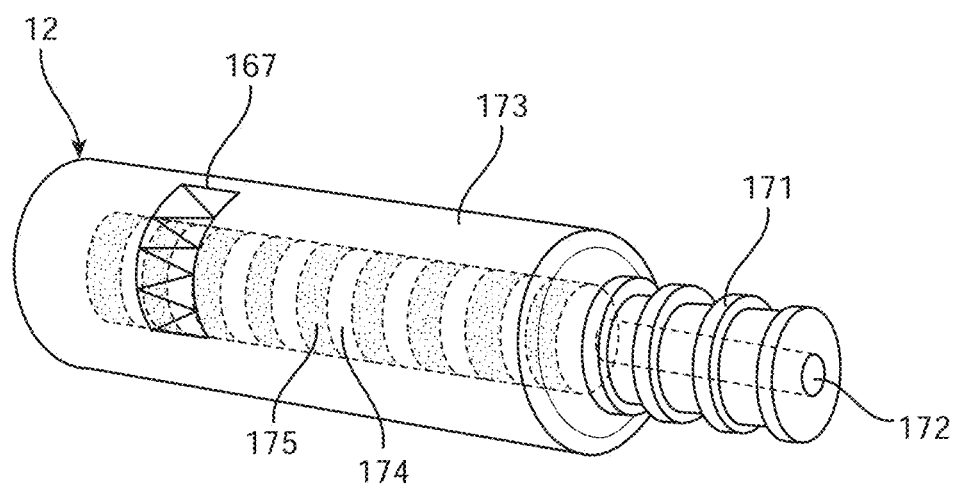

An alternative embodiment of the ground electrode 167 is shown in FIG. 28. Ground electrode 167 on the outside of the controller 12.

Figure 37:
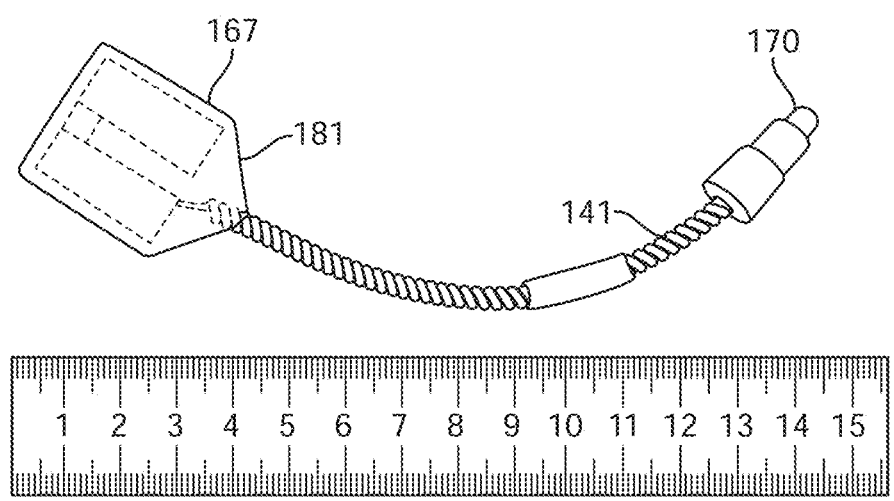
FIG. 37 is a photo of a C-shaped ground electrode.

The platinum C-shaped ground electrode 167 shown in FIG. 37 is embed in silicone 181 with a red helical lead wire 141 that is attached to a standard electrical terminal 169. Dacron mesh is used to assist secure the electrode and wire to tissue.

Figure 29:
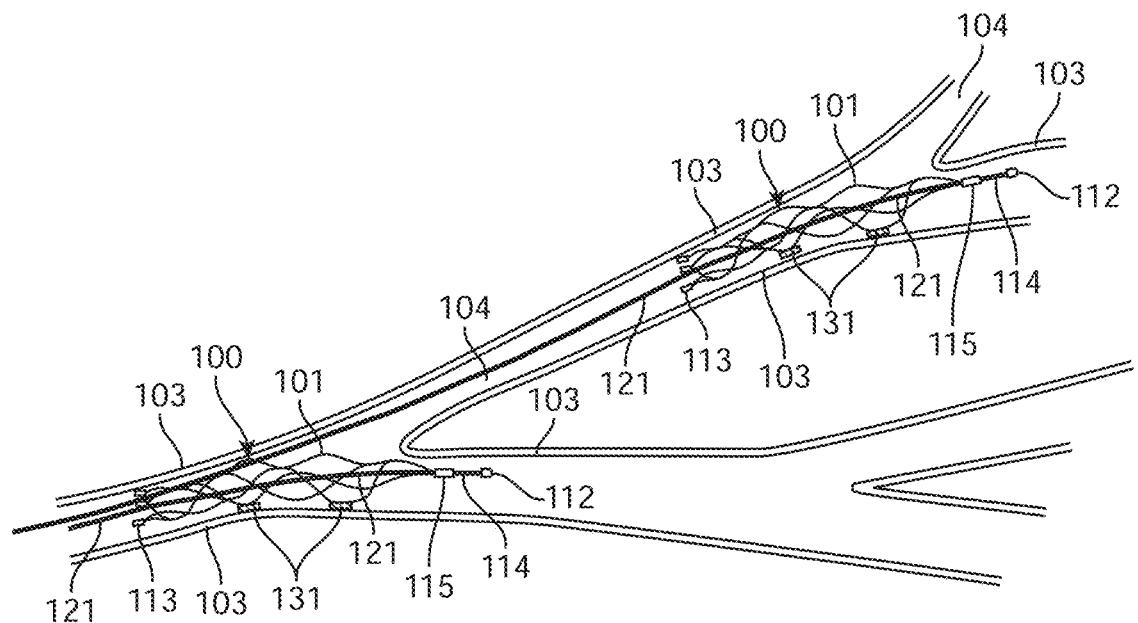
FIG. 29 is a diagrammatic illustration showing multiple vessels with multiple devices.

FIG. 29 shows a vessel with multiple devices 100 inserted in different vessels 104 to access different areas.

Figure 30:
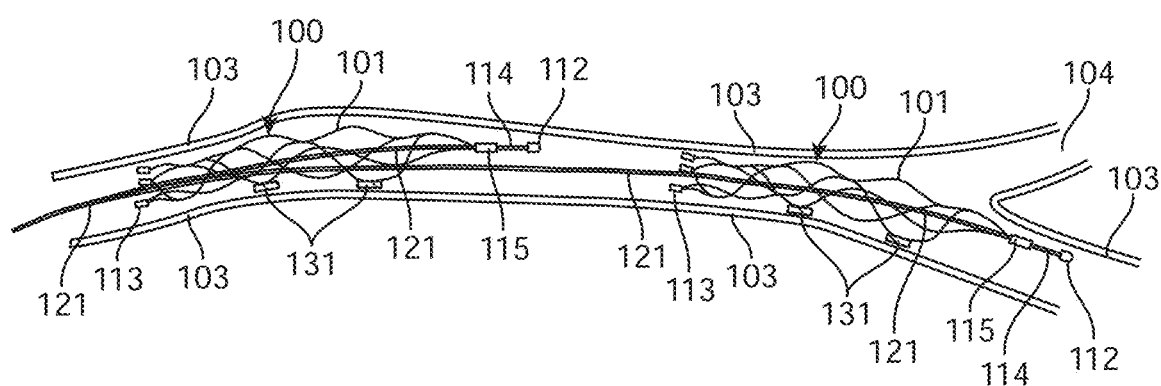
FIG. 30 is a diagrammatic illustration showing a single vessel with multiple devices.

FIG. 30 shows a single vessel 104 with multiple devices 100 implanted to cover a larger area.

Figure 31:
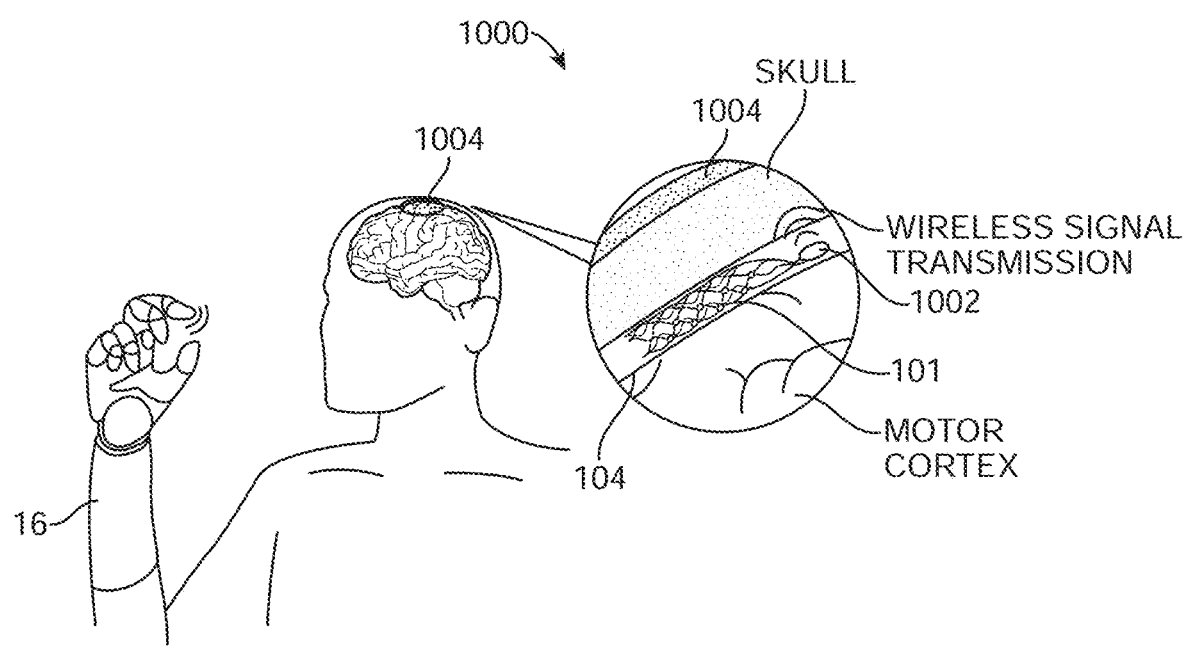
FIG. 31 is a diagrammatic illustration of a wireless electrode system.

FIG. 31 a wireless electrode system 1000 showing electrodes mounted on a stent 101 within a blood vessel 104 overlying the motor cortex in a human that are picking up neural information and relaying this information to a wireless transmitter 1002 located on the stent 101. Note the stent 101 has been deployed and the stylet has been removed (ie, only the stent 101, electrodes, electrode wires and wireless system 1002 remains). The information is wirelessly transmitted through the skull to a wireless received 1004 placed on the head, which in turn, decodes and transmits the acquired neural information to a prosthetic limb 16.

Figure 32:
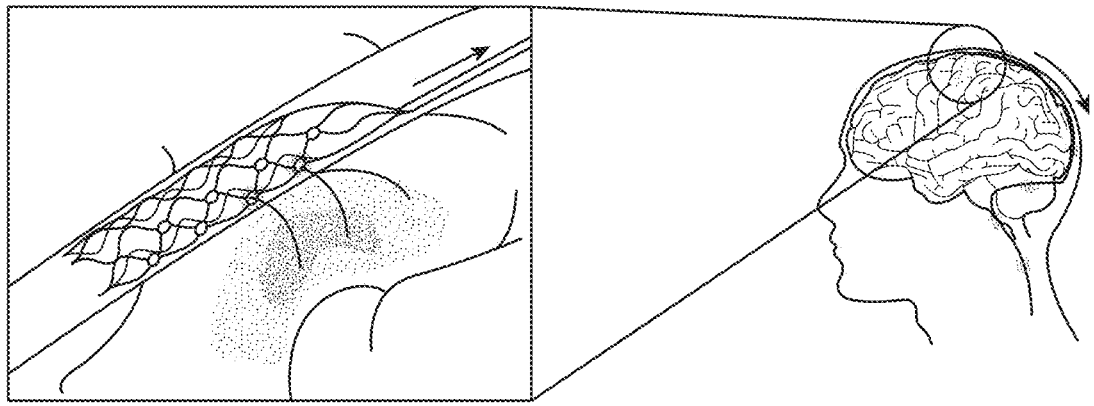
FIG. 32 is a diagrammatic illustration of the system being used to record neural information or stimulation of neurons from the superior sagittal sinus (SSS) or branching cortical veins of a patient using the device.

As shown in FIG. 32, the device 100 can be used to record neural information or stimulation of neurons from the superior sagittal sinus (SSS) or branching cortical veins of a patient using the device 100, including the steps of: (a) implanting the device in either the superior sagittal sinus or branching cortical veins; (b) receiving activity; and (c) generating data representing said activity; and (d) transmitting said data to a control unit. Stent 101 implanted in SSS over motor cortex acquiring (i.e. receives) signals that are fed through the wire to external equipment 12.

Figure 33:
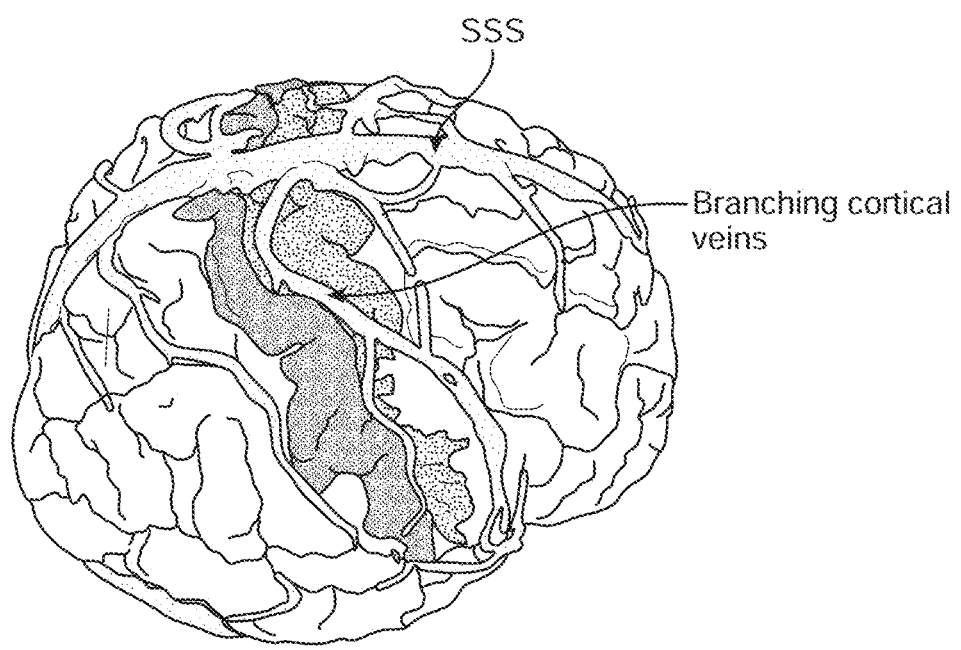
FIG. 33 shows an image reconstruction of a human brain (eyes facing left) demonstrating superior sagittal sinus and branching cortical veins near the motor cortex (red) and sensory cortex (yellow).

FIG. 33 shows an image reconstruction of a human brain (eyes facing left) demonstrating superior sagittal sinus and branching cortical veins near the motor cortex (red) and sensory cortex (yellow)

Figure 34:
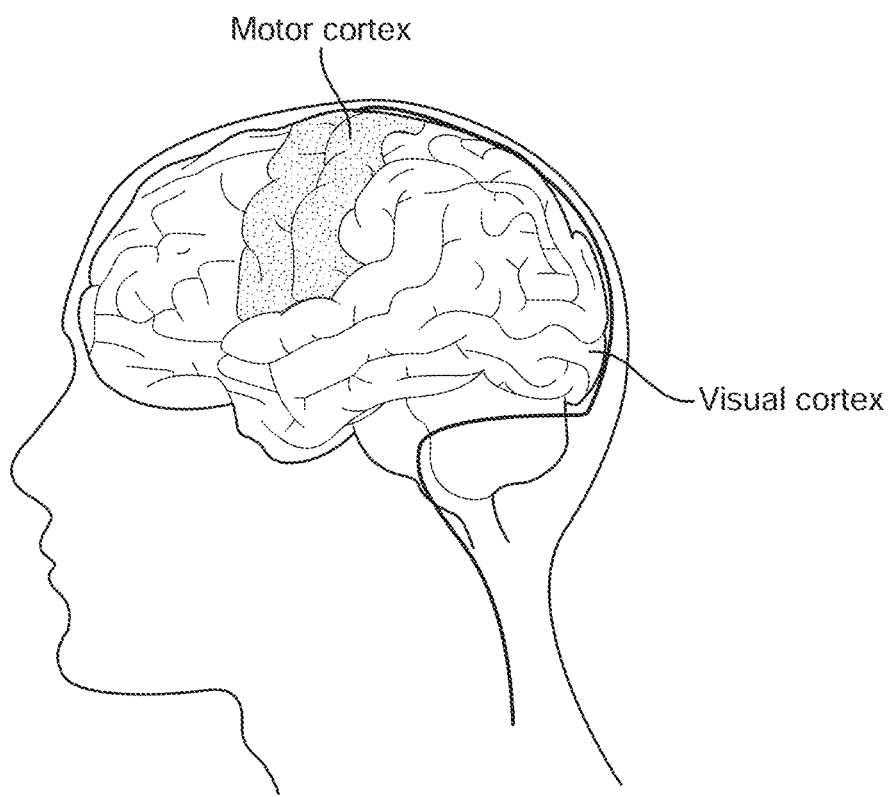
FIG. 34 is a diagrammatic illustration showing a method for stimulation and recording neural information or stimulation of neurons from the visual cortex of a patient using the device.

FIG. 34 shows a method of for stimulation and recording neural information or stimulation of neurons from the visual cortex of a patient using the device 100, including the steps of: (a) implanting the device in a vessel in the visual cortex of the patient; and (b) recording neural information associated with the vessel or stimulating neurons in accordance with received stimulation data.

Figure 35:
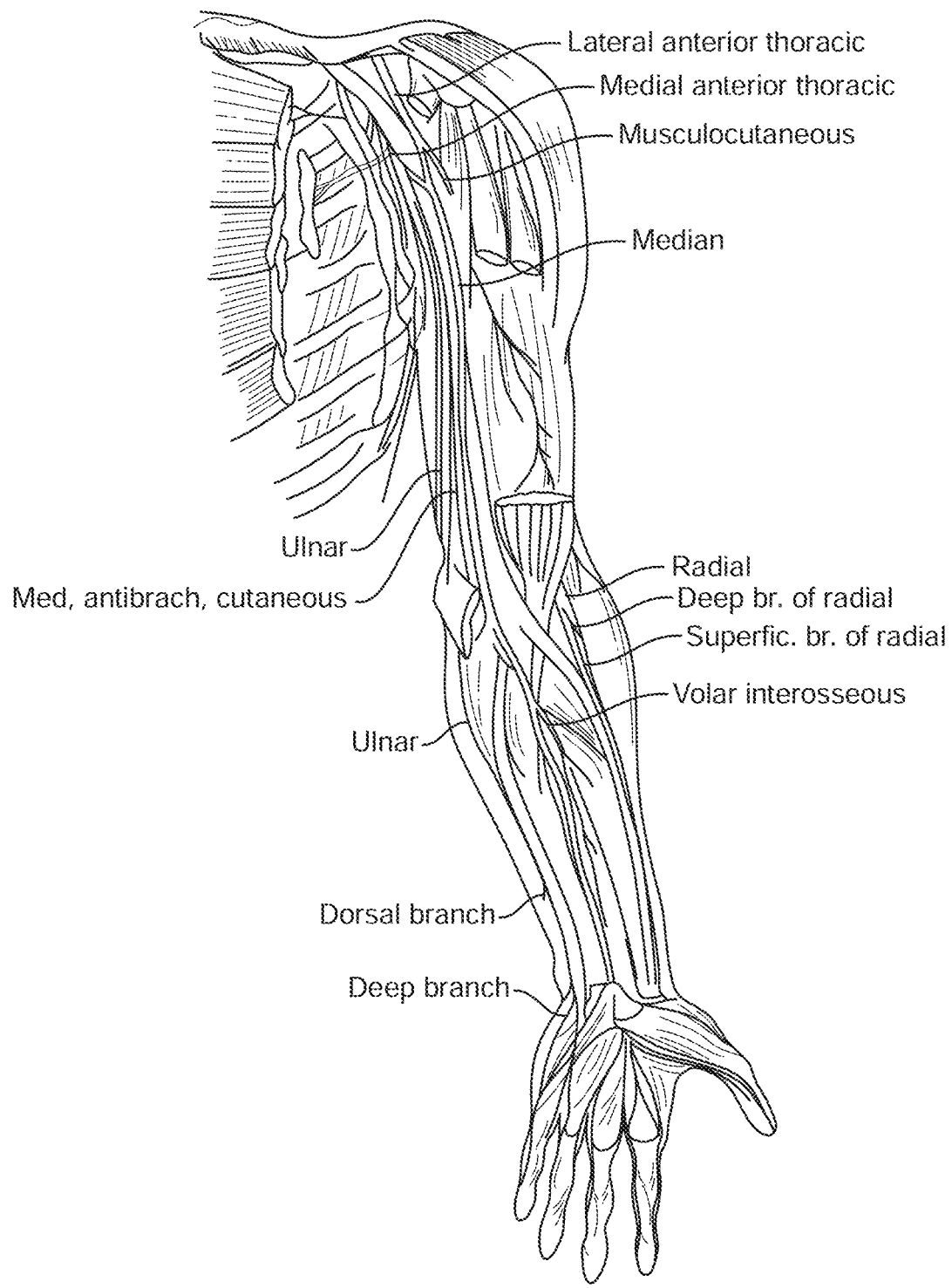
FIG. 35 is a diagrammatic illustration showing vessels and muscles in a human arm.

As particularly shown in FIG. 35, the device 100 is delivered through a vessel 104 deposited in a muscle for direct muscular stimulation or recording.

The device 100 can be delivered through a vessel adjacent to a peripheral nerve (such as shown in FIG. 35) for stimulation or recording.

Figure 36:
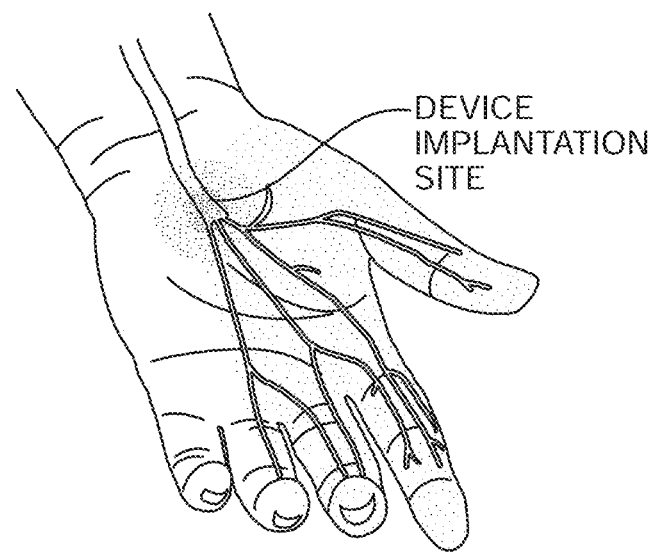
FIG. 36 is an illustration of a human hand showing possible implant location to enable neural stimulation or measurement.

The device is delivered through a vessel adjacent to a sympathetic or parasympathetic nerve for stimulation or ablation As shown in FIG. 36, one example of a peripheral nerve (the median nerve in this example) showing possible implant location to enable neural stimulation or measurement.

Figure 38A:
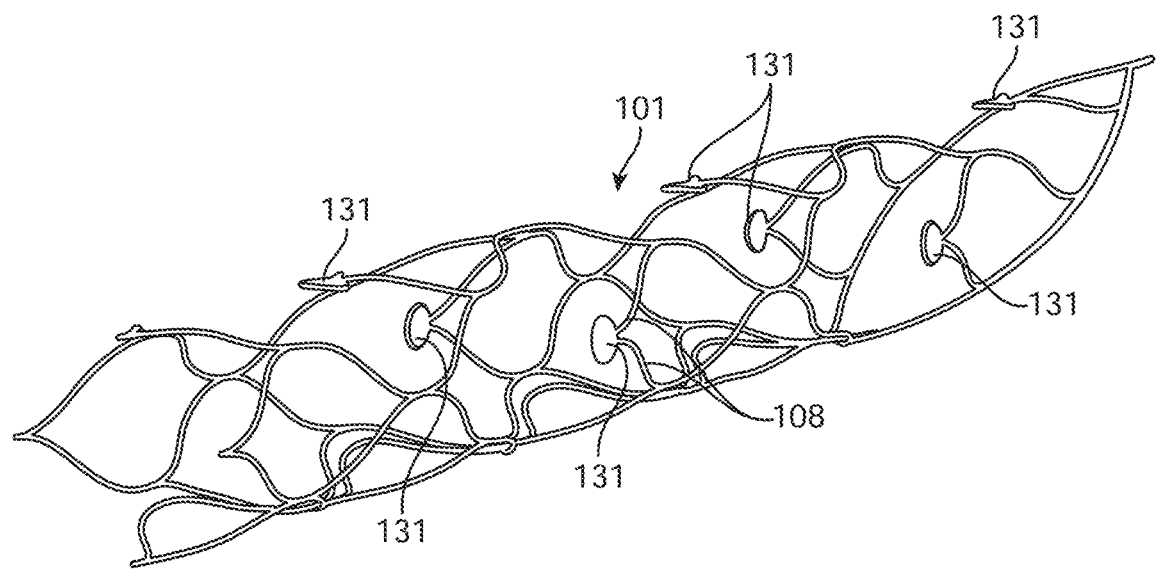
FIGS. 38A-38D illustrate examples of stents or scaffoldings having a plurality of electrodes disposed about the stent body.

FIG. 38A illustrates another example of a stent or scaffolding 101 having a plurality of electrodes 131 disposed about the stent 101 body. For purposes of illustration, the stent 101 is shown without any connecting structure that electrically couples the electrodes to leads or other such structure that allows electrical communication between the electrodes and control unit as described above. In the illustrated variation, the electrodes 131 are dispersed about the body of the stent 101 and are located at the joining or apex of joining struts 108. In such a configuration, where instead of having cells shaped like diamonds, the cells are shaped like a 'V'. This configuration can enhance the apposition between the electrodes 131 and the tissue or vessel wall.

FIG. 38A also illustrates a variation of a stent 101 that can be fabricated where stent structure comprises an integrated conductive layer that extends through a portion or more of the stent strut 108 and where the electrode 131 is formed through an exposed portion of the integrated conductive layer. Such a stent configuration, as described in detail below, permits a stent 101 electrode 131 assembly, which embeds electrodes and conductive electrode tracks into the stent lattice or strut itself. Such a construction reduces or eliminates the requirement to use fixation methods (i.e., adhesives, glues, fasteners, welds, etc.) to mount electrodes to the body of the stent. Such a construction further reduces or eliminates the need to further weld or electrically connect electrodes to wires. Another benefit is that conventional wire-connected-electrodes require accommodation of the wires about the stent struts and through the body of the stent.

Figure 38B:
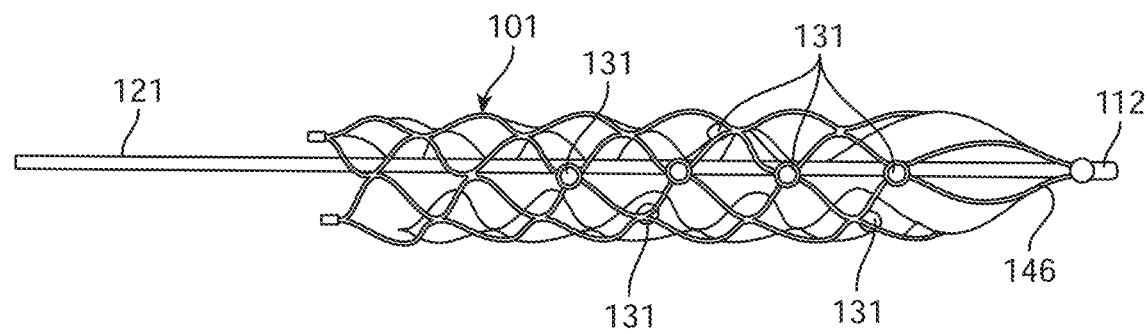
Figure 38C:
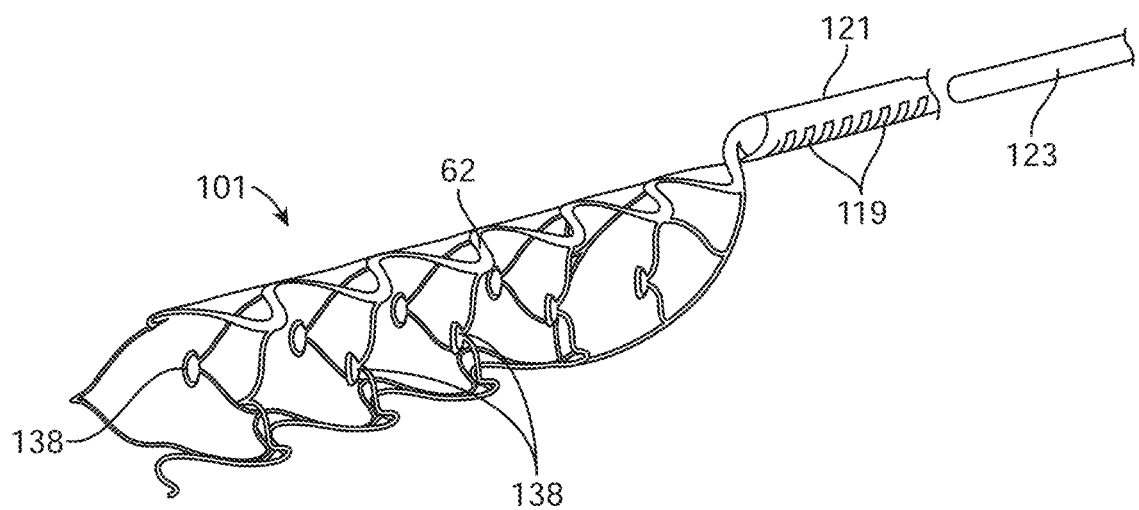
Figure 38D:
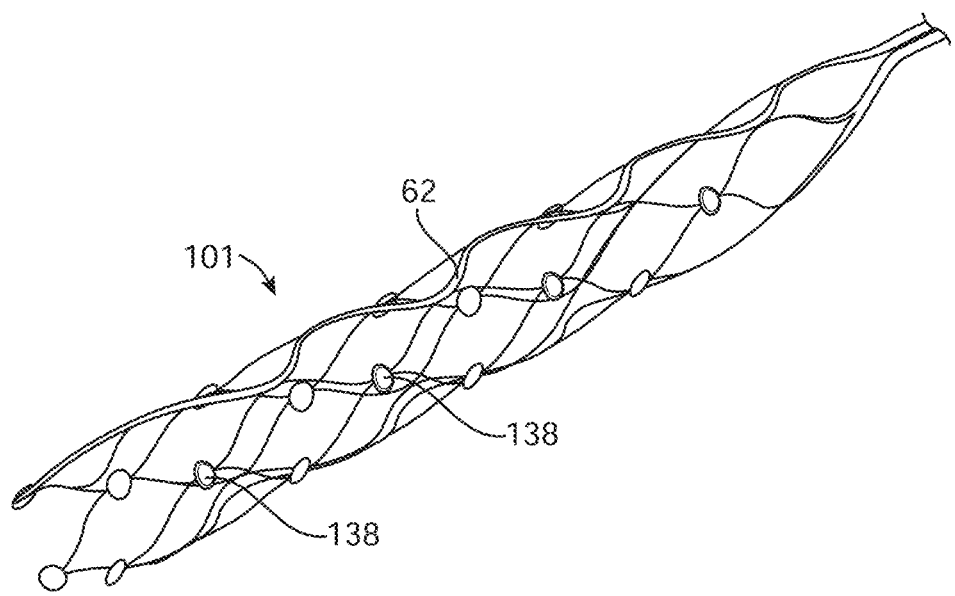

FIG. 38B illustrates a stent structure 101 with integrated electrodes 131, where the stent structure is coupled to a shaft 121 at a distal end 146. The shaft, as described herein, can electrically couple the electrodes 131 to one or more control units (not shown) as described herein. In one example, the shaft 121 can comprise a guidewire, push wire other tubular structure that contains wires or conductive members extending therein and are coupled to the conductive layer of the stent at the distal end 146. Alternatively, FIGS. 38C and 38D shows a variation of stents 101 that can be fabricated such that the shaft 121 is part of or integral with the stent structure, where the conductive layer extends through a portion or all of the stent to the shaft 121. Such a construction further eliminates the need for joining the shaft to the stent structure at the working end of the stent. Instead, the joining of the stent structure (forming the shaft) to a discrete shaft can be moved proximally along the device. Such a construction allows the working end of the stent and shaft to remain flexible. The stent structures shown in FIGS. 38C and 38D can also include an optional reinforced section 62 as discussed above. FIG. 38C further illustrates a hollow shaft 121, which allows insertion of a stylet 123 therethrough to assist in positioning of the device or permits coupling of wires or other conductive members therethrough. Furthermore, the shaft 121 can include any number of features 119 that improve flexibility or pushability of the shaft through the vasculature.

The electrical connection of the electrodes 131 to leads extending through the device can be accomplished by the construction of one or more connection pads (similar in construction to the electrodes described below) where the size of the pads ensures sufficient contact with the wire/lead, the type of pads ensures robustness and reduces track fatigue when crimped and attached. The section containing the pads can be compressed into a tube at, for example, distal section 146 to enable insertion of a cable 121.

In certain variations, the connection pads should be able to feed through the catheter. Furthermore, the connection pads 132 can include one or more holes or openings that enable visual confirmation that the pads are aligned with contacts on the lead. These holes/openings also enables direct/laser welding or adhesion of the contact leads (inside tube 121) and the contact pads (on the inside of the tube spanning through the hole to the outside)

In one example, a coaxial-octofilar cable (i.e. an inner cable with 8 wires positioned inside an outer cable having 8 wires) is used to enhance fatigue resistance and to ensure that wires can fit within constraints (i.e., can be inserted through a sufficiently small catheter, and can have an internal stylet as required).

Figure 39A:
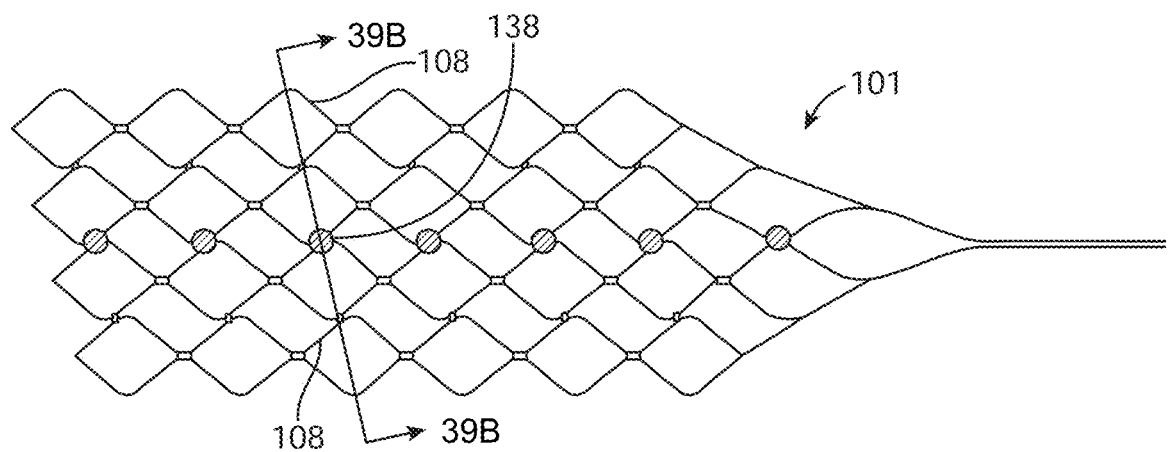
FIGS. 39A-39C illustrate an example of integrated or embedded electrodes.
Figure 39B:
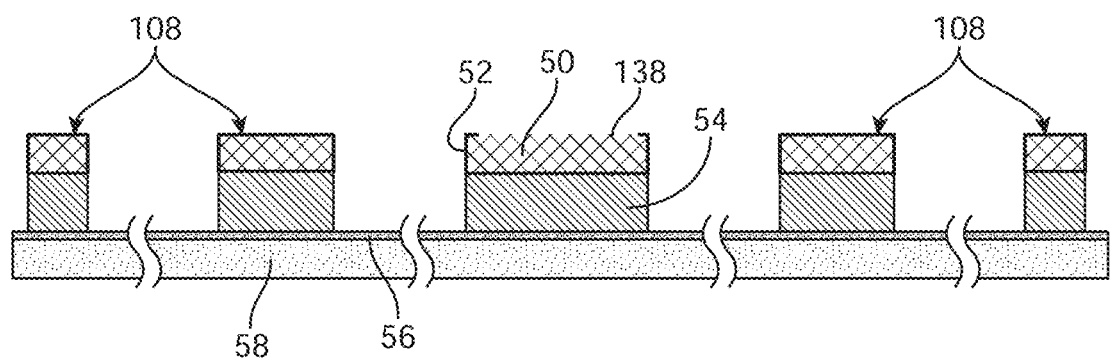
Figure 39C:
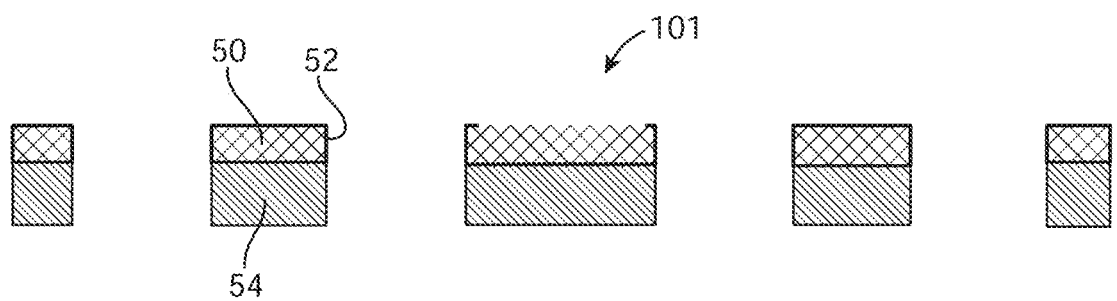

FIGS. 39A-39C illustrate one example of a stent structure 101 constructed with an embedded electrode and conductive path. FIG. 39A illustrates an example of a stent structure 101 with electrodes 138 in a linear arrangement for purposes of illustration only. Clearly, any configuration of electrodes is within the scope of this disclosure. Specifically, in those variations of stent structures useful for neurological applications, the stent structure can comprise a diameter that is traditionally greater than existing neurological stents. Such increased diameter can be useful due to the stent structure being permanently implanted and while requiring apposition of electrodes against the vessel/tissue wall. Moreover, in some variations, the length of such stent structures can include lengths up to and greater than 20 mm to accommodate desired placement along the human motor cortex. For example, variations of the device require a stent structure that is sufficiently long enough to cover the motor cortex and peripheral cortical areas. Such lengths are not typically required for existing interventional devices aimed at restoring flow or addressing aneurysms or other medical conditions. In addition, in certain variations, the electrical path between certain electrodes can be isolated. In such a case, the electrically conductive material 50 can be omitted from certain stent struts to form a pattern that allows an electrode to have an electrical conduction path to a contact pad or other conductive element but the electrical conduction path is electrically isolated from a second electrode having its own second electrically conductive path.

Placement of the electrodes in a specific pattern (e.g., a corkscrew configuration or a configuration of three linear (or corkscrew oriented) lines that are oriented 120 degrees from each other) can ensure a deployed electrode orientation that directs electrodes towards the brain. Once implanted, orientation is not possible surgically (i.e., the device will be implanted and will be difficult if not impossible to rotate). Therefore, variations of the device will be desirable to have an electrode pattern that will face towards the desired regions of the brain upon delivery.

Electrode sizing should be of a sufficient size to ensure high quality recordings and give large enough charge injection limits (the amount of current that can be passed through the electrodes during stimulation without damaging the electrodes which in turn may damage tissue). The size should also be sufficient to allow delivery via a catheter system.

FIGS. 39B and 39C illustrates a cross-sectional view of the stent structure of FIG. 39A taken along line 39B-39B to further illustrate one variation of a manufacturing technique of using MEMS (microelectrical mechanical systems) technology to deposit and structure thin film devices to fabricate a stent structure with electrodes and a conductive path embedded into the stent lattice or struts. The spacing of the struts in FIGS. 39B and 39C are compressed for illustrative purposes only.

As discussed above, embedding the electrode and conductive path presents advantages in the mechanical performance of the device. Furthermore, embedding of electrodes provides the ability to increase the number of electrodes mounted on the structure give that the conductive paths (30-50 μm×200-500 nm) can be smaller than traditional electrode wires (50-100 μm).

Manufacture of thin-film stents can be performed by depositing Nitinol or other superelastic and shape memory materials (or other materials for deposition of electrodes and contacts (including but not limited to gold, platinum, iridium oxide) through magnetron sputtering in a specific pattern (56) using a sacrificial layer (58) as a preliminary support structure. Removal of the support structure (54) enables the thin film to be further structured using UV-lithography and structures can be designed with thicknesses corresponding with radial force required to secure the electrodes against a vessel wall.

Electrical insulation of electrodes is achieved by RF sputtering and deposition of a non-conductive layer (52) (eg, SiO) onto the thin-film structure (54). Electrodes and electrode tracks (50) are sputter deposited onto the non-conductive layer (using conductive and biomedically acceptable materials including gold, Pt, Ti, NiTi, PtIr), with an additional non-conductive layer deposited over the conductive track tfor further electrical isolation and insulation. As shown, conducting path 50 is left exposed to form the electrode 138 (similarly, a contact pad area can remain exposed). Finally, the sacrificial layer 56 and substrate are removed leaving the stent structure 101 as shown in FIG. 39C.

In certain variations where the base structure 54 comprises superelastic and shape-memory materials (i.e. Nitinol), the stent structure 101 can be annealed in a high vacuum chamber to avoid oxidation during the annealing process. During heat treatment, the amorphous Nitinol structure 54 crystallizes to obtain superelasticity and can be simultaneously shape set into a cylindrical or other shape as desired. The structure 101 can then be heat treated.

Figure 40A:
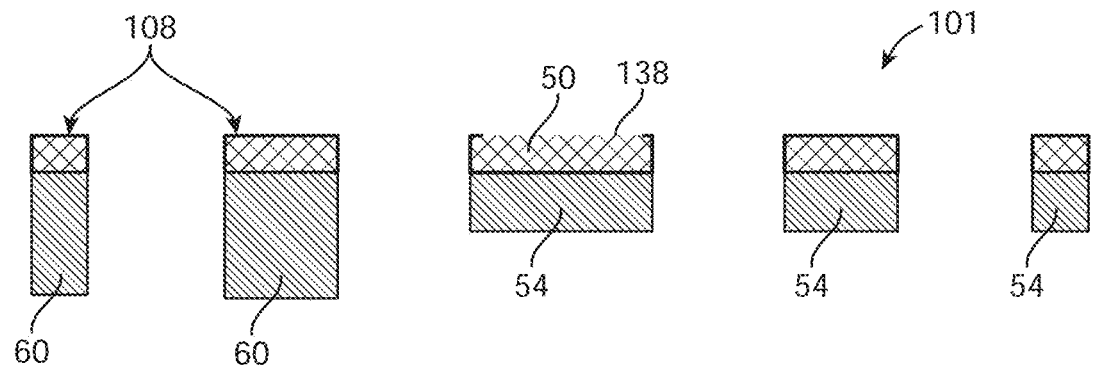
FIGS. 40A-40B show an example of a stent structure fabricated with dimensional variation to impart specific characteristics to the stent.
Figure 41A:
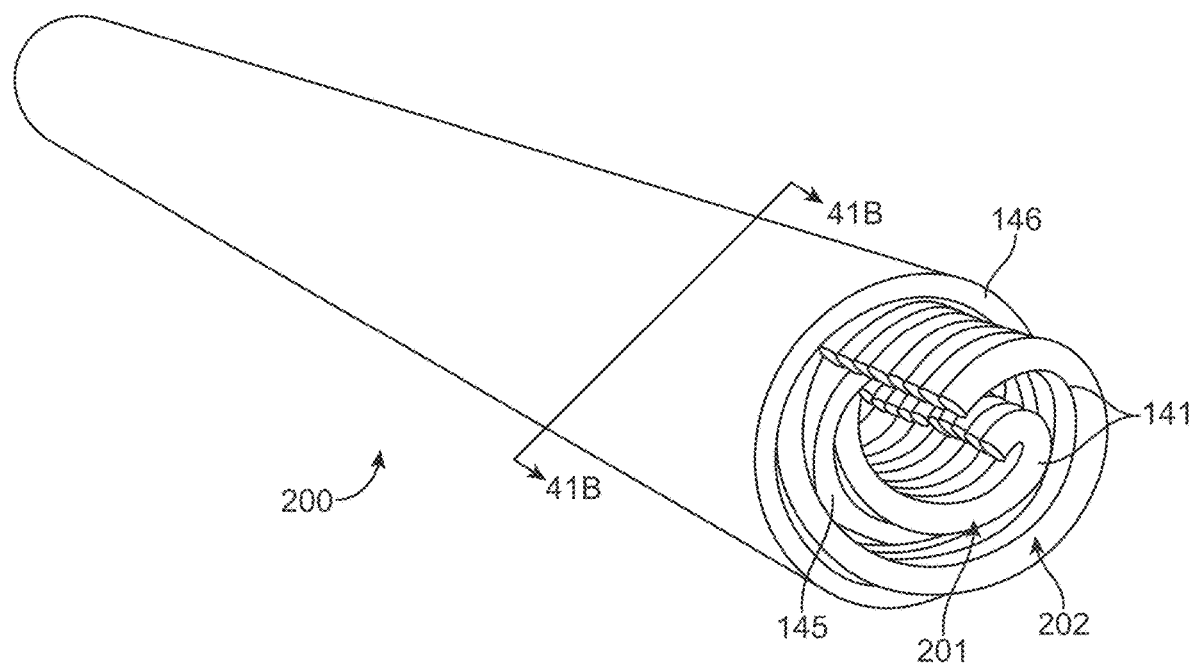
FIGS. 41A-41E illustrate a variation of a connector.
Figure 41B:
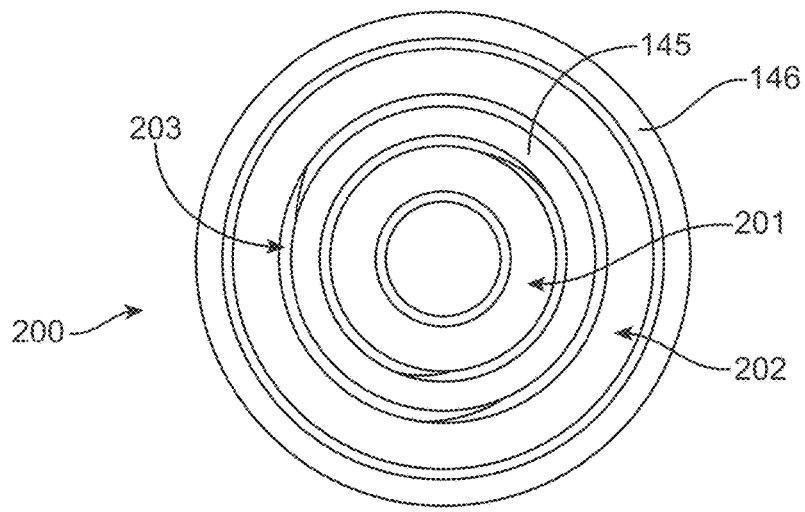

FIG. 40A, which is a partial sectional view of taken along lines 40A-40A of FIG. 41B, illustrate an additional variation of a stent structure 101 fabricated via MEMS technology where one or more stent struts 108 can be dimensionally altered to impart desired structural or other aspects to the stent structure 101. For example, in the illustrated variation, certain stent struts 108 are dimensionally altered such that the support material 60 comprises a greater thickness than adjacent stent structures 108. However, such dimensional variation is not limited to thickness but can also include width, shape, etc.

Figure 40B:
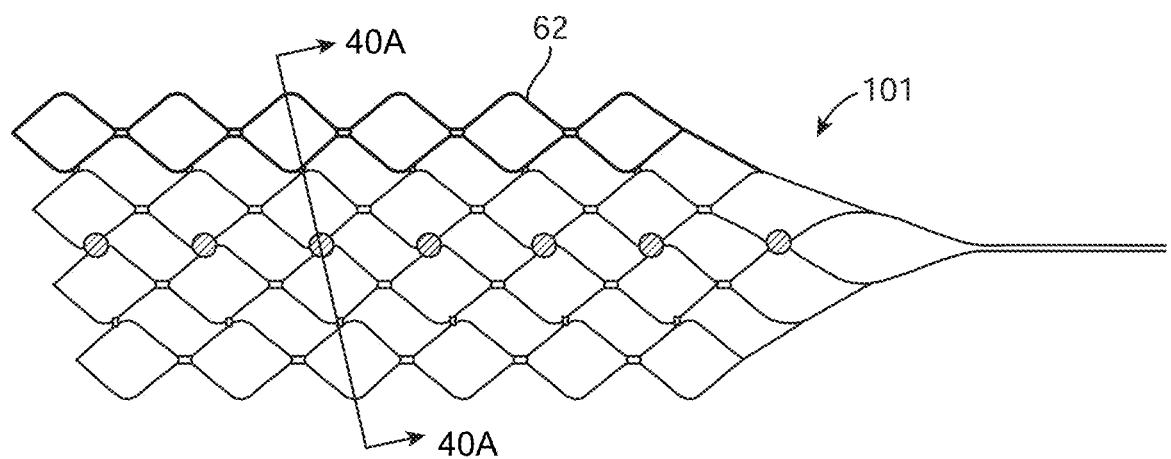

FIG. 40B illustrates the stent structure 101 resulting from the dimensionally altered struts resulting in a sinusoidal section 62 of the stent structure 101 that comprises a greater stiffness (resulting from the increased thickness). Such a configuration allowing the stent device to be pushed through a catheter rather than conventional requirements to be unsheathed (where the sheath is pulled back over the stent). Conventional stents are made from a thin lattice of Nitinol diamonds or cells. This sinusoidal section 62 can function like a backbone and gives forward pushing strength to the device without restricting super-elasticity and the ability for the stent to compress and expand. Clearly, any number of variations of dimensionally altered strut sections are within the scope of this disclosure.

FIGS. 41A-41E illustrate various aspects of a variation of a connector 200 that can be in electrical communication with a stent (e.g., stent 101) and a receptacle (e.g., control unit 12). For purposes of illustration, the connector 200 is shown isolated from the stent 101 and the receptacle 12. As described above, the connector 200 can allow electrical communication between the electrodes and the control unit.

FIG. 41A illustrates that the connector 200 can have a dual-octofiler cable (also referred to as a coaxial-octofiler cable). The dual-octofiler cable can have a first coil 201 (e.g., inner coil) and a second coil 202 (e.g., outer coil). The first and second coils 201, 202 can each have 8 wires 141. Other numbers of wires, more or less, are also appreciated. The first coil 201 can be positioned within a lumen of the second coil 202. The first coil can be positioned within a lumen of an internal tubing 145. The first and/or second coils 201, 202 can be positioned within a lumen of an external tubing 146. The first and second coils 201, 202 can be wound coils. The first and second coils 201, 202 can be helical coils. For example, the first coil 201 can be wrapped along an inner surface of the internal tube 145 and the second coil 202 can be wrapped along an outer surface of the internal tube 145. As described above, the dual-octofiler configuration can be used to enhance fatigue resistance and to ensure that wires can fit within constraints (i.e., can be inserted through a sufficiently small catheter, and can have an internal stylet as required).

An insulator (e.g., polyurethane) can cover one or more wires 141 of the coils 201, 202 (i.e., the wires 141 can be insulated). An insulator (e.g., polyurethane) can be positioned between the first and second coils 201, 202. For example, the internal tube 145 can be an insulator that can be positioned between the first and second coils 201, 202. An insulator (e.g., polyurethane) can cover the first and/or second coils 201, 202 (i.e., the first and second coils 201, 202 can be insulated).

The first coil 201 can have a length that is less than, greater than, or equal to the length of the second coil 202. For example, the first coil 201 can be longer than the second coil 202. The first coil 201 can have a diameter that is less than, greater than, or equal to the diameter of the second coil 202. The first and/or second coils 201, 202 can each have one or more diameters. For example, the first coil 201 can have two diameters and the second coil 202 can have one diameter. The first coil 201 can have a first diameter and a second diameter. The first diameter can correspond to where the first coil 201 is positioned within the second coil 202 and the second diameter can correspond to where the first coil 201 is not positioned within the second coil 202 (e.g., where it extends past the first coil 201). Other arrangements are also appreciated.

Although not shown in FIG. 41A, the external shaft 146 can comprise contacts 151 and separators 174 (e.g., insulators). The separators 174 can be positioned next to contacts 151 to keep the contacts 151 electrically insulated from one another. The wires 141 of the first and second coils 201, 202 can be electrically connected to the contacts 151. For example, the 8 wires 141 of the first coil 201 and the 8 wires 141 of the second coil 202 can each be electrically coupled to a corresponding contact 151.

The first coil 201 can allow a stylet 148 (not shown) to travel through it. For example, the first coil 201 can define a lumen that allows a stylet 148 to pass through the first coil 201. The inner surface of the first coil 201 can be insulated and/or not insulated.

The first and second coils 201, 202 can have a wound section and an unwound section. For example, the first and second coils 201, 202 can transition from a wound section to an unwound section. The wound section have helical wires and the unwound section can have straight, curved (e.g., have one or more bends), and/or angled (e.g., have one or more bends) wires. The wound and unwound sections can be flexible and/or rigid. For example, the wound section can be flexible and the unwound section can be rigid.

The first and second coils 201, 202 can have a helical section and a non-helical section. For example, the first and second coils 201, 202 can transition from a helical section (e.g., where the wires 141 define a helix) to a non-helical section (e.g., where the wires 141 do not define a helix). For example, the wires 141 in the non-helical section can be unwound to no longer form a coil. The wires 141 in the non-helical section can be straight, curved (e.g., have one or more bends), and/or angled (e.g., have one or more bends). The helical and non-helical sections can be flexible and/or rigid. For example, the helical section can be flexible and the non-helical section can be rigid.

The first and second coils 201, 202 can each have one or more channels. For example, the first and second coils 201, 202 can each have 8 channels. Other numbers of channels, more or less, are also appreciated (e.g., 9 to 16 channels, or more). Other numbers of coils are also appreciated, for example, 3 or more coils. For example, it will be appreciated that another coil can be positioned within the lumen of the first coil 201 and/or on the outside of the second coil 202.

FIG. 41B illustrates a cross-sectional view of the connector 200 shown in FIG. 41A taken along the line 41A-41A to further illustrate the first and second coils 201, 202 of the dual-octofiler coil configuration. FIG. 41B also illustrates that the first coil 201 can step-up 203 in diameter to match or otherwise approach the diameter of the second coil 202. The step-up 203 can occur somewhere along the length of the first coil 201 and somewhere along the length of the second coil 202. For example, the first coil 201 can step-up 203 at about the midpoint of the first coil 201 and at an end of the second coil 202 (e.g., a terminal end). The first coil 201 can step-up 203 to contact the leads 151, for example, so that uniformly sized leads 151 can be used. The first coil 201 can step-up 203 to attach to the leads 151. However, it will be appreciated that the leads 151 can have one or more sizes. With or without the step-up 203, the receptacle 12 can have a step in it so that the contacts 175 of the receptacle 12 can make contact with the contacts 151 in contact with the first coil 201. The various components of the dual octofilar cable can have the various dimensions shown (in inches).

Figure 41C:
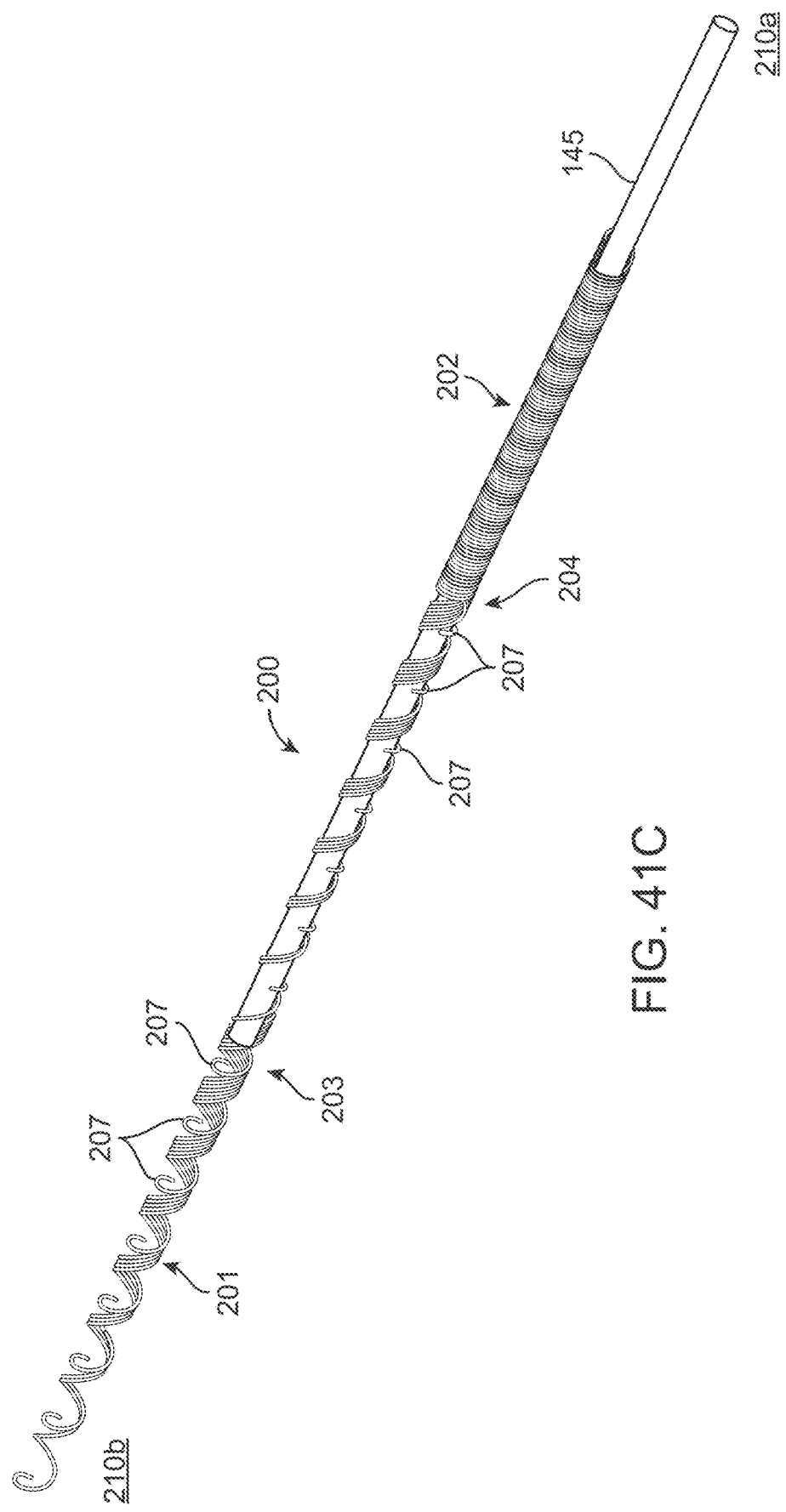

FIG. 41C illustrates another perspective view of the connector 200 of FIG. 41A, but with the outer shaft 146 made transparent for purposes of illustration. As described above, the second coil 202 can be wrapped around the inner shaft 145 and the first coil 201 can have a step-up 203. FIG. 41C illustrates that the 8 wires 141 of the first and second coils 201, 202 can have terminal ends 207. As shown, the wires 141 of the second coil 202 can terminate first, followed by the wires 141 of the first coil 201. The terminal ends 207 of the second coil 202 can attach to the first 8 leads 151 of the connector 200 and the terminal ends 207 of the first coil 201 can attach to the second 8 leads 151 of the connector 200. The first 8 leads 151 can be closer to a first end 210a of the connector 200 and the second 8 leads 151 can be closer to a second end 210b of the connector 200. Any connection sequence is appreciated, including, for example, connecting from proximal to distal (e.g., from first end 210a to second end 210b) as shown, from distal to proximal, alternating, etc. The terminal ends 207 can be electrically coupled to contacts 151 as described above (e.g., by welding). The terminal ends 207 can be exposed to the contacts 151 to establish an electrical path between the leads 151 and the electrodes 131, 138.

FIG. 41C also illustrates that the helix angle of the second coil 202 can change, for example, at position 204. The helix angle of the second coil 202 can increase or decrease. For example, the helix angle can increase near where the second coil 202 makes contact with the first contact 151. Other numbers of changes in the helix angle of the second coil 202, more or less, are also appreciated (e.g., including zero change to two or more changes).

Figure 41D:
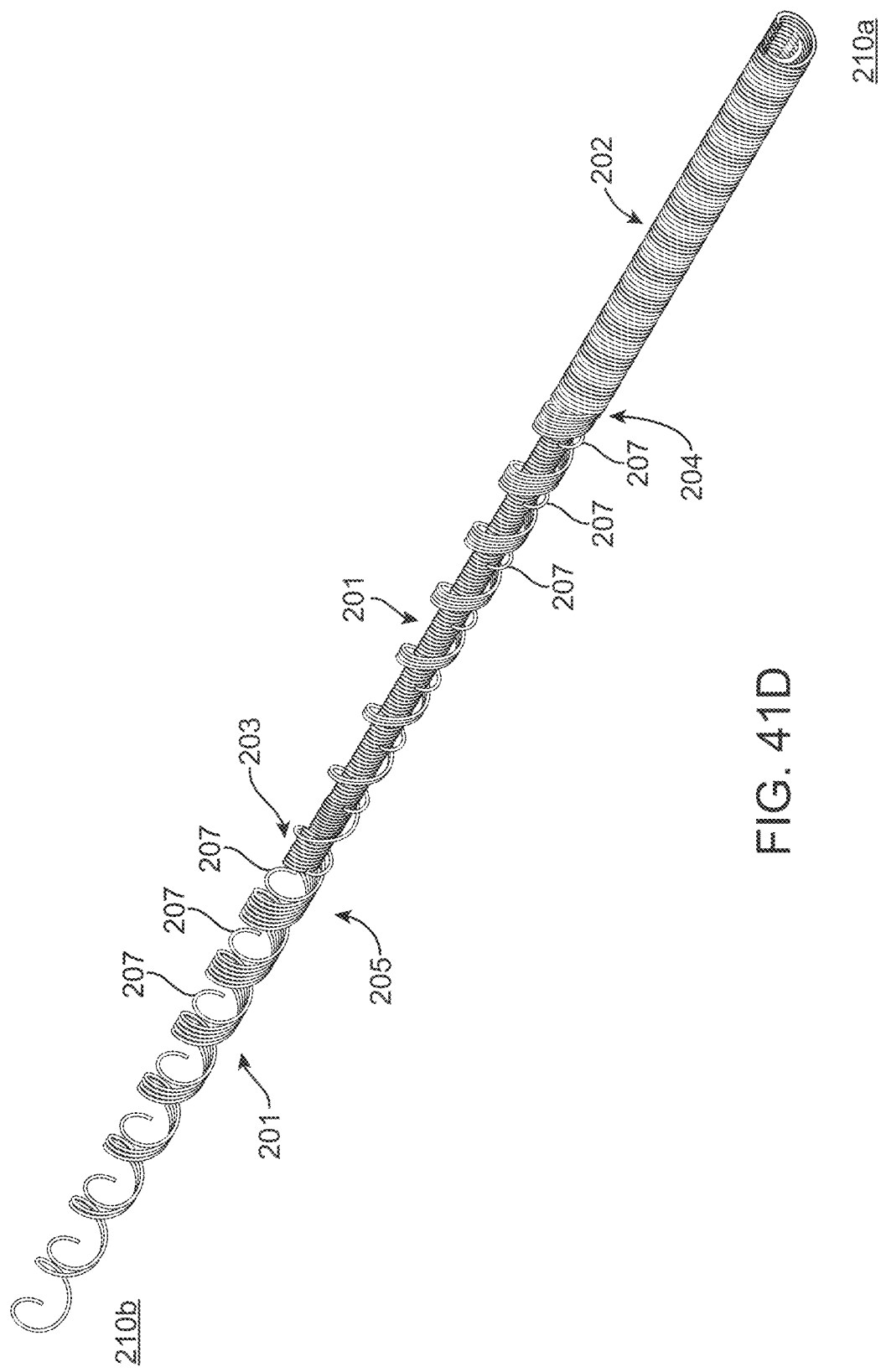

FIG. 41D illustrates another perspective view of the connector 200 of FIG. 41A, but with the inner and outer shafts 145, 146 made transparent for purposes of illustration. FIG. 41D illustrates that the helix angle of the first coil 201 can change, for example, at position 205. The helix angle of the first coil 201 can increase or decrease. For example, the helix angle can increase near where the last terminal end 207 of the second coil 202 makes electrical contact with an eighth contact 151. Other numbers of changes in the helix angle of the first coil 16, more or less, are also appreciated (e.g., including zero change to two or more changes).

Figure 41E:
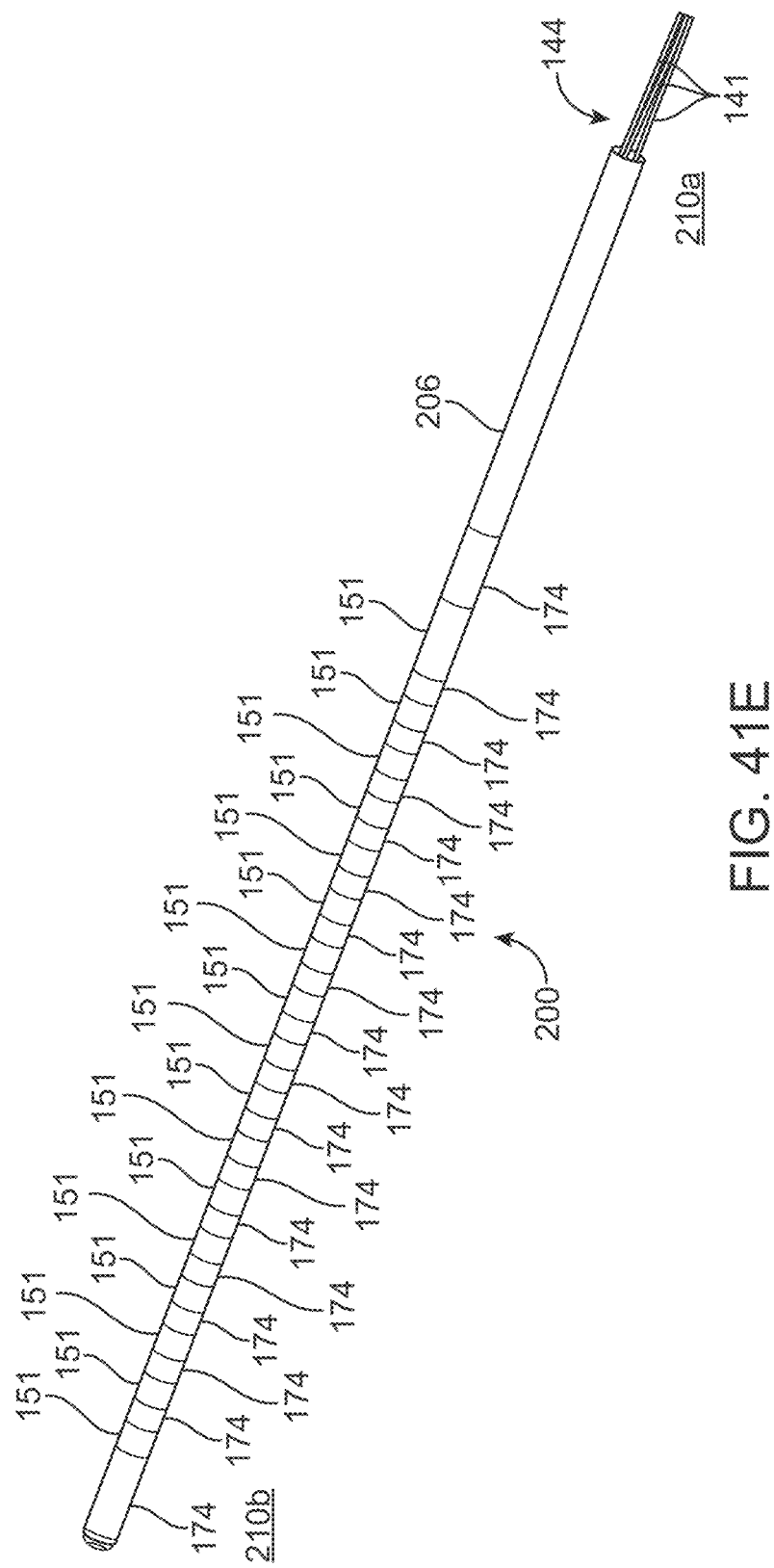

FIG. 41E illustrates the connector 200 of FIG. 41A with the leads 151 and separators 174 shown. The leads and separators 151, 174 can be positioned relative to one another in an alternating pattern. As described above, each wire 141 of the first and second coils 201, 202 terminate on a contact 151. The wires/filars 141 are exposed and attached (e.g., welded) to the inner surface (e.g., inner diameter) of the leads 151.

The connector 200 can be inserted into and/or attached to a receptacle 12 as described above. The connector 200 can be plugged into a receptacle 12 as described above. FIG. 41E illustrates that the connector 200 can have a retention member 206 (e.g., retention ring 206) that can engage with and/or attach to the receptacle 12. To accomplish this, the retention member 206 can form a ring or a ring-like structure, although other shapes are also appreciated. For example, the receptacle 12 can be screwed onto the retention member 206. The retention member 206 can have internal and/or external screw threads. For example, the retention member 206 can comprise a set screw. The retention member 206 can have a longer longitudinal dimension than one of the contacts 151.

The retention member 206 can be rigid to provide the connector 200 with structural support before, during and after implantation. Other parts of the connector 200 can be flexible so that the connector 200 can navigate or otherwise conform to the tortuosity of a blood vessel. For example, the portion of the connector 200 that is between the retention member 206 and the second end 210b of the connector 200 can be flexible (this portion is also referred to here as the lead body). The lead body of the connector 200 can flex 90 degrees around a 6 mm radius. Other angles and radii, more or less, are also appreciated. The connector 200 (e.g., the second end 210b of the connector 200) can flex 45 degrees around a radius of 0.5 mm. Other angles and radii, more or less, are also appreciated. The connector 200 can be looped around a 1 cm radius. Other loop radii, more or less, are also appreciated.

In the lead body portion of the connector 200, the coils 201, 202 can be allowed to float such that they are not embedded in insulation. The coils 201, 202 can be embedded in insulation within the retention member 206 and/or within the lead body portion. The separators 174 can be overmolded to ensure a uniform diameter is present between contacts.

FIG. 41E illustrates that the lead wires 141 can extend beyond the first end 210a of the connector 200. The lead wires 141 that extend beyond the first end 210a of the connector 200 can be unwound (e.g., uncoiled) such that each wire 141 can individually connect to a connection panel (e.g., connection panel 220 described below), or otherwise connect to the connection panel in one or more bundles 144 of wires 141. For example, the lead wires 141 can transition from coiled configurations into 16 tailed ends that can connect to the connection panel. The 16 tailed ends can be straight and/or curved. The connection panel can electrically couple the connector 200 to the electrodes 131, 138. For example, FIG. 41E illustrates that the first and second coils 201, 202 can be unwound and grouped into three bundles 144 of lead wires 141. Other numbers of bundles, more or less, are also appreciated. Wires from the first and second coil 201, 202 can be bundled with first coil 201 wires 141 and/or with second coil 202 wires 141. It is appreciated that individual wires 141 and one or more bundles of wires 144 can extend from the connector 200 to connect with the connection panel. The wires 141 can unwind/uncoil over some dimension within the retention member 206 and/or over some dimension within the rest of the connector 200. The wires 141 and/or bundles 144 that extend from the connector toward the stent 101 can be rigid and/or flexible.

The wires 141 can be directly connected to the stent 101, for example, with laser welding. For example, the wires 141 can be directly connected to pads on the stent 101. The wires 141 can be indirectly connected to the stent 101, for example, with wire bonding. For example, the wires 141 can be indirectly connected to pads on the stent 101 via connection to intermediate pads. The pads on the stent 101 can be wire bonded to the intermediate pads, for example, with jumper wires.

Figure 42:
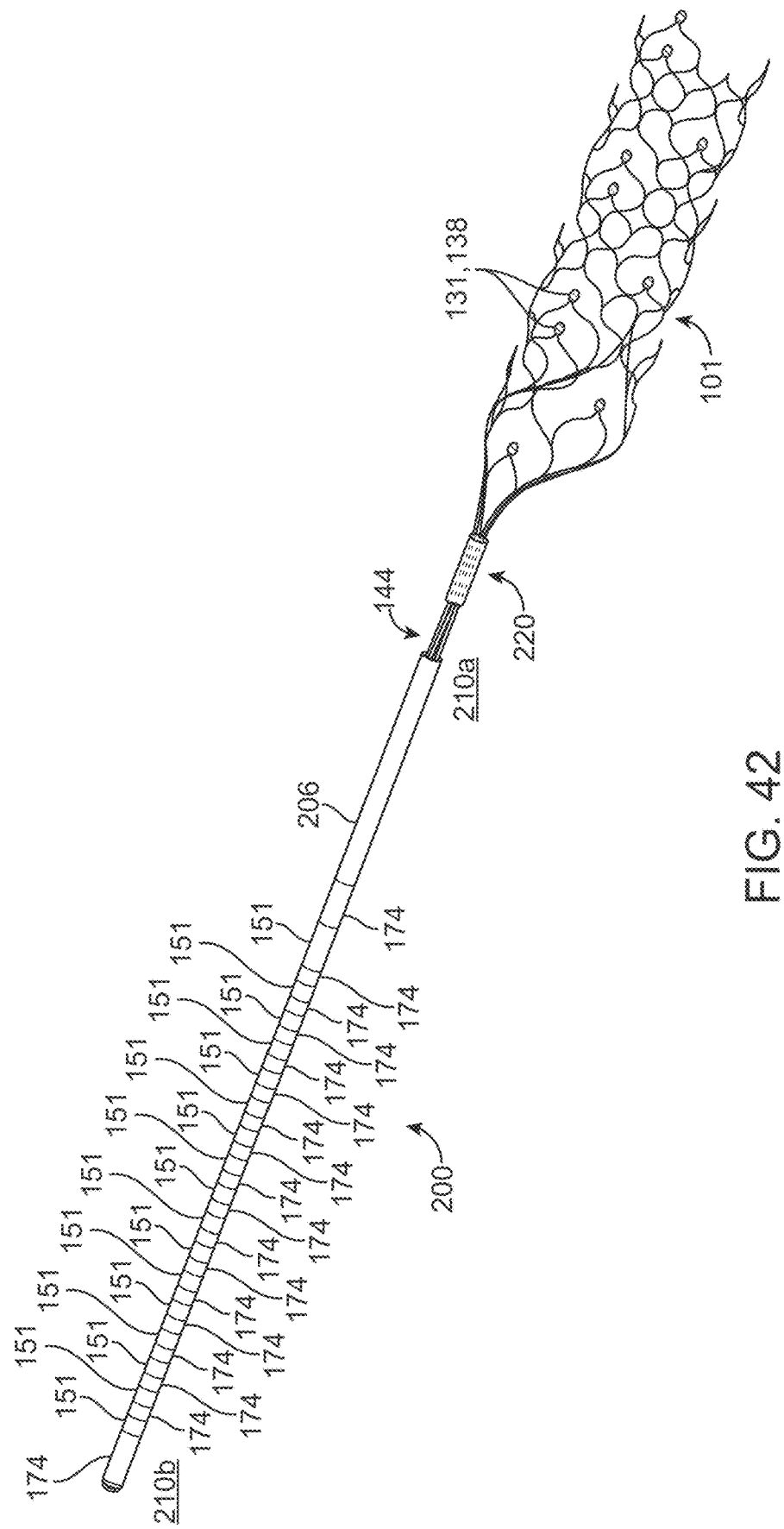
FIG. 42 illustrates a variation of a stent electrically coupled to a control panel and a connector.

FIG. 42 illustrates that the connector 200 of FIGS. 41A-41E can be electrically coupled to the electrodes 131, 138 of the stent 101 via a connection panel 220. FIG. 42 illustrates that the wires 141 of the connector 200 can be indirectly connected to the stent 101 via the connection panel 220. The connection panel 220 can have a first panel (e.g., an overlay) and a second panel (e.g., a stentrode panel) electrically coupled together. The first and second panels can each have one or more connection pads. The pads can be made of platinum or other conductive materials. The wires 141 of the connector 200 can be electrically connected to one or more pads of the first panel and the conductive paths (also referred to as electrode tracks) of the stent 101 can be electrically connected to one or more pads of the second panel. One or more jumpers can be used to electrically connect the first panel to the second panel. For example, one or more jumpers can be used to electrically connect the first panel pads to the second panel pads. The one or more jumpers can electrically connect the pads of the first panel to the pads of the second panel, thereby electrically connecting the leads 151 of the connector 200 to the electrodes 131, 138 of the stent 101. Attaching the wires/filars 141 to the first panel can advantageously provide a more stable and reliable connection than directly attaching the wires/filars 141 to the stentrode pads (e.g., to the second panel pads). The first and/or second panels can be attached to the connector 200, for example, by welding or other attachment method. The first and second panels can each have 16 pads. Other numbers of pads, more or less, are also appreciated (e.g., 1 pad to 32 or more pads). An insulating material (e.g., epoxy) can cover the connection panel 220.

More than one connection panel 220 can be used. For example, two connection panels 220 can be used. The use of two connection panels 220 can advantageously make connections easier and give more space for wire management relative to the use of only one connection panel 220 since not all 16 wires 141 are connected to the same area when two connection panels are used. The use of multiple connection panels can help provide structural support to the connection panel region when the stentrode is being pushed out of the delivery system. For example, the use of multiple connection panels can help distribute the force/axial load that is applied when the system is pushed through a delivery system (e.g., a catheter). The use of multiple connection panels is also advantageous from a processing and fatigue resistance standpoint.

The one or more connection panels 220 can be aligned with a backbone of the stent 101. For example, the one or more connection panels 220 can be aligned with struts 108, thicker struts 108, and/or with a reinforced section 62.

The transition from the dual coils 201, 202 to the leads 141 extending toward the panel 220 can include unwinding/uncoiling the first and second coils 201, 202 as described above.

The connector 200 (also referred to as an endovascular implantable lead) can be configured to transmit neural interface sensor data to an implantable telemetry unit (e.g., control unit 12). The dual-octofiler coils 201, 202 can advantageously withstand long term repetitive movement and trauma due to neck movements, among other movements. The use of dual-octofiler coils 201, 202 can advantageously reduce noise due to muscle artifacts.

The pads on the stent can be connected to the conductors in the lead body by a variety of methods including but not limited to resistance welding, laser welding (each involving direct contact between the pads on the Stentrode and the lead), and/or wire bonding (connection between the Stentrode and the lead via an intermediate pad).

FIGS. 43A-43F illustrate various views of a variation of a portion of a connection panel 220. As shown, the connection panel 220 can have a first panel 222 (e.g., an overlay) attached to a portion of the stent 101, for example, a second panel 224. The second panel 224 can be a connection paddle. The second panel 224 can be integrated with or attached to the stent 101. The second panel 224 can have multiple pads (not shown) and multiple electrode tracks 236. The electrode tracks 236 can be electrically connected to the pads of the second panel 224. The first panel 222 can have multiple pads 226 and multiple openings 228 (also referred to as windows or holes). The pads can be made of platinum or other conductive materials. The openings 228 can be aligned with or otherwise placed over the pads on the stent 101. The first panel 222 can have the same number or a different number of pads 226 and openings 228. For example, the first panel 222 can have 16 pads 226 and 16 openings 228, although other numbers of pads and openings, more or less, are also appreciated (e.g., 1 to 32 or more pads and openings). As another example, the first panel 222 can have more pads 226 than openings 228. As yet another example, the first panel 222 can have fewer pads 226 than openings 228. The stent 101 can have the same number or a different number of pads as the number of openings 228 in the first panel 222. For example, the stent 101 can have 16 pads and the first panel 222 can have 16 openings 228. As another example, the stent 101 can have 16 pads and the first panel 222 can have fewer than 16 openings 228 (e.g., 4 or 8 openings).

FIGS. 43A and 43B illustrate that the windows 228 can have a reduced cross-sectional area relative to the cross-sectional area of the pads 226. This can advantageously increase/optimize the operating space on the first panel 222 for wire management. The pads and windows 226, 228 can be arranged in various patterns to increase/optimize the operating space on the first panel for wire management. The pattern shown in FIGS. 43A and 43B is non-limiting, as any suitable pattern of pads and windows 226, 228 is appreciated. FIG. 43G illustrates a variation of the pads and openings 226, 228. The pads 226 can have, for example, a pad first dimension and a pad second dimension. The pad first dimension can be a pad length and the pad second dimension can be a pad width. The pad first dimension can be greater than, less than or the same as the pad second dimension. For example, FIG. 43G illustrates that the pad first dimension can be greater than the pad second dimension. The pad first dimension can be, for example, about 0.05 mm to about 1.00 mm, less than 10.00 mm, including every 0.01 mm increment within these ranges (e.g., 0.50 mm). The pad second dimension can be, for example, about 0.04 mm to about 1.00 mm, less than 10.00 mm, including every 0.01 mm increment within these ranges (e.g., 0.13 mm). The openings 228 can have, for example, an opening first dimension and an opening second dimension. The opening first dimension can be an opening length and the opening second dimension can be an opening width. The opening first dimension can be greater than, less than or the same as the opening second dimension. For example, FIG. 43G illustrates that the opening first dimension can be greater than the opening second dimension. The opening first dimension can be, for example, about 0.05 mm to about 1.00 mm, less than 10.00 mm, including every 0.01 mm increment within these ranges (e.g., 0.24 mm). The opening second dimension can be, for example, about 0.04 mm to about 1.00 mm, less than 10.00 mm, including every 0.01 mm increment within these ranges (e.g., 0.08 mm).

FIGS. 43C and 43D illustrate that wire bonds 230 can be made between the pads on the stent 101 and the pads 226 on the overlay 222. FIG. 43D is a magnified view of the wire bonds 230 of FIG. 43C at section 43D-43D. One or multiple wires 232 can pass through each of the windows 228. For example, two wires 232 are shown in FIGS. 43C and 43D passing through two different windows 228.

FIGS. 43E and 43F illustrate that the wires 141 can be attached (e.g., welded) to the pads 226 on the overlay 222. FIG. 43F is a magnified view of the wires 141 attached to the pads 226 of FIG. 43E at section 43E-43E. An insulating material 234 (e.g., epoxy) can cover at least a portion of the wires 141.

Figure 44A:
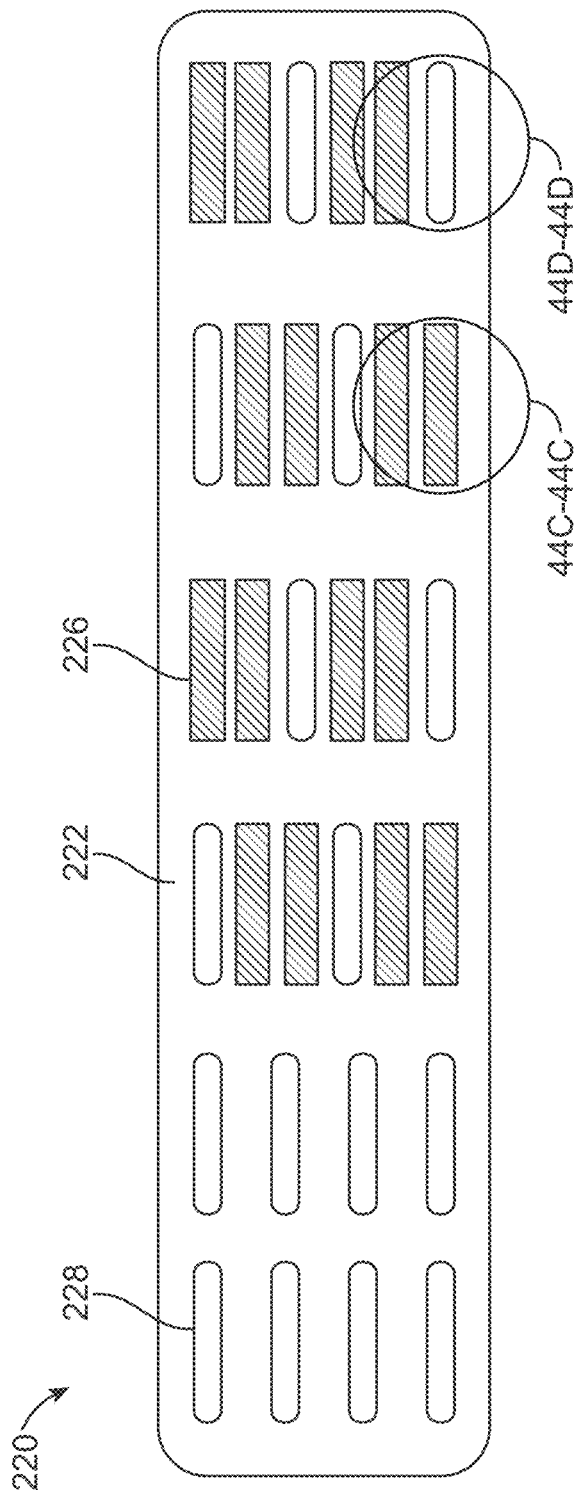
FIGS. 44A-44D illustrate a variation of an overlay.
Figure 44D:
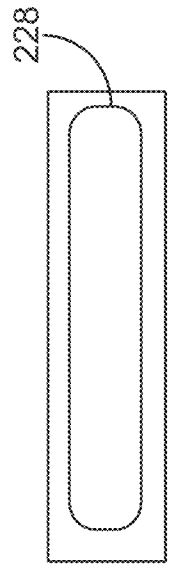
Figure 44C:
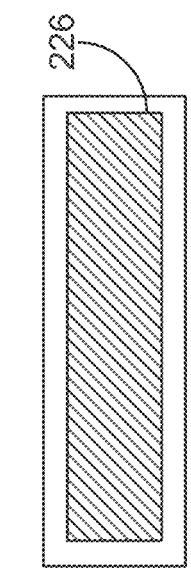
Figure 44B:
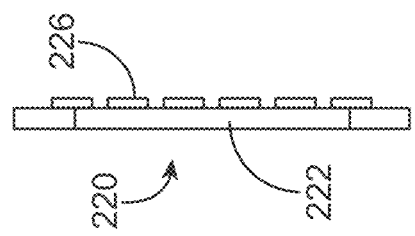

FIGS. 44A-44D illustrate a variation of an overlay 222 for wire bonding to a stent 101. The overlay 222 can have the various dimensions shown (in inches). The overlay 222 of FIGS. 44A-44D is similar to the overlay 222 of FIGS. 43A-43F except the pattern of the pads and openings 226, 228 is different, and the openings 228 are larger. FIG. 44C is a magnified view of one of the pads 226 of FIG. 44A at section 44C-44C. FIG. 44D is a magnified view of the opening 228 of FIG. 44A at section 44D-44D. The pads and openings 226, 228 can have the various dimensions shown (in inches). Wire bond pads can be placed in specific locations to enable all 16 electrode tracks to fit within the 900 μm width with enough separation that unwanted electrical connection is avoided. The overlay 222 can have a similar width to enable deployment through a 1 mm internal diameter catheter.

Figure 45A:
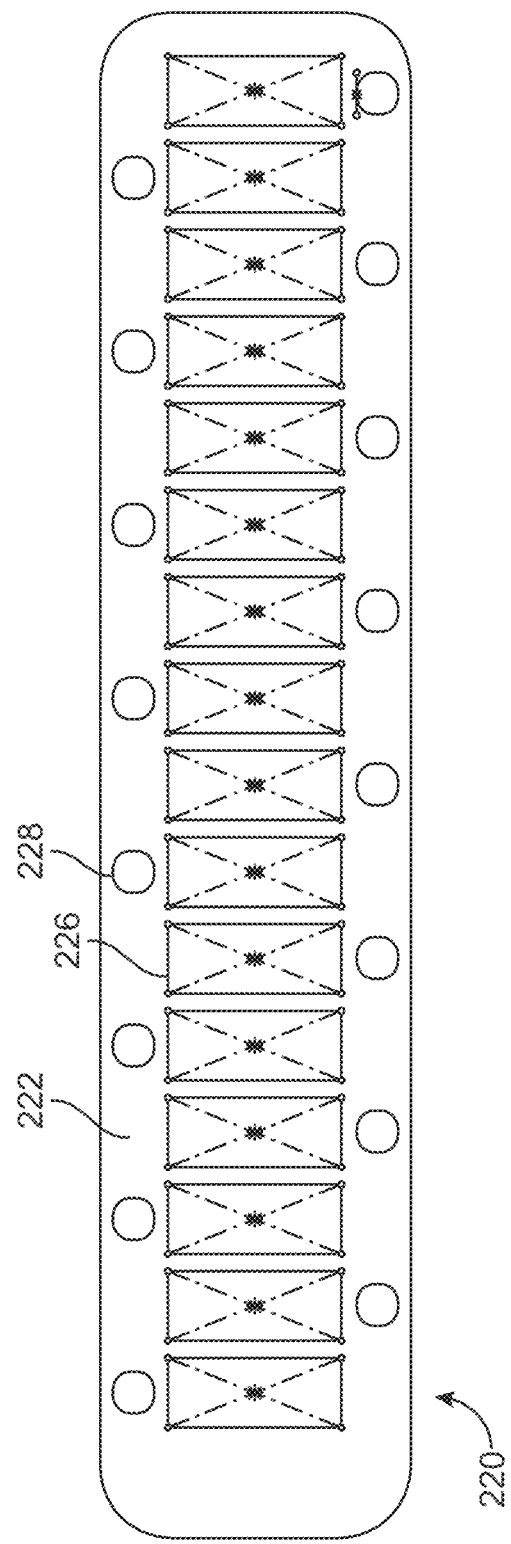
FIGS. 45A and 45B illustrate a variation of an overlay.
Figure 45B:
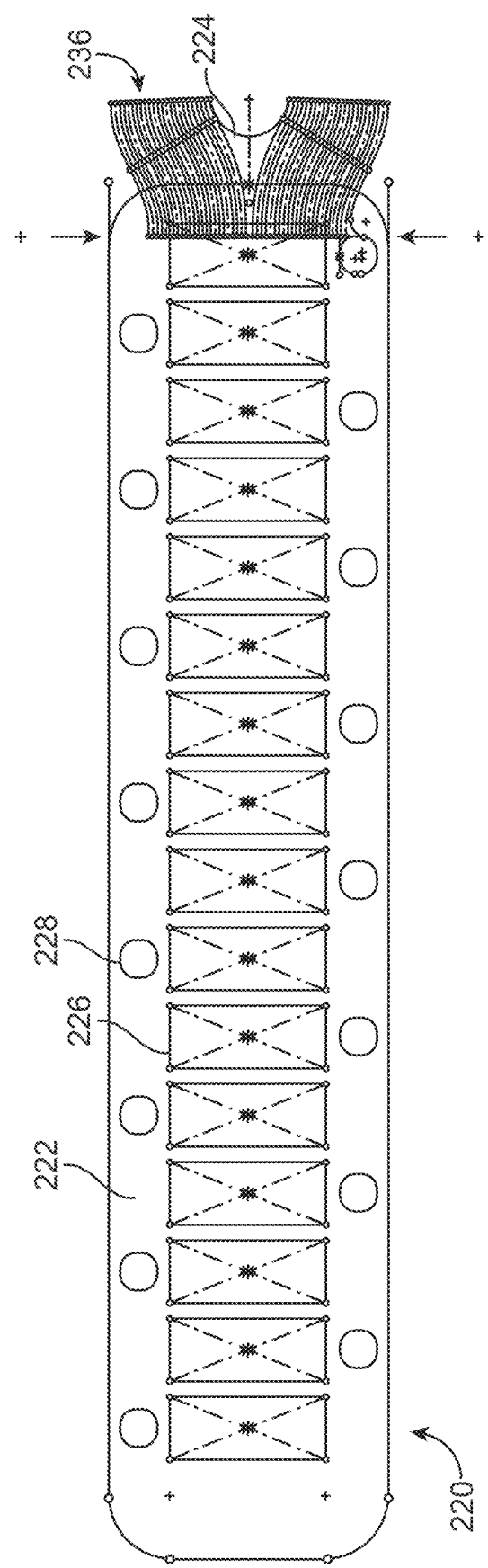

FIGS. 45A and 45D illustrate a variation of an overlay 222 for wire bonding to a stent 101. FIG. 45A illustrates a top view of the overlay 222 and FIG. 45B illustrates that the overlay 222 can be placed over the portion of the stent 101 having pads. The pads of the stent can be electrically connected to the electrodes 131 (not shown) via the electrode tracks 236. The pads and openings 226, 228 can have the various dimensions shown. This design, and similar changes to the pads on the stent 101, can advantageously allow for linear attachment of the pads 226 to the wire bonding holes 228, which can make manufacturing the connection panel 220 easier than, for example, the connection panel associated with FIGS. 44A-44D.

FIGS. 43A-45D illustrate that the wires 141 can be indirectly connected to the stent 101, for example, with wire bonding. The wires 141 can be indirectly connected to pads on the stent 101 via connection to intermediate pads 226 on the overlay 222. Such an intermediate connection method can advantageously allow for thicker/stronger wires 141 to be used to connect the lead 200 to the overlay 222. Welds from the overlay 222 to the stent 101 can overcome limitations on the stent 101 of having a small amount of platinum to weld to. This is advantageous relative to, for example, laser welding because laser welding typically requires more material which is melted to form a pool during welding. With a small amount of material, the melted pool can cause the track material to be sucked up into the pool, causing the tracks to break during manufacture.

FIGS. 46A-46F illustrate variations of stents 101 having various electrode 131 configurations. Each of these stents 101 can advantageously position electrodes 131 in a manner that, regardless of the manner in which the stent 101 is delivered into a vessel, there will always be sufficient electrodes 131 pointing to an information rich area of the brain (e.g., motor cortex, sensory cortex, among others) upon expansion from a compressed configuration. For purposes of illustration, the stents 101 are shown without any connecting structure that electrically couples the electrodes 131 to leads or other such structure that allows electrical communication between the electrodes 131 and the control unit 12 as described above.

As shown, the electrodes 131 can be dispersed about the body of the stents 101a t various locations. FIGS. 46A-46F illustrate that the stents 101 can have one or more cell sizes and/or shapes (e.g., diamond-shaped, V-shaped, among others). For example, the stents 101 can have cells that are longer than they are wide (L>W). This can advantageously allow for greater compression and reduce the force required to retract the stents 101 into a delivery instrument (e.g., a stylet or delivery catheter) and reduce the force required to deploy the stents 101 from within the delivery instrument. The stents 101 can have one or more cells that are wider than they are long (W>L). The stents 101 can have some cells that are longer than they are wide (L>W) and some cells that are wider than they are long (W>L). Such cell variations can advantageously accommodate various vessel physiologies.

One or more of the electrodes 131 can be attached to, embedded into, and/or otherwise integrated with the stents 101 as described above. For example, the stents 101 can have one or more integrated conductive layers (also referred to as electrode tracks and electrical tracks). The electrode tracks can have a thickness from about 200 μm to about 1000 μm. Other track thicknesses, more or less, as well as other ranges, narrower or wider, are also appreciated. Electrode tracks with these thicknesses can advantageously decrease the electrical resistance of the electrode track and provide more material (at the connection end) for welding. In FIGS. 46A-46F, the electrode track thickness is the dimension into the page (i.e., not width or length, which can remain constant to reduce the overall thickness of the Stentrode struts where multiple tracks are present, such as the fork 302 on the far left of the figures). The thickness of the struts 108 (i.e., the material underneath the insulation layers and electrical tracks) can be from about 50 μm to about 100 μm, for example, 50 μm, 85 μm, or 100 μm. Other strut thicknesses, more or less, as well as other ranges, narrower or wider, are also appreciated. The strut 108 thickness can increase or decrease gradually and/or in a step-wise manner along the stent 101 (e.g., gradually increase from 50 μm to 85 μm or step up from 50 μm to 85 μm). Thicker struts can have a larger radial and axial force relative to thinner struts. The thicker struts can therefore advantageously increase the apposition between the stent 101 and a vessel wall. The thicker struts can therefore increase the ability of the stent 101 to be pushed forward and deployed from within a delivery instrument (e.g., a catheter). The stents 101 can be thickest near the forks 302 on the proximal end of the stents 101 and can be thinnest at the distal end of the stents 101. The stents 101 can become thinner from the proximal end to the distal end. The stents 101 can have any suitable thickness(es), including a constant thickness.

The configurations of struts 108 and cells shown in FIGS. 46A-46F can enhance the apposition between the electrodes 131 and tissue or vessel walls when the stents 108 are in their expanded configuration. The strut and electrode configurations 108, 131 can advantageously allow the stents 101 to be compressed into a catheter. The strut and electrode configurations 108, 131 can advantageously allow the stents 101 to be expanded after being compressed in a catheter. The cells (e.g., their size and/or shape) and the electrode 131 positions can allow the stents 101 to compress and/or expand so that the struts and electrodes 108, 131 do not physically interfere with the compression and/or expansion of the stents 101. For example, the relative positions of the cells and the electrodes 131 can allow the stents 101 to compress and/or expand without getting stuck in a partially compressed configuration or a partially expanded configuration. The cells and the electrode 131 positions can help prevent electrodes and struts 131, 108 from becoming snagged with one another during compression or expansion of the stents 101. The relative positions of the cells and electrodes 131 can facilitate expansion and/or compression of the stents 101. The struts can be curved and/or straight. The struts that define the cells can be curved and/or straight.

To reduce the number of leads/wires from the stent 101 to external equipment, a multiplexing unit (not shown) can be used. The multiplexing unit can be placed on the connection panel/paddle of the stent 101 (e.g., second panel 224). The multiplexing unit can be placed on the stent 101, for example, on a strut 108. One or multiple multiplexors can be used. The multiplexing unit can be small enough so that it does not impede the radial force and flexibility of the stent 101. Multiplexing can reduce the number of wires required. One or more wires can be used with a multiplexor to power and switch between the electrodes 131 as required. The stent 101 can be wirelessly powered.

FIGS. 46A-58D illustrate various arrangements of stent cells, but any open cell configuration is appreciated. Moreover, although not shown, one or more of the stent cells can be closed such that there is not an opening in the cell. For purposes of illustration, the stents 101 shown in FIGS. 46A-58D are illustrated as having various lengths and various numbers of electrodes 131. However, other lengths, greater or smaller, as well as other numbers of electrodes, more or less, are also appreciated. The stent lengths shown in FIGS. 46A-58D is not limiting. The length of the stents 101 can be increased, for example, by including more stent in the longitudinal direction. For example, the length of the stents 101 can be increased by increasing the number of cells and/or by increasing the length and/or width of the cells. Similarly, length of the stents 101 can be decreased, for example, by having less stent in the longitudinal direction.

For example, the length of the stents 101 can be decreased by decreasing the number of cells and/or by decreasing the length and/or width of the cells. The open cell designs in FIGS. 46A-58D are for illustrative purposes only as well. The cell arrangements shown can be repeated, changed, and/or altered to achieve the desired length of the stents 101 and/or the desired open cell design. FIGS. 46A-58D illustrate various cell shapes and sizes, but any open cell configuration for the stents 101 is appreciated. For example, any of the cells in FIGS. 46A-58D can be combined with one another to form a stent (e.g., stent 101). The numbers of electrodes in FIGS. 46A-58D can be increased or decreased as needed. For example, the stents 101 in FIGS. 46A-58D can have between 1 and 32 or more electrodes 131 (the numbers of electrodes 131 in the figures are exemplary only). In this way, the stents 101 can advantageously accommodate various vessel physiologies and sense and/or stimulate various tissues in one or multiple locations.

The stents 101 can have one or more sections of electrodes 131. The one or more sections can be separated by one or more sections of struts 108 that do or do not have electrodes.

As described above, the stents 101 disclosed and contemplated herein, for example, the stents 101 shown in FIGS. 46A-56D, can stimulate and/or sense various activity of media (e.g., tissue and/or fluids). For example, the stents 101 can stimulate and/or sense activity of fluid inside a lumen of a vessel, activity of a vessel itself, and/or activity of media (e.g., tissue and/or fluids) outside of the vessel such as the motor and/or sensory cortex of the brain.

Figure 46A:
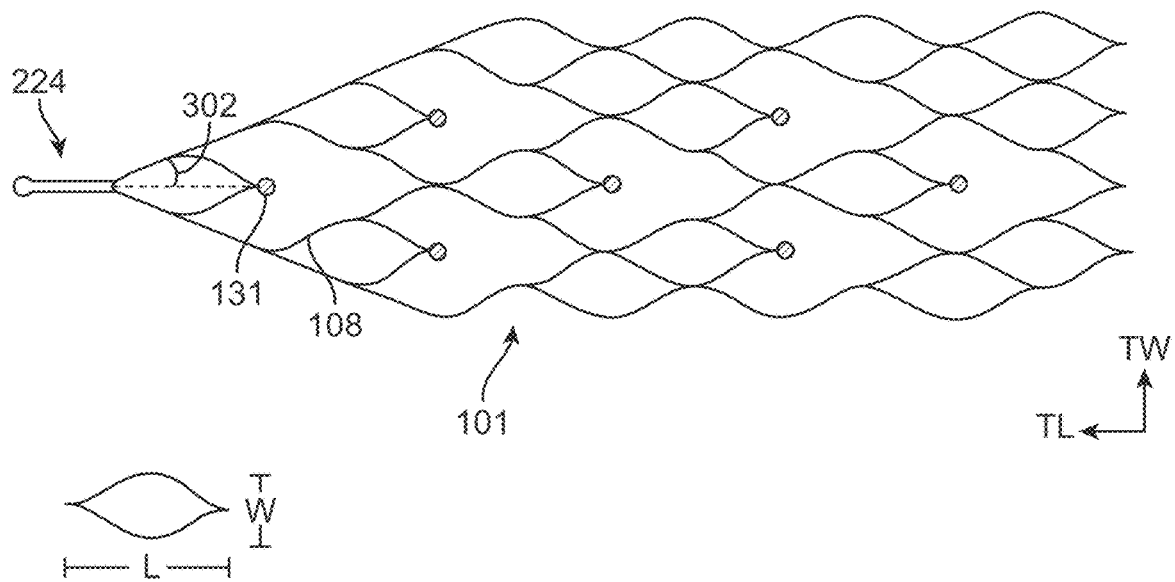
FIGS. 46A-46F illustrate variations of stents having various electrode configurations.

FIG. 46A illustrates that the stent 101 can have seven electrodes 131 arranged as shown. Other numbers of electrodes, more or less, are also appreciated (e.g., between 1 and 32 or more electrodes). The seven electrodes 131 can span radially across a length of the vessel with no electrode overlap. For example, the seven electrodes 131 can span radially across a length of an 8*mm* vessel with no electrode overlap. The seven electrodes 131 can be at different radial positions along a length of the stent 101 such that there is no overlap of electrodes 131 when the stent 101 is expanded in a vessel. The seven electrodes 131 can be at different circumferential positions along the length of the stent 101 such that there is no overlap of electrodes 131 when the stent 101 is expanded in a vessel. As described above, this can advantageously ensure that the stent 101 has a sufficient number of electrodes 131 pointing to information rich areas of the brain (e.g., the motor cortex, the sensory cortex, among other areas) upon expansion from a compressed configuration.

FIG. 46A illustrates that the stent 101 can have large cells and small cells. The small cells can be inside the large cells. The struts 108 can define the cells. Some of the struts 108 can define at least a portion of a small cell and at least a portion of a large cell. Some of the struts 108 can define at least a portion of a small cell or at least a portion of a large cell. The electrodes 131 can be located on the small cells and/or the large cells. For example, the electrodes 131 can be integrated with the small cells. The electrodes 131 can be located anywhere on the small cells. For example, the electrodes 131 can be located at an apex of the small cells. The electrodes 131 can be located anywhere on the struts 108. As shown, the electrodes 131 can be located at the distal longitudinal apexes of the small cells. Although not shown, the electrodes 131 can be located on a portion of the small cells away from the distal longitudinal apexes, including for example, the transverse and proximal apexes. The electrodes 131 can be indirectly coupled to the large cells. The small cells can be inside the large cells for advantageous electrode placement and to assist with electrode-vessel wall apposition. The stent 101 can have a full set of small closed cells on top for stent overlap (e.g., the top row of small closed cells in FIG. 46A). The small cells can have a cell length L and a cell width W. The stent 101 can have a total length TL and a total width TW. The configuration in FIG. 46A can enhance the apposition between the electrodes 131 and the tissue of a vessel wall.

Figure 46B:
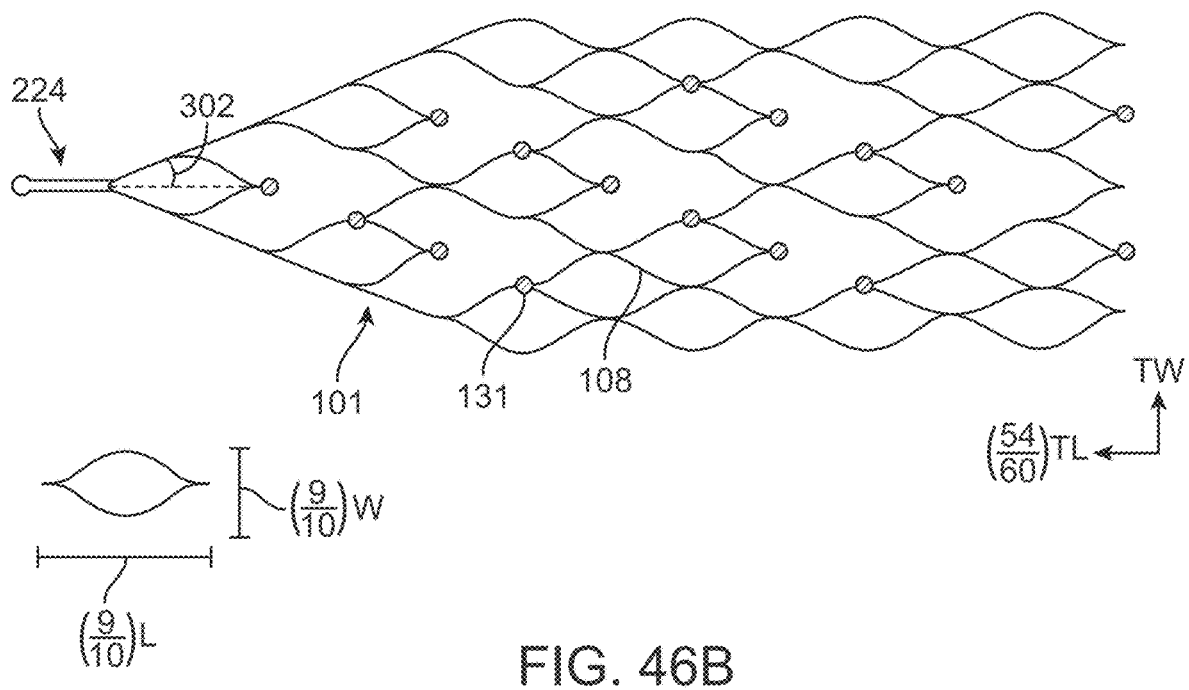

FIG. 46B illustrates that the stent 101 can have sixteen electrodes 131 arranged as shown. Other numbers of electrodes, more or less, are also appreciated. The electrodes 131 can be positioned in bipolar pairs for neural recording and stimulation efficiency. The bipolar pair arrangement can advantageously enable direct stimulation or recording from one electrode to another (e.g., between any two electrodes 131). This can elicit a response or record a signal from a focal region of the brain in a region between the electrodes 131 that form the bipolar pair (as opposed to an electrode 131 and a distant ground, with the second or return electrode placed off the stent). The electrodes 131 can be independent from one another. The electrodes 131 can be used in pairs. The electrodes 131 can be used in multiple pairs, for example, by switching among the electrodes 131. The electrodes 131 can be used in pairs and can be independent from one another. The configuration in FIG. 46B can enhance the apposition between the electrodes 131 and the tissue of a vessel wall.

Figure 46C:
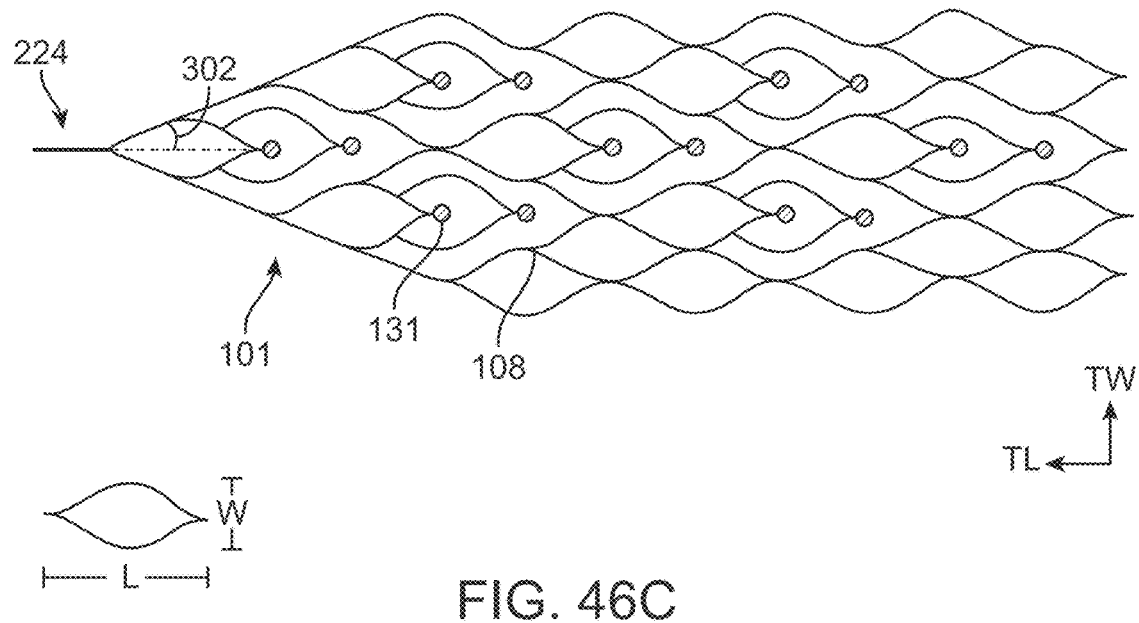

FIG. 46C illustrates that the stent 101 can have 14 electrodes 131 arranged as shown. Other numbers of electrodes, more or less, are also appreciated. The electrodes 131 can be positioned in bipolar pairs. The stent 101 of FIG. 46C is similar to the stent 101 of FIG. 46B, except that the bipolar electrode pairs are constructed with one electrode mounted to an open cell and another electrode mounted in an open cell style to that electrode to enhance electrode apposition while ensuring known distance between electrodes.

Figure 46D:
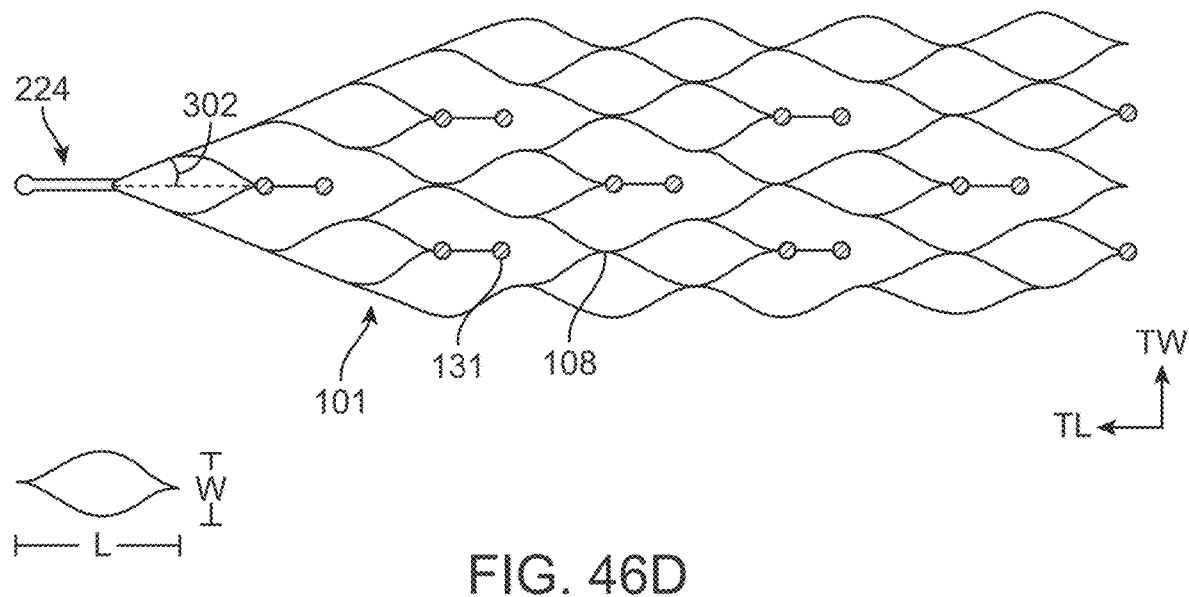

FIG. 46D illustrates that the stent 101 can have 16 electrodes 131 arranged as shown. Other numbers of electrodes, more or less, are also appreciated. The electrodes 131 can be positioned in bipolar pairs. FIG. 46D illustrates that the stent 101 can have a straight, single strut bipolar pair open cell design. The electrodes 131 can be mounted on the inside of open cell struts with a bipolar pair electrode 131 attached with single linear strut 108. This can reduce the amount of material required (compared, for example, to the amount of material required for the stent 101 illustrated in FIG. 46C). The configuration in FIG. 46D can enhance the apposition between the electrodes 131 and the tissue of a vessel wall.

Figure 46E:
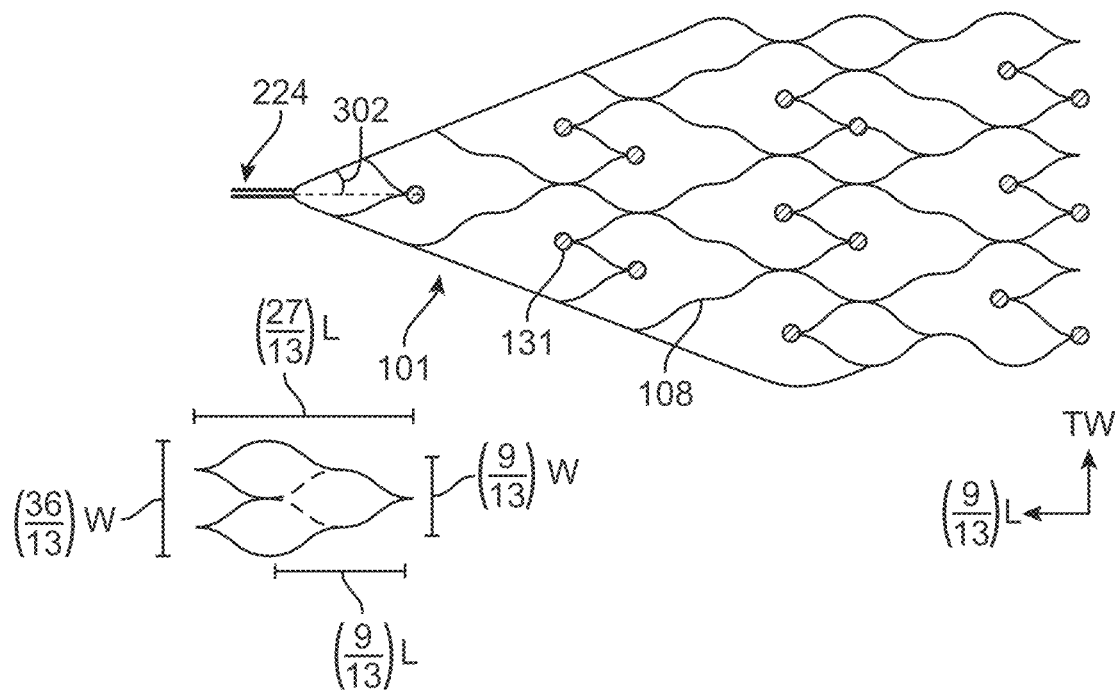

FIG. 46E illustrates that the stent 101 can have 16 electrodes 131 arranged as shown. Other numbers of electrodes, more or less, are also appreciated. The electrodes 131 can be positioned in bipolar pairs. The cells of the stent 101 can have the shapes shown. The electrodes can have the locations shown, although any location on struts 108 defining the cells is appreciated. The stent 101 can be flexible and require less material that the stents 101 illustrated in FIGS. 46A-46D. The configuration in FIG. 46E can enhance the apposition between the electrodes 131 and the tissue of a vessel wall. For example, the configuration in FIG. 46E can appose the vessel wall around vascular chordae which maintaining superelasticity, at least partly to the large open cell design.

Figure 46F:
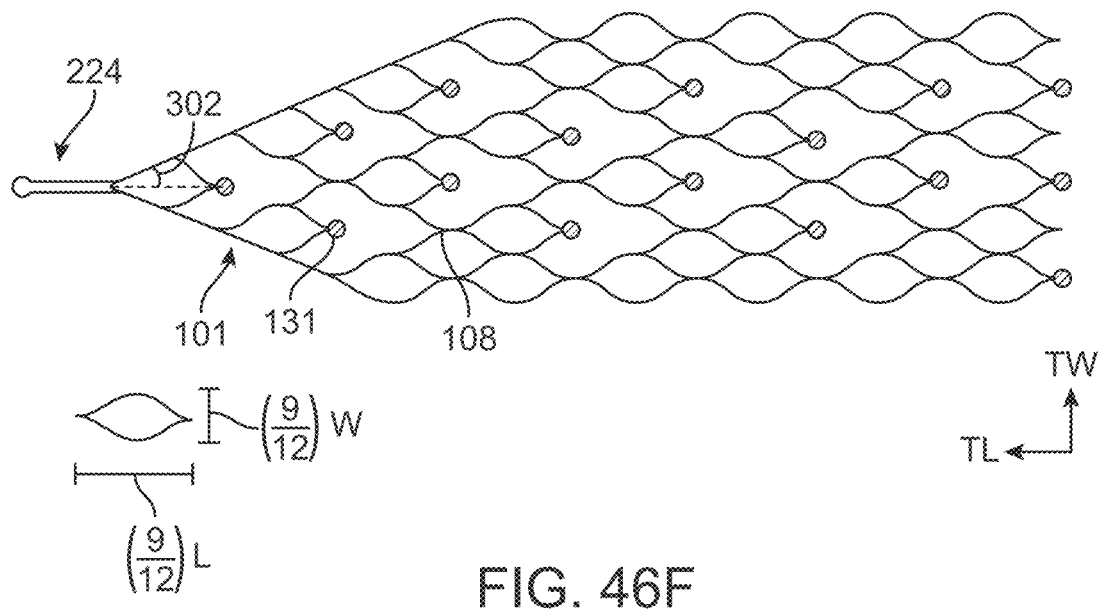

FIG. 46F illustrates that the stent 101 can have sixteen electrodes 131 arranged as shown. Other numbers of electrodes, more or less, are also appreciated. The stent 101 of FIG. 46F is similar to the stent 101 of FIG. 46A except that the stent 101 of FIG. 46F can have a greater length and is illustrated with more electrodes 131.

FIGS. 47A-47F illustrate variations of stents 101 having various electrode 131 configurations. The stents 101 of FIGS. 47A-47F are similar to the stents 101 of FIGS. 46A-46F except for the different cell configurations and electrode 131 locations. FIGS. 47A-47F illustrate that the stents 101 can have strut crosslinks 109 that are offset from one another, for example, by offset angles 304. The offset crosslinks 109 can advantageously allow the stents 101 to be compressed without having any stent overlap. This can, in turn, advantageously allow the stents 101 to be more easily expanded by preventing or otherwise reducing the risk of cells and/or electrodes 131 from becoming entangled or snagged with one another when the stents 101 are expanded. For purposes of illustration, the stents 101 in FIGS. 47A-47E have been illustrated with linearly arranged struts 108, forming various diamond- and rectilinear-shaped cells. However, the cells of the stents 101 can be shaped as shown in the lower left insets of FIGS. 47A-47F, which are similar to the small cells of FIGS. 46A-46F except for the offset angles 304 described above. The offset angle can be, for example, 101 degrees (e.g., 101.3 degrees), although other offset angles, more or less, are also appreciated (e.g., 80 degrees to 120 degrees, or narrower or wider ranges).

FIGS. 47A-47F illustrate that the length to width ratio of the cells can be 7:5. The 7:5 ratio helps ensure that the stents 101 can compress and expand.

Figure 47A:
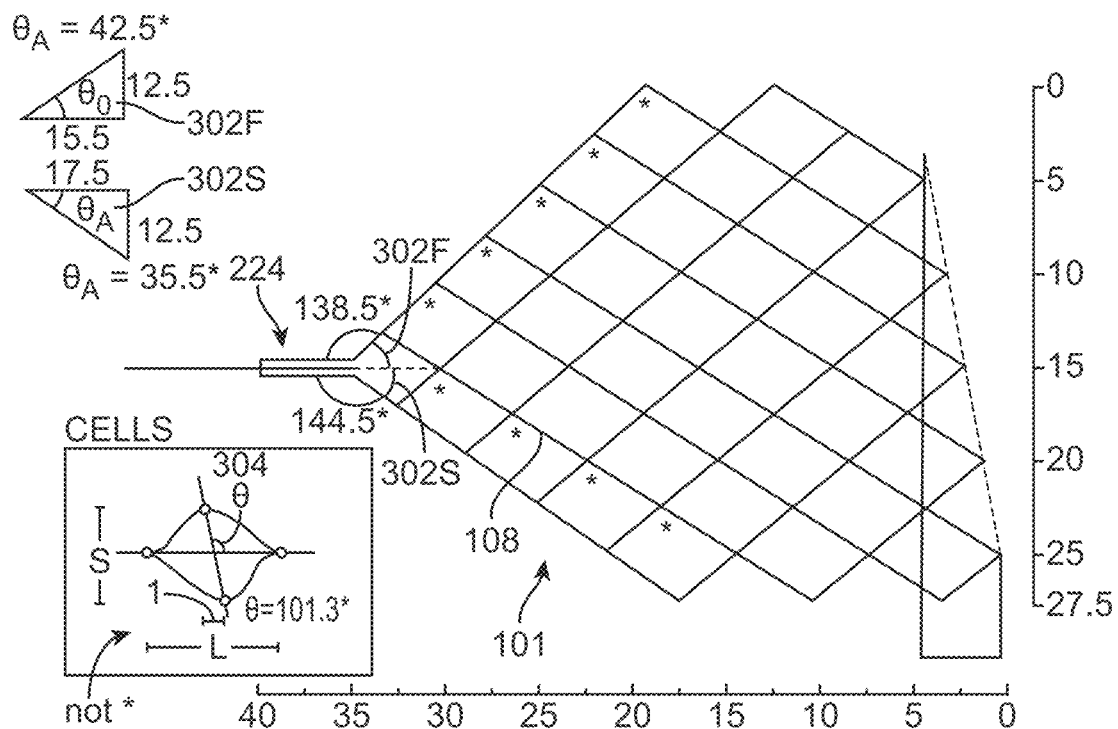
FIGS. 47A-47F illustrate variations of stents having various electrode configurations.

FIGS. 47A-47F illustrate that the stents 101 can have a fork angle 302. FIG. 47A shows that the stents 101 can have a first fork angle 302F and a second fork angle 302S. The first and second fork angles 302F, 302S can be the same or different from one another. As shown, the first and second fork angles 302F, 302F can be measured, for example, between a center axis and first and second struts (not separately labeled) that extend from the connection panel 224. The first and second fork angles 302F, 302S can each be from about 30 degrees to about 50 degrees. For example, the first fork angle 302F can be about 41.5 degrees and the second fork angle 302S can be about 35.5 degrees. Other fork angles, more or less, as well as other fork angle ranges, narrower or wider, are also appreciated. The fork angle 302 can advantageously allow for easier deployment (e.g., expansion) and retraction (e.g., compression) of the stents 101.

Figure 47B:
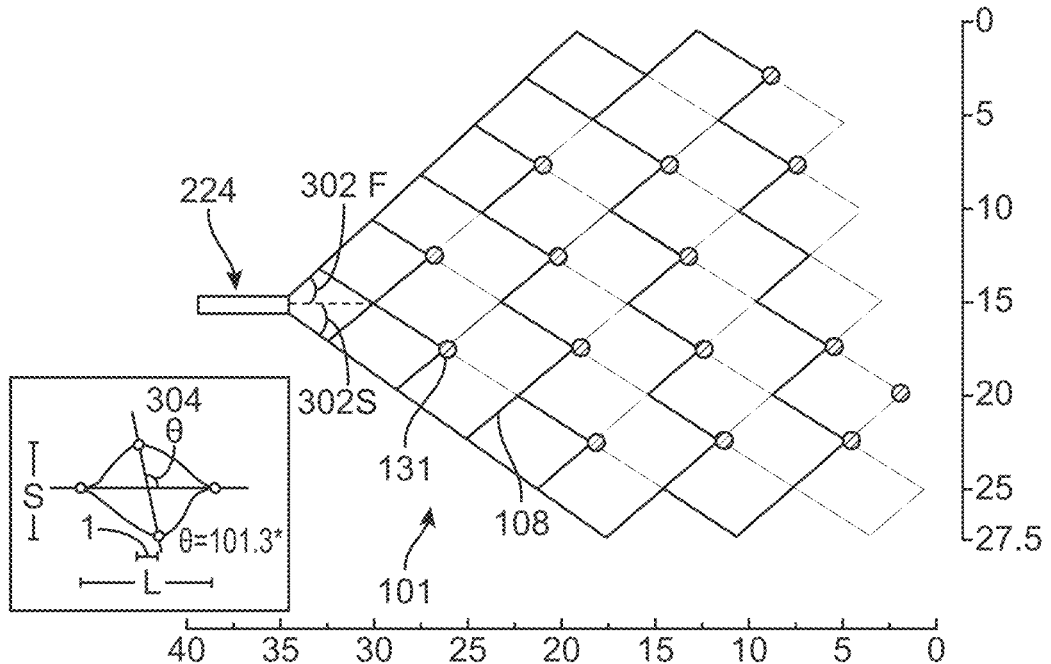
Figure 47C:
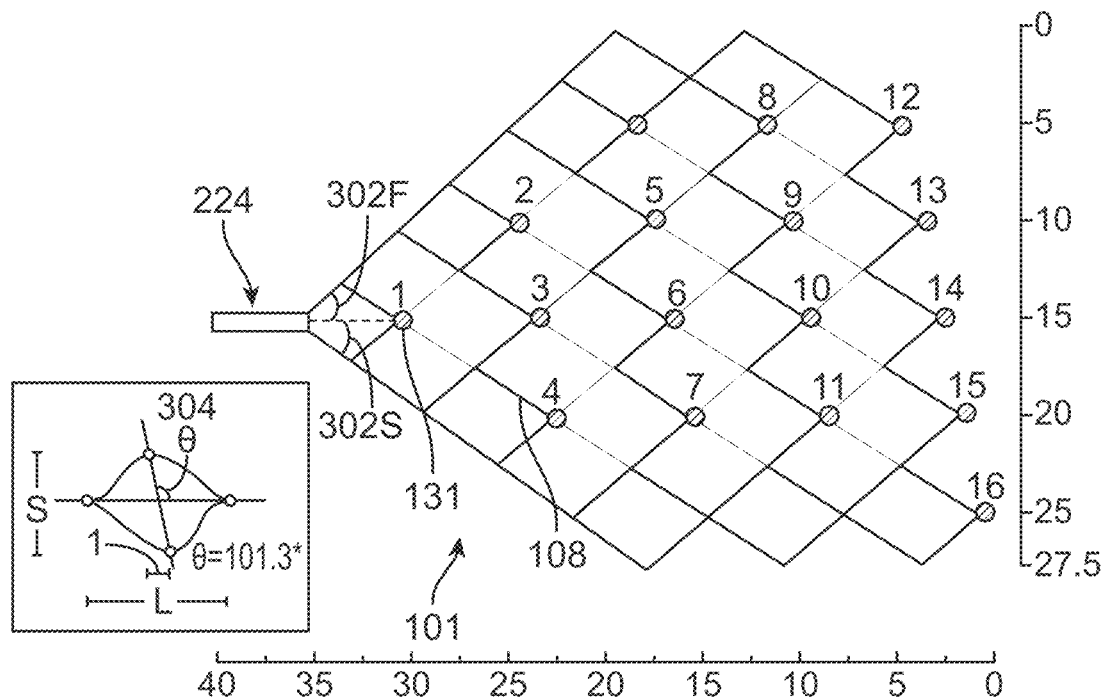

FIG. 47B illustrates that the stent 101 can have sixteen electrodes 131 arranged as shown. Other numbers of electrodes, more or less, are also appreciated. The sixteen electrodes can be arranged in a ladder style having two or more "rungs." For example, the sixteen electrodes can be arranged in five rungs of electrodes 131 having a 2-4-4-5-1 pattern. The stent 101 can have any number of rungs and any number of electrodes 131 in each of the rungs, including four rungs having a 2-4-5-5 electrode pattern. As another example, FIG. 47C illustrates that the stent 101 can have sixteen electrodes arranged in five ladder rungs having a 1-3-3-4-5 electrode pattern. The 1-3-3-4-5 pattern of FIG. 47C can advantageously provide additional electrical evaluation length (e.g., stimulation and/or recording length) relative to shorter ladder configurations, for example, the 2-4-5-5 pattern of FIG. 47B. The ladder style can advantageously assist with delivery through vascular tortuosity and enable navigation of vascular chordae whilst ensuring electrode apposition and self-expansion.

Figure 47D:
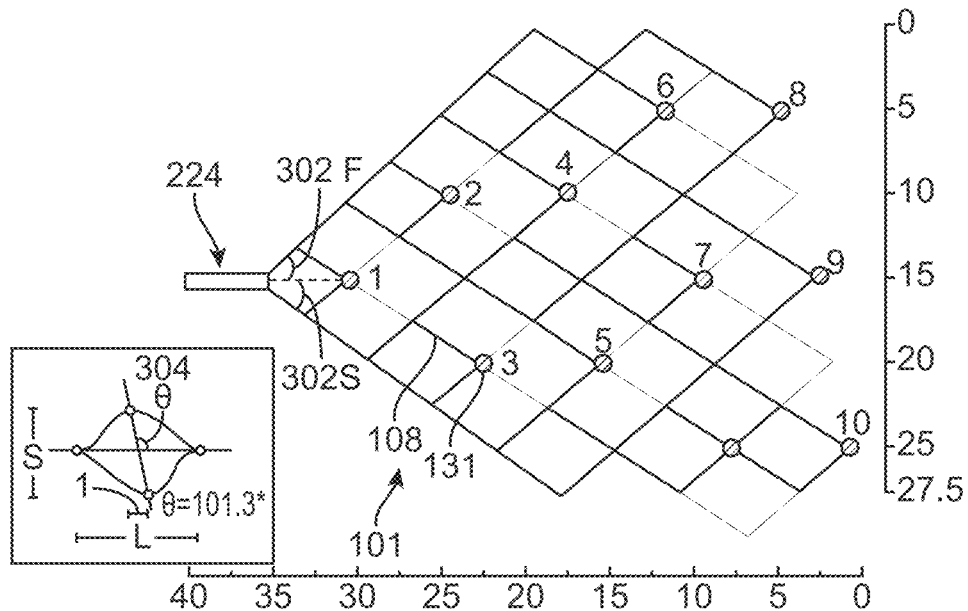

FIG. 47D illustrates that the stent 101 can have ten electrodes 131 arranged as shown. The ten electrodes 131 are shown in a 1-2-2-2-3 five rung ladder pattern, although any ladder pattern having ten electrodes is appreciated. The stent 101 can have relative cell sizes similar to the large and small cells described above with reference to FIG. 46A.

Figure 47E:
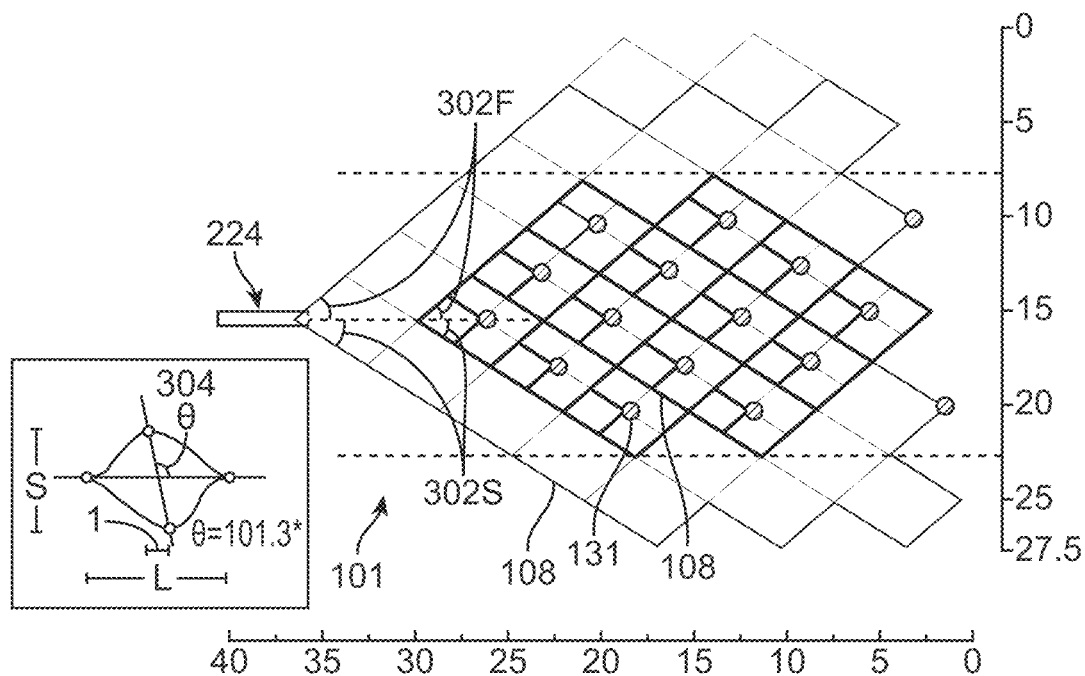

FIG. 47E illustrates that the stent 101 can have sixteen electrodes 131 arranged as shown. FIG. 47E illustrates that the stent 101 can have larger cells on the border (e.g., perimeter) of the stent 101 and more dense cells closer to the center (e.g., in the center) of the stent 101. This arrangement of cells and electrodes 131 can advantageously provide an enhanced region for recording or stimulation closer to the center of the stent 101. As shown, the electrodes 131 can be arranged in an eight rung 1-2-3-2-3-2-1-2 ladder pattern, although any ladder pattern having sixteen electrodes 131 is appreciated.

Figure 47F:
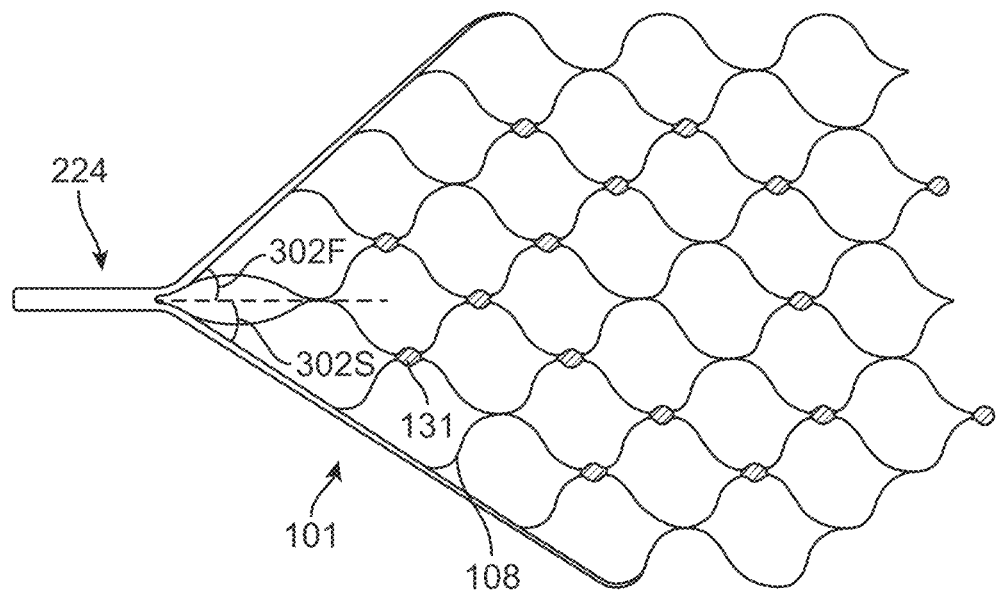

FIG. 47F illustrates that the stent 101 can have sixteen electrodes arranged in seven ladder rungs having a 2-1-4-2-2-2 electrode pattern. The 2-1-4-2-2-3-2 pattern of FIG. 47F can advantageously provide additional electrical evaluation length (e.g., stimulation and/or recording length) relative to shorter ladder configurations, for example, relative to the ladder patterns of FIG. 47B-47D. FIG. 47F illustrates fork angles 302F, 302S that assist with delivery, retraction and deployment, skewed electrode locations for improved deliverability and reducing overlap, interleaved cells for overlap and radial force, cell aspect ratio for deliverability and self-expansion.

For purposes of illustration, the stents 101 in FIGS. 46A-47F described above and FIGS. 48A-48B, 46B-46C, 51B, 52B, 53B-53C, 54A-57 and 58C described below are shown flat so that the cells, struts 108, electrodes 131, and/or electrode tracks 236 can be easily seen. However, the stents 101 are curved in practice (e.g., when in the compressed and/or expanded configuration). The top of the stents 101 can be directly joined to the bottom of the stents 101 (the top and bottom as shown in FIGS. 46A-47F) to form cylindrical tube-like stent structures that can exert radial outward forces against a vessel wall. The top of the stents 101 can curve around to meet (with or without permanent attachment) the bottom of the stents 101. A portion of the top and bottom of the stents 101 can overlap or there can be a gap therebetween.

FIGS. 48A-48D illustrate a variation of a stent 101. FIG. 48A illustrates that the stent 101 can have eight electrodes 131 arranged as shown. The stent 101 can have a proximal end 250 and a distal end 260. The proximal end 250 can include a second panel 224 as described above. The second panel 224 can have stent pads 238. FIG. 48B illustrates the struts 108 of FIG. 48A that have electrode tracks 236. For purposes of illustration, the stent 101 is shown flat in FIGS. 48A and 48B but can be curved as described above. FIG. 48C is a magnified view of the proximal end 250 of the stent 101 of FIG. 48A at section 48C-48C and shows the electrode tracks 236 electrically connected to the stent pads 238. An overlay 222 can be placed over the stent pads 238. FIG. 48D is a magnified view of an electrode 131 of FIG. 48A at section 48D-48D.

Figure 49A:
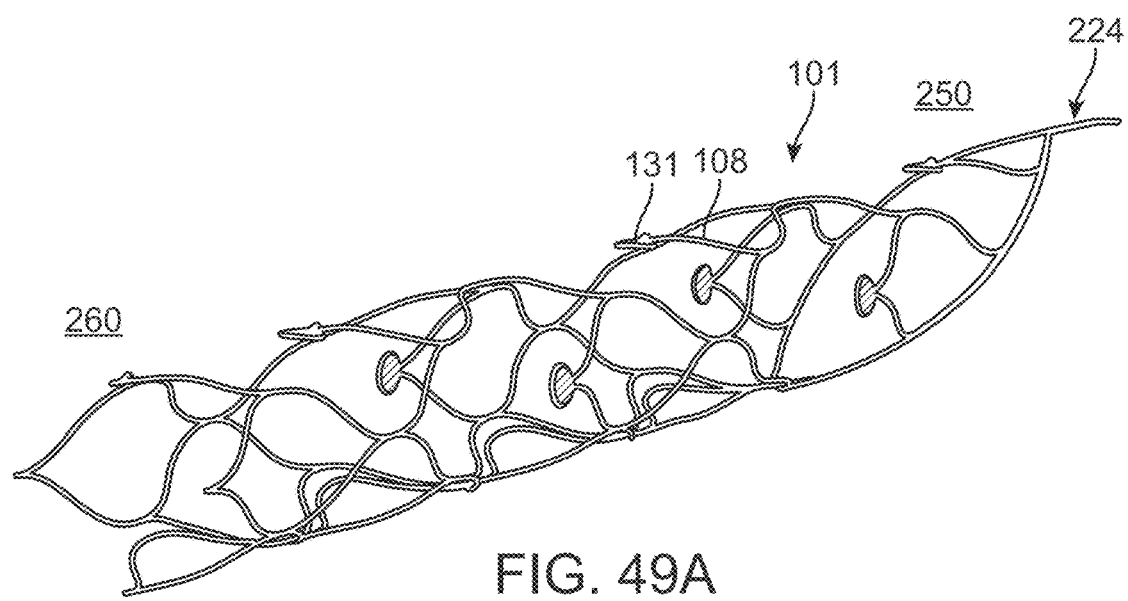
FIGS. 49A-49C illustrate a variation of a stent.
Figure 49B:
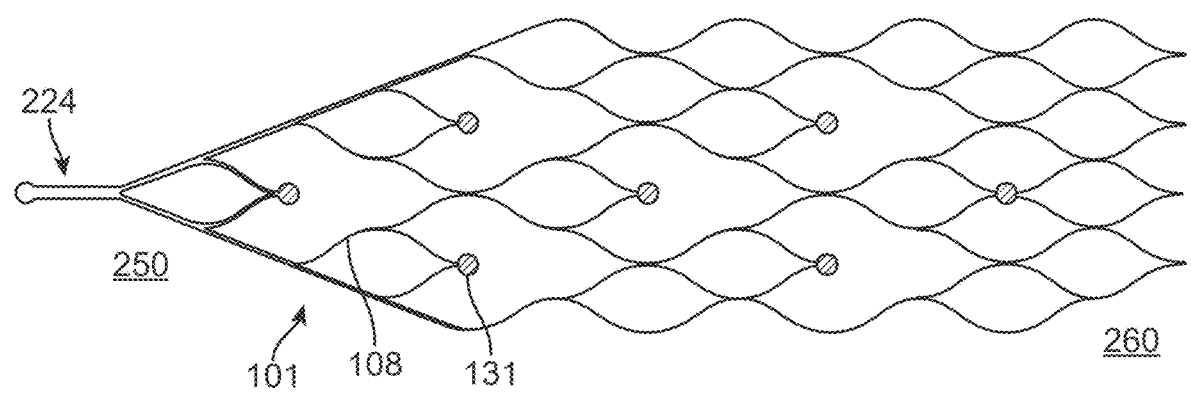
Figure 49C:
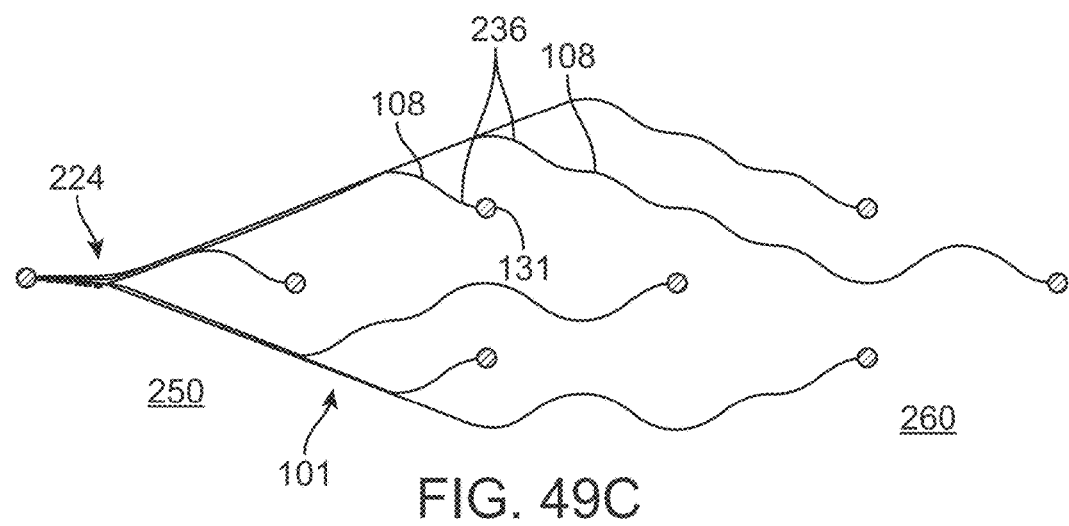

FIGS. 49A-49C illustrate a variation of a stent 101 having seven electrodes 131 arranged as shown. The stent 101 of FIGS. 49A-49C is similar to the stent 101 of FIG. 46A. FIG. 49A illustrates a perspective view of the stent 101 having a curved profile in an expanded configuration. FIG. 49B illustrates the stent 101 in a flat configuration. FIG. 49C illustrates the struts 108 of FIGS. 49A and 49B that have the electrode tracks 236. FIGS. 49B and 49C illustrate that the struts 108 can get thicker from the distal end 260 to the proximal end 250, for example, to accommodate multiple electrode tracks 236 as they merge into a common strut and/or to increase the axial and radial forces/resilience of the stent 101. Multiple electrode tracks 236 on a common strut can be parallel to each other.

FIGS. 50A-50C illustrate front perspective, rear perspective and top views of a variation of a stent 101 connected to a connection panel 220. The stent 101 can have eight electrodes 131 arranged as shown.

Figure 51A:
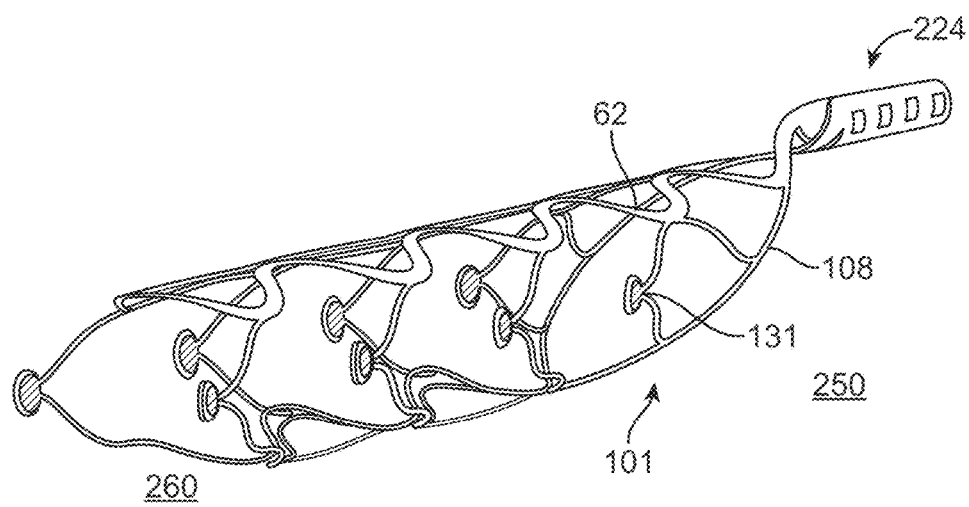
FIGS. 51A and 51B illustrate a variation of a stent.
Figure 51B:
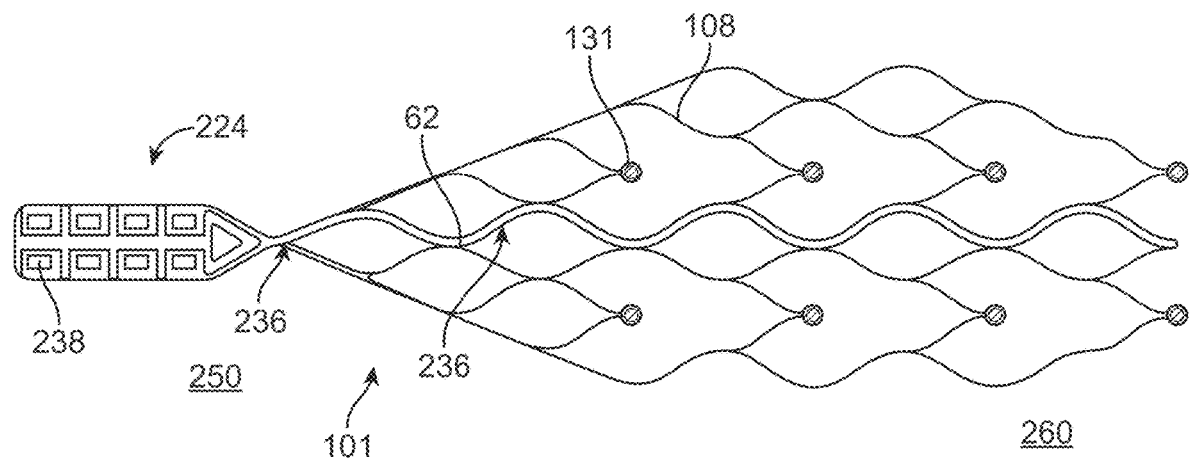

FIGS. 51A and 51B illustrate a variation of a stent 101 having eight electrodes 131 arranged as shown. FIG. 51A illustrates a perspective view of the stent 101 having a curved profile in an expanded configuration and FIG. 51B illustrates the stent 101 in a flat configuration. The stent 101 can have a reinforced section 62. As shown, the electrode tracks 236 from each of the electrodes 131 can merge into the reinforced section 62. The multiple electrode tracks 236 in the reinforced section 62 can be parallel to each other. Some of the struts 108 and/or the reinforced section 62 can get thicker from the distal end 260 to the proximal end 250. The stent pads 238 can be directly connected to the lead wires 141 of a connector 200 (not shown). The stent pads 238 can be indirectly connected to the lead wires 141 of a connector 200 (not shown).

Figure 52A:
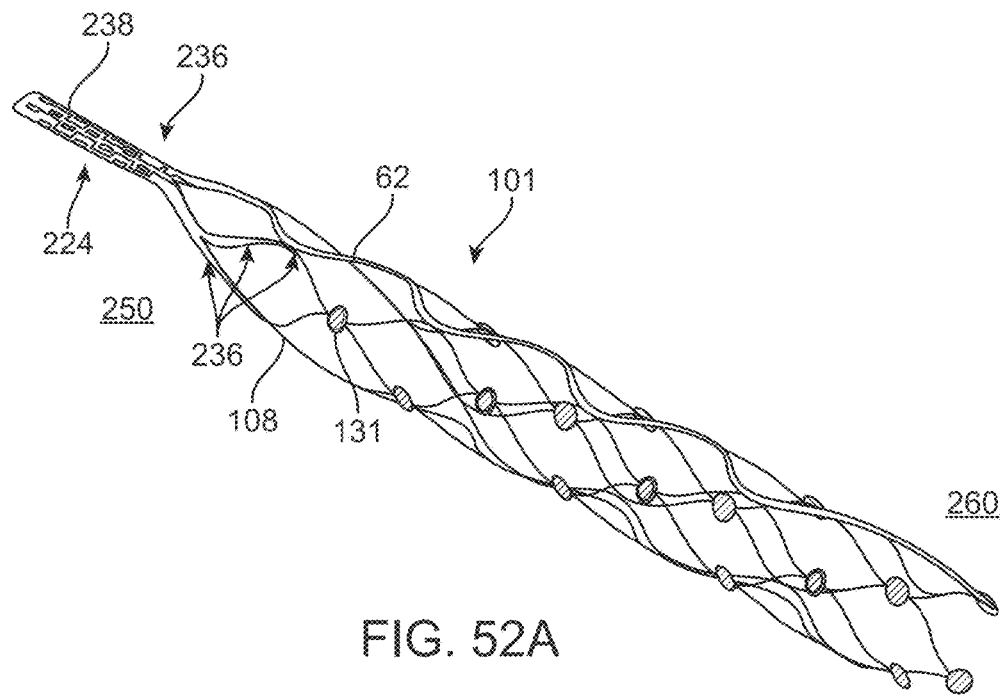
FIGS. 52A-52C illustrate a variation of a stent.
Figure 52B:
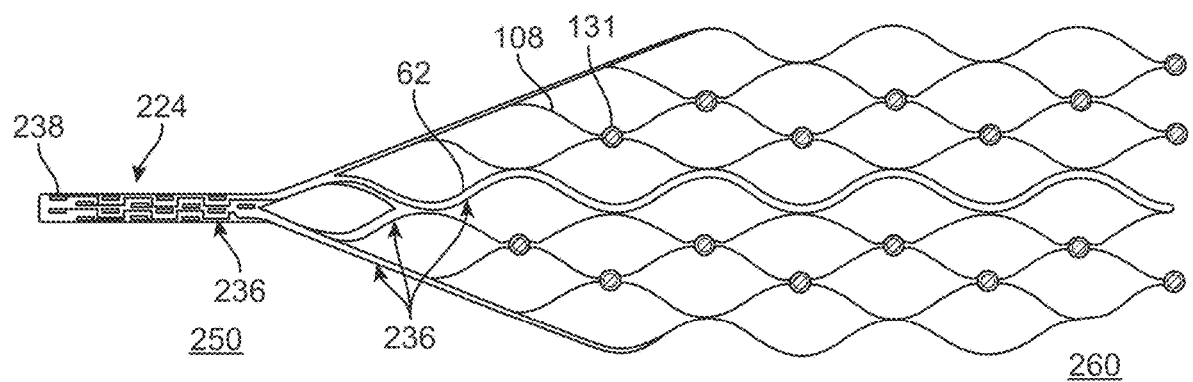
Figure 52C:
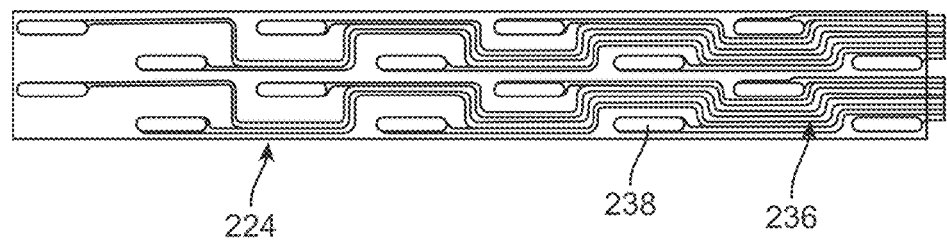

FIGS. 52A-52C illustrate a variation of a stent 101 having sixteen electrodes 131 arranged as shown. The proximal end 250 can include a second panel 224 as described above. The second panel 224 can have stent pads 238. FIG. 52A illustrates a perspective view of the stent 101 having a curved profile in an expanded configuration and FIG. 52B illustrates the stent 101 in a flat configuration. The stent 101 can have a reinforced section 62. FIG. 52B illustrates that some of the electrode tracks 236 can merge into a top, bottom, or middle strut 108, or any other strut. The middle strut 108 can be the reinforced section 62. Some of the struts 108 and/or the reinforced section 62 can get thicker from the distal end 260 to the proximal end 250. FIG. 52C is a magnified view of the proximal end 250 of the stent 101 of FIGS. 52A and 52B and shows the electrode tracks 236 electrically connected to the stent pads 238. An overlay 222 can be placed over the stent pads 238. The stent pads 238 can be directly connected to the lead wires 141 of a connector 200 (not shown). The stent pads 238 can be indirectly connected to the lead wires 141 of a connector 200 (not shown).

Figure 53B:
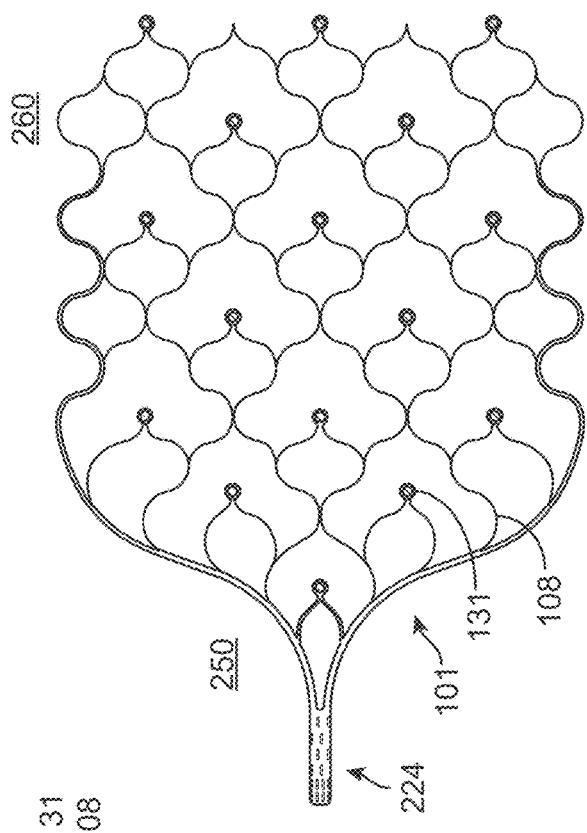
FIGS. 53A-53D illustrate a variation of a stent.
Figure 53D:
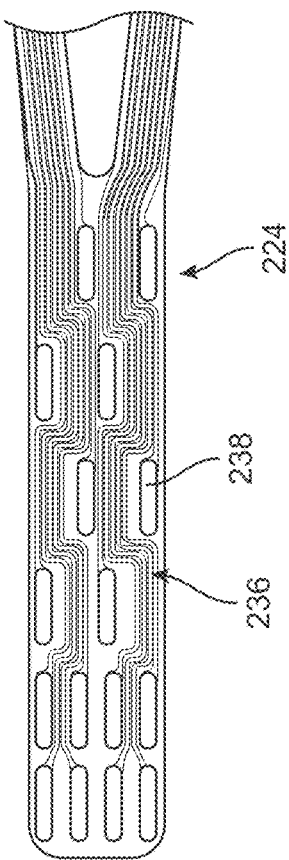
Figure 53A:
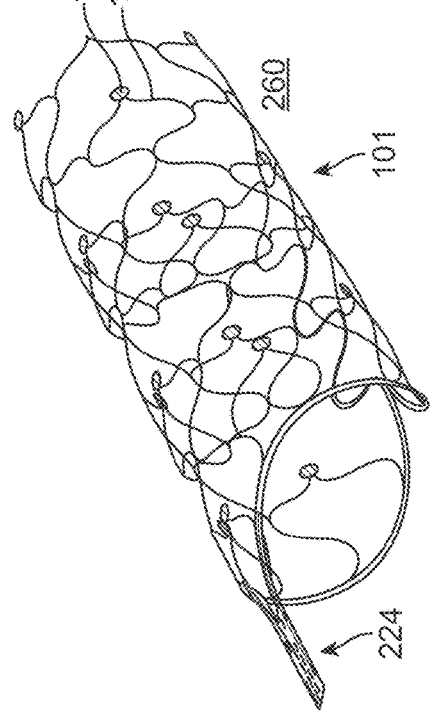
Figure 53C:
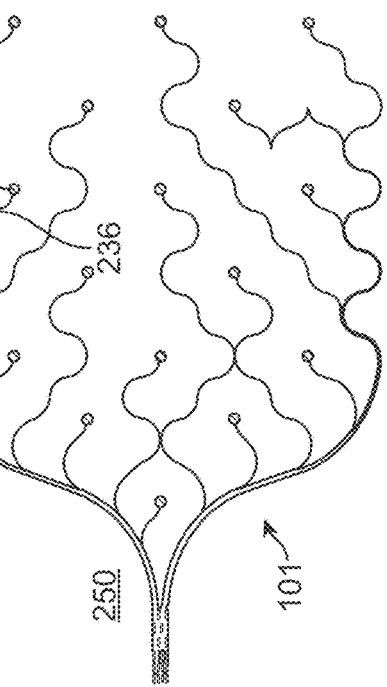

FIGS. 53A-53D illustrate a variation of a stent 101 having sixteen electrodes 131 arranged as shown. FIG. 53A illustrates a perspective view of the stent 101 having a curved profile in an expanded configuration. FIG. 53B illustrates the stent 101 in a flat configuration. FIG. 53C illustrates the struts 108 of FIGS. 53A and 53B that have electrode tracks 236. FIG. 53C illustrates that some of the electrode tracks 236 can merge into a top strut and some of the electrode tracks 236 can merge into a bottom strut. FIG. 53D is a magnified view of the proximal end 250 of the stent 101 of FIGS. 52A and 52B and shows the electrode tracks 236 electrically connected to the stent pads 238.

FIGS. 54A and 54B illustrate a variation of a stent 101. FIG. 54A illustrates that the stent 101 can have eight electrodes 131 arranged as shown. Other numbers of electrodes, more or less, are also appreciated. FIG. 54B illustrates the struts 108 of FIG. 54A that have electrode tracks 236. FIG. 54B illustrates that some of the electrode tracks 236 can merge into a top strut and some of the electrode tracks 236 can merge into a bottom strut.

Figure 55A:
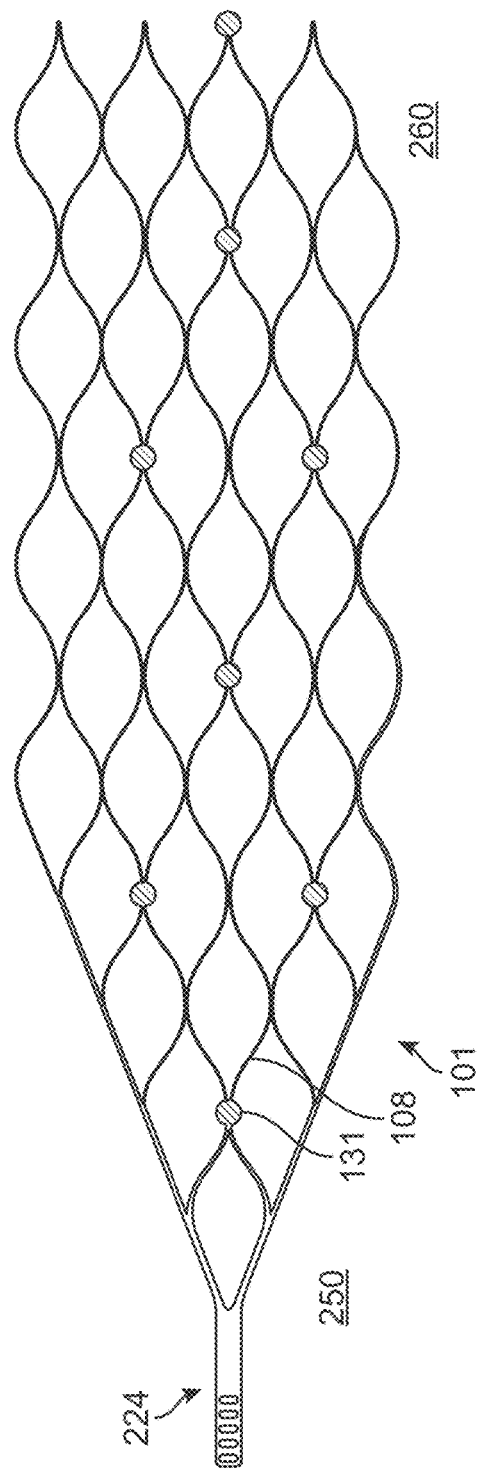
FIGS. 55A and 55B illustrate a variation of a stent.
Figure 55B:
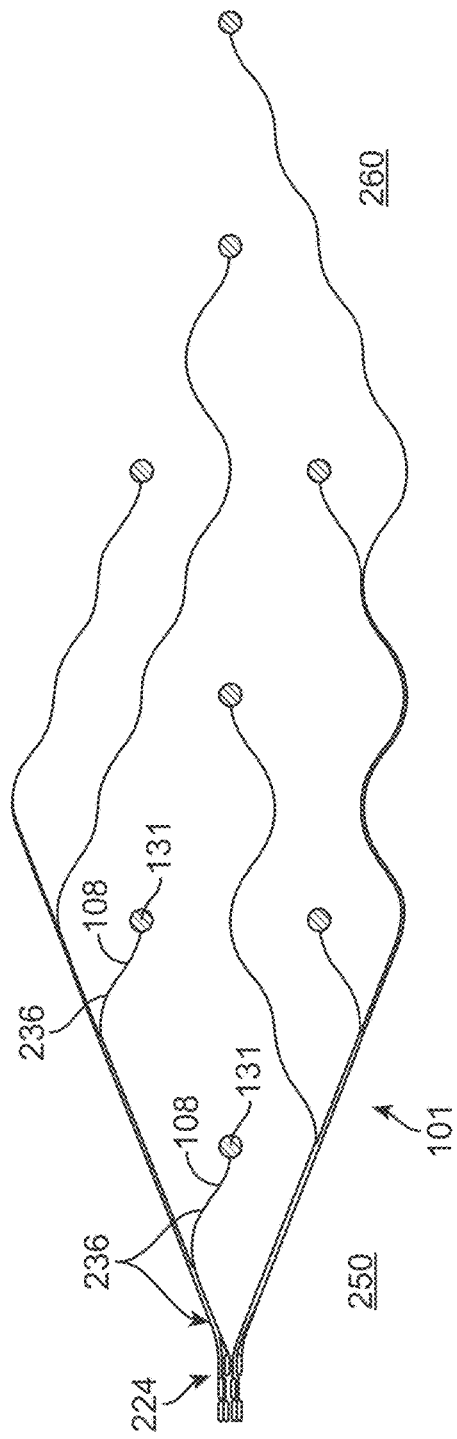
Figure 56A:
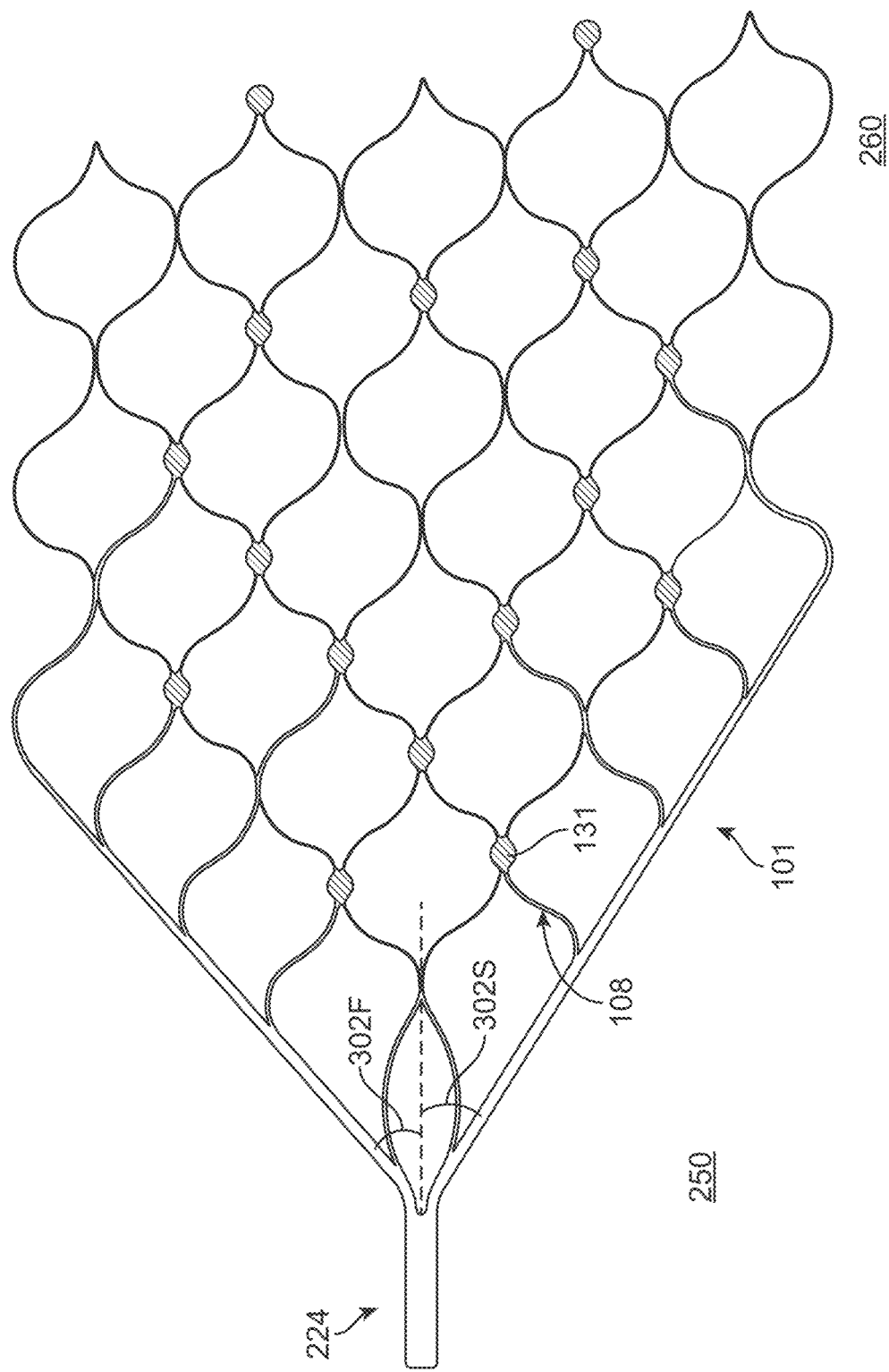
FIGS. 56A-56D illustrate variations of stents having various electrode configurations.
Figure 56B:
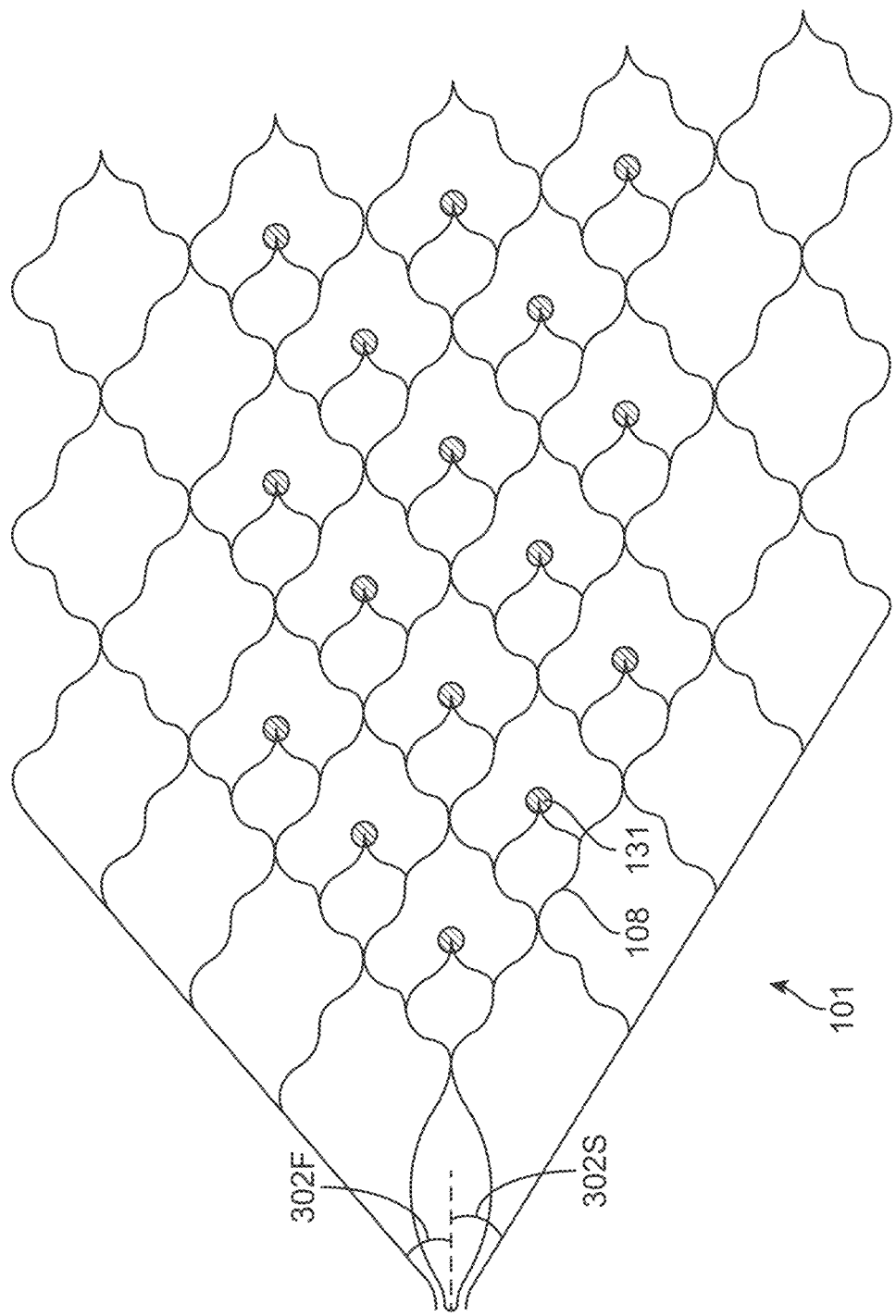
Figure 56C:
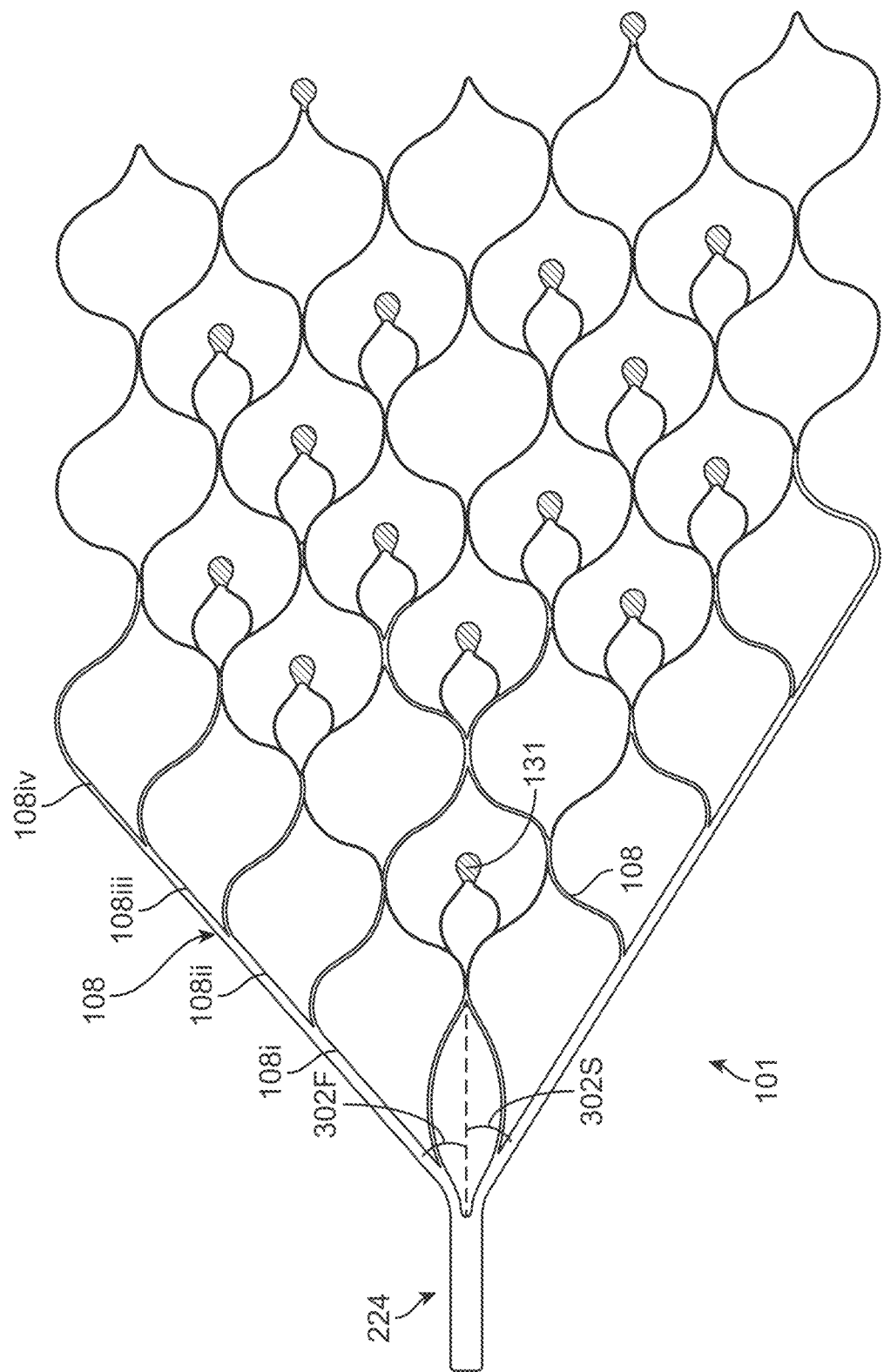
Figure 56D:
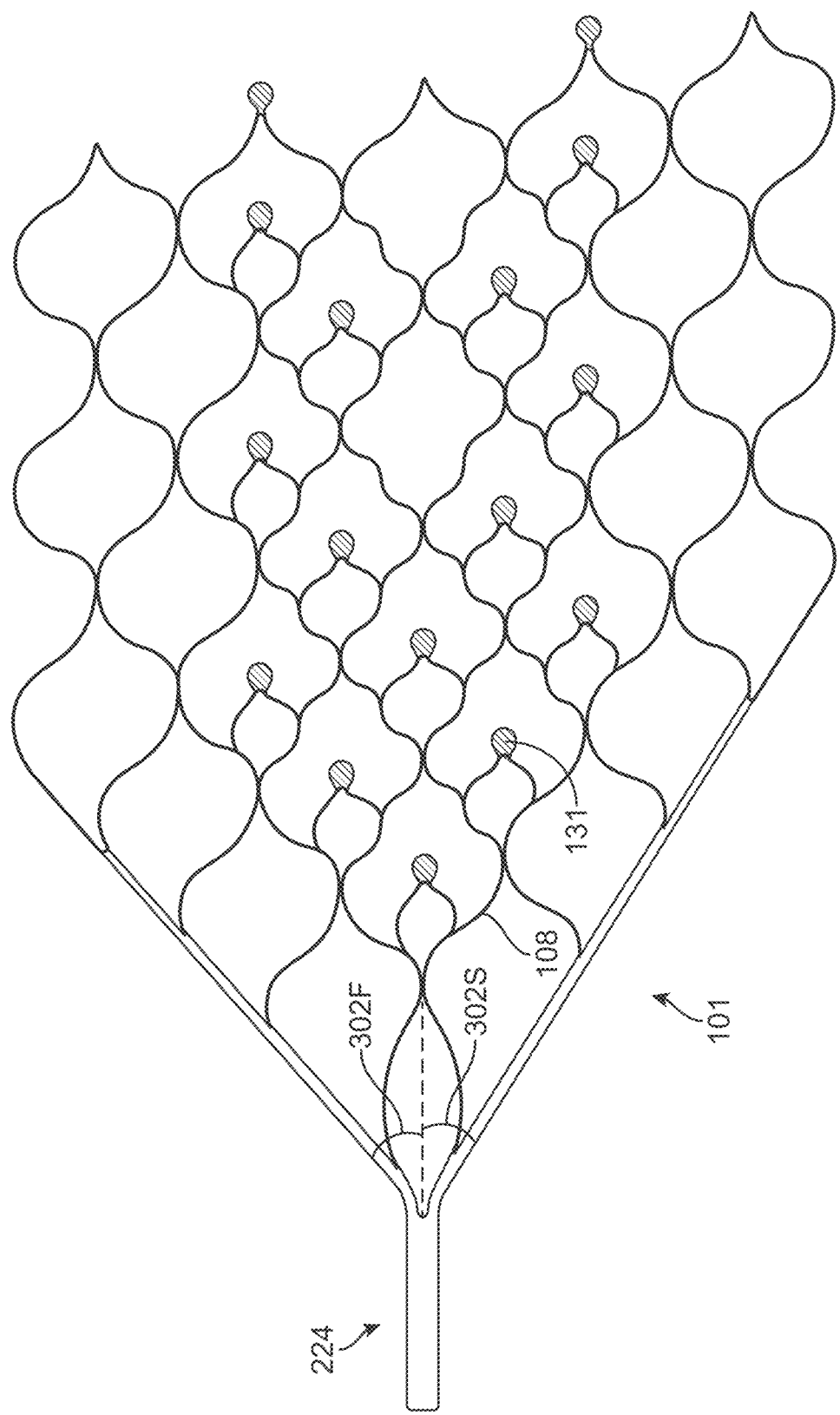

FIGS. 55A and 55B illustrate a variation of a stent 101. The stent 101 of FIGS. 55A and 55B is similar to the stent 101 of FIGS. 54A and 54B except that the cells in FIG. 55A have a uniform size.

FIGS. 56A-56D illustrate various variations of stents 101 without electrode tracks. The stents 101 can have electrodes 131 arranged as shown. Other numbers of electrodes, more or less, are also appreciated.

FIG. 57 illustrates a variation of a lattice structure for a stent 101.

FIGS. 58A-58C illustrate a variation of a stent 101 having sixteen electrodes 131 arranged as shown. The stent 101 of FIGS. 58A-58C is similar to the stent 101 of FIG. 47F. FIGS. 58A and 58B illustrate perspective and side views of the stent 101 having a curved profile in an expanded configuration. The curved profile can have a gap 240. FIG. 58C illustrates the stent 101 in a flat configuration. The stent 101 can have the various dimensions shown (in millimeters) in FIG. 58C.

Any of the stents 101 disclosed and/or contemplated herein can be wireless stents (also referred to as wireless electrode systems). The stents 101 can have one or more wireless transmitters (e.g., the wireless transmitter 1002 of FIG. 31). The wireless transmitters can be attached to or integrated with the stents 101. The wireless transmitters can be a separate device and/or can be an arrangement of one or more electrodes 131 of the stents 101. For example, an arrangement of one or more electrodes 131 can form a wireless antenna that can send and/or receive information. The electrodes 131 can record or pick up neural information and relay this information to a wireless transmitter. This recorded information can be wirelessly transmitted through the skull to a wireless receiver (e.g., the wireless receiver 1004 of FIG. 31). The wireless receiver can decode and transmit the acquired neural information to a device such as a prosthetic limb or a visual prosthesis.

The wireless stents (e.g. stents 101) can be configured for the transmission of both power and data. Power can be wirelessly transmitted to the wireless stents to operate the circuitry of the stents and data can be wireless transmitted from the wireless stents to, for example, a control unit (e.g., control unit 12). In addition to or in lieu of the wireless power, the stents can be powered with a piezoelectric energy power generator that generates energy from blood flow and/or from vascular constriction and dilation.

The wireless stent systems can be fully or partly wireless. Fully wireless means that no portion of the stent (e.g., stents 101), including the electrodes 131 and wireless circuitry, extends beyond a vessel wall after implantation. Semi-wireless means that at least a portion of the stent (e.g., stents 101), electrodes 131 and/or wireless circuitry extends beyond a vessel wall after implantation. The stent 101 of FIG. 31 is an example of a fully wireless stent system. As shown in FIG. 31, the entire device (stent and electronics) can be within the blood vessel, or otherwise become embedded within the blood vessel over time. The stent 101 of FIG. 2A is an example of a semi-wireless system, where the wireless electronics sit outside the vessel in the pectoral region. The system of FIG. 2A is similar to, for example, a pacemaker where the wireless system sits outside of the vessel. Semi wireless systems can have a wire that passes from within a blood vessel to outside a blood vessel.

As described above, the stents 101 can be used to scaffold the electrodes 131 against the vessel wall. Wireless stent systems can have one or more stents (e.g., stents 101), for example, between one and ten stents (e.g., 1, 2, or 3 or more stents 101). Other numbers of stents, more or less, as well as ranges, narrower or wider, are also appreciated. If the wireless electronics cannot be mounted on or integrated with a first stent 101 having electrodes 131 (e.g., due to space or functional requirements), the wireless electronics can be mounted or integrated with a second stent 101 (e.g., which can have the same or a different number of electrodes than the first stent 101, or no electrodes). Such multi-stent systems (e.g., dual-stent systems) can advantageously carry the circuitry away from the center of the vessel where it has a chance of causing occlusion or blockage. The first and second stents of a dual-stent system can advantageously form a dipole antenna, which can improve wireless transmission of the system. The second stent can be under the skull connected directly (but not electrically) to the first stent, or can be placed in the neck, tethered to the first stent. Other arrangements are also appreciated (e.g., the first and second stents can be electrically connected to one another). A benefit of placing the second stent in the neck includes a reduction in distance to the body surface. Placement in the neck is also expected to cause less interference to the acquisition and amplification of the neural signals.

The system (e.g., system 10) can have one or more stents 101 in wired and/or wireless communication with a telemetry unit (e.g., control unit 12). For example, the system can be an endovascular telemetry and closed loop cortical recording and/or stimulation system for the diagnosis, prediction and treatment of epilepsy. Endovascular telemetry systems for epilepsy (also referred to as epilepsy care systems) can advantageously record brain activity 24 hours/day 7 days/week. This 24/7 monitoring offers a critical advantage to doctors and patients alike, as traditionally the ability of the treating physician to determine the number of seizures a patient is suffering depends on the patient recording a seizure diary, which can be, and are notoriously, inaccurate. Knowing how many and the nature of seizures occurring in a patient can be critical in determining the correct dosing for anti-seizure treatment by the physician, which the endovascular telemetry system provides. The epilepsy care systems can receive inputs that can modulate treatment doses of medications/drugs.

For recording telemetry, a stent 101 can be implanted in cortical venous targets (including the transverse sinus) to achieve proximity to cortical regions of interest for seizure detection (including the temporal lobe). The stent 101 can be or can be part of an implantable telemetry unit (ITU). The ITU can house a data unit that can collect brain recordings 24/7. The ITU can be accessed wirelessly by the user or physician to review the neural information over a time period of interest. The ITU can be accessed wirelessly for real-time assessment of the neural information. For example, in periods of higher-risk (including when the patient is unwell, or having to make modifications to their treatment regimen) the physician is able to assess neural signal in real time. The neural data collected by the ITU can be streamed into a range of apps that allow various real time functions. For example, the neural data collected can be communicated to third party applications that apply software analysis of the neural data (including for seizure prediction). In this way, the collected data can be made available to third party users to generate information or modulation information to the patients upon use of the collected data. The epilepsy care systems can have closed loop feedback. For example, the collected data can be utilized in an input loop into a treatment-delivery system to enable precise dosage determinations based upon data containing real-time seizure detection (including vagal nerve stimulator, drug delivery systems). The epilepsy care systems can perform neuromodulation. For example, responsive neural stimulation can be achieved by the endovascular systems described herein having stents 101. This can advantageously enable a closed loop system by utilizing the stent system to record and deliver treatment by stimulating across the vessel wall (e.g., from one or more electrodes 131 of one or more stents 101) to achieve seizure termination.

FIGS. 59A-59C illustrate a telemetry unit lead 400 having a snake and rung design connected to a telemetry device 12. The snake and rung design can advantageously reduce the surgical manipulation required to shorten the lead 400, for example, if the lead is too long. Typically, leads are shortened by winding the lead on itself; however, such winding can cause fatigue as the lead rubs on itself and wears away and/or can require a larger incision into muscles during surgery. The snake and rung design prevents/avoids these risks. As shown in FIGS. 59A-59C, the telemetry unit lead 400 can be a set overall size (e.g., overall length) that is curled into a snake form 404 connected by one or more rungs 402. The rungs 402 can be made of silicone or other biocompatible material that has some flex. If a longer lead is required, one or more of the rungs 402 can be detached (e.g., through surgical cutting or otherwise) so that the lead length can be increased. In this way, the length of a generic telemetry unit lead 400 can be tailored/customized to a patient and to the surgical placement of the telemetry device 12 during surgery. For example, FIGS. 59A-59C illustrate that the lead length can be increased from $L_1$ to $L_2$ by detaching four rungs 402, for example, during surgery. One or more rungs 402 (e.g., one, two, or three or more) can be placed centrally or on the left and/or right edges of the snaked portion 404 of lead 400, or somewhere in between.

As described above, the telemetry unit (e.g., control unit 12) can communicate information (using wires or wirelessly) to and/or from an external apparatus 16, which can include (but is not limited to) one or more of the following: (a) an exoskeleton; (b) wheelchair; (c) computer; and/or (d) other electrical or electro-mechanical device.

For example, FIGS. 60a-60d illustrate a variation of a system 10 having a stent 101 implanted in the vascular of a person's brain, for example, a vessel traversing the person's superior sagittal sinus. FIG. 60a illustrates the system 10 and FIGS. 60b-60c illustrate three magnified views of the system 10 as shown. The stent 101 can be implanted for example, via the jugular vein, into the superior sagittal sinus (SSS) overlying the primary motor cortex to passively record brain signals and/or stimulate tissue. The stent 101 can record and interpret brain signals that are associated with intentions to move, so that people who are paralyzed due to neurological injury or disease, can communicate, improve mobility and potentially achieve independent through direct brain control of assistive technologies such as computer software and/or apparatuses 16 (e.g., robotic upper limb prostheses, motorized wheelchairs, and the like). Other applications for the stent 101 as described throughout this disclosure are also appreciated.

The system 10 can have one or multiple telemetry units. The system 10 can have one or multiple internal and/or external telemetry units. FIGS. 60a and 60d illustrate that the system can have an internal telemetry unit (e.g., control unit 12) in wired or wireless communication with an external telemetry unit 15. For example, the external telemetry unit 15 can be wirelessly connected to the internal telemetry unit 12 across the user's skin. The internal telemetry unit 12 can be in wireless or wired communication with the stent 101. For example, FIGS. 60a-60d illustrate that the stent 101 can be electrically connected to the internal control unit 12 via a communication conduit 14. The communication conduit 14 can be a stent lead. As shown in FIG. 60c, the stent lead can extend from the stent 101, pass through a wall of the jugular, and tunnel under the skin to a subclavian pocket. In this way, the communication conduit 14 can facilitate communications between the stent 101 and the internal control unit 12.

As shown in FIGS. 60a-60d (as well as FIGS. 1-2B), the one or multiple telemetry units can be located/implanted in and/or on the chest of a user. However, the telemetry unit can be located in any suitable location. For example, the telemetry unit can be located/implanted behind the ear of a user. For example, one or multiple telemetry units can be located/implanted behind the ear of the user at, or otherwise proximate to, location 19 shown in FIG. 60*a*. Relative to placement in and/or on the chest, positioning the control unit behind a user's ear can advantageously reduce artifacts and noise due to neck and muscle movement, for example, because the communication conduit 14 (e.g., stent lead) would not need to be located in the neck of a user.

The internal telemetry unit 12 can be connected to one or multiple external apparatuses 16. The internal telemetry unit 12 can be connected to one or multiple internal apparatuses (not shown), for example, visual prosthetics and other controllable devices implanted partially or completely within or on a person's body. The external telemetry unit 15 can be connected to one or multiple external apparatuses 16. The external telemetry unit 15 can be connected to one or multiple internal apparatuses (not shown), for example, visual prosthetics and other controllable devices implanted partially or completely within or on a person's body.

As described above, the system (e.g., system 10) can have one or more stents 101. The stents 101 can be in wired and/or wireless communication with a telemetry unit (e.g., control unit 12). The stents 101 can record and or stimulate areas of the cortex associated with vision. For example, the system can be an endovascular visual prosthesis neural interface having one or more stents 101. The stent 101 can be used to access deep, folded areas of cortex in the occipital lobe (e.g., the primary visual cortex) that are not reachable via open brain surgery, and which cannot be targeted by current technology (i.e., technology that is implanted directly onto the cortical surface of the occipital lobe). FIG. 34 shows a method for stimulation and the recording neural information or the stimulation of neurons from the visual cortex of a patient using the device 100, including the steps of: (a) implanting the device in a vessel in the visual cortex of the patient; and (b) recording neural information associated with the vessel or stimulating neurons in accordance with received stimulation data. The stents 101 can be implanted in the superior sagittal sinus and/or the transverse sinus to advantageously achieve transvascular stimulation of the occipital region of interest, although any implant location is appreciated. Information from the visual world can be captured in a video capture. The information can be translated into a stimulation algorithm. The translated information can be delivered into the occipital lobe via stimulation via one or more stents 101. The visual prosthetic system can contain a large number of electrodes embedded into the wall of the transverse and superior sagittal sinus via the one or more stents 101.

The one or more stents 101 can be used for an endovascular neural interface system for deep brain stimulation treatment. Current deep brain stimulation requires a craniotomy for implantation of the leads. Craniotomy procedures are associated with myriad complications and risks including hemorrhage. The stents 101 can eliminate the need for craniotomies. The stents 101 can access to deep structures suitable as targets for deep brain stimulation is viable through deep venous and arterial vessels in the brain. A catheter can be used to access the deep blood vessels. The stents 101 can enable stimulation of targeted brain tissue. Implantation of an endovascular lead into a deep structure can enable stimulation of the brain tissue. The stents 101 and systems disclosed herein can treat a range of conditions with deep brain stimulation, including Parkinson's disease, dystonia, obsessive compulsive disorder, depression, among others.

Figure 61A:
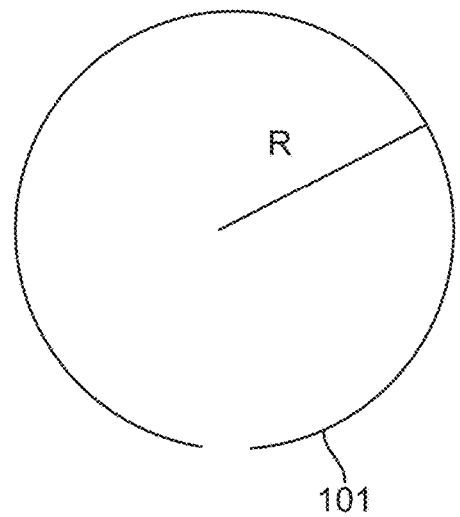
FIGS. 61A-61B illustrate cross sectional views of stent designs with open cross sections as well as cross sections with a first portion of the stent having a first radius and a second portion of the stent having a second radius.
Figure 61B:
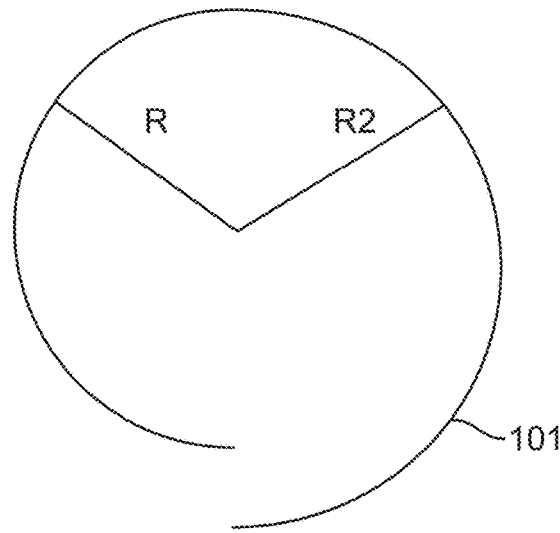

FIG. 61A illustrates a variation to the overall stent structure. In this variation, the stent structure 101 includes a single radius R but the stent structure is spaced or contiguous. This configuration allows the stent structure to accommodate a greater size range of vessels. FIG. 61B illustrates a stent structure 101 having a first portion (such as a half) with a greater radius R2 than the radius R of the other portion (or other half). This configuration allows the structure 101 to curl on itself in one direction preferentially, which is anticipated to: reduce the force to retract into catheter; reduce the likelihood of electrodes or struts catching; and/or enable a larger diameter (increased radial force) without requiring an increase in overall physical stent size or oversizing of stent.

Figure 62A:
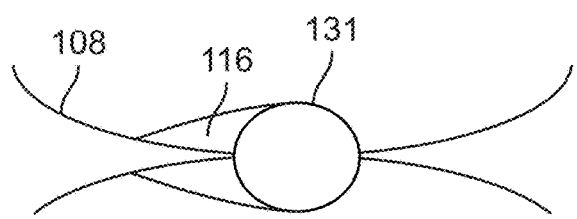
FIGS. 62A-62B illustrate an improved electrode design with filleted edges that gradually taper to the strut.
Figure 62B:
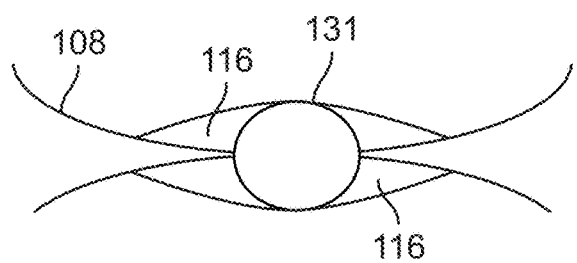

FIGS. 62A-62B illustrate an improvement to the electrodes 131 are configured with one or more filleted edges 116 that transition from the electrode to adjacent struts 108. FIGS. 62A and 42B illustrate respective filleted edges on a single side of the electrode and both sides of the electrode respectively. The filleted edges 116 can be configured as a gradual thickening from the strut towards the electrode, thereby removing a sharp corner and creating a slower, shallower transition between strut and electrode. Thickening of the strut transition 116 and creating that "smooth corner" reduces the prospect of wires or other items being caught in the intersection adjacent to the electrodes.

In some variations of the device, the filleted edges 116 can add to the conductive surface of the electrode. However, in those applications where primary purpose of the edge 116 is to prevent the electrode catching on alternate stent struts or other structures, the filleted edge 116 can be non-conductive.

Figure 63:
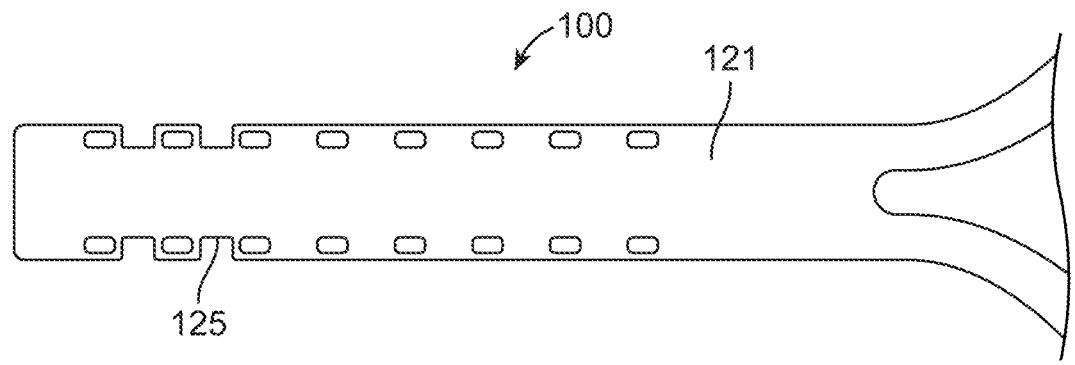
FIG. 63 illustrates a variation of a stent device with a stent shaft that has grooves or pockets to assist in joining the shaft to a lead.

FIG. 63 illustrates a variation of a stent device 100 with a stent shaft 121 that has grooves or pockets 125 (e.g., areas of the shaft 121 that are removed.) The grooves or pockets 125 allow for the epoxy/adhesive to reduce movement in multiple planes (i.e., both left/right and forward/backwards). The toothed pattern increases the grip when attached to a lead because epoxy/adhesive can be deposited between the teeth. This makes the attachment to the lead more secure and stable, while maintaining the existing geometric profile and width.

Figure 64:
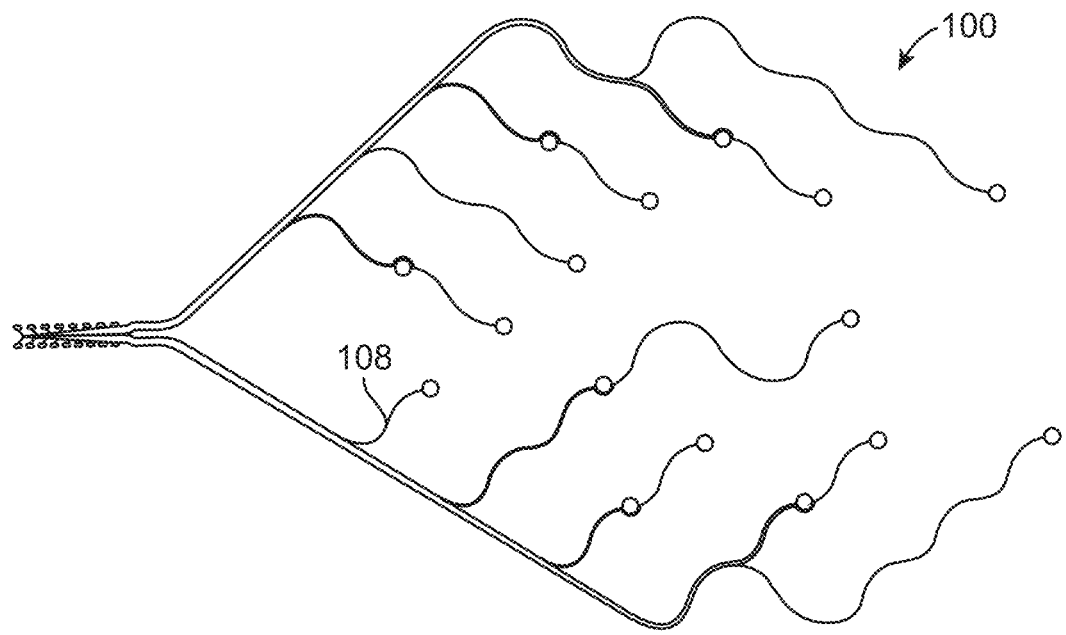
FIG. 64 illustrates a planar view of a variation of a stent device where the electrodes are specifically designed to limit the number of tracks per strut.

FIG. 64 illustrates a planar view of a variation of a stent device 100 where the electrodes 131 are specifically designed to limit the number of tracks per strut 108. Limiting the number of tracks per strut 108 reduces potential crosstalk and noise caused with/by parallel tracks and also reduces the width of the strut that is required to support multiple tracks. In certain variations, the tracks/struts are located/positioned in a unidirectional arrangement to: reduce thermal heating generated by high angle turns and reduce fatigue caused during flexion/extension. The track thickness can be optimized to minimise the electrical resistance/impedance (where large tracks better) as well as minimize the overall strut thickness (where small tracks are better).

Figure 65:
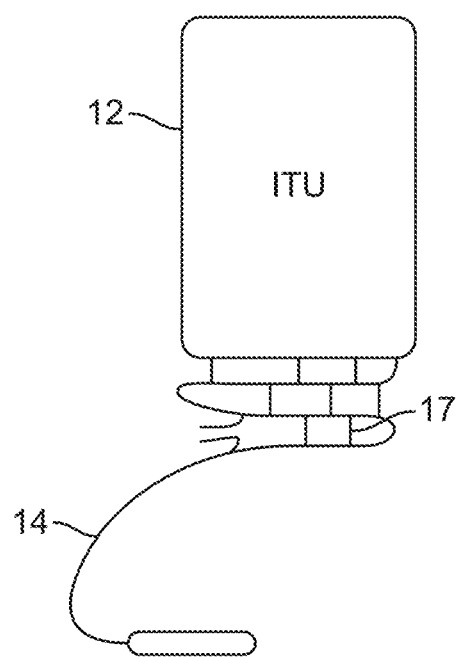
FIG. 65 illustrates a variation of an implantable telemetry unit coupled to a connector via an extension lead arranged in a serpentine fashion.

FIG. 65 illustrates an implantable telemetry unit 12 coupled to a connector via an extension lead 14. In this variation, the lead 14 is arranged in a serpentine fashion, connected by a thin (possibly polymer) layer, with thicker 'bridges' 17 across each lead pass. This allows a surgeon to pull the required length of lead from the ITU body, without risking fatigue due to lead rubbing, and minimising the depth of a surgical pocket needed for implantation of the device.

Other Applications

The methods, device, and systems described herein are discussed in terms of controlling computers, wheelchairs, exoskeletons, robotic prosthesis, cameras, vehicles and other electrical stimulation, diagnostic and measurement hardware and software. However, specific applications of these methods, systems and devices can provide language communicators/translators, gaming and (house) device controller, enhancements to applied intelligence and memory, sleep modifications, integrated communication devices, as well as enhanced cognitive output devices.

In some variations, the implants record neural activity, which transmits signals representing the neural activity to another source (whether external or internal). Next, feedback is provided to the patient/user. In one basic variation, the signals representing neural activity can be transmitted to a processing unit that includes a database of previously determined activity. Where the processing unit identifies or compares the recorded neural activity to the database of previously determined activity and generates a signal to control or trigger an external device.

In the variations discussed above, the neural activity can be monitored in different areas brain areas that are being recorded from indicative of different ways that information can be acquired from the brain (i.e., signals relating to speech, movement, sight, vision, memory, emotions, touch).

Transmitting the signals to the source can include delivering the information contained in the signals to a useful external source. This could be a prosthetic limb, or could be more advance (such as a database consisting of information, or language translations etc.). In some variations, the transmission of signals could comprise the final step (as is the case with rudimentary prostheses such as a wheelchair, for speech translation or for recording memories, dreams or previous visual information).

Various examples of sending feedback to the patient/user can vary based on the specific application. For example, sophisticated prostheses could provide information in the form of tactile feedback to sensory cortices within the brain. Alternatively, systems for treatment of moods, depression, or post-traumatic stress disorder provide feedback that stimulates an area of the brain that provides a feeling of happiness. Feedback could also come in the form of auditory cues (i.e., stimulation could be delivered back to the person which is interpreted as left, right, straight ahead etc.). Similarly for visual feedback, directions in the form of arrows could be presented to the visual cortex to inform which direction to take, or for other applications such as memory, could provide a complete (or near complete) scene of what you need to recall (where you live, where your car is parked, what was on the shopping list etc.). Signals generating low resolution images (e.g., around 1500 pixels), which could be used to spell words or general shapes that provide the desired feedback/Other useful cues can be delivered to justify electrical stimulation as visual feedback (i.e., flashing of numbers or symbols representing numbers). Clearly, the systems described herein can apply to medical applications as well as non-medical applications.

Universal Translators

The applications of one or more neural implants can assist those individuals who cannot communicate verbally by enabling direct brain control of speech or other communication. In such a case, the implants described above can function with a device that provides universal translator capabilities such as enabling people with speech difficulties to have a voice through a computer. Alternatively, or in combination, the universal translator can sense neural activity and cause stimulation of the individual's own muscles to enable communication. The implants described herein can record brain activity or signals specific to speech, relay such activity to an external device that uses signals to control a computer speech processor, a speaker, the user's own muscles, or even cause direct stimulation of a different implant in a different individual. For example, the systems can allow for signals of certain neural activity to be transmitted to another person's auditory cortex (e.g., hearing aid, cochlear implant, etc.) so that the neural activity of a first individual can be received by a second individual without traditional sounds/speech.

Further, processing of this information can enable communication in any language by translating between two or more different languages. It is known that neural commands generated by the brain control the muscles used for speech (tongue, lips, mouth etc.). An implant placed in a specific cortical location, can record signals the brain sends to these muscles. Different muscles have a large, but finite, number of different combinations meaning that a finite number of commands can drive a speech or control the muscles directly.

Such systems can include applications for people who are mute or have speech difficulties (stutter, lisp), suppression of unwanted speech (Tourette's), universal translator between different languages.

Gaming and Device Controllers

The systems, methods and devices of the present disclosure can also receive neural activity that controls muscles during high intensity gaming. Such neural activity can be processed to control an external gaming device or various house appliances and devices (e.g., light switches, appliances, locks, thermostats, security systems, garage doors, windows, shades, etc.) Again, the implants would detect brain signals specific to acts in which such devices are operated. The system can then generate signals to control one or more networked external device that to allow for neural control of the devices.

Memory Assist Systems

The systems described herein can also aid in memory recall of past activities. For example, one or more electrode devices can be implanted in regions of the brain that receive information sent by the eyes to the visual cortex. Neural signals that are generated through the eyes or during sleep can be acquired within the visual cortex. The visual cortex is retinotopically mapped (i.e. fields of view in the eye have specific cortical locations). Major regions of visual cortex are inaccessible by conventional electrode arrays as it is hidden beneath a large vessel. The sensory devices described herein can access one or more regions that are otherwise inaccessible by the conventional electrode arrays. These neural signals can be relayed to a recording device. At a later time, the recorded signals can then be re-stimulated in various locations in the brain to replay the visual or other input. Such recording and replay methods can be applied to any sensory input in addition to visual. In variations where the system records multiple sensory inputs, the system can later relay a sensory recording in isolation or in combination with other sensory recordings. In addition, visual information can be delivered to a person through stimulation of the visual cortex or other accessory areas. This would enable use as a restorative visual implant for the blind or to enable people to visualise pre-developed scenes (i.e., could see and be immersed in a movie or scenery of a different location.

These systems can assist in individuals where the recall of past activities is difficult, such as for people with Alzheimer's or dementia, people who experience physical or psychological trauma which causes memory loss. In addition, such a memory assist system can be used on a temporary basis where a device is implanted only for a short period of time.

Intelligence Enhancement Systems

Another application of the systems described in this disclosure includes establishing a connection between the brain and a database, server, and/or an internet site. The system can include using an existing networked appliance such as a cell phone and/or networked appliance that accesses information. As with the other systems described herein, an electrode device can be positioned in a region of the brain to sense neural activity and determine the intent of the neural activity (such as by comparing the neural activity to previously determined actions), which allows control of the system similar to a spoken command. The system can then stimulate the brain directly based on information provided by the database, server, and/or an internet site for applications including: augmented intelligence, non-verbal communication, etc. In this variation, there is two way communication—information or a request coming from the sensors located in the brain, sent via a computer, database or server, then information is fed back into the brain (potentially to different targets (i.e. for sight, smell, taste, memory, vision etc.). For example, an individual can ask a question to a voice activated/recognition computer interface. The computer would then provide feedback using a visual (i.e. arrows to the visual cortex) or auditory (tones or full commands for left, right, straight etc.) presentation/descriptions of a map or directions to the nearest place.

The networks described herein can comprise a traditional a computer network comprising is a set of computers connected together for the purpose of sharing resources. Alternatively, or in combination, the network can comprise a directly attached equipment (i.e., a robotic limb can provide information to tell the user that they are touching something). Furthermore, there are databases that may be required to be accessed (i.e., maps, or general knowledge).

Sleep Stimulation/Suppression Systems

Another application of the systems described in this disclosure includes implantation of a device within a sleep center of the brain to stimulate or assist in accelerating neural reconfiguration where the stimulation and neural reconfiguration reduce the hours needed to sleep. Alternatively, the systems can be used to keep people awake where required.

Integrated Communication Systems

The systems described herein can also function as integrated communication systems. The disclosed and contemplated systems can augment communication for those who cannot communicate, can augment communication for those who can communicate normally, can augment communication for those who can communicate but in a diminished capacity, or any combination thereof. For example, the device (e.g., stent 100) can record neural activity in the motor cortex associated with making a call. The neural activity can then be relayed to circuitry either wired or wirelessly that connects to network and places the required call. Speech commands, generated through set commands (i.e., one action for hello, one action for goodbye acquired from motor cortex) or vocal activation can be acquired and sent to receiver. As with previous descriptions, the voice on the other end of the line could then relay words back to the auditory or visual cortex (via electrodes) directly.

As another example, the device (e.g., stent 100) can record neural activity in the motor cortex associated with communicating with an electronic device such as a computer, a database, a server (e.g., a web server, an internet server, a cloud server), or any combination thereof, as well as with the internet in general, including web pages, websites, search engines, or any combination thereof. The device 100 can record neural activity in the motor cortex associated with communicating with software stored on one or multiple electronic devices (e.g., on a computer, in the cloud). For example, for a subject to communicate with and/or navigate the internet, the device 100 can be in communication with an intermediary device (e.g., an electronic device) in communication with the internet. The device 100 can be in wired or wireless communication with an electronic device. The electronic device can be a remote electronic device. However, regardless of the proximity to the subject, the electronic devices can be assistive devices that the device 100 (also referred to as a brain machine interface) can communicate with and/or can be assistive technology such as assistive software that the device 100 can communicate with. A closed communication loop can be formed between the device 100 and the computers and/or assistive software that the device 100 is configured to communicate with.

A subject can communicate with electronic devices and software by controlling a moveable control such as a cursor. The device 100 can record neural activity in the motor cortex associated with such control. For example, subjects who have the device 100 can communicate with electronic devices and software by willing cursor movement (e.g., by willing a mouse cursor to move) and by willing cursor selection (e.g., by willing a mouse click, including left mouse click functionality, right mouse click functionality, mouse wheel functionality, mouse wheel functionality for scrolling, click and drag functionality, or any combination thereof). In this way, the device 100 can enable a subject through the power of their thought to move a cursor on an electronic display (e.g., computer screen), to make selections on the electronic display via the cursor, or any combination thereof. Subjects can make selections with a cursor, for example, by "clicking" on a selection, by hovering over a selection for a threshold time period such as 5 seconds, by clicking and then enclosing the selection with a selection shape (e.g., a selection box), or any combination thereof. The electronic display can be a screen of a computer, for example, of a smartphone, tablet, laptop, desktop monitor, television, virtual reality system, augmented reality system, graphic display goggles, graphic display glasses, graphical user interface, or any combination thereof. The device 100 can record neural signals such that the subject can move one or multiple cursors and can make one or multiple selections (also referred to as decisions). Where the subject is controlling multiple cursors, the subject can move the multiple cursors sequentially or simultaneously relative to one another. Where the subject is making multiple decisions, the subject can make such decisions sequentially or simultaneously relative to one another.

A subject's decisions associated with neural activity recorded in their motor cortex by the device 100 can include any decision people without a device 100 can make while interacting with a computer or the internet, such as, for example, selecting links, opening and closing documents, opening and closing emails, browsing websites, selecting links on websites, opening and closing software programs, using the software programs (e.g., graphical programs such as graphical word processing programs, internet browsers, email programs, video games), initiating and terminating internet connections, or any combination thereof. In this way, subjects having the device 100 can control electronic devices, for example, to browse the internet and use software programs.

An example of a software program that a subject can interact with via the device 100 is communicating software such as a speller. A subject having a device 100 can move a cursor on a display to make letter and word selections in the speller to spell and communicate with others via one or multiple electronic devices, for example, using programs having letters, words, and/or drawing features (e.g., a word processing program). The speller software can display letters on a screen and the subject can will a cursor to move on the screen to select the letters that they want.

The device 100 can be unidirectional (record only or stimulate only) or can be bi-directional (record and stimulate). Once the device 100 records neural activity, the recorded neural activity can then be relayed to circuitry either wired or wirelessly that directly or indirectly connects to an electronic device or first to a processing unit that includes a database of previously determined activity. The processing unit identifies or compares the recorded neural activity to the database of previously determined activity and generates a signal to control or trigger an external device. For communication with an electronic device, feedback may (e.g., when using a bi-directional device 100) or may not (e.g., when using a unidirectional device 100 or when using a bi-directional device 100) be sent back to the brain. Visual feedback can be provided on the electronic display of the electronic device when the subject is communicating with the electronic device via the device 100 such that feedback to the brain is not required.

Enhanced Cognitive Output

Systems described herein can be used to enhance cognitive output, for improvements in such areas as: learning, memory, training, motor tasks, etc. Transcranial Direct-Current Stimulation (TDCS) and Transcranial Magnetic Stimulation (TMS) have been shown to have potential applications in improved attention, learning, and motor outputs. Implantation of an intravascular stimulation device into the appropriate area could potentially create more reliable, long term improvements to cognitive outputs using less energy due to increased access and proximity to the regions of interest.

Neural Signal Processing

The systems and implants described herein can record and process neural activity to control devices that are internal and/or external to a user's body via a brain machine interface. Such processing can be done with one or more processors or microprocessors that are, for example, integrated or otherwise in communication with one or more stent devices 100 and/or with the telemetry unit 12. The processors can be programmed with or be capable of calling a variety of control algorithms to process the neural signals received from the brain and/or from elsewhere in the body. This includes neural signals received from both the sympathetic and/or parasympathetic pathways. For example, an electrode array (e.g., the stent based electrode array 100) can sense cortical and/or sub-cortical neural activity, and can relay such activity to a processor to control a brain machine interface. The brain machine interface can be linked to internal and/or external devices. Cortical and subcortical locations can include, for example, the primary motor cortex (M1), the supplementary motor area (SMA), the posterior parietal cortex (PPC), the primary somatosensory cortex (S1), the cerebellum, the thalamus and the brain stem. Neural activity in areas outside of the brain can also be sensed and processed, for example, from the spinal cord, muscles and organs such as the heart, lungs, stomach, kidneys and pancreas. The control algorithms can process neural activities that are sensed or recorded by the system to generate control signals. The generated control signals can allow for the neural control of one or multiple external devices, internal devices, parts of the body, or any combination thereof. For example, the algorithms can produce control signals that actuate some part of a device and/or that stimulate tissue.

The algorithms can process sensed neural activity from one or more neural areas to determine, for example, whether a user intends to act, and if so how much. If the sensed neural signals correspond to intended action, the brain machine interface can generate control signals that actuate a device associated with the action intended. For example, where a user has a prosthetic arm linked to a brain machine interface, the user can think about raising their arm and the system can detect this intent by processing the neural signals that are associated with this action. The system can transform this detected intent into a control signal to raise the prosthetic arm according to the user's intended action.

Various algorithms can be used to decode or otherwise determine a user's intent as well as determine whether the sensed or decoded intent corresponds to a user's intended action. For example, the system can sense signals from multiple brain areas to rely on and detect natural synergies that exist between multiple brain areas when a user mentally forms an intent (e.g., a motor intent). Such an intent determination algorithm relies on the fact that any given intent will be replicated in multiple areas of the brain and be supplemented with additional information. For example, the system can detect and use natural cortical and/or subcortical synergies for informing the outputs of the brain machine interface when determining intent. In such a case, the system can determine a user's intent by processing neural signals from two or more neural areas and then making a determination of whether the two or more sets of neural signals are associated with one another before generating an output signal. Sensing and analysing neural synergies can reduce the risk of accidentally activating devices in communication with the brain machine interface since such a decoding process relies on multiple areas of the brain as opposed to just one, and takes advantage of the neural redundancies or lack thereof that naturally result. Utilizing such synergies can therefore enable for more accurate and reliable identification of a person's intent. This can in turn allow for the generation of more accurate and reliable control signals, as well as instil greater confidence in users for the device. The system can also determine a user's intent without relying on neural synergies, for example, by processing neural signals from a single area without associating or comparing the signals to signals from other neural areas.

Figure 66:
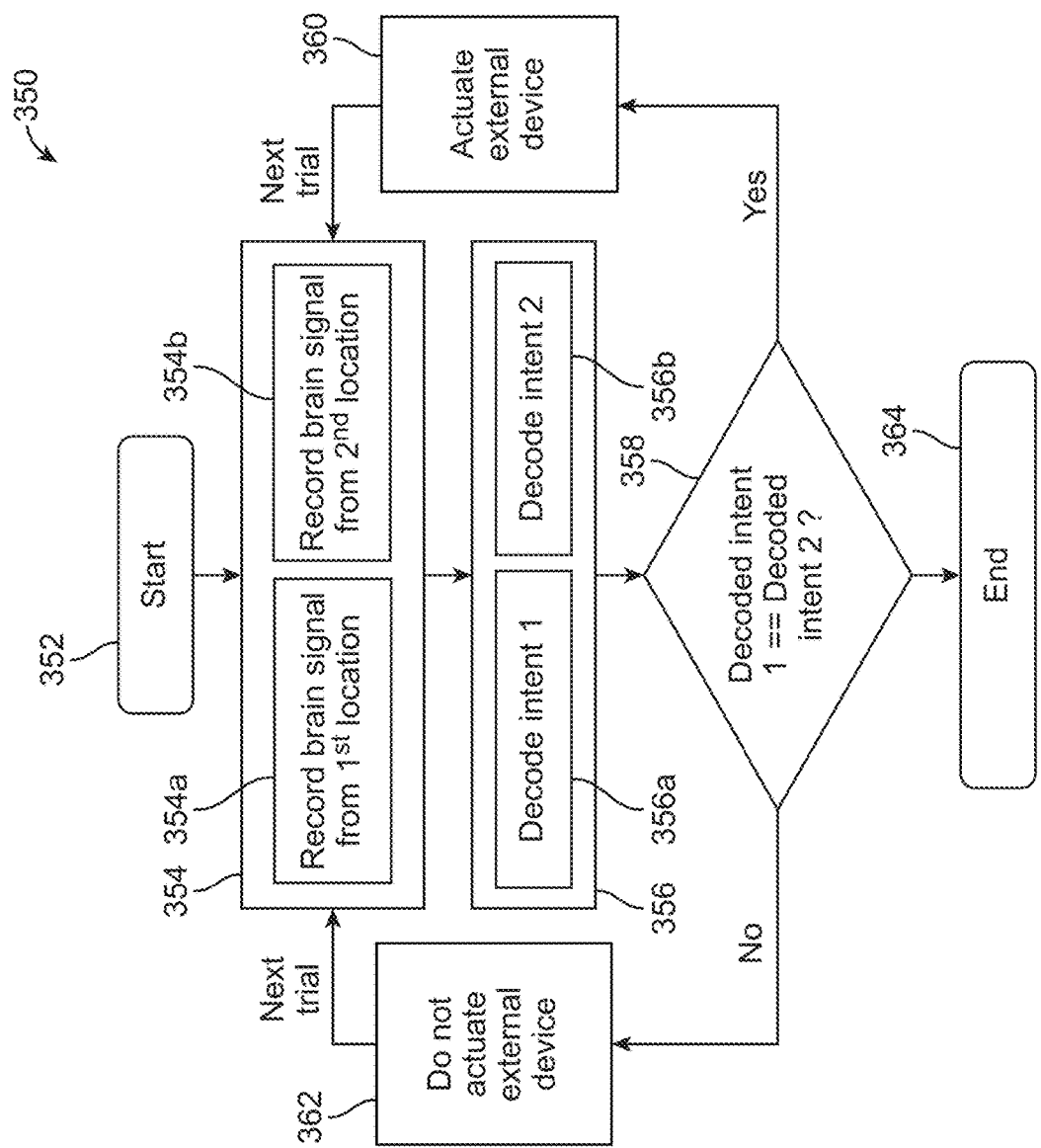
FIG. 66 illustrates a variation of an algorithm for processing neural signals from two or more neural areas.

FIG. 66 illustrates a variation of an algorithm 350 for processing neural signals from two or more neural areas that are received, for example, from one or more stent devices 100. The algorithm 350 can process the received neural signals to determine whether the signals correspond to a user's intended action. Upon starting at block 352, the algorithm 350 can record brain signals 354 from multiple neural locations, decode intents 356 from the recorded signals, and perform a correlation analysis 358 on the intents decoded. For example, FIG. 66 illustrates that the algorithm 350 can record brain signals 354 from a first location 354a and a second location 354b. The neural activity in different areas can be recorded simultaneously or sequentially relative to activity recorded in one or more other areas (e.g., the signals at the second location 354b can be recorded at the same time as the signals at the first location 354a or at a later time).

Recording signals from multiple neural areas 354 makes the algorithm 350 multimodal and enhances the intent determination process 356 and improves error detection 358. The recorded signals can be measured, for example, with one or more sensors (e.g., one or more electrodes 131 of one or more stent devices 100). For example, the brain signals in the first location 354a can be recorded with a first sensor and the brain signals in the second location can be recorded with the first sensor or a second sensor. The first sensor can be proximate or in the first neural area 354a and the second sensor can be proximate or in the second neural area 354b. Further, although FIG. 66 illustrates that the first and second neural areas 354a, 354b are in the brain, the neural areas 354 can be in and/or outside of the brain including, for example, the cortex, the subcortex, the cerebellum, the thalamus, the brain stem, the spinal cord, organs, muscles, or any combination thereof. The first and second neural activities 354a, 354b can be measured with the same or different implants, for example, with first and second stent devices 100.

Once the first and second signals 354a, 354b are received in step 354, the algorithm 350 can determine the intents 356 that are associated with each of the recorded signals. For example, FIG. 66 illustrates that a first intent 356a can be determined from the first neural signal 354a and that a second intent 356b can be determined from the second neural signal 354b. The first and second intents 356a, 356b can be determined by decoding the recorded first and second neural activities 354a, 354b, respectively. Alternatively, or in combination, the intents 356 (e.g., first and second intents 356a, 356b) can be determined by referencing previously measured neural activities stored in a memory. The neural activities stored in the memory can be obtained from the user, another person, and/or from multiple people. In this way, the stored neural activities can be user specific, specific to another person, and/or be a compilation of data from multiple users. In this way, the memory can be patient-specific and/or be a global library of neural data. Where neural data from one or more other people who are different from the user is stored on and/or referenced from the memory, this data can represent a benchmark standard and/or the next neural goal for the user at any stage in their neural development and training. The memory can be configured to store new measurements, purge old measurements, organize the stored data, or any combination.

Once the intents 356 are determined, the algorithm 350 can perform a correlation analysis 358 to determine whether to actuate 360 or not actuate 362 a device associated with or otherwise controllable by the algorithm 350. The correlation analysis 358 can ascertain error between two or more of the neural areas being recorded, for example, between two or more of the measured signals 354 and/or between two or more of the determined intents 356. FIG. 66 illustrates that if the correlation analysis 358 determines that the first intent 356a is the same as or substantially the same as (also referred to as associated with or substantially associated with) the second intent 356b, a processor can be programmed to generate one or more control signals configured to actuate 360 a device. Likewise, if the correlation analysis 358 determines that the first and second intents 356a, 356b are not associated with one another, the processor can be programmed to not actuate 362 the device. Stated differently, if the algorithm 350 confirms that two or more decoded intents 356 are associated with one another, one or more control signals can be generated and delivered to the device to actuate 360 the device, after which the algorithm 350 can return to the recording step 354 or end 364. Likewise, if the algorithm 350 is unable to confirm that two or more decoded intents 356 are associated with one another (e.g., if an error is detected between the two or more decoded intents 356), the algorithm 350 can proceed to the recording step 354 or end 364 without actuating 362 the device.

For example, the correlation analysis 358 can calculate an error between the measured first and second activities 354a, 354b and/or between the decoded first and second intents 356a, 356b. For example, the algorithm 350 can deliver one or more control signals to the device upon determining that the calculated error between the first and second decoded intents 356a, 356b is below a pre-determined error, upon determining that the calculated error is below multiple pre-determined errors, upon determining that multiple calculated errors are below the pre-determined error, upon determining that an average of multiple calculated errors is below the pre-determined error, upon determining that an average of multiple calculated errors is below an average of multiple pre-determined errors, or any combination thereof. The predetermined error or errors can be determined, for example, using prediction class matching and/or instrumented class matching. For example, the prediction class matching can be binary (e.g., classes can be class 1-n, where each class can activate a switch). For example, if the intended class (e.g., the first decoded intent)=the predicted class (e.g., second decoded intent), then the processor can generate and deliver control signals to the device. The instrumented class matching can also be binary but the intended class can instead be provided by an external sensor (e.g., from a proximity sensor or other such device).

FIG. 66 illustrates that the processor can be configured to make a "Yes" and a "No" decision. A "Yes" signal can prompt the processor to transmit one or more control signals to the device to actuate 362 the device. A "No" signal can prompt the processor to return to step 354 of the algorithm 350. The steps 354, 356, 358 of the algorithm 350 can be repeated until at least one control signal is delivered to the device. The algorithm 350 can start 352 automatically when the stent devices 100 are in communication with the devices being controlled, or can be controlled by the user or another party such as a care provider. The algorithm 350 can be used to control one or more parameters of the device, for example, a first parameter, a second parameter, a third parameter, or more parameters. The parameters can correspond to a position, velocity, or trajectory of the device (e.g., a first parameter can be a position of the device, a second parameter can another position of the device, and a third parameter can be a velocity of the device). As described above, the device can be an exoskeleton, a prosthetic limb, a speller, a wheelchair, a computer, an electrical or electromechanical device, or any combination thereof. Additionally, or in combination, the device can be a web browser and/or the device can be in communication with a web browser. For example, the device can be a processor in control of a web browser, the device can have a processor in control of a web browser, the device can be in wired or wireless communication with a processor in control of a web browser, or any combination thereof.

Although not illustrated in FIG. 66, the algorithm 350 can record more than two neural activities, for example, 3, 4, 5, 6, 7, 8, 9, 10, or more neural activities in 3, 4, 5, 6, 7, 8, 9, 10, or more corresponding neural locations using the first and/or second sensors and/or by using one or more other sensors (e.g., 3, 4, 5, 6, 7, 8, 9, 10, or more other sensors).

The algorithm 350 can sense neural signals specific to one or more devices for one or more of the parameters being controlled.

For example, the algorithm 350 can measure one or more third and fourth neural activities. In such a case, the algorithm 350 can prompt the processor to deliver one or more control signals to a device upon confirming in the correlation analysis step 358 that one or more of the fourth measured neural activities are associated with at least one first, second, and/or third intent, upon confirming that multiple fourth neural activities are associated with one or more first, second, and/or third intents, upon confirming that at least one of the one or more fourth neural activities is associated with multiple first, second, and/or third intents, upon confirming that an average of the fourth neural activities is associated with an average of the first, second, and/or third intents, or any combination thereof. The steps 354, 356, 358 of the algorithm 350 can be repeated for each neural area being recorded until at least one control signal is delivered to the device.

Figure 67:
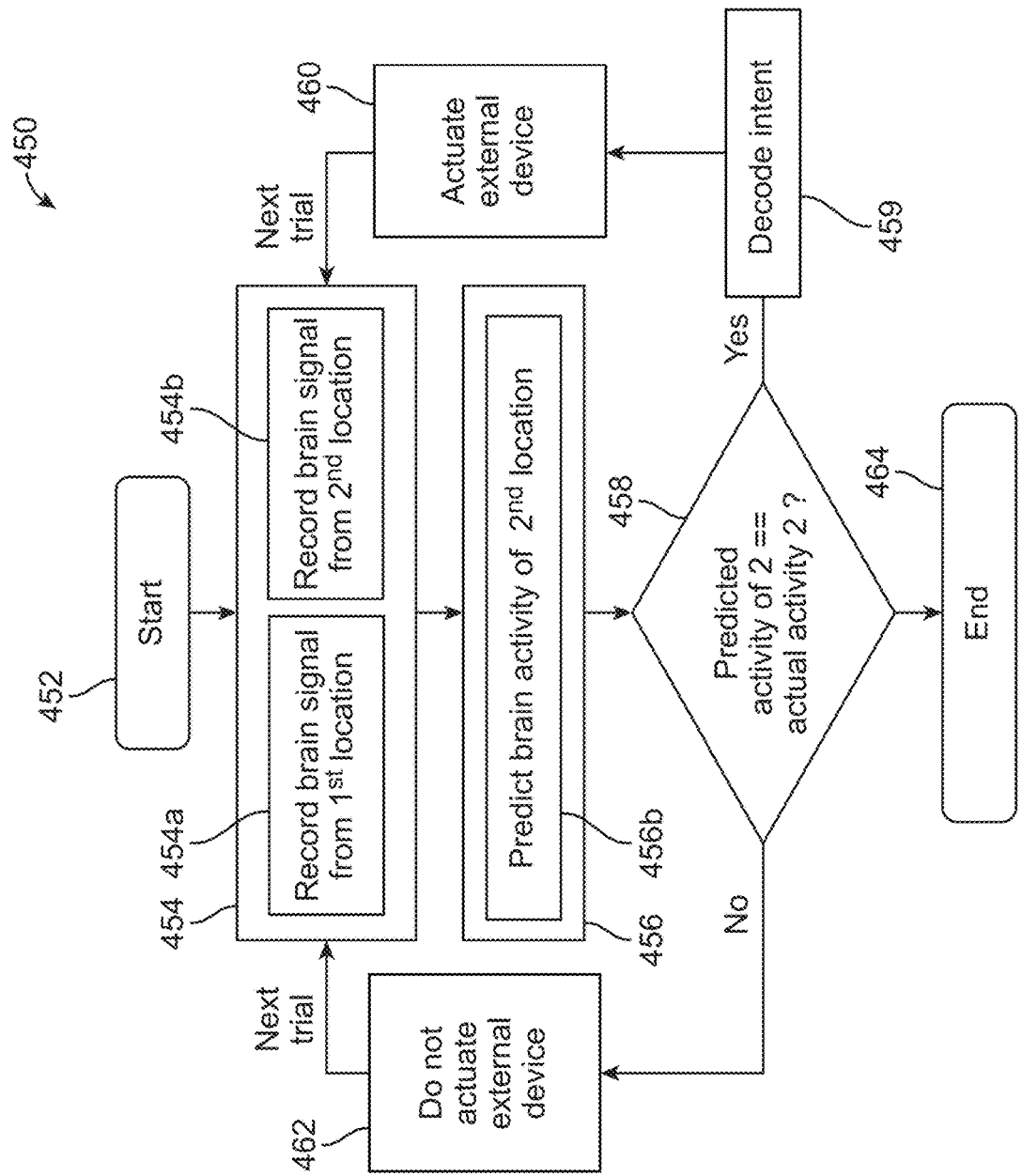
FIG. 67 illustrates a variation of an algorithm for processing neural signals from two or more neural areas.

FIG. 67 illustrates a variation of another algorithm 350 for processing neural signals from two or more neural areas that are received, for example, from one or more stent devices 100. The algorithm 450 can process the received neural signals to determine whether the signals correspond to a user's intended action. Upon starting at block 452, the algorithm 450 can record brain signals 454 from multiple neural locations, predict the neural activity 456 of at least one of the measured brain signals 454, and perform a correlation analysis 458 between at least one of the measured activities and at least one of the predicted activities. For example, FIG. 67 illustrates that the algorithm 450 can record brain signals 454 from a first location 454a and a second location 454b. The neural activity in different areas can be recorded simultaneously or sequentially relative to activity recorded in one or more other areas (e.g., the signals at the second location 454b can be recorded at the same time as the signals at the first location 454a or at a later time). The recorded signals 454 can be measured with one or more sensors on one or multiple implants, can be measured with the same or different implants (e.g., first and second stent devices 100), and can record signals in the brain and/or outside of the brain, for example, as described above with reference to algorithm 350.

Once the first and second signals 454a, 454b are received in step 454, the algorithm 450 can predict 456 the neural activity of one or more of the measured brain signals 454 (e.g., the first and/or second brain signals 454a, 454b). In the prediction step 456, activity from one of the measured neural areas can be used to predict 456 the activity in another neural area. Alternatively, or in combination, multiple measured activities of one of the neural areas can be used to predict 456 the activity in another neural area. Alternatively, or in combination, measured activities from multiple neural areas can be used to predict 456 the activity in one or multiple other neural areas. For example, FIG. 67 illustrates that the algorithm 450 can predict 456 the neural activity of the second location 456b using the activity measured in the first neural area 454a. Other information can also be used to predict neural activities, including neural data stored in the memory described above with reference to the algorithm 350.

Once the activity of one of the neural areas is predicted 456 based at least partly on the activity measured 454 in another neural area and/or on stored neural data, the algorithm 450 can perform a correlation analysis 458 to determine whether to actuate 460 or not actuate 462 a device associated with or otherwise controllable by the algorithm 450. The correlation analysis 458 can ascertain error between one or more of the recorded activities 454 and one or more of the predicted activities 456. For example, the correlation analysis 458 can calculate an error between the measured first activity 454a and a predicted first activity 456a and/or between the measured second activity 454b and the predicted second activity 456b. The predicted first activity 456a is not shown in FIG. 67. This activity can be predicted based on the measured second activity or on any other measured activity different from the measured first activity. Similarly, the predicted second activity can be based on the measured first activity or on any other measured activity different from the measured second activity.

FIG. 67 illustrates that if the correlation analysis 458 determines that the predicted second activity 456b is the same as or substantially the same as (also referred to as associated with or substantially associated with) the measured second activity 454b, a processor can be programmed to determine the intent 459 of the first and/or second measured activities 454a, 454b to determine the executed action of the device. The algorithm 450 can then generate one or more control signals configured to actuate 460 the device, for example, in the decoding step 459 or subsequent to the decoding step 459. Likewise, if the correlation analysis 358 determines that the measured and predicted second activities 454b, 456b are not associated with one another, the processor can be programmed to not actuate 462 the device. Stated differently, if the algorithm 450 confirms that the measured and predicted second activities 454b, 456b are associated with one another, one or more control signals can be generated and delivered to the device to actuate 460 the device, after which the algorithm 450 can return to the recording step 454 or end 464. Likewise, if the algorithm 450 is unable to confirm that the measured and predicted second activities are associated with one another (e.g., if an error is detected between them), the algorithm 450 can proceed to the recording step 454 or end 464 without actuating 462 the device.

For example, the algorithm 450 can determine the intent 459 of the measured activities 454 and/or deliver the one or more control signals to the device upon determining that the calculated error is below a pre-determined error, upon determining that the calculated error is below multiple pre-determined errors, upon determining that multiple calculated errors are below the pre-determined error, upon determining that an average of multiple calculated errors is below the pre-determined error, upon determining that an average of multiple calculated errors is below an average of multiple pre-determined errors, or any combination thereof. The predetermined error or errors can be determined, for example, using prediction class matching and/or instrumented class matching as described above. Here, if the intended class (e.g., the first measured neural activity)=the predicted class (e.g., the predicted neural activity), then the processor can decode one or more of the associated intents in step 459 as described above.

FIG. 67 illustrates that the processor can be configured to make a "Yes" and a "No" decision. A "Yes" signal can prompt the processor to decode 459 the measured first and/or second activities 454a, 454b and then transmit one or more control signals to the device to actuate 462 the device. A "No" signal can prompt the processor to return to step 454 of the algorithm 450. The steps 454, 456, 458 of the algorithm 450 can be repeated until at least one control signal is delivered to the device. The algorithm 450 can start 452 automatically when the stent devices 100 are in communication with the devices being controlled, or can be controlled by the user or another party such as a care provider. The algorithm 450 can be used to control one or more parameters of the device as described above with reference to algorithm 350. The device can be an exoskeleton, a prosthetic limb, a speller, a wheelchair, a computer, an electrical or electro-mechanical device, or any combination thereof.

Although not illustrated in FIG. 67, the algorithm 450 can record more than two neural activities, for example, 3, 4, 5, 6, 7, 8, 9, 10, or more neural activities in 3, 4, 5, 6, 7, 8, 9, 10, or more corresponding neural locations using the first and/or second sensors and/or by using one or more other sensors (e.g., 3, 4, 5, 6, 7, 8, 9, 10, or more other sensors). The algorithm 450 can sense neural signals specific to one or more devices and one or more of the parameters being controlled. For example, the algorithm 350 can measure one or more third and fourth neural activities, and determine one or more intents to control the device. The steps 454, 456, 458 of the algorithm 450 can be repeated for each neural area being recorded until at least one control signal is delivered to the device.

Figure 68:
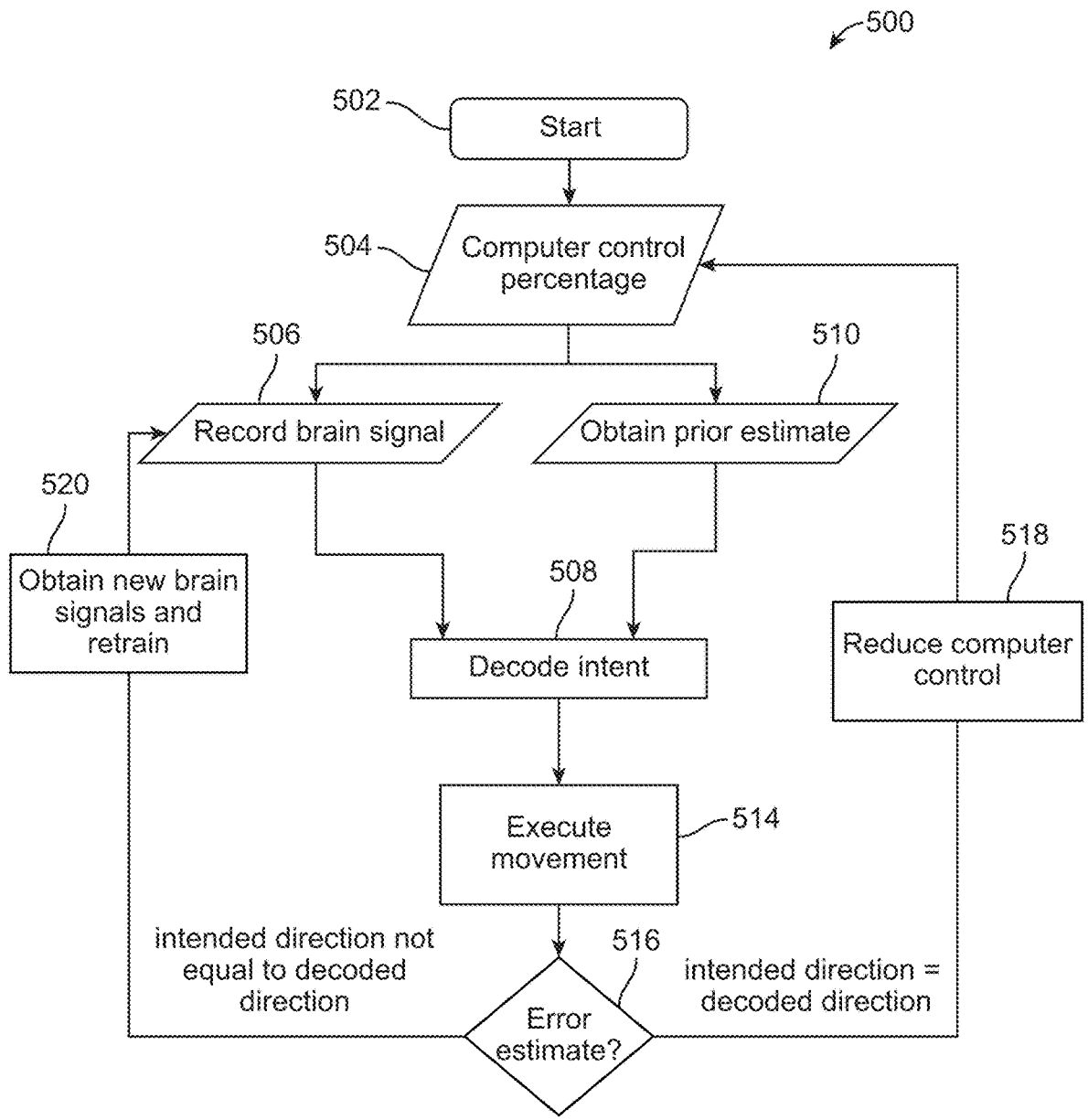
FIG. 68 illustrates a variation of an adaptive control algorithm.

FIG. 68 illustrates a variation of an adaptive control algorithm 500 that allows for dual control of a device via both the user and the device itself. The algorithm 500 can enable both machine learning and human learning to occur as opposed to just one or the other. The algorithm 500 can be used alone without another algorithm or with another algorithm, for example, with algorithm 350, with algorithm 450, or any combination thereof. For example, the algorithm 500 can be a subroutine of the algorithms 350, 450.

As shown in FIG. 68, the algorithm 500 can start at block 502 and then establish 504 a computer control percentage and a user control percentage that can be subsequently increased and/or decreased, for example, based on a determination of a user's competence or proficiency with the device. When the algorithm 500 is initially started 502, the computer control percentage can be about 75% to about 100% (e.g., about 95%) and the user control percentage can be about 0% to about 25% (e.g., about 5%). The total percentage of both control percentages added together can be about 100%. Where multiple devices are used or otherwise in neural communication with a user, a separate computer control percentage can be established 504 for each device. Additionally, or in combination, a single computer control percentage can be split among multiple devices and/or among multiple control sources associated with a single device.

The algorithm 500 can be used to adjust the user's and computer's control of one or more parameters of a device. For example, the control of one or more kinematic parameters can be monitored and adjusted by the algorithm 500, including the control of trajectory, speed, velocity, position, or changes thereof. After the control percentages are set at block 504, a neural signal associated with a parameter can be recorded 506 and an estimate of the parameter can be obtained 510. The estimate 510 can be obtained from the device that the user is controlling or trying to control, or can be obtained from another separate device. The neural activity recorded 506 and the machine estimate 510 can be used to decode a user's intent 508.

Once the user's intent 508 is decoded, a filter (e.g., a Kalman filter) can be trained by executing the parameter 514 (e.g., movement) associated with the decoded neural activity 508. The filter can be used to calculate an error 516, for example, an error estimate, by comparing the executed parameter 514 with the decoded intent 508 (also referred to as the decoded parameter 508 or the intended parameter 508). The calculated error/error estimate 516 can be based at least partly on the decoded and estimated parameters 508, 510. The calculated error can correspond to a calculated control correlation (also referred to as a calculated control proficiency) between the measured neural activity 506 and the desired intended parameter 510. The algorithm 500 can perform the error calculation 516 to determine whether to adjust the user and computer control percentages.

FIG. 68 illustrates that if the error analysis 516 determines that the intended parameter 508 is the same as or substantially the same as the executed parameter 514, a processor can decrease the computer control percentage 518 and correspondingly increase the user control percentage. Likewise, if the error analysis 516 determines that the intended and executed parameters 508, 510 are not the same, the processor can be programmed to obtain new neural signals to retrain the user at block 520 and/or increase the computer control percentage and correspondingly decrease the user control percentage. The algorithm 500 can adjust a user control percentage and a computer control percentage upon determining that the calculated control correlation is below or above a pre-determined error. For example, a processor can increase the user control percentage and decrease the computer control percentage upon determining the calculated control correlation is below the pre-determined. decrease the user control percentage and increase the computer control percentage upon determining that the calculated control correlation is above the pre-determined error or another pre-determined error, vice versa, or any combination thereof. Alternatively, or in combination, the processor can be programmed to provide no adjustment to the user and computer control percentages upon determining the control correlation is above the pre-determined error, above another pre-determined error, below the pre-determined error below another pre-determined error, or any combination thereof. The predetermined error or errors can be determined, for example, using prediction class matching and/or instrumented class matching as described above.

The adaptive training paradigm 500 can gradually and/or rapidly adjust the control percentages by training both the user and the computer. For example, the user and computer control percentages can be adjusted by a processor in percentage increments of about 1% to about 25%, for example, 1% increments, 2% increments, 10% increments, 25% or more increments, or any combination thereof. The algorithm 500 can incrementally increase the user control percentage from an initial percentage of about 0% to about 25% to a final percentage of about 75% to about 100%, with the computer control percentage being correspondingly decreased from an initial percentage of about 75% to about 100% to a final percentage of about 0% to about 25%. For example, the algorithm can start with about a 90% computer control percentage and about a 10% user control percentage, and then can gradually and/or rapidly increase the user's control leading to about 90% or more user control, for example, 100% user control. The algorithm 500 can be iterated from 1 time to 10,000 or more times for the adaptive training to transition from the initial control percentages to the final control percentages. At every change in the user control percentage, the algorithm 500 can be programmed to correspondingly change its error/error estimate calculations. The training can be tailored to each individual whereby the time between algorithm adaptation and user adaptation can be altered.

For example, the time interval between user adaptation and algorithm can be varied based on individual subjects performance. As another example, the signals used for adaptation can be varied. For example the ratio of incorrect predictions to accurate prediction by the algorithm can be varied to optimize accuracy of a subject's or user's control of the external device, or any device or platform linked to the one or multiple implanted stentrodes.

The algorithms 350, 450, 500 in FIGS. 66-68 can each provide discrete and/or continuous control of the device. The adaptive algorithm 500 in FIG. 68 can enhance user and machine learning and plasticity using one or more stent devices 100 as discussed above. Neural activities can be recorded and the associated intents decoded in algorithms 350, 450, 500, for example, as follows: (1) record the neural signal, filter at about 2 Hz to about 200 Hz, and remove artifacts, (2) obtain features of interest, e.g., power in frequency bands 4 Hz to 12 Hz, 13 Hz to 28 Hz, 29 Hz to 45 Hz, 55 Hz to 80 Hz, 81 Hz to 120 Hz, 121 Hz to 180 Hz, (3) apply a linear regression model to the results, for example, $y(t)=X(t)\times A+E(t)$, where A represents the linear parameters, $E(t)$ is the error term, $X(t)$ is the feature vectors and $y(t)$ is the desired output.

Dual Phased Multipolar Neural Stimulation

The methods, devices, and systems described herein can be capable of providing dual multipolar stimulation to neural tissue. In such variations, the two multipolar signals can be phased with one another to achieve dual phased multipolar stimulation. Dual phased multipolar stimulation can be provided in addition to traditional monopolar, traditional bipolar, and traditional multipolar stimulation. The use of dual phased multipolar stimulation can allow neural tissue to be more accurately targeted, for example, by allowing the stimulation to be focused on one or more regions of neural tissue (e.g., one or more regions in the brain) without affecting other adjacent regions. The location, direction and depth of stimulation can be controlled with dual multipolar stimulation by focusing one or more currents on a target area, summing one or more of the currents in the target area, and/or adjusting the amplitude of one or more currents. Traditional stimulation techniques that do not allow for current summation. Dual multipolar stimulation can also reduce the stimulation current required to achieve the desired stimulation level by utilizing multiple current sources instead of, for example, just one current source. The total current delivered can be divided among the multiple current sources such that the desired stimulation current is only achieved or is otherwise most focused in the target area. For example, instead of a single current source at full strength, two current sources can be used in a dual phased polar stimulation arrangement where each of the two current sources has half the current strength (50% and 50%) as compared to the current strength of the single current source. However, any percentage current distribution among the two sources is appreciated, for example, 10% and 90%, 20% and 80%, 30% and 70%, 40% and 60%. When the system has multiple current sources (e.g., 2 to 50 or more current sources), one or more of the current sources can have a current strength that is less than the current strength of variations where current summation is not utilized. The current can be distributed among multiple current sources evenly or unevenly such that all the current sources deliver current having the same current strength, or such that at least two current sources deliver current having current strengths different from one another. The multiple current sources can be independent from one another and/or one or more of the current sources can be dependent on one or more other current sources. Dual phased multipolar current delivery can function similar to dual phased multipolar ultrasound delivery.

Figure 69A:
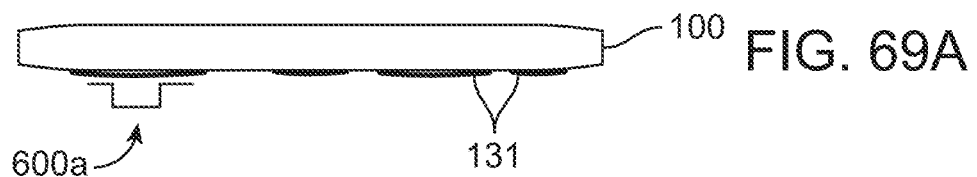
FIGS. 69A-69E illustrate schematic variations of stent devices delivering stimulation to a target location.
Figure 69B:
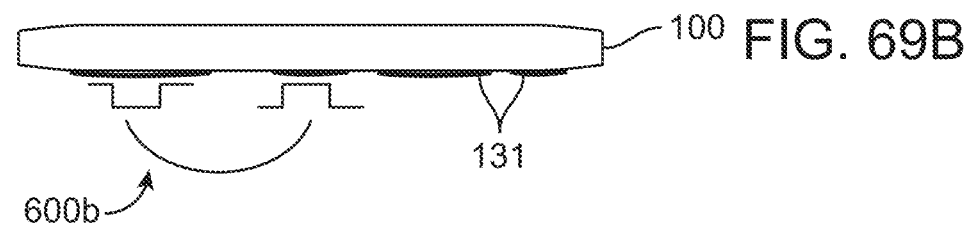
Figure 69C:
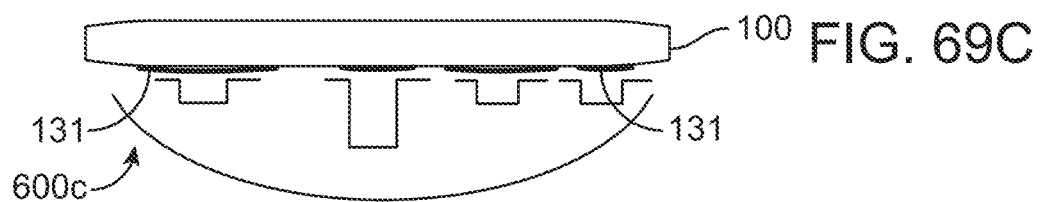
Figure 69D:
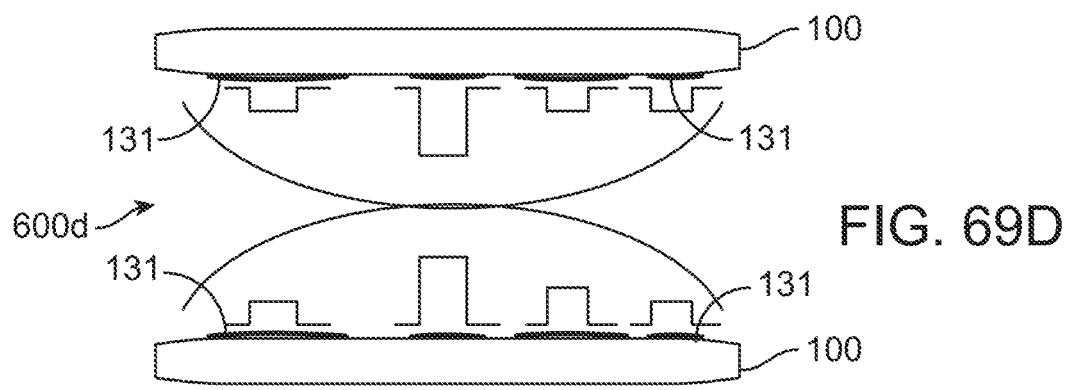
Figure 69E:
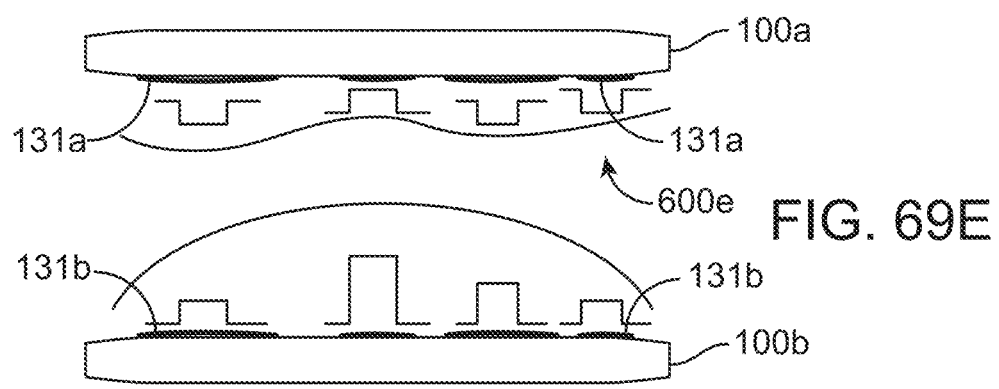

To stimulate neural tissue, one or more stent devices 100 can be configured to deliver one or more currents to a target area by passing current from one or more current sources to one or more current sinks. Each current source can be distributed among one or more electrodes 131 of a stent device 100. The current from one or more of the one or more current sources can be steered to or otherwise focused on one or more of the one or more current sinks such that the delivered currents pass through one or multiple target areas. With dual phased multipolar stimulation, the currents in the target areas can sum to achieve the desire stimulation level. For example, FIGS. 69A-69D illustrate a schematic variation of electrodes 131 of a stent device 100 delivering traditional monopolar stimulation 600a in FIG. 69A, delivering traditional bipolar stimulation 600b in FIG. 69B, delivering traditional multipolar stimulation 600c in FIG. 69C, and delivering dual multipolar stimulation 600d in FIG. 69D. FIG. 69E illustrates a schematic variation of electrodes 131a of a first stent device 100a and electrodes 131b of a second stent device 100b delivering dual multipolar stimulation 600e. The patterns and polarity of the stimulations 600a, 600b, 600c, 600d, 600e shown in FIGS. 69A-69E are exemplary and illustrate the area of neural activation (also referred to as the current spread). The patterns and polarities of a stimulation can be static or dynamic such that the stimulation being delivered can be held constant or adjusted in real-time, for example, based on a user's responsiveness to the stimulation and/or based on criteria unrelated to a user's responsiveness (e.g., predetermined stimulation times, pre-determined stimulation sequences, pre-determined stimulation strengths). Additionally, or in combination, the patterns and polarities can be pulsed or have another delivery protocol that is variable in nature.

One or more currents can pass through one or multiple target areas and be summed with one or more other currents in each target area that can likewise pass through one or multiple target areas. For example, a first current and a second current can pass through and sum in a target area to a stimulation current. As another example, a first current can pass through a first target area and a second target area, a second current can sum with the first current in the first target area but not in the second target area, and a third current can sum with the first current in the second target area but not in the first target area. The first and second currents can sum to a first stimulation current and the first and third currents can sum to a second stimulation current equal to or different from the first stimulation current.

As described above, the current from one or more of the one or more current sources can be steered to one or more of the one or more current sinks. Steering can include pulling the current from one or more of the one or more current sources with one or more of the one or more current sinks, where each current sink can be configured to pull current from one or more designated current sources. A designated current source is a current source that is configured to deliver current to one or more specific current sinks. Steering can include pushing the current from one or more of the one or more current sources to one or more of the one or more current sinks, where each current source can be configured to push current to one or more designated current sinks. A designated current sink is a current sink that is configured to receive current from one or more specific current sources. For example, a first current can be delivered to the target area by steering the first current from a first current source to a first current sink or multiple first current sinks.

At least two currents can be simultaneously delivered to a target area via pulling or pushing. For example, two or more of the at least two currents can be steered to the target area such that at least two currents sum in the target area to a stimulation current having an energy sufficient to stimulate neural tissue in the target area. As another example, a first current can be delivered to a target area by steering the first current from a first current source to a first current sink and simultaneously delivering a second current to the target area by steering the second current from a second current source to a second current sink.

The one or more current sources can be independent from one another and the one or more current sinks can be independent from one another.

The devices described herein can have any arrangement of current sources, current sinks, and electrodes. For example, one or more implants (e.g., stent devices 100) can have one or more current sources and current sinks such that the current sources and current sinks are all on the same implant. In such variations, each implant can have multiple electrodes (e.g., electrodes 131) where each current source can be one or multiple current source electrodes and each current sink can be one or multiple current sink electrodes. As another example, a first implant (e.g., first stent device 100a) can have the one or more current sources and a second implant (e.g., second stent device 100b) can have one or more current sinks such that the one or more current sources are on a different implant than the one or more current sinks. In such variations, the first implant can have one or multiple electrodes and each current source can be one or multiple current source electrodes. The second implant can likewise have one or multiple electrodes and each current sink can be one or multiple current sink electrodes. As yet another example, a first implant (e.g., first stent device 100a) can have at least one current source and at least one current sink and a second implant (e.g., second stent device 100b) can have at least one current source and at least one current sink such that each of the first and second implants have one or more current sources and one or more current sinks. In such variations, the first and second implants can each have electrodes where each current source can be one or multiple current source electrodes and where each current sink can be one or multiple current sink electrodes.

The devices described herein can selectively target, simultaneously or sequentially, one or more target areas by selectively activating one or more of the one or more current sources and/or by selectively activating one or more of the one or more current sinks. For example, the devices described herein can selectively target, simultaneously or sequentially, one or more target areas by selectively activating one or more of the one or more current source electrodes and/or by selectively activating one or more of the one or more current sink electrodes.

When delivering dual phased multipolar stimulation, for example, a first current source can be in a first location and a first current sink can be in a second location. The first location can correspond to a vessel first location and the second location can correspond to a vessel second location. The vessel first location can be in a first vessel and the vessel second location can be in a second vessel different from the first vessel. The vessel first and second locations can be on opposite sides of a plane that passes through the target area.

As another example, a first current source can be in a first location, a second current source can be in a second location and a first current sink can be in a third location. The first location can correspond to a vessel first location, the second location can correspond to a vessel second location and the third location can correspond to a vessel third location. The vessel first, second and/or third locations can be in the same or different vessels from one another. The vessel first and/or second locations and the vessel third location can be on opposite sides of a plane that passes through the target area.

As yet another example, a first current source can be in a first location, a second current source can be in a second location, a first current sink can be in a third location and a second current sink can be in a fourth location. The first location can correspond to a vessel first location, the second location can correspond to a vessel second location, the third location can correspond to a vessel third location, and the fourth location can correspond to a vessel fourth location. The vessel first, second, third and/or fourth locations can be in the same or different vessels from one another. The vessel first and/or second locations and the vessel third and/or fourth locations can be on opposite sides of a plane that passes through the target area. The vessel first and third locations can be on opposite sides of a first plane that passes through the target area and the vessel second and fourth locations can be on opposite sides of a second plane that passes through the target area.

The devices described herein can be configured to limit a first current to limit a stimulation depth of a first implant and to limit a second current to limit a stimulation depth of a second implant.

As described above, the devices described herein can adjust a strength of at least one of the one or more current sources to adjust a stimulation strength and/or a stimulation depth. Such adjustments can be accomplished by increasing and/or decreasing the amperage of at least one of the one or more current sources and/or by increasing and/or decreasing the number of currents that sum in the target area.

Similarly described above, one or more currents can be sequentially and/or simultaneously delivered to one or multiple target areas by passing current from one or multiple current sources to one or multiple current sinks.

Dual phase multipolar stimulation can be used to target neural tissue anywhere in the body, for example, in and/or outside of the brain including, for example, the cortex, the subcortex, the cerebellum, the thalamus, the brain stem, the spinal cord, organs (e.g., heart, lungs, stomach, kidneys and pancreas), muscles, or any combination thereof. The cortical and subcortical locations can include, for example, the primary motor cortex (M1), the supplementary motor area (SMA), the posterior parietal cortex (PPC), the primary somatosensory cortex (S1), the cerebellum, the thalamus and the brain stem.

Although the foregoing description refers to dual phased multipolar stimulation throughout, any single stent and/or multi-stent n-phased multipolar stimulation can be provided, for example, with one or multiple implants. In addition to dual phase multipolar stimulation, 3-phase, 4-phase, 5-phase, 6-phase, or n+1 phase multipolar stimulation can be delivered to one or more neural target areas. Alternatively, or in combination, the devices described herein can be configured to deliver two or more dual phased multipolar stimulations to one or multiple target areas. For example, FIGS. 70A-70H illustrate schematic variations of stent devices 100 implanted in the brain in various locations delivering various types of stimulation. FIGS. 70A-70H illustrate various MRI images with stent devices 100 delivering neural stimulation.

Figure 70A:
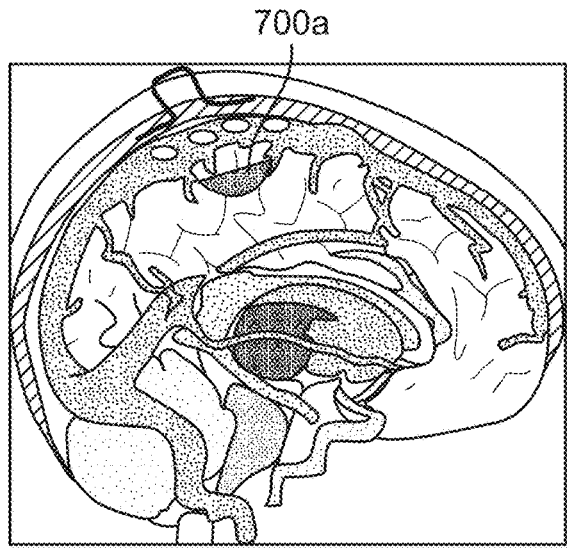
FIGS. 70A-70H illustrate schematic variations of stent devices implanted in the brain in various locations delivering various types of stimulation to various target locations.

FIG. 70A illustrates a stent device 100 located in the superior sagittal sinus delivering monopolar stimulation 700a. External return stimulation is also shown.

Figure 70C:
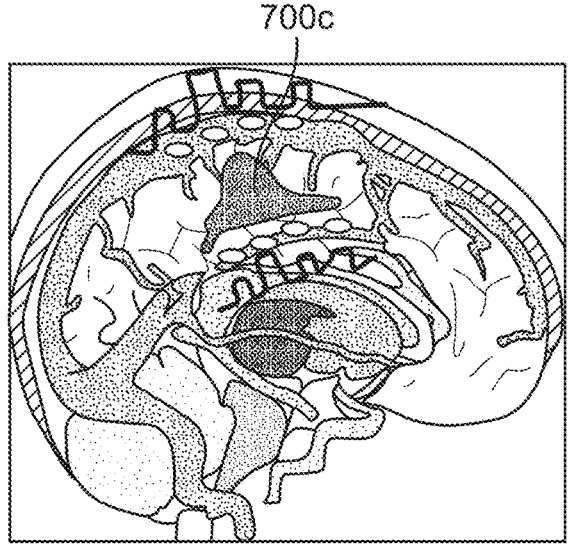
Figure 70B:
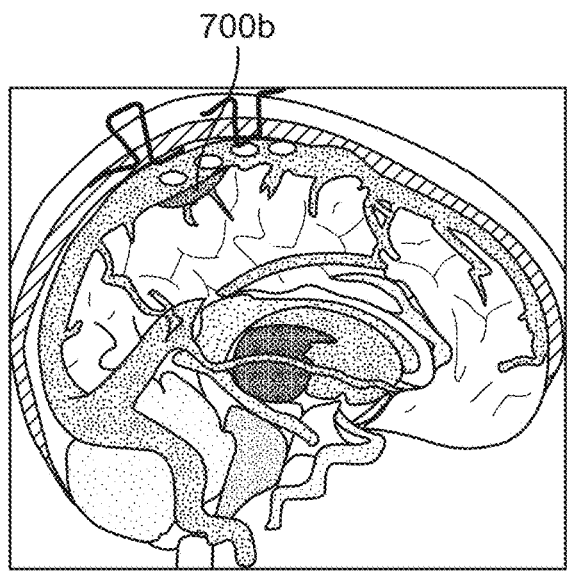

FIG. 70B illustrates a stent device 100 located in the superior sagittal sinus delivering bipolar stimulation 700b.

FIG. 70C illustrates a dual stent implementation delivering multipolar stimulation 700c. A first stent device (e.g., a first stent 100a) is shown located in the superior sagittal sinus and a second stent device (e.g., a second stent 100b) is shown located in the inferior sagittal sinus.

Figure 70D:
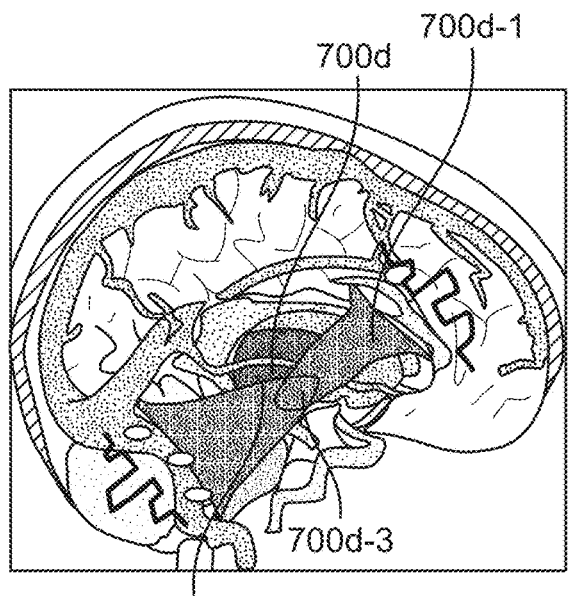

FIG. 70D illustrates a dual stent implementation delivering dual multipolar stimulation 700d. A first stent device (e.g., a first stent 100a) is shown located in the transverse sinus delivering stimulation 700d-1 and a second stent device (e.g., a second stent 100b) is shown located in the pericallosal artery delivering stimulation 700d-2. The first and second stimulations 700d-1, 700d-2 can sum where the two stimulations overlap in region 700d-3. Neural tissue can be stimulated in region 700d-1, region 700d-2, and/or region 700d-3. For example, neural tissue can be stimulated in region 700d-1 but not in the portion of regions 700d-1 and 700d-2 that do not overlap with each other in region 700d-3. As another example, neural tissue can be stimulated in region 700d-1 at a first stimulation magnitude, in region 700d-2 at a second stimulation magnitude, and in region 700d-3 at a third stimulation magnitude. The first and second stimulation magnitudes can be the same or different from one another. The third stimulation magnitude can be the sum of the first and second stimulation magnitudes that are in the overlap region 700d-3. The strength of the stimulation delivered by the first and second stents (e.g., 100a, 100b) can decay as the distance from each respective stent increases, for example, as a result of energy being absorbed by tissue. The stimulation delivered can therefore naturally vary within each stimulation region 700d-1, 700d-2, 700d-3. The stimulation in region 700d-3 can be held substantially constant or can be varied.

Figure 70E:
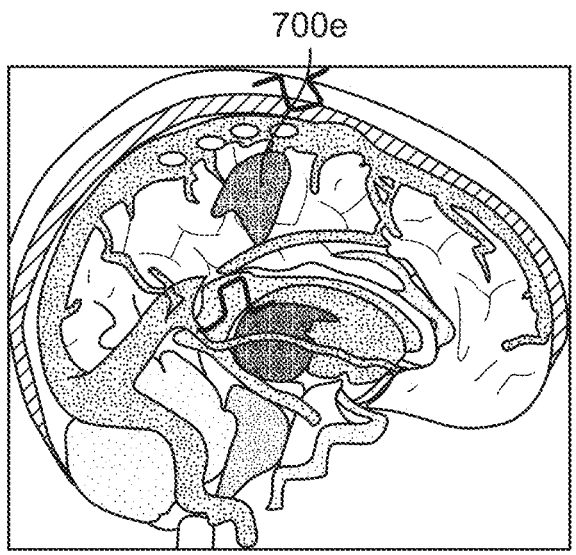

FIG. 70E illustrates a dual stent implementation delivering monopolar stimulation 700e. A first stent device (e.g., a first stent 100a) is shown located in the superior sagittal sinus and a second stent device (e.g., a second stent 100b) is shown located in the inferior sagittal sinus.

Figure 70G:
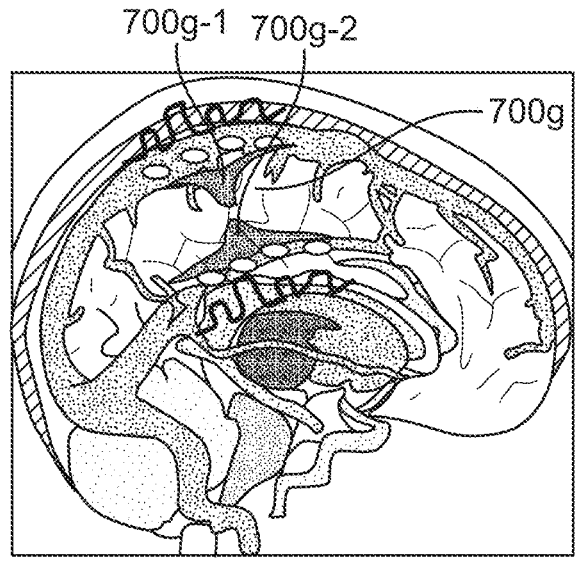
Figure 70F:
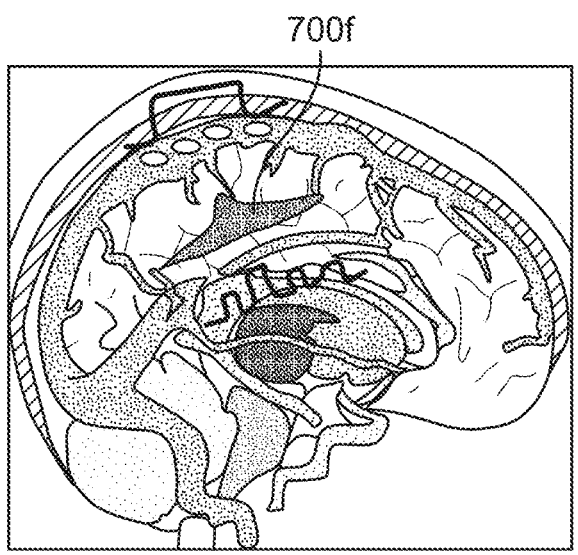

FIG. 70F illustrates a dual stent implementation delivering mono multipolar stimulation 700f. A first stent device (e.g., a first stent 100a) is shown located in the superior sagittal sinus and a second stent device (e.g., a second stent 100b) is shown located in the inferior sagittal sinus.

FIG. 70G illustrates a dual stent implementation delivering dual multipolar stimulation 700g. A first stent device (e.g., a first stent 100a) is shown located in the superior sagittal sinus delivering stimulation 700g-1 and a second stent device (e.g., a second stent 100b) is shown located in the inferior sagittal sinus delivering stimulation 700g-2.

Figure 70H:
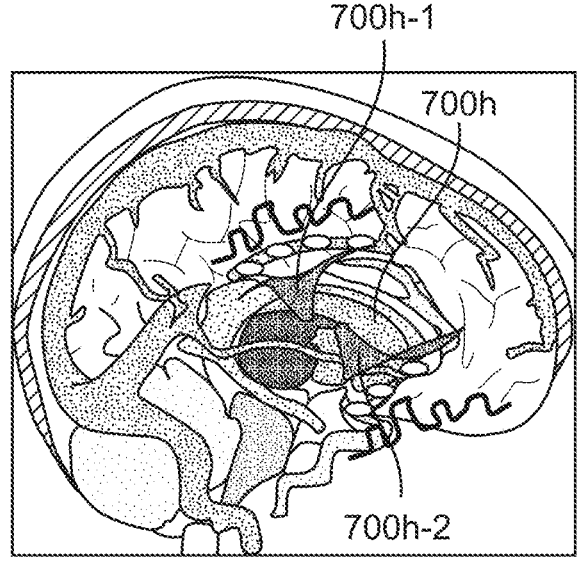

FIG. 70H illustrates a dual stent implementation delivering dual multipolar stimulation 700h. A first stent device (e.g., a first stent 100a) is shown located in the inferior sagittal sinus delivering stimulation 700h-1 and a second stent device (e.g., a second stent 100b) is shown located in the internal carotid artery delivering stimulation 700h-2.

Figure 70I:
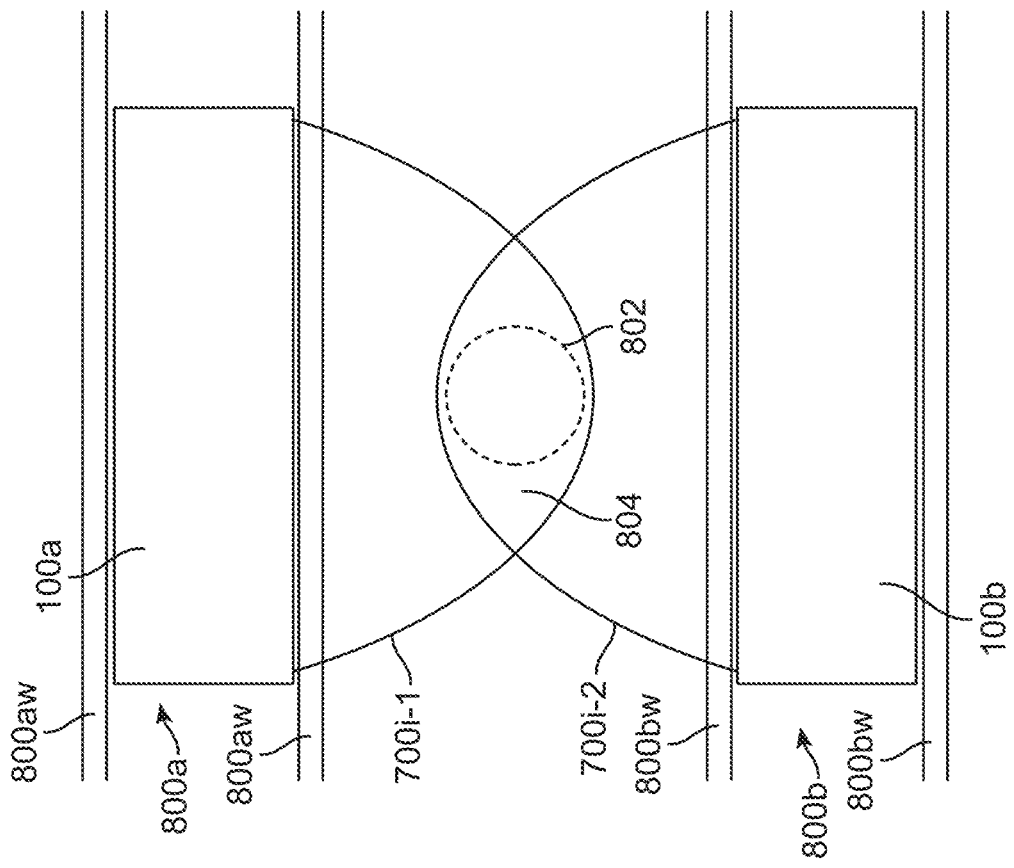
FIGS. 70I(a)-70I(g) illustrate schematic variations of stent devices implanted in vessels delivering various types of stimulation to various target locations.
Figure 70I:
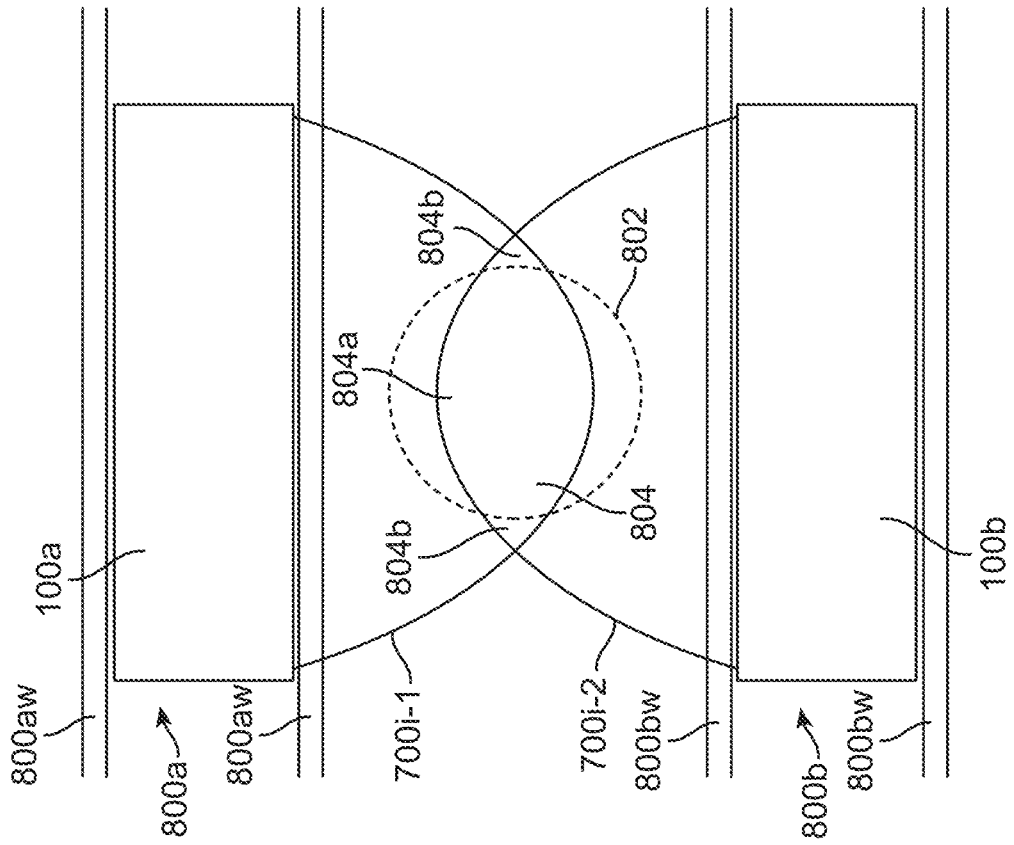
Figure 70I:
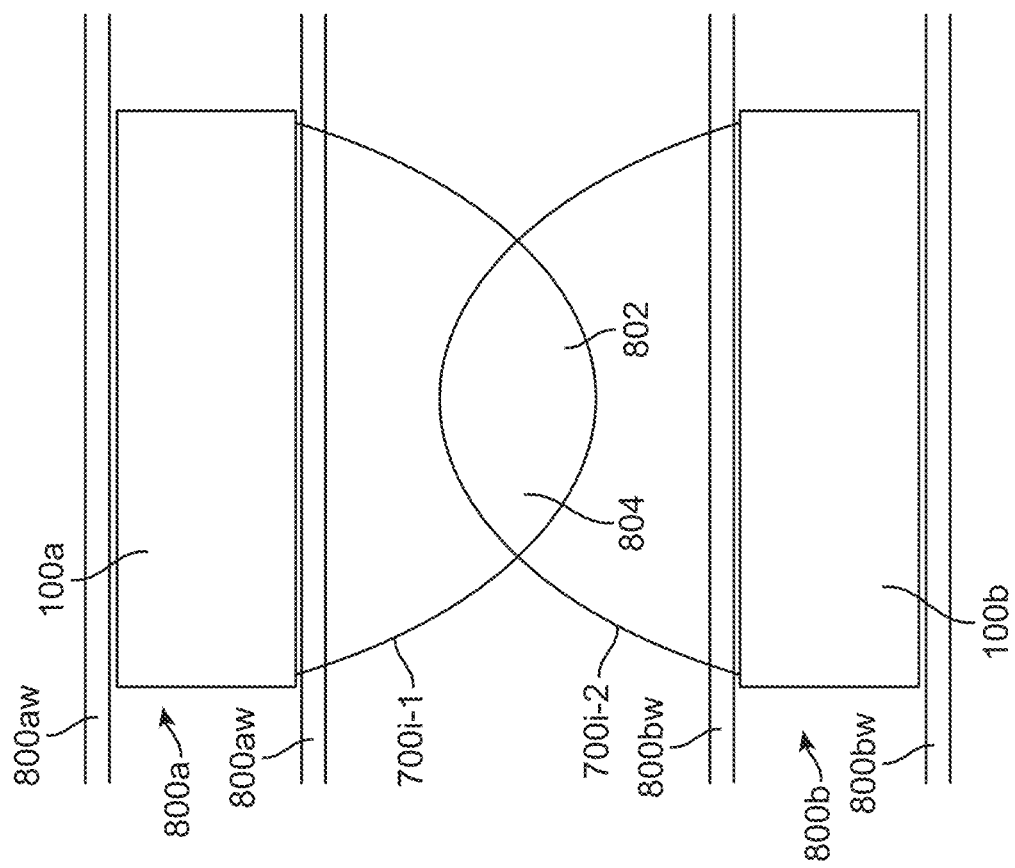
Figure 70I:
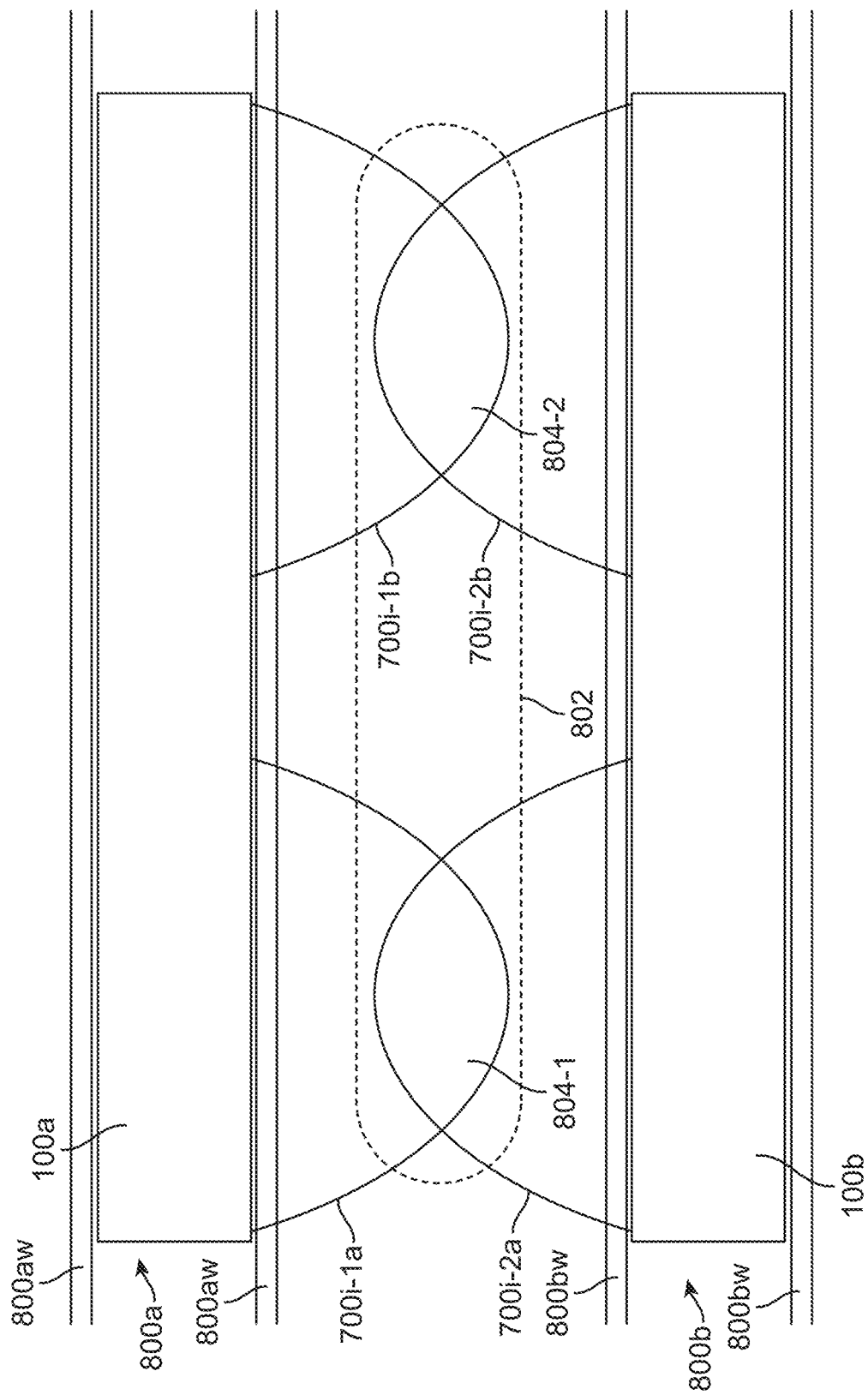
Figure 70I:
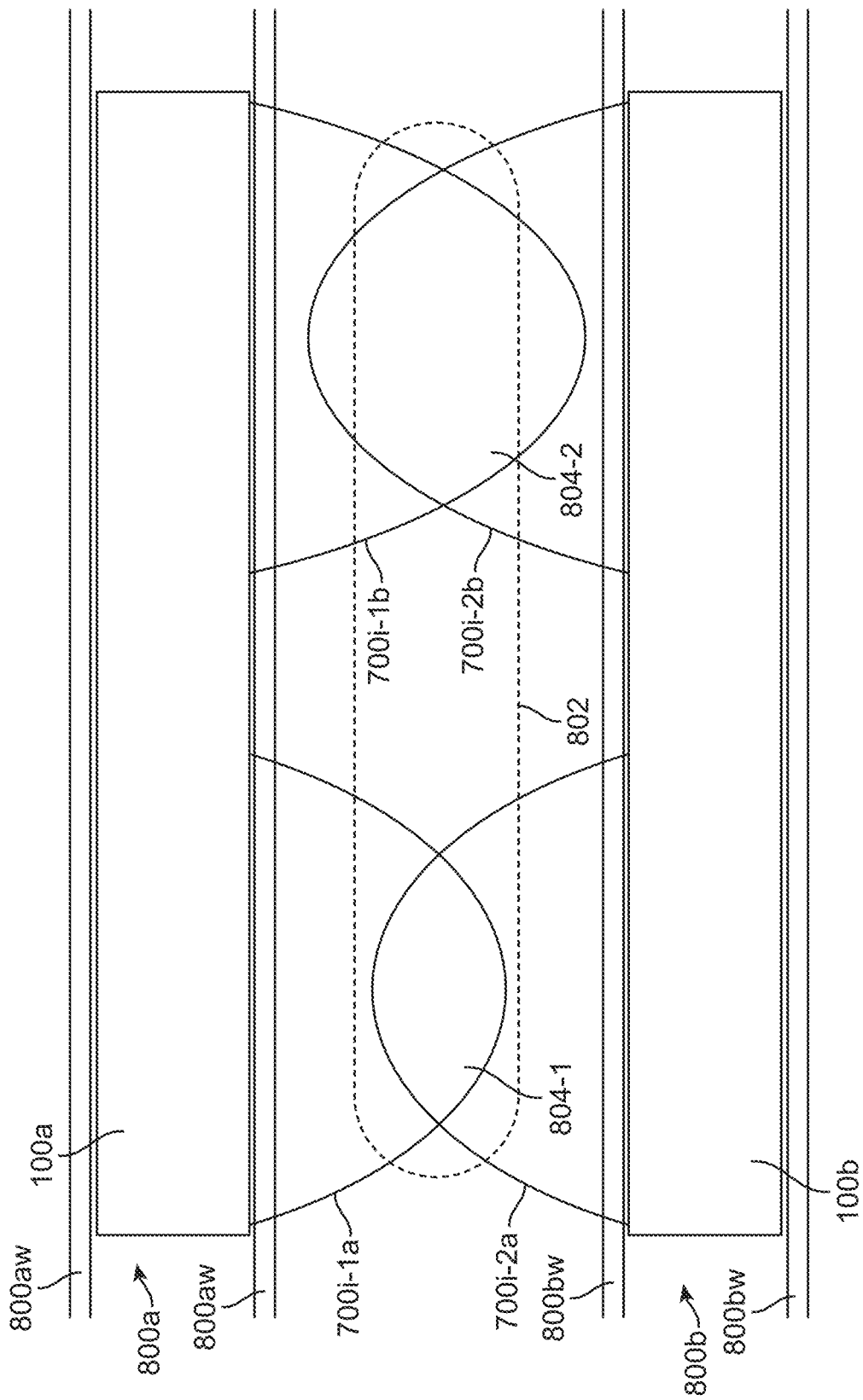
Figure 70I:
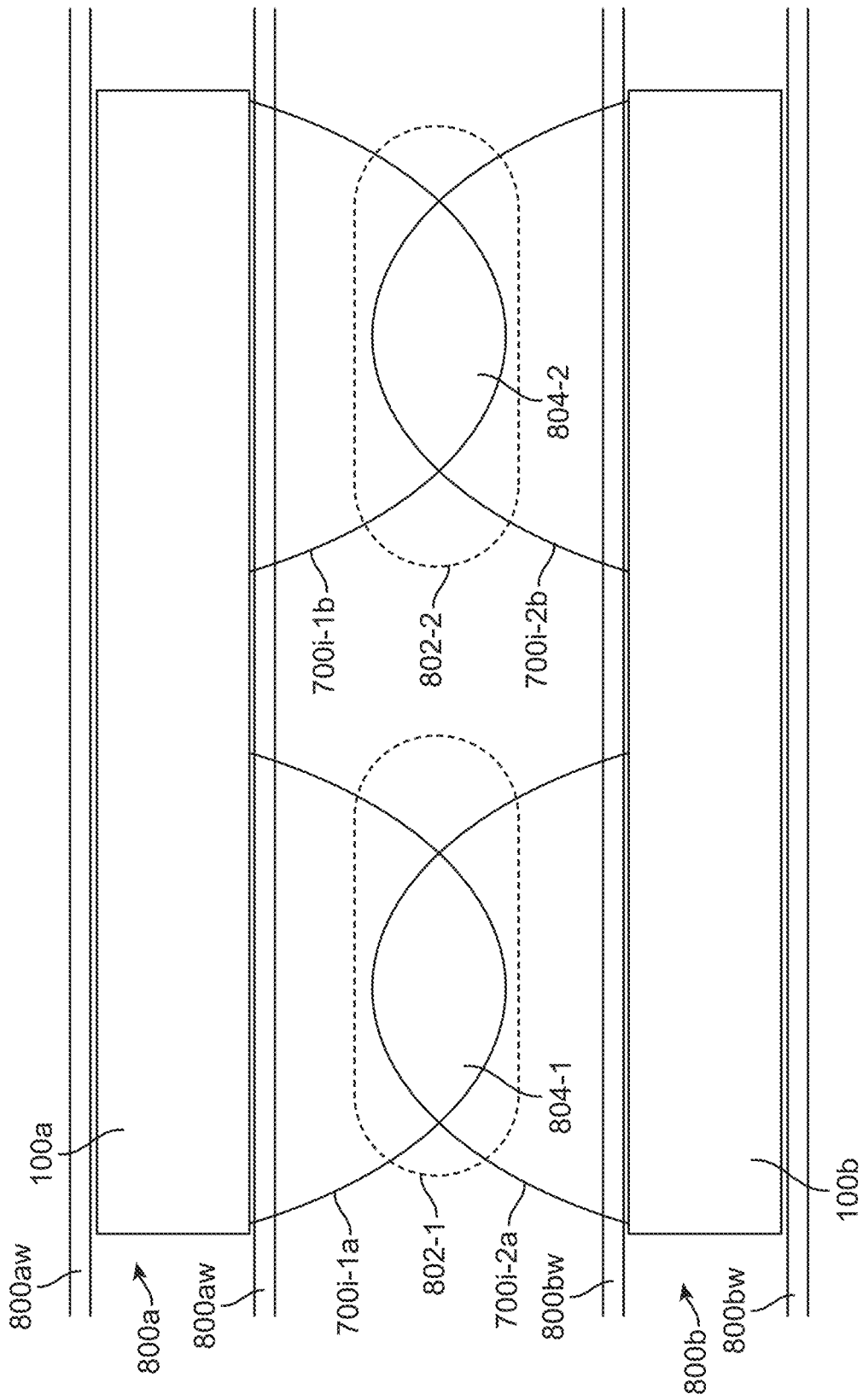
Figure 70I:
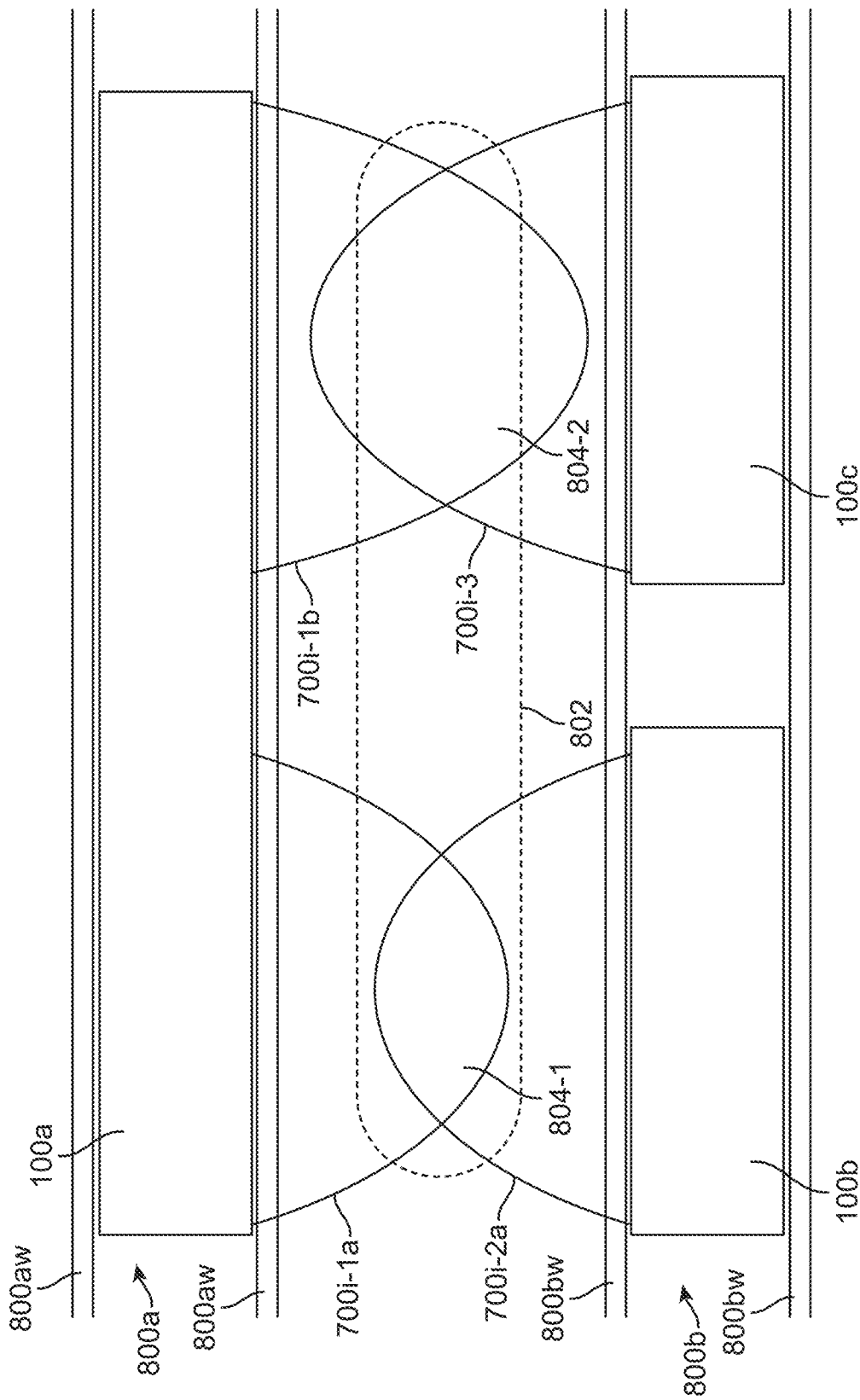

FIG. 70I(a) illustrates a first stent device 100a in a first vessel 800a having a first vessel wall 800aw and a second stent device 100b in a second vessel 800b having a second vessel wall 800bw, where the first and second stents 100a, 100b are configured to deliver signals (e.g., stimulation signals) to a target location 802. For example, the first stent 100a can deliver a first stent signal 700i-1 and the second stent 100b can deliver a second stent signal 700i-2 to the target location 802. The signals can be, for example, electrical impulses, ultrasound signals, or both, including any other type of tissue stimulating signals. The signals 700i-1 and 700i-2 can sum in a signal region 804. The summed signals in the signal region 804 can stimulate tissue. The signal region 804 can be a tissue activation area. The signal region 804 can be a tissue activatable area. Tissue in the activatable area 804 can be activated, for example, when the devices (e.g., 100a, 100b) deliver or emit a signal or signals toward the target area 802. When the two signals (e.g., 700i-1, 700i-2) add together tissue can be activated, for example, in the signal region 804. The summed signal in the signal region 804 can be equal to or greater than a neural tissue activation threshold required to activate neurons and/or neuron bundles in the target area 802. The signal region 804 can be in, can overlap with, or can coincide with some or all of the tissue in the desired target area 802. As another example, the signal region 804 can be in, can overlap with, or can coincide with some or all of the tissue in an undesired or suboptimal target area 802, for example, where anatomical constraints, medical conditions (e.g., aneurysms), surgical complications, or other mitigating factors can result in placement of the stent or stents (e.g., devices 100a, 100b) in the vessel or vessels in secondary, tertiary or unplanned locations.

Neural tissue inside and/or outside the signal region 804 can be stimulated by the first stent first signal 700i-1, by the second stent signal 700i-2, by the combination of the first and second signals 700i-1 and 700i-2, or by any combination thereof. For example, FIG. 70I(a) illustrates that the first and second signals can sum in the signal region 804 to stimulate neural tissue in the target area 802 but that neural tissue outside of region 804 may (e.g., in a device and/or system first variation, for example, the variation shown in FIG. 70I(a)) or may not (e.g., in the device and/or system first variation and/or in a device and/or system second variation) be stimulated by the first and second stents 100a, 100b outside the signal region 804. As a first example, FIG. 70I(a) illustrates that the first and second signals can sum in the signal region 804 to stimulate neural tissue in the target area 802 but that neural tissue outside of the signal region 804 is not stimulated by the first and second stents 100a, 100b. As a second example, FIG. 70I illustrates that neural tissue in and outside the signal region 804 can be stimulated by the first and second stents 100a, 100b, whereby the neural tissue outside of the signal summation region 804 can be, for example, stimulated to a lesser extent than the tissue inside the signal region 804. As a third example, multiple bell-shaped signals or signal spikes (e.g., signals 700i-1 and 700i-2) can be delivered from the stents (e.g., 100a, 100b) to control the shape of the signal summation region 804, to create multiple signal summation regions 804 (e.g., 2 to 50, 2 to 100, 2 to 1000, including every 1 region increment within these ranges), or both, to achieve the desired shape and/or number of stimulation regions 804.

The first and second devices 100a, 100b can have any of the features disclosed, contemplated and/or illustrated herein. The first and second vessels 800a, 800b can be the same or a different vessel and can be any blood vessel in the body. The target location 802 can be any tissue location disclosed, contemplated and/or illustrated herein. The devices 100a and 100b can emit signals away from the devices 100a and 100b, respectively, for example, to stimulate tissue (e.g., tissue in the target area 802), the devices 100a and 100b can record signals received from the tissue (e.g., tissue in the target area 802), or both (e.g., the devices 100*a* and/or 100*b* can stimulate tissue and/or can record signals from tissue).

The devices 100 (e.g., devices 100*a*, 100*b*) can emit signals away from itself, toward itself, or both. The device 100*a* can emit signals toward itself, for example, where the devices (e.g., 100*a*, 100*b*) have a longitudinal curvature such that one or more portions of the device 100 can be oriented or directed to face back onto itself. A longitudinal axis of the device 100*a* can be straight, curved, or both. The device 100*a* can emit signals toward itself, for example, where the device 100*a* has a longitudinal curvature such that one or more first portions of the device 100 (e.g., struts, electrodes) are oriented or directed to face back onto one or more second portions of the device 100 (e.g., struts, electrodes). The energy emitters of the device 100 (e.g., the electrodes of the device 100) can emit energy at any angle away from the device longitudinal axis, where the device longitudinal axis can be, for example, a center axis through the blood flow channel defined by the device, or as another example, a center axis through one or more of the struts. The energy emitters (e.g., electordes) can emit energy along an emission axis that extends away from or toward the device longitudinal axis at an emission angle of, for example, about 1 degree to about 360 degrees, including every 1 degree increment within this range (e.g., 15 degrees, 45 degrees, 60 degrees, 75 degrees, 90 degrees, 105 degrees, 120 degrees, 135 degrees, 150 degrees, 165 degrees). The emission axis can intersect with or not intersect with the device longitudinal axis. Although two devices 100*a* and 100*b* and two vessels 800*a* and 800*b* are shown in FIG. 70I(a), the device 100*b* can be a second portion of the device 100*a* in the vessel 800*a* such that the device 100*b* in FIG. 70I(a) is another part of the device 100*a* and such that the blood vessel 800*b* is another portion of the blood vessel 800*a*, for example, where device 100*a* is curved in the vessel 800*a*. In such cases, the device first portion 100*a* can be a first longitudinal end of the device or any segment of the device 100*a* between the first longitudinal terminal end of the device and the second longitudinal terminal end of the device. The device second portion (illustrated as 100*b* in this portion of the detailed description) can be a second longitudinal end of the device or any segment of the device 100*a* between the first longitudinal terminal end of the device and the second longitudinal terminal end of the device.

FIG. 70I(a) further illustrates that some or all of the signal summation region 804 can overlap with the target area 802. For example, FIG. 70I(a) illustrates that the signal region 804 can have a signal region first region 804*a*, a signal region second region 804*b* and a signal region third region 804*c*, where the region 804*a* is inside the target area 802 and the regions 804*b* and 804*c* are outside of the target area 802.

FIG. 70I(b) illustrates that all of the target area 802 can be within the signal summation region 804.

FIG. 70I(c) illustrates that the target area 802 can have the same exact shape and size as the signal summation region 804. The stent or stents (e.g., 100*a* and 100*b*) can be controlled to emit signals which sum to approximate the desired shape, size, and number of target areas 802.

FIG. 70I(d) illustrates that the one or multiple devices (e.g., stentrodes 100*a*, 100*b*) can emit multiple bell-shaped signals, signal spikes, signals, or any combination thereof (e.g., signals 700*i*-1 and 700*i*-2) having different strengths. Multiple signals can be delivered from the stents (e.g., 100*a*, 100*b*), for example, to control the size and/or shape of the signal summation region 804, to create multiple signal summation regions 804 (e.g., 2 to 50, 2 to 100, 2 to 1000, including every 1 region increment within these ranges), or both, to advantageously achieve the desired size, shape, and/or number of stimulation regions 804. For example, FIG. 70I(d) illustrates that the first stent 100*a* can deliver a first stent first signal 700*i*-1*a* and a first stent second signal 700*i*-1*b* to the target location 802 and that the second stent 100*b* can deliver a second stent first signal 700*i*-2*a* and a second stent second signal 700*i*-2*b* to the target location 802. The signals 700*i*-1*a* and 700*i*-2*a* can sum in a first signal region 804-1. The signals 700*i*-1*b* and 700*i*-2*b* can sum in a second signal region 804-2. The first signal region 804-1 can be the same or different size and shape than the second signal region 804-2. The first and second signal regions 804-1, 804-2 can stimulate the same tissue or different tissues (e.g., the same brain regions or different brain regions). The summed signals in the signal regions 804-1 and 804-2 can stimulate tissue in these respective regions.

FIG. 70I(e) illustrates that the signal first and second regions 804-1, 804-2 can be different sizes. For example, the second signal region 804-2 is shown larger than the first signal region 804-1.

FIG. 70I(f) illustrates that the one or multiple devices (e.g., stentrodes 100*a*, 100*b*) can stimulate multiple target areas 802 (e.g., 2 to 10 target areas, 2 to 100 target areas, 2 to 1000 target areas, including every 1 target area increment within these ranges, for example, a first target). For example, the first and second devices 100*a*, 100*b* can stimulate a first target area 802-1 and the first and second devices 100*a*, 100*b* can stimulate a second target area 802-2. For example, the first and second devices 100*a*, 100*b* can sum in a first activation region 804-1 and in a second activation region 804-2.

FIG. 70(g) illustrates that the stimulation system can include three or more stentrode devices, for example, stent 100*a*, 100*b* and 100*c*, where a signal from the first stent 100*a* can sum with the signals from the second stent 100*b* and/or from the third stent 100*c*, where a signal from the second stent 100*b* can sum with the signals from the first stent 100*a* and/or from the third stent 100*c*, and where a signal from the third stent 100*c* can sum with the signals from the first stent 100*a* and/or from the second stent 100*b*. For example, FIG. 70I(g) illustrates that the first stent first signal 700*i*-1*a* can sum with the second stent signal 700*i*-2 and that the first stent second signal 700*i*-1*b* can sum with a third stent signal 700*i*-3.

Although two devices 100*a* and 100*b* and two vessels 800*a* and 800*b* are shown in FIGS. 70I(a)-70(g), the device 100*b* can be a second portion of the device 100*a* in the vessel 800*a* such that the device 100*b* in these figures is another part of the device 100*a* and such that the blood vessel 800*b* is another portion of the blood vessel 800*a*, for example, where device 100*a* is curved in the vessel 800*a*. In such cases, the device first portion 100*a* can be a first longitudinal end of the device or any segment of the device 100*a* between the first longitudinal terminal end of the device and the second longitudinal terminal end of the device. The device second portion (illustrated as 100*b* in this portion of the detailed description) can be a second longitudinal end of the device or any segment of the device 100*a* between the first longitudinal terminal end of the device and the second longitudinal terminal end of the device.

Each stent device in FIGS. 70A-70H is shown schematically as four dots, with the exception of FIG. 70D in which the illustrated stent devices are each shown schematically as three dots. The various stimulation patterns 700*a*-700*h* shown in FIGS. 70A-70I(g) are exemplary and illustrate the area of neural activation (also referred to as the current spread). The stimulation patterns 700a-700h illustrated by the shaded regions in FIGS. 70A-70H are exemplary cross-sectional schematic variations of a portion of the three-dimensional current spread being delivered by the illustrated stent devices 100. The stimulation patterns in FIGS. 70I(a)-(g) are likewise exemplary. FIGS. 70A-70H illustrate that one or multiple neural areas can be targeted simultaneously. As described above, the patterns and polarities of a stimulation can be static or dynamic such that the stimulation being delivered can be held constant or adjusted in real-time, for example, based on a user's responsiveness to the stimulation and/or based on criteria unrelated to a user's responsiveness (e.g., predetermined stimulation times, pre-determined stimulation sequences, pre-determined stimulation strengths). Additionally, or in combination, the patterns and polarities can be pulsed or have another delivery protocol that is variable in nature. The energy emitted from a first device in these figures can sum with energy emitted from a second device to activate tissue (e.g., in any of the configurations shown in FIGS. 70A-70H). As another example, the energy emitted from the devices shown in FIGS. 70A-70H can activate tissue with or without the emitted energy from the different energy sources (e.g., devices 100) summing together, for example, from multiple devices 100 (e.g., a first device, a second device, a third device, or more devices, or any combination thereof). For example, where there are multiple summation regions 804, these multiple regions can be stimulated independently from one another, sequentially, simultaneously, or any combination thereof, for example, over an energy delivery period.

Figure 71B:
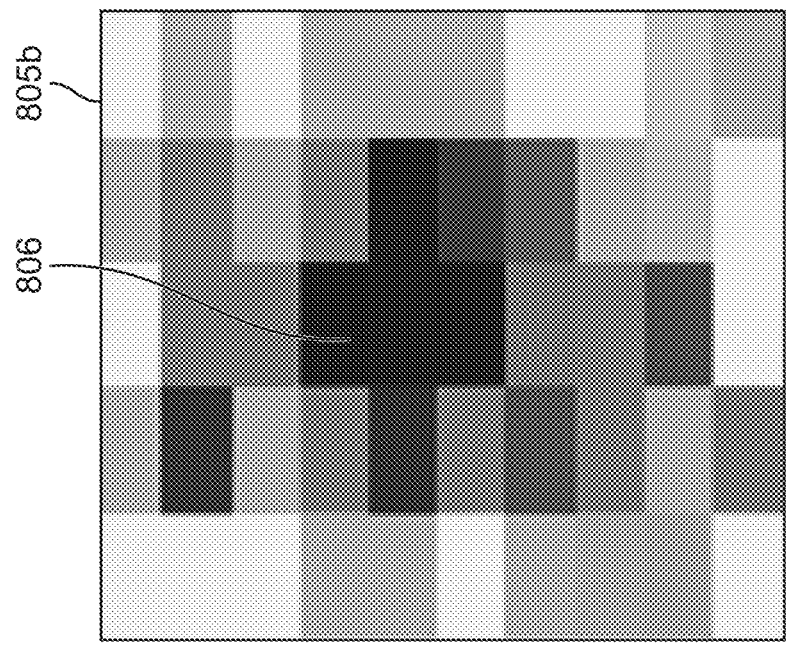
FIGS. 71A and 71B illustrate variations of stimulation heat maps.
Figure 71A:
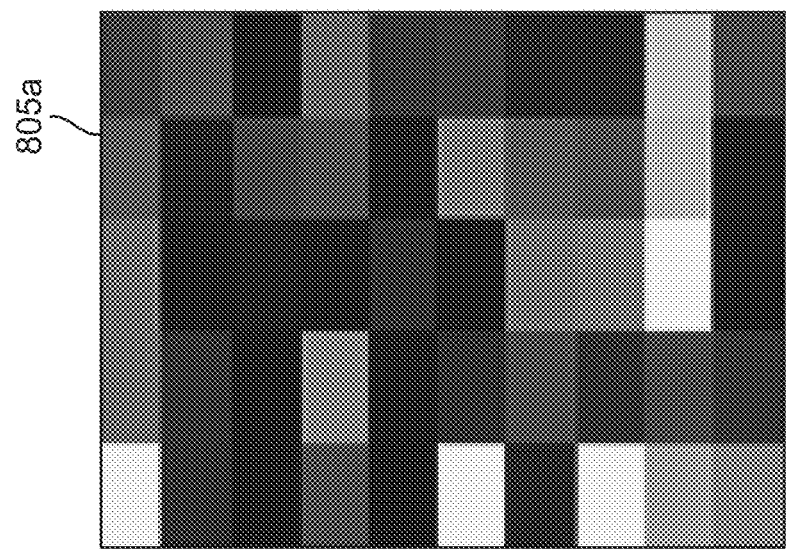

FIG. 71A illustrates an exemplary heat map 805a when the device or devices (e.g., 100a, 100b) stimulate tissue with monopolar stimulation, where the heat map 805a shows large current spreads (e.g., the darker areas).

FIG. 71B illustrates an exemplary heat map 805b when the device or devices (e.g., 100a, 100b) stimulate tissue with dual multipolar stimulation, where the heat map 805b shows focal current distributions, for example, showing a focused current distribution 806. Focused current distributions can advantageously allow more focused treatment of subjects and give more granularity to subjects in regards to control and accuracy, for example, when compared to the monopolar stimulation heat map 805a of FIG. 71A. The focused current distributions that the device or devices (e.g., 100a, 100b) can provide can advantageously give subjects more control and/or more accurate control of the external devices or systems linked to their one or more stentrodes (e.g., 100a, 100b).

The heat maps 805a and 805b can be the heat maps in the target area 802. The heat maps 805a and 805b can be the heat maps in the signal summation regions 804. The heat maps 805a and 805b can be the heat maps that span the target area 802 inside and outside of the signal summation regions 804.

Power Generation

The devices described herein (e.g., the stent devices 100) can be powered with blood flow, thermoelectricity, electromagnetism, piezoelectricity, or any combination thereof.

Many modifications will be apparent to those skilled in the art without departing from the scope of the present invention.

The reference to any prior art in this specification is not, and should not be taken as, an acknowledgment or any form of suggestion that the prior art forms part of the common general knowledge in Australia In this specification and the claims that follow, unless stated otherwise, the word "comprise" and its variations, such as "comprises" and "comprising", imply the inclusion of a stated integer, step, or group of integers or steps, but not the exclusion of any other integer or step or group of integers or steps.

References in this specification to any prior publication, information derived from any said prior publication, or any known matter are not and should not be taken as an acknowledgement, admission or suggestion that said prior publication, or any information derived from this prior publication or known matter forms part of the common general knowledge in the field of endeavor to which the specification relates.

Any elements described herein as singular can be pluralized (i.e., anything described as "one" can be more than one). Like reference numerals in the drawings indicate identical or functionally similar features/elements. Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All dimensions shown in the drawings are exemplary.

We claim:

1. A method of controlling an apparatus in communication with a brain machine interface, the method comprising:
    measuring a first neural activity in a first neural area, where the first neural activity is associated with a first intent to control the apparatus, where measuring the first neural activity comprises using a first sensor of the brain machine interface;
    measuring a second neural activity in a second neural area using a second sensor of the brain machine interface;
    receiving, via a processor in wired or wireless communication with the brain machine interface, the first neural activity and the second neural activity;
    processing, via the processor, the received first neural activity and the second neural activity; and
    creating and delivering, via the processor, one or more first control signals to the apparatus upon comparing the second neural activity with the first neural activity, and confirming, based on this comparison, that the second neural activity is associated with the first intent.

2. The method of claim 1, where measuring a first neural activity in a first neural area comprises measuring the first neural activity from the first sensor at a machine interface location, and where measuring a second neural activity in a second neural area comprises measuring the second neural activity from the second sensor at the same brain machine interface location.

3. The method of claim 2, where the brain machine interface location is a blood vessel.

4. The method of claim 1, where the first sensor is a first portion of the brain machine interface and the second sensor is a second portion of the brain machine interface.

5. The method of claim 1, further comprising:
    decoding, via the processor, the first intent from the measured first neural activity; and
    decoding, via the processor, a second intent from the measured second neural activity,
    where the delivering comprises delivering the one or more first control signals to the apparatus upon confirming that the second intent is associated with the first intent.

6. The method of claim 5, where decoding the first and second intents comprises referencing previously measured neural activities stored in a memory.

7. The method of claim 1, further comprising repeating the measuring until at least one of the one or more first control signals is delivered to the apparatus.

8. The method of claim 1, where the delivering comprises delivering the one or more first control signals to the apparatus to control a first parameter and/or a second parameter of the apparatus.

9. The method of claim 1, where the first sensor is proximate or in a first neural area and where the second sensor is proximate or in a second neural area.

10. The method of claim 9, wherein the first and second neural areas are in a brain.

11. The method of claim 1, further comprising:
determining, via the processor, a desired parameter of the apparatus from a signal received from a sensor of the apparatus;
calculating, via the processor, a control correlation between the measured first neural activity and the desired parameter; and
adjusting, via the processor, a brain machine interface control percentage of the apparatus and an apparatus control percentage of the apparatus upon determining the control correlation is below a predetermined error, where the brain machine interface control percentage is the percentage control of the apparatus via signals detected by the first and second sensors of the brain machine interface, and where the apparatus control percentage of the apparatus is the percentage control of the apparatus via signals detected by the sensor of the apparatus.

12. The method of claim 11, where the adjusting comprises increasing the brain machine interface control percentage and decreasing the apparatus control percentage upon determining the control correlation is below the predetermined error and/or where the adjusting comprises decreasing the brain machine interface control percentage and increasing the apparatus control percentage upon determining the control correlation is above the predetermined error.

13. The method of claim 12, where the brain machine interface control percentage is initially 0% to 25% and the apparatus control percentage is initially 75% to 100%, further comprising incrementally increasing the brain machine interface control percentage from an initial percentage of 0% to 25% to a final percentage of 75% to 100%.

14. The method of claim 11, wherein the brain machine interface control percentage of the apparatus is associated with a user of the apparatus using the brain machine interface such that the brain machine interface is configured to record, via the first or second sensor, brain activity of the user when the user attempts to control the apparatus, and wherein the apparatus control percentage of the apparatus is associated with the apparatus such that the apparatus determines, via an apparatus processor, an estimate of the first parameter.

15. A method of controlling an apparatus in communication with a brain machine interface, the method comprising:
measuring a first neural activity in a first neural area, where the first neural activity is associated with a first intent to control the apparatus, where measuring the first neural activity comprises using a first sensor of the brain machine interface in a first area of the brain;
measuring a second neural activity in a second neural area using a second sensor of the brain machine interface in the first area of the brain;
receiving, via a processor in wired or wireless communication with the brain machine interface, the first neural activity and the second neural activity;
processing, via the processor, the received first neural activity and the second neural activity; and
creating and delivering, via the processor, one or more first control signals to the apparatus upon confirming that the second neural activity is associated with the first intent.

16. The method of claim 15, where the creating and delivering comprises creating and delivering, via the processor, one or more first control signals to the apparatus upon comparing the second neural activity with the first neural activity, and confirming, based on this comparison, that the second neural activity is associated with the first intent.

17. The method of claim 15, where the delivering comprises delivering the one or more first control signals to the apparatus to control a first parameter and/or a second parameter of the apparatus.

18. A method of controlling an apparatus in communication with a brain machine interface, the method comprising:
measuring a first neural activity in a first neural area, where the first neural activity is associated with a first intent to control the apparatus, where measuring the first neural activity comprises using a first sensor of the brain machine interface in a first area of the brain;
measuring a second neural activity in a second neural area using a second sensor of the brain machine interface in the first area of the brain;
receiving, via a processor in wired or wireless communication with the brain machine interface, the first neural activity and the second neural activity;
processing, via the processor, the received first neural activity and the second neural activity; and
creating and delivering, via the processor, one or more first control signals to the apparatus upon comparing the second neural activity with the first neural activity, and confirming, based on this comparison, that the second neural activity is associated with the first intent.

19. The method of claim 18, where the delivering comprises delivering the one or more first control signals to the apparatus to control a first parameter and/or a second parameter of the apparatus.

20. The method of claim 18, where the first sensor is a first portion of the brain machine interface and the second sensor is a second portion of the brain machine interface.

* * * * *